US008097625B2

(12) United States Patent
Lalji et al.

(10) Patent No.: US 8,097,625 B2
(45) Date of Patent: Jan. 17, 2012

(54) COMBINATION OF SEDATIVE AND A NEUROTRANSMITTER MODULATOR, AND METHODS FOR IMPROVING SLEEP QUALITY AND TREATING DEPRESSION

(75) Inventors: Karim Lalji, Sudbury, MA (US); Timothy J. Barberich, Concord, MA (US); Judy Caron, Westwood, MA (US); Thomas Wessel, Lenox, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 8 days.

(21) Appl. No.: 11/761,235

(22) Filed: Jun. 11, 2007

(65) Prior Publication Data

US 2007/0299055 A1 Dec. 27, 2007

Related U.S. Application Data

(63) Continuation of application No. 11/007,795, filed on Dec. 8, 2004, now abandoned.

(60) Provisional application No. 60/529,156, filed on Dec. 11, 2003, provisional application No. 60/541,614, filed on Feb. 4, 2004, provisional application No. 60/633,213, filed on Dec. 3, 2004.

(51) Int. Cl.
*A01N 43/58* (2006.01)
*A01N 43/40* (2006.01)
*A61K 31/50* (2006.01)
*A61K 31/497* (2006.01)
*A61K 31/435* (2006.01)

(52) U.S. Cl. ............ 514/247; 514/252.1; 514/277; 514/449; 514/461

(58) Field of Classification Search .......... 514/217, 514/247, 252.1, 277, 449, 461
See application file for complete search history.

(56) References Cited

U.S. PATENT DOCUMENTS

| | | | |
|---|---|---|---|
| 4,278,676 | A | 7/1981 | Krogsgaard-Larsen |
| 4,419,345 | A | 12/1983 | Wyatt |
| 4,505,914 | A | 3/1985 | Metz et al. |
| 5,430,029 | A | 7/1995 | Biella et al. |
| 5,786,357 | A | 7/1998 | Young et al. |
| 5,929,065 | A | 7/1999 | Lancel |
| 6,211,173 | B1 | 4/2001 | Fink-Jensen et al. |
| 6,258,814 | B1 | 7/2001 | Martin |
| 6,319,926 | B1 * | 11/2001 | Cotrel et al. |
| 6,319,927 | B1 | 11/2001 | Martin |
| 6,342,533 | B1 | 1/2002 | Jerussi et al. |
| 6,348,485 | B1 | 2/2002 | Ohkawa et al. |
| 6,436,936 | B1 | 8/2002 | Young et al. |
| 6,444,673 | B1 * | 9/2002 | Cotrel et al. |
| 6,864,257 | B2 * | 3/2005 | Cotrel et al. |
| 7,125,874 | B2 | 10/2006 | Cotrel et al. |
| 7,381,724 | B2 * | 5/2008 | Cotrel et al. |
| 7,465,729 | B2 * | 12/2008 | Wessel et al. |
| 7,776,858 | B2 * | 8/2010 | Wessel et al. |
| 2002/0019398 | A1 | 2/2002 | Jerussi et al. |
| 2002/0143016 | A1 | 10/2002 | Jerussi et al. |
| 2002/0193378 | A1 | 12/2002 | Cotrel et al. |
| 2003/0119841 | A1 | 6/2003 | Jerussi et al. |
| 2003/0166657 | A1 | 9/2003 | Jerussi et al. |
| 2004/0122104 | A1 | 6/2004 | Hirsh et al. |
| 2004/0132826 | A1 | 7/2004 | Hirsh et al. |
| 2004/0147521 | A1 | 7/2004 | Jerussi et al. |
| 2004/0192764 | A1 * | 9/2004 | Sanchez et al. ............ 514/469 |
| 2005/0031688 | A1 | 2/2005 | Ayala |
| 2005/0038042 | A1 | 2/2005 | Codd et al. |
| 2005/0164987 | A1 | 7/2005 | Barberich et al. |
| 2005/0176680 | A1 | 8/2005 | Lalji et al. |
| 2005/0215521 | A1 | 9/2005 | Barberich et al. |
| 2005/0267176 | A1 * | 12/2005 | Barberich et al. |
| 2008/0175903 | A1 * | 7/2008 | Hopkins et al. |
| 2008/0293726 | A1 * | 11/2008 | Caron et al. |
| 2009/0111817 | A1 * | 4/2009 | Caron et al. |
| 2009/0111818 | A1 * | 4/2009 | Caron et al. |
| 2010/0004251 | A1 * | 1/2010 | Barberich et al. |
| 2010/0280038 | A1 | 11/2010 | Wessel et al. |

FOREIGN PATENT DOCUMENTS

| | | |
|---|---|---|
| WO | WO 99/37303 A | 7/1999 |
| WO | WO 2004/000326 | 12/2003 |
| WO | WO 2004/112786 A2 | 12/2004 |
| WO | 2005/060968 A1 * | 7/2005 |
| WO | 2005/063248 | 7/2005 |
| WO | 2005/063297 | 7/2005 |
| WO | 2005/079851 A3 * | 9/2005 |
| WO | 2005/097132 | 10/2005 |
| WO | 2005097132 | 10/2005 |
| WO | 2007/005940 A2 * | 1/2007 |
| WO | 2007/005961 A2 * | 1/2007 |
| WO | 2007/005962 A2 * | 1/2007 |
| WO | 2007/006003 A2 * | 1/2007 |
| WO | 2008/070000 A2 * | 6/2008 |

OTHER PUBLICATIONS

Drugs of the Future; Drugs Fut 2003, 28(7):640.* Asnis, G. M. et. al.; J. Clin. Psychiatry, 60: 10, 1999.*
Roth T. The relationship between psychiatric diseases and insomnia. Int J Clin Pract Suppl 2001;3-8.
Roth T. New developments for treating sleep disorders. J Clin Psychiatry 2001;62 Suppl 10:3-4.
McCall WV. A psychiatric perspective on insomnia. J Clin Psychiatry 2001;62 Suppl 10:27-32.

(Continued)

*Primary Examiner* — Yong Chong
(74) *Attorney, Agent, or Firm* — Heslin Rothenberg Farley & Mesiti P.C.

(57) ABSTRACT

One aspect of the present invention relates to pharmaceutical compositions containing two or more active agents that when taken together can be used to treat, e.g., insomnia and/or depression. The first component of the pharmaceutical composition is a GABA receptor modulating compound. The second component of the pharmaceutical composition is a serotonin reuptake inhibitor, a norepinephrine reuptake inhibitor, a 5-HT$_{2A}$ modulator, or dopamine reuptake inhibitor. In certain embodiments, the pharmaceutical composition comprises eszopiclone. In a preferred embodiment, the pharmaceutical composition comprises eszopiclone and fluoxetine. The present invention also relates to a method of treating a sleep abnormality, treating insomnia, treating depression, augmenting antidepressant therapy, eliciting a dose-sparing effect, reducing depression relapse, improving the efficacy of antidepressant therapy or improving the tolerability of antidepressant therapy, comprising co-administering to a patient in need thereof a GABA-receptor-modulating compound; and a SRI, NRI, 5-HT$_{2A}$ modulator or DRI.

9 Claims, 16 Drawing Sheets

OTHER PUBLICATIONS

Mellinger GD, Baiter MB, Uhlenhuth EH. Insomnia and its treatment. Prevalence and correlates. Arch Gen Psychiatry 1985;42:225-232.

Ancoli-Israel S, Roth T. Characteristics of insomnia in the United States: results of the 1991 National Sleep Foundation Survey. I. Sleep 1999;22 Suppl 2:S347-S353.

Shochat T, Umphress J, Israel AG, et al. Insomnia in primary care patients. Sleep 1999;22 Suppl 2:S359-S365.

Doghramji K. The need for flexibility in dosing of hypnotic agents. Sleep 2000;23 Suppl I:S16-S20.

Liu X, Uchiyama M, Kim K, et al. Sleep loss and daytime sleepiness in the general adult population of Japan. Psychiatry Res 2000;93: 1-11.

Nugent AM, Gleadhill I, McCrum E, et al. Sleep complaints and risk factors for excessive daytime sleepiness in adult males in Northern Ireland. J Sleep Res 2001;10:69-74.

Ohayon MM, Zulley J. 1. Correlates of global sleep dissatisfaction in the German population. Sleep 2001;24:780-787.

National Sleep Foundation. 2002 Sleep in America Poll. Washington, DC: WB & A Market Research; 2002: 1-43.

Reite M, Ruddy J, Nagel K. Insomnia complaints. In: Concise Guide to Evaluation and Management of Sleep Disorders. 2nd ed. Washington, DC: American Psychiatric Press, Inc.; 1997:47-112.

Szuba MP, Fernando AT, Groh-Szuba G. Sleep abnormalities in treatment-resistant mood disorders. In: Amsterdam JD, Nierenberg AA, eds. Treatment Resistant Mood Disorders. Cambridge, UK: Cambridge University Press; 2001:96-110.

McCall WV. Management of primary sleep disorders among elderly persons. Psychiatr Serv 1995;46:49-55.

Reynolds CF, III. Sleep disorders. In: Sadavoy J, Lazarus LW, Jarvik LF, et al., eds. Comprehensive Review of Geriatric Psychiatry-II. 2nd ed. Washington, DC: American Psychiatric Press, Inc.; 1996:693-712.

Webb WB. Sleep in older persons: sleep structures of 50- to 60-year-old men and women. J Gerontol 1982;37:581-586.

Gislason T, Almqvist M. Somatic diseases and sleep complaints. An epidemiological study of 3,201 Swedish men. Acta Med Scand 1987;221:475-481.

McCrae CS, Lichstein KL. Managing insomnia in long-term care. Annals of Long-term Care 2002; 10:38-43.

Dorrepaal KL, Aaronson NK, van Dam FS. Pain experience and pain management among hospitalized cancer patients. A clinical study. Cancer 1989;63:593-598.

Strang P. Emotional and social aspects of cancer pain. Acta Oncol 1992;31 :323-326.

Boyle GJ, Murrihy R. A preliminary study of hormone replacement therapy and psychological mood states in perimenopausal women. Psychol Rep 2001;88: 160-170.

Mitchell ES, Woods NF. Symptom experiences of mid life women: observations from the Seattle Midlife Women's Health Study. Maturitas 1996;25: 1-10.

Moe KE. Reproductive hormones, aging, and sleep. Semin Reprod Endocrinol 1999; 17:339-348.

Bonnet MH. Infrequent periodic sleep disruption: effects on sleep, performance and mood. Physiol Behav 1989;45: 1049-1055.

Hohagen F, Kappler C, Schramm E, et al. Sleep onset insomnia, sleep maintaining insomnia and insomnia with early morning awakening—temporal stability of subtypes in a longitudinal study on general practice attenders. Sleep 1994;17:551-554.

Ford DE, Kamerow DB. Epidemiologic study of sleep disturbances and psychiatric disorders. An opportunity for prevention? JAMA 1989;262:1479-1484.

Breslau N, Roth T, Rosenthal L, et al. Sleep disturbance and psychiatric disorders: a longitudinal epidemiological study of young adults. Biol Psychiatry 1996;39:411-418.

Chang PP, Ford DE, Mead LA, et al. Insomnia in young men and subsequent depression. The Johns Hopkins Precursors Study. Am J Epidemiol 1997; 146: 105-114.

Asnis GM et al. Zolpiderm for Persistent Insomnia in SSRI-Treated depressed Patients. J. Clin Psychiatry 1999; 60 (10):668-676.

Doghramji PP. Detection of insomnia in primary care. J Clin Psychiatry 2001;62 Suppl 10: 18-26.

National Institutes of Health. Consensus conference. Drugs and insomnia. The use of medications to promote sleep. JAMA 1984;251:2410-2414.

Londborg PD, Smith WT, Glaudin V, et al. Short-term cotherapy with clonazepam and fluoxetine: anxiety, sleep disturbance and core symptoms of depression. J Affect Disord 2000;61:73-79.

Nolen, WA et al. Hypnotics as concurrent medication in depression. J of Affective Disorders 1993; 28:179-188.

Richardson GS, Roth T. Future directions in the management of insomnia. J Clin Psychiatry 2001;62 Suppl 10:39-45.

Rajput V, Bromley SM. Chronic insomnia: a practical review. Am Fam Physician 1999;60: 1431-1438.

Benca RM. Consequences of insomnia and its therapies. J Clin Psychiatry 2001;62 Suppl 10:33-38.

Roth T, Ancoli-Israel S. Daytime consequences and correlates of insomnia in the United States: results of the 1991 National Sleep Foundation Survey. II. Sleep 1999;22 Suppl 2:S354-S358.

Chevalier H, Los F, Boichut D, et al. Evaluation of severe insomnia in the general population: results of a European multinational survey. J Psychopharmacol 1999; 13: S21-S24.

Dinges DF, Pack F, Williams K, et al. Cumulative sleepiness, mood disturbance, and psychomotor vigilance performance decrements during a week of sleep restricted to 4-5 hours per night. Sleep 1997;20:267.

Erman MK. Sleep architecture and its relationship to insomnia. J Clin Psychiatry 2001;62 Suppl10:9-17.

Carskadon MA, Brown ED, Dement WC. Sleep fragmentation in the elderly: relationship to daytime sleep tendency. Neurobiol Aging 1982;3:321-327.

Levitan RD, Shen JH, Jindal R, et al. Preliminary randomized double-blind placebocontrolled trial of tryptophan combined with fluoxetine to treat major depressive disorder: antidepressant and hypnotic effects. J Psychiatry Neurosci 2000;25:337-346.

Nowlin-Finch NL, Altshuler LL, Szuba MP, et al. Rapid resolution of first episodes of mania: sleep related? J Clin Psychiatry 1994;55:26-29.

Agargun MY, Kara H, Solmaz M. Sleep disturbances and suicidal behavior in patients with major depression. J Clin Psychiatry 1997;58:249-251.

Thase ME, Simons AD, Reynolds CF, III. Abnormal electroencephalographic sleep profiles in major depression: association with response to cognitive behavior therapy. Arch Gen Psychiatry 1996;53:99-108.

Krystal AD, et al: Sustained efficacy of eszopiclone over 6 months of nightly treatment: Results of a randomized, double-blind, placebo-controlled study in adults with chronic insomnia. Sleep 2003;26:793-9.

Holbrook AM, Crowther R, Lotter A, et al. The diagnosis and management of insomnia in clinical practice: a practical evidence-based approach. CMAJ 2000; 162:216-220.

Shochat T, Loredo J, Ancoli-Israel S. Sleep Disorders in the Elderly. Curr Treat Options Neurol 2001;3:19-36.

Wagner , J.; Wagner, M.L.; Hening, W.A. The Annals of Pharmacotherapy 1998, 32, 680-691.

Doghramji, P. "Treatment of Insomnia with Zalepon, A Novel Sleep Medication" International Journal of Clinical Practice 2001, 55(5), 329-334.

Dieperink, M.E. et al. "Zopiderm for Insomnia related to OTSD" Psychiatric Services 1999, 50(3), 421.

Valuck,R.J. "Treatment of depression with citalopram, fluoxetine, paroxetine, sertraline, and venlafaxine in managed care" Drug Benefit Tredns 2002 US 2002, 14(8), 33-40.

Ambien Package Insert.

International Search Report, mailed May 2, 2005.

Trivedi et al. "Do bupropion SR and sertraline differ in their effect on anxiety in depressed patients?". J. Clin. Psychiatry, Oct., 62(10), 776-781 (2001).

Vaswani, M, et al. Role of selective serotonin reuptake inhibitors in psychiatric disorders: a comprehensive review. Progress in Neuro-Psychopharmacology & Biological Psychiatry 2003; 27: 85-102.

Pollack, M, et al. Eszopiclone Coadministered With Escitalopram in Patients With Insomnia and Comorbid Generalized Anxiety Disorder. Arch Gen Psychiatry 2008. 65(5): 551-562.

Fava, M, et al. Eszopiclone Co-Administered With Fluoxetine in Patients With Insomnia and Coexisting With Major Depressive Disorder. Biol Psychiatry 2006. 59:1052-1060.

* cited by examiner

Figure 14

| Insomnia Severity Index (ISI) | | | | | |
|---|---|---|---|---|---|
| Date subject completed: ⎣__⎦/⎣__⎦/⎣__⎦ (dd) (mmm) (yy) | | | | | |
| 1. Please rate the current (last 2 weeks) SEVERITY of your insomnia problem(s). | | | | | |
|  | None | Mild | Moderate | Severe | Very Severe |
| a. Difficulty falling asleep | 0☐ | 1☐ | 2☐ | 3☐ | 4☐ |
| b. Difficulty staying asleep | 0☐ | 1☐ | 2☐ | 3☐ | 4☐ |
| c. Problem waking up too early | 0☐ | 1☐ | 2☐ | 3☐ | 4☐ |
| 2. How SATISFIED/dissatisfied are you with your current sleep pattern? | | | | | |
| Very satisfied | Satisfied | Neutral | | Dissatisfied | Very dissatisfied |
| 0☐ | 1☐ | 2☐ | | 3☐ | 4☐ |
| 3. To what extent do you consider your sleep problem to INTERFERE with your daily functioning (e.g., daytime fatigue, ability to function at work/daily chores, concentration, memory, mood, etc)? | | | | | |
| Not at all interfering | A little | Somewhat | | Much | Very much interfering |
| 0☐ | 1☐ | 2☐ | | 3☐ | 4☐ |

Figure 15

| The SF-36v2™ Acute Health Survey |
|---|
| *INSTRUCTIONS: Please answer every question. Some questions may look like others, but each one is different. Please take the time to read and answer each question carefully by placing an "X" in the square that best represents your response. Check only one response.* |

Date subject completed: ☐☐ / ☐☐☐ / ☐☐
                        (dd)   (mmm)  (yy)

1. In general, would you say your health is:

| Excellent | Very Good | Good | Fair | Poor |
|---|---|---|---|---|
| 1 ☐ | 2 ☐ | 3 ☐ | 4 ☐ | 5 ☐ |

2. Compared to one year ago, how would you rate your health in general now?

| Much better now than one year ago | Somewhat better now than one year ago | About the same as one year ago | Somewhat worse now than one year ago | Much worse than one year ago |
|---|---|---|---|---|
| ☐ | ☐ | ☐ | ☐ | ☐ |

Figure 16

| The SF-36v2™ Acute Health Survey |
|---|

| INSTRUCTIONS: *Please answer every question. Some questions may look like others, but each one is different. Please take the time to read and answer each question carefully by placing an "X" in the square that best represents your response. Check only one response.* |
|---|
| Date subject completed: ⬜⬜/⬜⬜⬜/⬜⬜ <br> (dd)   (mmm)   (yy) |

1. In general, would you say your health is:

| Excellent | Very Good | Good | Fair | Poor |
|---|---|---|---|---|
| 1☐ | 2☐ | 3☐ | 4☐ | 5☐ |

2. Compared to one year ago, how would you rate your health in general now?

| Much better now than one year ago | Somewhat better now than one year ago | About the same as one year ago | Somewhat worse now than one year ago | Much worse than one year ago |
|---|---|---|---|---|
| ☐ | ☐ | ☐ | ☐ | ☐ |

COMBINATION OF SEDATIVE AND A NEUROTRANSMITTER MODULATOR, AND METHODS FOR IMPROVING SLEEP QUALITY AND TREATING DEPRESSION

RELATED APPLICATIONS

This application is a divisional of U.S. application Ser. No. 11/007,795, filed Dec. 8, 2004. U.S. Ser. No. 11/007,795 claimed the benefit of priority to U.S. Provisional Patent Application Ser. No. 60/529,156, filed Dec. 11, 2003; U.S. Provisional Patent Application Ser. No. 60/541,614, filed Feb. 4, 2004; and U.S. Provisional Patent Application Ser. No. 60/633,213, filed Dec. 3, 2004; These applications are hereby incorporated by reference in their entirety.

BACKGROUND F THE INVENTION

Sleep is controlled by two biological processes, the homeostatic drive and the circadian rythym. The homestatic drive manifests itself as an increased drive for sleep. This drive for sleep accumulates across the period of wakefulness (typically daytime) and dissipates across the sleep period. The circadian rhythm of sleep-wake shows a biphasic curve with the greatest drive for sleep occurring between midnight and 5 AM, and between 2 PM and 4 PM. It is believed that major circadian influences are an alerting pulse in the evening and in the morning. It is the interaction of these processes which give rise to the 24-hour sleep schedule. For individuals with a usual sleep period of 11 PM to 7 AM, sleep onset in the evening occurs primarily as a function of homeostatic drive. After about four hours of sleep (at about 3 AM) homeostatic drive dissipates significantly and wakefulness begins to intrude into the sleep period. This propensity to increased wakefulness is further increased by the rise in the circadian alerting pulse at about 5 AM. In terms of the pharmacological management of insomnia, two vulnerabilities have been recognized. The first is difficulty initially falling asleep, with the second being reawakening in the middle of the night.

Many physiological functions are characterized by diurnal rhythms, in which levels of circulating hormones, catecholamines and other compounds fluctuate during the day and/or night. Certain medical disorders, such as insomnia, are associated with abnormalities in these rhythms. The time, within a 24 hour period, of administration of drugs for the prevention and treatment of such disorders can be a critical factor in determining efficacy of the therapy.

The term "insomnia" refers to the perception of inadequate or non-restful sleep by a patient. Insomnia is a frequent complaint, reported by 32% of the adult population surveyed in the Los Angeles area (Bixler et al, Amer. Journal of Psychiatry 136:1257-1262, 1979), and 13% of the population surveyed in San Marino, Italy (Lugaresi et al., Psychiatric Annals 17:446-453, 1987). Fully 45% of the surveyed adult population of Alachua County, Fla., reported trouble getting to sleep or staying asleep (Karacan et al., Social Science and Medicine 10:239-244, 1976). The prevalence of insomnia has also been shown to be related to the age and sex of the individuals, being more prevalent in older individuals, especially adults aged 65 and over, and in females.

Early treatments for insomnia commonly employed central nervous system (CNS) depressants such as barbiturates. These compounds are typically long acting (on the order of 8-50 hours) due to long terminal half-lives, and have a well-known spectrum of side effects, including lethargy, confusion, depression and next day hangover effects. In addition, chronic use has been associated with a high potential for addiction involving both physical and psychological dependence.

During the 1980s, the pharmaceutical treatment of insomnia shifted away from barbiturates and other CNS depressants toward the benzodiazepine class of sedative-hypnotic agents. This class of compounds produces a calming effect that results in a sleep-like state in humans and animals, with a greater safety margin than prior hypnotics. However, many benzodiazepines possess side effects that limit their usefulness in certain patient populations. These problems include synergy with other CNS depressants (especially alcohol), the development of tolerance upon repeat dosing, dependency, withdrawal, rebound insomnia following discontinuation of dosing, hangover effects the next day and impairment of psychomotor performance and memory. Next day sleepiness and memory impairment, which can include amnesia for events occurring prior to and after drug administration, is of particular concern in the elderly whose cognitive functions may already be impaired by the aging process.

More recent treatments for insomnia have used non-benzodiazepine compounds, which show an improved side effect profile over the benzodiazepine class of sedative-hypnotics. The first of these agents to be approved by the United States Food and Drug Administration (FDA) for marketing in the United States was zolpidem, marketed by Sanofi-Synthelabo as AMBIEN® (zolpidem tartrate), which is based on the imidazopyridine backbone (see U.S. Pat. Nos. 4,382,938 and 4,460,592). In addition to zolpidem, zaleplon, which is marketed by Jones Pharma as SONATA®, was been approved by the FDA; zaleplon is a pyrazolopyrimidine-based compound (see U.S. Pat. No. 4,626,538). Other non-benzodiazepine compounds and/or methods for making or using the same have also been reported (see, e.g., U.S. Pat. Nos. 4,794,185, 4,808,594, 4,847,256, 5,714,607, 4,654,347; 5,538,977, 5,891,891). Attempts have also been disclosed to provide controlled-release dosage forms, particularly in the context of zolpidem and salts thereof (see WO 00/33835 and EP 1 005 863 A1).

Norepinephrine and serotonin are mammalian neurotransmitters that play important roles in a wide variety of physiological processes. Norepinephrine, also called noradrenaline, is a neurotransmitter that doubles part-time as a hormone. As a neurotransmitter, norepinephrine helps to regulate arousal, dreaming, and moods. As a hormone, it acts to increase blood pressure, constrict blood vessels and increase heart rate—responses that occur when we feel stress.

Serotonin (5-hydroxytryptamine, 5-HT) is widely distributed in animals and plants, occurring in vertebrates, fruits, nuts, and venoms. A number of congeners of serotonin are also found in nature and have been shown to possess a variety of peripheral and central nervous system activities. Serotonin may be obtained from a variety of dietary sources; however, endogenous 5-HT is synthesized from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA).

Serotonin is implicated in the etiology or treatment of various disorders, particularly those of the central nervous system, including anxiety, depression, obsessive-compulsive disorder, schizophrenia, stroke, obesity, pain, hypertension, vascular disorders, migraine, and nausea. Recently, understanding of the role of 5-HT in these and other disorders has advanced rapidly due to increasing understanding of the physiological role of various serotonin receptor subtypes.

Neurotransmitters (NTs) produce their effects as a consequence of interactions with cellular receptors. Neurotransmitters, including serotonin, are synthesized in brain neurons and stored in vesicles. Upon a nerve impulse, they are released into the synaptic cleft, where they interact with various postsynaptic receptors. The actions of 5-HT are terminated by three major mechanisms: diffusion; metabolism; and uptake back into the synaptic cleft through the actions of specific amine membrane transporter systems. The major mechanism by which the action of serotonin is terminated is by uptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Thus, the actions of 5-HT, or any neurotransmitter, can be modulated by agents that: stimulate or inhibit its biosynthesis; agents that block its storage; agents that stimulate or inhibit its release; agents that mimic or inhibit its actions at its various postsynaptic receptors; agents that inhibit its reuptake into the nerve terminal; and agents that affect its metabolism.

Accordingly, there is a need in the art for serotonin reuptake inhibitor-sedative, norepinephrine reuptake inhibitor-sedative, 5-HT$_{2A}$ modulator-sedative, and dopamine reuptake inhibitor-sedative compositions that induce and maintain sleep as single dose nocturnal formulations, but without the side effects associated with the longer-acting hypnotics. The present invention fulfills this need and further provides other related advantages.

SUMMARY OF THE INVENTION

The present invention generally relates to pharmaceutical compositions comprising a sedative agent; and an antidepressant, including without limitation serotonin reuptake inhbitors, norepinephrine reuptake inhibitors, dopamine reuptake inhibitors, CRS antagonists and 5-HT$_{2A}$ receptor modulators. The sedative agent is a GABA receptor modulating compound. In a preferred embodiment, the sedative agent is eszopiclone, or a pharmaceutically acceptable salt, solvate, clathrate, polymorph, or co-crystal thereof. The pharmaceutical compositions of the invention are useful in the treatment of various sleep disorders. In addition, the present invention also relates to a method of treating a patient suffering from a sleep abnormality, insomnia, or depression comprising administering a therapeutically effective amount of a pharmaceutical composition of the invention.

In addition, the present invention relates to a method for augmentation of antidepressant therapy in a patient comprising administering to the patient a therapeutically effective amount of a sedative agent. In a preferred embodiment, the sedative agent is eszopiclone, or a pharmaceutically acceptable salt, solvate, clathrate, polymorph, or co-crystal thereof. The present invention also relates to a method for eliciting a dose-sparing effect in a patient undergoing treatment with an antidepressant comprising administering to the patient a therapeutically effective amount of a sedative agent. In a preferred embodiment, the sedative agent is eszopiclone, or a pharmaceutically acceptable salt, solvate, clathrate, polymorph, or co-crystal thereof.

Furthermore, the present invention relates to a method for reducing depression relapse in a patient who received antidepressant treatment comprising administering to the patient a therapeutically effective amount of a sedative agent. In one embodiment, the sedative agent is administered chronically or long-term. In a preferred embodiment, the sedative agent is eszopiclone, or a pharmaceutically acceptable salt, solvate, clathrate, polymorph, or co-crystal thereof.

BRIEF DESCRIPTION OF THE FIGURES

FIG. 14 depicts an Insomnia Severity Index (ISI) questionnaire used in the clinical-study protocol to assess the safety and efficacy of compositions and methods of the present invention.

FIG. 15 depicts a portion of an Acute Health Survey questionnaire used in the clinical-study protocol to assess the safety and efficacy of compositions and methods of the present invention.

FIG. 16 depicts a portion of an Acute Health Survey questionnaire used in the clinical-study protocol to assess the safety and efficacy of compositions and methods of the present invention.

DETAILED DESCRIPTION OF THE INVENTION

Figure 1:
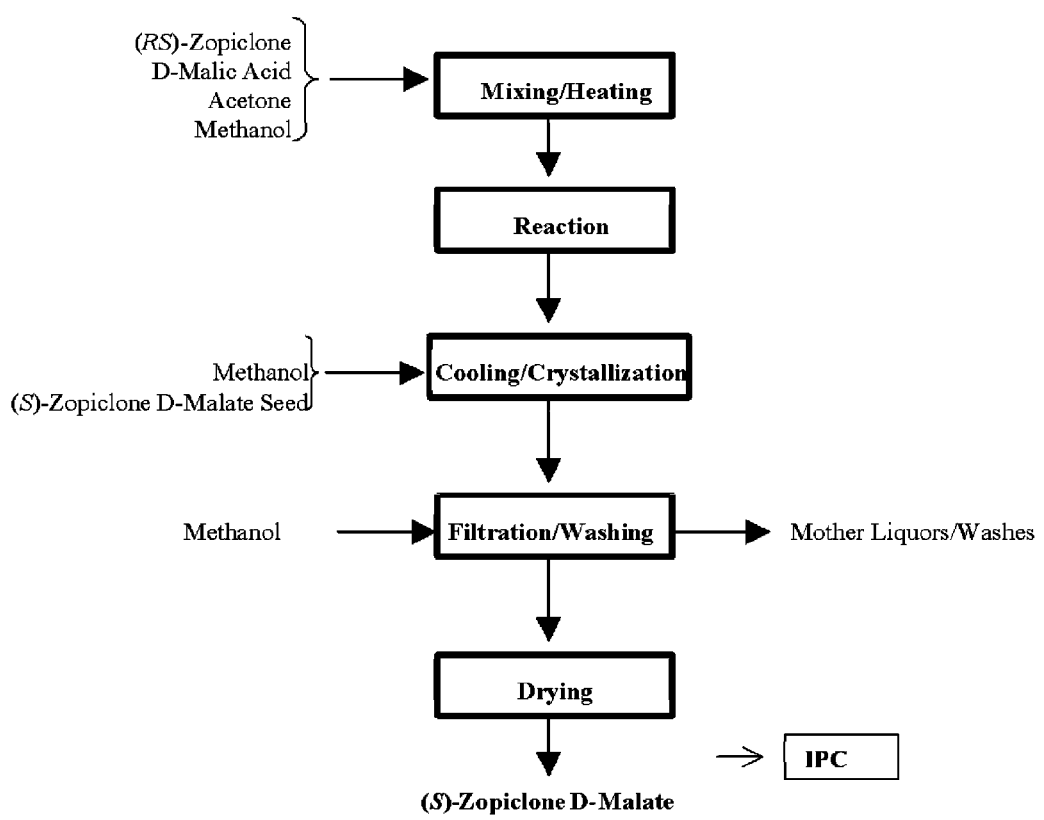
FIG. 1 depicts a schematic diagram of a method for preparing (S)-zopiclone D-malate (IPC=in-process control testing).

The present invention relates generally to pharmaceutical compositions containing two or more active agents that when taken together improve the quality of sleep for a patient. In certain embodiments, the present invention relates to a pharmaceutical composition comprising an antidepressant and a sedative agent. In certain embodiments, the present invention relates to a pharmaceutical composition comprising a serotonin reuptake inhibitor and a sedative agent. In certain embodiments, the present invention relates to a pharmaceutical composition comprising a NRI and a sedative agent. In certain embodiments, the present invention relates to a pharmaceutical composition comprising a 5-$HT_{2A}$ modulator and a sedative agent. In certain embodiments, the present invention relates to a pharmaceutical composition comprising a dopamine reuptake inhibitor and a sedative agent. The sedative agent is a GABA receptor modulating compound. In a preferred embodiment, the sedative agent is eszopiclone, or a pharmaceutically acceptable salt, solvate, clathrate, polymorph, or co-crystal thereof. Another aspect of the present invention relates to a method of treating a patient suffering from a sleep disorder comprising the step of administering to said patient a therapeutically effective dose of a pharmaceutical composition containing two or more active agents that when taken together improve the quality of sleep or sleep disorders for said patient. Another aspect of the present invention relates to a method of treating a patient suffering from depression comprising the step of administering to said patient a therapeutically effective dose of a pharmaceutical composition of the invention.

In certain embodiments, said pharmaceutical composition comprises aserotonin reuptake inhibitor and a sedative agent. In certain embod pharmaceutical composition comprises a norepinephrine reuptake inhibitor and a sedative agent. In certain embodiments, said pharmaceutical composition comprises a 5-$HT_{2A}$ modulator and a sedative agent. In certain embodiments, said pharmaceutical composition comprises a dopamine reuptake inhibitor and a sedative agent. In a preferred embodiment, the sedative is eszopiclone, or a pharmaceutically acceptable salt, solvate, clathrate, polymorph, or co-crystal thereof. In another embodiment, said pharmaceutical composition comprises eszopiclone and a SRI. In yet another embodiment, said pharmaceutical composition comprises eszopiclone and fluxetine, or a pharmaceutically acceptable salt, solvate, clathrate, polymorph, or co-crystal of any one or both of them.

In another embodiment, the present invention relates to a method for augmentation of antidepressant therapy in a patient comprising administering to the patient a therapeutically effective amount of a sedative agent. In a preferred embodiment, the sedative agent is eszopiclone, or a pharmaceutically acceptable salt, solvate, clathrate, polymorph, or co-crystal thereof.

The present invention also relates to a method for eliciting a dose-sparing effect in a patient undergoing treatment with an antidepressant comprising administering to the patient a therapeutically effective amount of a sedative agent. In a preferred embodiment, the sedative agent is eszopiclone, or a pharmaceutically acceptable salt, solvate, clathrate, polymorph, or co-crystal thereof.

Furthermore, the present invention relates to a method for reducing depression relapse in a patient who received antidepressant treatment comprising administering to the patient a therapeutically effective amount of a sedative agent. In one embodiment, the sedative agent is administered chronically or long-term. In a preferred embodiment, the sedative agent is eszopiclone, or a pharmaceutically acceptable salt, solvate, clathrate, polymorph, or co-crystal thereof.

Sleep Difficulties and Insomnia

Several epidemiologic studies suggest that 10% to 15% of adults suffer from chronic insomnia, and an additional 25% to 35% have transient or occasional insomnia (Roth T. *Int. J Clin. Pract. SuppL.* 2001,3-8).

The National Sleep Foundation's 2002 Sleep in America survey assessed the occurrence of four symptoms of insomnia in adults in the United States: difficulty falling asleep; waking a lot during the night; waking up too early and not being able to get back to sleep; and waking up feeling unrefreshed. In the survey, 58% of the respondents reported experiencing at least one of these symptoms a few nights a week or more, and 35% reported difficulties every night or almost every night within the past year (National Sleep Foundation. 2002 Sleep in America Poll. Washington, DC: WB & A Market Research, 2002,1-43). In addition, of those reporting insomnia symptoms at least a few nights a week, 40% reported feeling unrefreshed upon awakening, 36% reported being awake a lot during the night, 25% reported difficulty falling asleep, and 24% reported waking up too early and being unable to fall back asleep.

The major types of insomnia are often described as primary and secondary insomnia (as in the American Psychiatric Association's *Diagnostic and Statistical Manual of Mental Disorders*, Text Revision. 4th ed. Washington, DC: American Psychiatric Publishing, Inc, 2000 [DSM]), chronic versus acute/transient insomnia, intrinsic versus extrinsic insomnia (as in the International Classification of Sleep Disorders [ICSD]), and sleep-onset versus sleep maintenance (Diagnostic Classification Steering Committee. International Classification of Sleep Disorders (ICSD): Diagnostic and Coding Manual. Rochester, Minn.: American Sleep Disorders Association, 1990). Many patients with sleep disturbance will fall into more than one of these categories or will have unspecified dissatisfaction with the quality of their sleep (Roth T. *Int. J Clin. Pract. Suppl.* 2001,3-8). The fourth edition of the DSM (DSM-IV) defines insomnia as difficulties in sleep onset (or initiation), difficulties in sleep maintenance, or sleep that is nonrestorative.

Chronic insomnia may result from several different sources (Rajput et al., *Am. Fam. Physician,* 1999, 60:1431-1438). Patients with chronic insomnia can often have several sleep complaints simultaneously and experience a range of sleep disturbances, including prolonged latency to sleep onset, increased time awake during the sleep period, and reduced total sleep time (Benca R M, *J. Clin. Psychiatry,* 2001, 62 *Suppl* 10:33-38).

Sleep maintenance problems may take several forms, including frequent awakenings, an increase in time spent awake after initially falling asleep (wake time after sleep onset, or WASO, which is a robust measure of sleep maintenance), sleep fragmentation (transient microarousals appearing on an EEG but not necessarily involving full wakefulness), and unrefreshing sleep. Of these, WASO is a particularly sensitive measure of sleep improvement. WASO may include a number of microarousals, as well as all periods of full wakefulness, and thus increases in WASO of only a few minutes may be indicative of substantially improved sleep continuity.

The severity of insomnia can be directly correlated to severity of next-day functional impairment. There is also strong evidence that, compared with patients without insomnia, patients with chronic insomnia experience a subjective deterioration in waking behaviors and psychosocial functioning, including impaired memory, concentration, ability to accomplish tasks, and enjoyment of interpersonal relationships (Roth et al., *Sleep,* 1999, 22 *Suppl* 2:S354-S358).

Sleep maintenance problems may cause decreases in next-day functioning. Bonnet studied healthy volunteers with normal sleep habits and found that, with increasing periods of induced arousal or insomnia during the night, residual effects of next-day performance on evaluations of vigilance, reaction time, sleepiness, and other measures experienced corresponding decreases (Bonnet M H, *Physiol. Behav.*, 1989, 45:1049-1055).

Depression

Psychiatric disorders are pathological conditions of the brain characterized by identifiable symptoms that result in abnormalities in cognition, emotion or mood, or the highest integrative aspects of behavior. These disorders may vary in severity of symptoms, duration, and functional impairment. Psychiatric disorders afflict millions of people worldwide resulting in tremendous human suffering and economic burden due to lost productivity. Mood disorders are a type of psychiatric disorder often defined as a group of heterogeneous, typically recurrent illnesses including unipolar (depressive) and bipolar (manic-depressive) disorders characterized by pervasive mood disturbances, psychomotor dysfunction, and vegetative symptoms. Suicide, the most serious complication in patients with mood disorders, is the cause of death in 15 to 25% of untreated patients with mood disorders; unrecognized or inadequately treated depression contributes to 50 to 70% of all completed suicides.

Depression is an affective disorder, the pathogenesis of which cannot be explained by any single cause or theory. The most widely accepted hypothesis involves abnormal function of the catecholamine (primarily norepinephrine) and/or serotonin transmitter systems. In this hypothesis, most forms of depression are associated with a deficiency of norepinephrine and/or serotonin at functionally important adrenergic or serotonergic receptors. Hence drugs that enhance the concentrations of norepinephrine (NE) and/or serotonin at these receptors should alleviate to an extent the symptoms of depression. Approaches to the treatment of depression over the years have involved the use of agents (stimulants) that mimic norepinephrine; agents (MAOIs) that increase the levels of NE and 5-HT by inhibiting their metabolism; and drugs that increase these levels at the receptor by inhibiting the uptake of NE and 5-HT.

The classical tricyclic antidepressants (TCAs) currently available block primarily the uptake of norepinephrine and also, to varying degrees, the uptake of 5-HT—depending on whether they are secondary or tertiary amines. Tertiary amines such as imipramine and amitriptyline are more selective inhibitors of 5-HT than catecholamines, compared with secondary amines such as desipramine. More recently, selective 5-HT reuptake inhibitors (SSRIs) have been investigated as potential antidepressants with the anticipation that these agents, unlike the first-generation TCAs, would possess fewer side effects, such as anticholinergic actions and cardiotoxicity, and would be less likely to cause sedation and weight gain.

Three selective 5-HT uptake inhibitors, also referred to as second-generation antidepressants, have been introduced to the U.S. market. Fluoxetine (PROZAC®), sertraline (ZOLOFT®), and paroxetine (PAXIL®) have gained immediate acceptance, each appearing in recent listings of the top 200 prescription drugs. Fluoxetine was approved also for the treatment of obsessive-compulsive disorder. These agents do not appear to possess greater efficacy than the TCAs, nor do they generally possess a faster onset of action; however, they do have the advantage of a lower side-effect profile. Of these three SSRIs, paroxetine is the most potent inhibitor of 5-HT uptake, fluoxetine the least. Sertraline is the most selective for 5-HT versus NE uptake, fluoxetine the least selective. Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, histamine, or 5-HT receptors.

Venlafaxine (EFFEXOR®) is a recently introduced antidepressant, differing from the classical TCAs and the SSRIs chemically and pharmacologically in that it acts as a potent inhibitor of both 5-HT and norepinephrine uptake, as well as weakly inhibiting dopamine uptake. Its major metabolite, O-desmethylvenlafaxine, shares a similar profile. Neither venlafaxine nor its major metabolite have significant affinity for muscarinic, histaminergic, benzodiazephine, mu opioid, or adrenergic alpha-1 receptors. It is administered as a racemic mixture. Both enantiomers inhibit 5-HT and NE uptake, but the (S)(+)-isomer is more selective for 5-HT uptake. Venlafaxine possesses an efficacy equivalent to that of the TCAs, and a benign side effect profile similar to those of the SSRIs.

Unfortunately, treatment options for depressed patients who have suboptimal clinical responses to therapy with an antidepressant are limited. Approximately thirty percent (30%) of patients initiating antidepressant therapy show suboptimal or delayed clinical responses to the first-line antidepressant agents that are commonly used to treat depression.

Typically, if a patient exhibits suboptimal or delayed clinical response after several weeks of therapy with an antidepressant, the clinician's initial approach is to increase the dose of the antidepressant. If the patient's response remains unsatisfactory after increasing the dose, the most common approaches that many clinicians will pursue are: a) switching to another antidepressant; or b) adding a second antidepressant; or c) attempting an augmentation therapy by administering agents such as lithium carbonate, thyroid hormone (triiodothyronine), psychostimulants, modafinil, atypical antipsychotics, buspirone, or pindolol.

There are very important, fundamental differences in these three approaches. The first involves switching the patient to another antidepressant agent that may have different pharmacodynamic and pharmacokinetic characteristics from the first agent. The second attempts to utilize an antidepressant agent that will produce synergistic effects with the first agent. Lastly, the third approach relies on potential augmentation of the concurrently administered original antidepressant by agents that in and of themselves may have limited or no direct antidepressant effect.

The pharmacological mechanism of action for any of the commonly used augmentation agents described above and in the literature is not established, and data from controlled clinical trials to support the use of these and other agents to bring about an augmentation of antidepressant treatment is sparse. The most thoroughly researched agents that are utilized in many patients with antidepressant-resistant depression are lithium and thyroid hormone. Several clinical trials with these two agents have shown that augmentation with lithium or thyroid hormone is effective.

Less reliable information in the literature suggests that central nervous system stimulants may also produce an augmentation effect in antidepressant therapy, but there is concern that these agents can produce tolerance and put the patient at risk for physical and psychological dependence and possible drug abuse. Some clinicians utilize atypical antipsychotics at low doses and buspirone which are generally well tolerated and may have additional utility in treating concomitant anxiety in depressed patients that are refractory to their antidepressants. Pindolol has also been shown to accelerate clinical responses in some but not all clinical studies reported.

Serotonin Reuptake Inhibitors (SRI)

In general, a dose of an SRI or a pharmaceutically acceptable salt thereof suitable for administration to a human will be in the range of 0.01 to 50 mg per kilogram body weight of the recipient per day, preferably in the range of 0.1 to 3 mg per kilogram body weight per day. Unless otherwise stated all weights of active ingredients are calculated in terms of drug per se. In certain embodiments, the desired dose is presented as two, three, four, five or more sub-doses administered at appropriate intervals throughout the day. These sub-doses may be administered in unit dosage forms, for example, containing about 5 to 50 mg.

Citalopram

Citalopram is a selective, centrally acting serotonin reuptake inhibitor having antidepressant activities. The antidepressant activity of the compound has been reported in several publications, e.g., J. Hyttel *Prog. Neuro-Psychopharmacol. & Biol. Psychiat.* 1982, 6, 277-295; and A. Gravem *Acta Psychiatr. Scand.* 1987, 75, 478-486. The compound has further been disclosed to show effects in the treatment of dementia and cerebrovascular disorders. See EP-A 474580. Christensen et al. reported on the pharmacology of citalopram in *Eur. J. Pharmacol.* 1977, 41, 153. Others have described the clinical effectiveness of citalopram, e.g., Dufour et al. *Int. Clin. Psychopharmacol.* 1987, 2, 225; and Timmerman et al., ibid., 239. In certain instances, citalopram is administered in the form of its hydrobromide salt marketed under the name Cipralmil.

Citalopram has the chemical name 1-[3-(dimethylamino)propyl]-1-(4-fluorophenyl)-1,3-dihydro-5-isobenzofuran carbonitrile. Citalopram was first disclosed in DE 2,657,271 and U.S. Pat No. 4,136,193. The structure of citalopram is presented below.

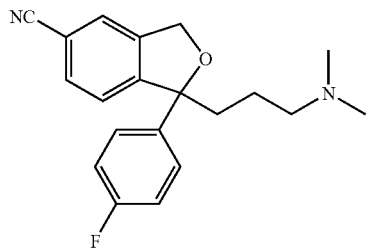

The size of a prophylactic or therapeutic dose of citalopram in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 80 mg. Preferably, a daily dose range should be between about 5 mg to about 50 mg. Most preferably, a daily dose range should be between about 10 mg to about 30 mg. In certain embodiments, a daily dosage of 15, 20, or 25 mg may be preferred depending upon patient response. In managing the patient, the therapy may be initiated at a lower dose, perhaps about 4 mg to about 6 mg and increased up to about 10 mg or higher depending-on the patient's global response. It may be necessary to use dosages outside these ranges in some cases.

Duloxetine (CYMBALTA®)

Duloxetine is an antidepressant that functions by inhibiting the reuptake of serotonin and norepinephrine. Duloxetine has the chemical name N-methyl-3-(1-naphthalenyloxy)-3-(2-thienyl)propanamine and is usually administered as the hydrochloride salt. In certain instances, duloxetine is administered as the (+) enantiomer. The word "duloxetine" will be used here to refer to any acid addition salt or the free base of the molecule. Duloxetine was first taught by U.S. Pat. No. 4,956,388, which discloses its high potency. Duloxetine is generally administered orally in the form of a tablet or a capsule full of enteric coated granules. The chemical structure of duloxetine is given below.

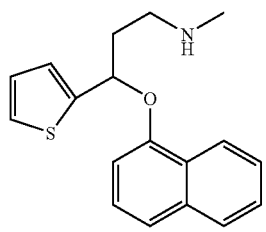

The size of a prophylactic or therapeutic dose of duloxetine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 150 mg. Preferably, a daily dose range should be between about 5 mg to about 80 mg. Most preferably, a daily dose range should be between about 5 mg to about 50 mg. In certain embodiments, a daily dosage of 10, 20, or 30 mg may be preferred depending upon patient response. In managing the patient, the therapy may be initiated at a lower dose, perhaps about 4 mg to about 6 mg and increased up to about 10 mg or higher depending-on the patient's global response. It may be necessary to use dosages outside these ranges in some cases.

Escitalopram

Escitalopram is the S-enantiomer of citalopram. Escitalopram is greater than 100 times more potent in inhibiting serotonin reuptake compared to the R-enantiomer. Escitalopram does significantly affect reuptake of norepinephrine or dopamine. In addition, escitalopram has negligible affinity for the adrenergic, dopamine ($D_{1-5}$), histamine ($H_{1-3}$), muscarinic ($M_{1-5}$), and benzodiazepine receptors. Generally, escitalopram is administered as its oxalate salt under the name LEXAPRO™.

Escitalopram has the chemical name (S)-(+)-1-[3-(dimethylamino)propyl]-1-(4-fluorophenyl)-1,3-dihydro-5-isobenzofuran carbonitrile oxalate. Citalopram was first disclosed in DE 2,657,271, corresponding to U.S. Pat No. 4,136,193. The structure of citalopram is presented below.

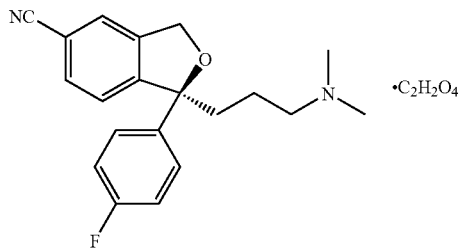

The size of a prophylactic or therapeutic dose of escitalopram in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 80 mg. Preferably, a daily dose range should be between about 5 mg to about 50 mg. Most preferably, a daily dose range should be between about 10 mg to about 30 mg. In certain embodiments, a daily dosage of 15, 20, or 25 mg may be preferred depending upon patient response. In managing the patient, the therapy may be initiated at a lower dose, perhaps about 4 mg to about 6 mg and increased up to about 10 mg or higher depending on the patient's global response. In elderly patients, a 10 mg dosage may be optimal. It may be necessary to use dosages outside these ranges in some cases.

Fluoxetine

Fluoxetine is a potent, highly selective reuptake inhibitor of serotonin and is indicated for the treatment of depression and obsessions and compulsions related to obsessive-compulsive disorder (OCD). The use of fluoxetine for indications other than treating depression is also disclosed in the following: U.S. Pat. Nos. 4,594,358, 4,647,591, 4,683,235, 4,940,585, 4,999,382, 5,151,448, 5,356,934, 5,446,070, 5,589,511, and PCT Application WO 92/18005. The anti-depressant action of fluoxetine appears to be based on its capacity to selectively inhibit the uptake of serotonin by the neurons of the central nervous system.

Fluoxetine is described in U.S. Pat. No. 4,314,081 and has the chemical name N-methyl-3-(p-trifluormethylphenoxy)3-phenylpropylamine. Fluoxetine is generally marketed as the racemic mixture of its two enantiomers in the form of a hydrochloride salt under the name Prozac. Fluoxetine hydrochloride is a white crystalline solid (molecular weight 345.79 g/mol) that has a solubility of 14 mg/mL in water. Other methods for the production of fluoxetine and new intermediates are disclosed in U.S. Pat. No. 5,225,585. The chemical structure of fluoxetine hydrochloride is shown below:

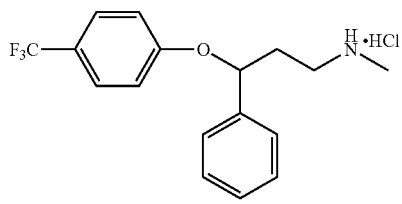

The oral administration of fluoxetine in the treatment of depression is often initiated with a 20 mg/day dose administered in the morning. If no improvement is observed over several weeks, the dosage may be increased, though generally to no more than 80 mg/day. Doses above 20 mg/day are often administered once a day in the morning or by a b.i.d. schedule (morning and noon). Following oral administration of fluoxetine hydrochloride (PROZAC®) in 10 mg or 20 mg daily doses, fluoxetine hydrochloride has an elimination half-life of from 1-9 days, averaging about 2-3 days. Additional product information, including dosage and administration, can be found in the Physicians' Desk Reference, 48th Edition, 1994, pp. 877-880.

Although fluoxetine is generally marketed as the racemic mixture, Robertson et al., *J. Med. Chem.* 1988, 31, 1412, taught the separation of the R- and S-enantiomers of fluoxetine and showed that their activity as serotonin uptake inhibitors is similar to each other. Additionally, U.S. Pat. No. 5,104,899 discloses a method of treating depression in a human patient comprising administering the S-(+)-enantiomer of fluoxetine in substantially optically pure form. PCT application WO 95/28152 discloses methods for treating or improving memory, and for treating sexual dysfunction.

The size of a prophylactic or therapeutic dose of fluoxetine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 150 mg. Preferably, a daily dose range should be between about 5 mg to about 80 mg. Most preferably, a daily dose range should be between about 10 mg to about 20 mg. In certain embodiments, a daily dosage of 30, 40, or 60 mg may be preferred depending upon patient response. In managing the patient, the therapy may be initiated at a lower dose, perhaps about 4 mg to about 8 mg and increased up to about 10 mg or higher depending-on the patient's global response. It may be necessary to use dosages outside these ranges in some cases.

Fluvoxamine

Fluvoxamine is an inhibitor of serotonin reuptake that is used to treat depression and obsessive-compulsive disorder. Fluvoxamine is described in U.S. Pat. No. 4,085,225 and Neth. Pat. Appl. 7,503,310. The therapeutic activity of fluvoxamine has been described by Claassen et al. in *Brit. J Pharmacol.* 1977, 60, 505; De Wilde et al. in *J. Affective Disord.* 1982, 4, 249; and Benfield et al. in *Drugs* 1986, 32, 313. The efficacy of fluvoxamine has been established for obsessive-compulsive outpatients in double-blind, placebo-controlled clinical trials. However, the utility of fluvoxamine for long-term care lasting longer than 10 weeks has not been evaluated in controlled trials. In certain instances, fluvoxamine is administered in form of its maleate salt under the name Luvox. Luvox is a crystalline solid that melts at 120-121.5° C. The chemical name of fluvoxamine is 5-methoxy-1-[4-(trifluoromethyl)-phenyl]-1-pentanone O-(2-aminoethyl)oxime and the structure is presented below.

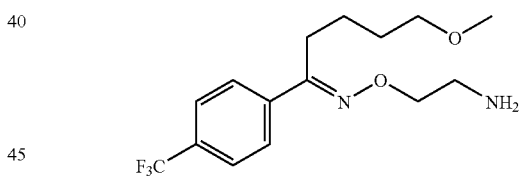

The size of a prophylactic or therapeutic dose of fluvoxamine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 600 mg. Preferably, a daily dose range should be between about 10 mg to about 300 mg. Most preferably, a daily dose range should be between about 50 mg to about 200 mg. In certain embodiments, a daily dosage of 75, 100, 125, or 150 mg may be preferred depending upon patient response. In managing the patient, the therapy may be initiated at a lower dose, perhaps about 20 mg to about 25 mg and increased up to about 50 mg or higher depending-on the patient's global response. It may be necessary to use dosages outside these ranges in some cases. In instances where the dosage is greater than 100 mg per day, the total dosage may need to be administered in two separate doses. A reduced dosage may be required for In elderly patients or patients suffering from liver conditions. Children of 8-17 years of age should be given a starting dose of 25 mg. In certain instances, young girls may need to be given a lower dosage than boys of similar age.

Milnacipran

Milnacipran is a inhibitor of serotonin and norepinephrine reuptake which is used to treat depression. Milnacipran is also known in the art as F2207, TN-912, dalcipran, midalcipran, and midalipran. The NE:5-HT selectivity of milnacipran is 2:1. See Moret et al. *Neuropharmacology* 1985, 24, 1211-1219 and Palmier et al. *Eur. J. Clin. Pharmacol.* 1989, 3, 235-238. Quite significantly, milnacipran has been used as an antidepressant in approximately 400,000 patients, and is known to be non-toxic in humans. Milnacipran was well tolerated and usually produced no more adverse effects than placebo in clinical trials at dosages of 100 mg/day or 200 mg/day (Spencer and Wilde *Drugs* 1998, 56, 405-427).

Milnacipran has the chemical name (N,N-diethyl-2-aminomethyl-1-phenylcyclo-propanecarboxamide). Procedures for the preparation of Milnacipran are given U.S. Pat. No. 4,478,836. The pharmacological activity of Milnacipran is described by Moret and coworkers in *Neuropharmacology* 1985, 24, 1211-19. Additional information regarding milnacipran may be found in the Merck Index, 12$^{th}$ Edition, at entry 6281. The structure of Milnacipran is presented below.

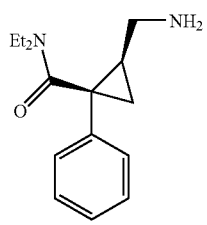

Those of skill in the art will recognize that compounds such as milnacipran may exhibit the phenomena of tautomerism, conformational isomerism, geometric isomerism and/or optical isomerism. It should be understood that the invention encompasses any tautomeric, conformational isomeric, optical isomeric and/or geometric isomeric forms of the NE 5-HT SNRI compounds having one or more of the utilities described herein, as well as mixtures of these various different forms. For example, as is clear from the above structural diagram, milnacipran is optically active. It has been reported in the literature that the dextrogyral enantiomer of milnacipran is about twice as active in inhibiting norepinephrine and serotonin reuptake than the racemic mixture, and that the levrogyral enantiomer is much less potent (see, Spencer and Wilde, 1998, supra; Viazzo et al. *Tetrahedron Lett.* 1996, 37, 4519-4522; Deprez et al. *Eur. J. Drug Metab. Pharmacokinet.* 1998, 23, 166-171). Accordingly, milnacipran may be administered in entantiomerically pure form (e.g., the pure dextrogyral enantiomer) or as a mixture of dextogyral and levrogyral enantiomers, such as a racemic mixture. Unless specifically noted otherwise, the term "milancipran" as used herein refers to both enantiomerically pure forms of milnacipran as well as to mixtures of milnacipran enantiomers. Methods for separating and isolating the dextro- and levrogyral enantiomers of milnacipran and other NE 5-HT SNRI compounds are well-known (see Grard et al. *Electrophoresis* 2000, 21, 3028-3034).

The size of a prophylactic or therapeutic dose of milancipran in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 400 mg. Preferably, a daily dose range should be between about 50 mg to about 250 mg. Most preferably, a daily dose range should be between about 100 mg to about 200 mg. In certain embodiments, a daily dosage of 110, 130, 150, or 170 mg may be preferred depending upon patient response. In managing the patient, the therapy may be initiated at a lower dose, perhaps about 20 mg to about 30 mg and increased up to about 50 mg or higher depending-on the patient's global response. It may be necessary to use dosages outside these ranges in some cases.

Paroxetine

Paroxetine is phenylpiperidine compound used to treat major depressive disorder, social anxiety disorder, obsessive compulsive disorder, panic disorder, generalized anxiety disorder, and posttraumatic stress disorder. The therapeutic properties of paroxetine are attributed to inhibition of neuronal reuptake of serotonin. Paroxetine is generally marketed as the hydrochloride salt under the name PAXIL®. Paroxetine is reported in U.S. Pat. Nos. 3,912,743 and 4,007,196 while the activity profile of the drug is given in Lassen et al. *Eur. J. Pharmacol.* 1978, 47, 351; Hassan et al. *Brit. J. Clin. Pharmacol.* 1985, 19, 705; Laursen et al. *Acta Psychiat. Scand.* 1985, 71, 249; and Battegay et al. *Neuropsychobiology* 1985, 13, 31. Dosage forms include immediate release tablets, extended release tablets, capsules and suspensions. The active substance in the commercial forms has been paroxetine hydrochloride and specifically with regard to tablets and other solid forms the active ingredient has been paroxetine hydrochloride hemihydrate as described in U.S. Pat. No. 4,721,723 and EP 223403.

Paroxetine hydrochloride is an off-white powder that has the chemical name (−)-trans 4R-(4'-fluorophenyl)-3S-[(3'4'-methylenedioxy-phenoxy)methyl]-piperidine hydrochloride. Paroxetine hydrochloride melts at 120-138° C., has a molecular weight of 374.8 g/mol, and has a solubility of 5.4 mg/mL in water. The structure of paroxetine hydrochloride is presented below.

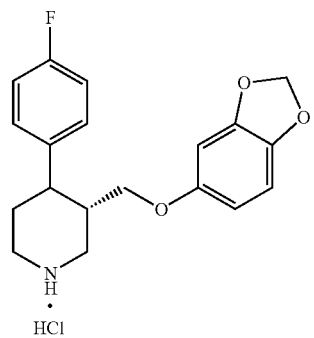

U.S. Pat. No. 5,874,447 describes paroxetine sulfonate salts, including paroxetine methane sulfonate also known as paroxetine mesylate. These sulfonate salts have advantageous properties in comparison to the known salts, including the hydrochloride salts. For example, the sulfonate salts have high water solubility and good thermal stability, making them useful in forming a commercial paroxetine dosage form. The U.S. Pat. No. 5,874,447 patent discloses that tablets can be made by any known method including a dry technique (direct compression, dry granulation) or a wet technique (wet granulation).

The size of a prophylactic or therapeutic dose of paroxetine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 90 mg. Preferably, a daily dose range should be between about 5 mg to about 50 mg. Most preferably, a daily dose range should be between about 10 mg to about 40 mg. In certain embodiments, a daily dosage of 15, 20, or 30 mg may be preferred depending upon patient response. In managing the patient, the therapy may be initiated at a lower dose, perhaps about 4 mg to about 8 mg and increased up to about 10 mg or higher depending-on the patient's global response. It may be necessary to use dosages outside these ranges in some cases.

Sertraline

Sertraline is a serotonin reuptake inhibitor which is marketed as an antidepressant. It is disclosed by U.S. Pat. No. 4,536,518. The therapeutic effect of sertraline is attributed to inhibition of CNS neuronal uptake of serotonin. Clinical studies in man indicate that sertraline blocks the uptake of serotonin in human platelets. In addition, in vitro studies indicate that it is a very poor inhibitor of norepinephrine and dopamine neuronal uptake. Sertraline is a naphthaleneamine that is generally marketed as the hydrochloride salt under the brand name ZOLOFT®.

Sertraline hydrochloride has the molecular formula $C_{17}H_{17}NCl_2 \cdot HCl$ and has the chemical name (1S-cis)-4-(3,4-dichlorophenyl)-1,2,3,4-tetrahydro-N-methyl-1-naphthalenamine hydrochloride. The preparation of sertraline may be carried using preparatory methods such as those described in Welch, et al. European Patent Application 30,081 and U.S. Pat. No. 4,536,518. The chemical structure of Sertraline hydrochloride is presented below.

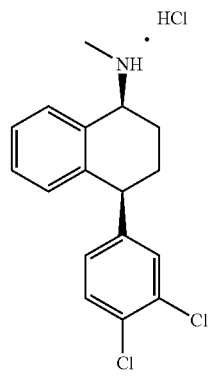

The size of a prophylactic or therapeutic dose of sertraline in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 500 mg. Preferably, a daily dose range should be between about 10 mg to about 200 mg. Most preferably, a daily dose range should be between about 20 mg to about 100 mg. In certain embodiments, a daily dosage of 30, 50, 70, or 80 mg may be preferred depending upon patient response. In managing the patient, the therapy may be initiated at a lower dose, perhaps about 10 mg to about 15 mg and increased up to about 20 mg or higher depending-on the patient's global response. It may be necessary to use dosages outside these ranges in some cases. Additional information for sertraline hydrochloride including product information, dosage amounts, and administration is given in Physicians' Desk Reference, 48th Edition, 1994, pp. 2000-2003.

Clomipramine

Clomipramine is an antidepressant described in U.S. Pat. No. 3,467,650. In certain instances, clomipramine may be administered in the form of a hydrochloride salt named Anafranil. Clomipramine has the chemical name 3-Chloro-10,11-dihydro-N,N-dimethyl-5H-dibenz[b,f]azepine-5-propanamine. The structure of clominpramine is presented below.

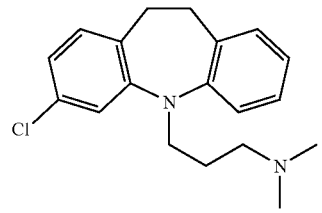

The size of a prophylactic or therapeutic dose of clominpramine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 300 mg. Preferably, a daily dose range should be between about 10 mg to about 200 mg. Most preferably, a daily dose range should be between about 25 mg to about 100 mg. In certain embodiments, a daily dosage of 40, 60, or 80 mg may be preferred depending upon patient response. In managing the patient, the therapy may be initiated at a lower dose, perhaps about 5 mg to about 10 mg and increased up to about 20 mg or higher depending-on the patient's global response. It may be necessary to use dosages outside these ranges in some cases.

Femoxetine

Femoxetine is an antidepressant reported in U.S. Pat. No. 3,912,743. The chemical name for femoxetine is (3R-trans)-3-[4-Methoxyphenoxy)-methyl]-1-methyl-4-phenylpiperidine. In certain instances, femoxetine may be administered in the form of a hydrochloride salt. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. The chemical structure of femoxetine is presented below.

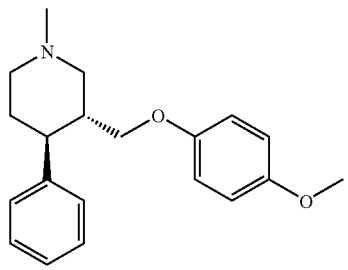

Indalpine (UPSTENE®)

Indalpine is serotonin reuptake inhibitor that may be used to treat depression. Indalpine was disclosed in U.S. Pat. No. 4,064,255. The pharmacological activity is discussed in G. LeFur et al. *Life Sci.* 1978, 23, 1959 and R. Ashkenazi et al. *Brit. J. Pharmacol.* 1983, 79, 765 and 915. In certain instances, indalpine can be administered as the monohydrochloride salt. Indalpine has the chemical name 3-[2-(4-Piperidinyl)ethyl]-1H-indole and has the structure presented below.

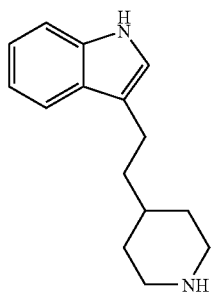

The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Alaproclate

Alaproclate is a serotonin reuptake inhibitor that has the chemical name 2-(4-chlorophenyl)-1,1-dimethyl 2-aminopropanoate. In certain instances, Alaproclate is administered as a hydrochloride salt. The size of a prophylactic or therapeutic dose in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Cericlamine

Cericlamine has the chemical name (+/−)3-(3,4-dichlorophenyl)-2-dimethylamino-2-methylpropan-1-ol. The preparation of cericlamine is described in EP 237 366, *J. Chem. Soc. Perkin Trans. I* 1996, 1495-1498, and U.S. Pat. No. 6,121,491. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Ifoxetine

Ifoxetine has the chemical name (+/−)-bis-[cis-3-hydroxy-4-(2,3-dimethyl-phenoxy)]-piperidine sulfate. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Additional serotonin reuptake inhibitors contemplated for the instant invention include buspirone, clovoxamine, cyanodothiepin, dapoxetine, imipramine, litoxetine, lofepramine, nefazodone, norzimeldine, trazodone, venlafaxine, viqualine, and zimeldine.

$5\text{-HT}_{2A}$ Modulators

Originally, four main subgroups of 5-HT receptors, named $5\text{-HT}_1$, $5\text{-HT}_2$, $5\text{-HT}_3$ and $5\text{-HT}_4$, were recognized based on receptor binding profiles, the biological activity of the ligands for the receptors, and secondary messenger coupling. Additional research has lead to the identification of $5\text{-HT}_{1F}$, $5\text{-HT}_5$, $5\text{-HT}_6$ and $5\text{-HT}_7$ receptors. The recognition that different subtypes of 5-HT exist is important for drug design because compounds which selectivity inhibit only one of the 5-HT subtypes may offer reduced side effects compared to a therapeutic agent that broadly inhibits many of the 5-HT subtypes.

The $5\text{-HT}_2$ receptor family is comprised of the $5\text{-HT}_{2A}$, $5\text{-HT}_{2B}$ and $5\text{-HT}_{2C}$ receptor subtypes. The $5\text{-HT}_{2C}$ receptor had been termed $5\text{-HT}_{1C}$ before researchers determined that it is structurally very similar to the $5\text{-HT}_2$ receptors. The $5\text{-HT}_{2A}$, $5\text{-HT}_{2B}$ and $5\text{-HT}_{2C}$ receptors are single protein molecules of 458-471 amino acids. Each of the receptors are thought to be linked to the phosphoinositol hydrolysis signal transduction system via the a subunit of the Gq GTP binding protein.

The $5\text{-HT}_{2A}$ receptor is located in the cortex, claustrum and basal ganglia. Biological testing in rodents revealed that stimulation or agonism of $5\text{-HT}_{2A}$ receptors causes head shaking and may mediate the effects of hallucinogens. $5\text{-HT}_{2A}$ modulators include compounds that are $5\text{-HT}_{2A}$ receptor antagonists, which block the activity of agonists and have little to no intrinsic activity on the receptor, and $5\text{-HT}_{2A}$ inverse agonists, which are compounds that have negative intrinsic activity on the receptor. $5\text{-HT}_{2A}$ receptor antagonists, e.g., ritanserin, have been reported to improve sleep quality. $5\text{-HT}_{2A}$ receptor antagonists are also useful in treating migraine, depression, and schizophrenia.

MDL 100,907

MDL 100,907 is a potent $5\text{-HT}_{2A}$ receptor antagonist and thus is useful for treating a variety of conditions. For example, MDL 100,907 has been evaluated for the treatment of various neurological disorders, including schizophrenia. WO 99/56750 and *J. Pharm. Exp. Ther.* 1996,277, 968-9881. MDL 100,907 has been shown to exert a tonic inhibitory influence on dopamine efflux in the medial prefrontal cortex. See *European Journal of Pharmacology* 1995, 273, 273-279. MDL 100,907 is highly selective in its activity at the $5\text{-HT}_{2A}$ receptor compared to other receptors, and, as such, has reportedly fewer side effects. It has been shown to have a better CNS safety index relative to the reference compounds haloperidol, clozapine, risperiodone, ritanserin, and amperozide in preclinical testing. JPET 1996, 277, 968-981. In addition, MDL 100,907 is useful in the treatment of sleep disorders, such as insomnia and obstructive sleep apnea. See U.S. Pat. Nos. 6,277,864 and 6,613,779.

MDL 100,907 has the chemical name (+)-α-(2,3-dimethoxyphenyl)-1-[2-(4-fluorophenyl)ethyl]-4-piperidine methanol and can be prepared as described in U.S. Pat. No. 5,134,149 and WO 91/18602. Compounds that are structurally similar to MDL 100,907 are described in EP 0208235. In addition, the present invention encompasses a composition-comprising mixture of MDL 100,907 and its enantiomer. The structure of MDL 100,907 is presented below:

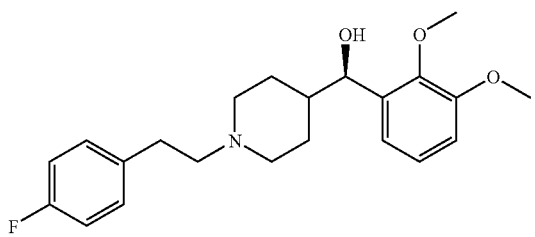

The dosage range at which MDL 100,907 exhibits its ability to block the effects of serotonin at the 5-$HT_{2A}$ receptor can vary depending upon the particular disease or condition being treated and its severity, the patient, the formulation, other underlying disease states that the patient is suffering from, and other medications that may be concurrently administered to the patient. Generally, MDL 100,907 will exhibit its serotonin 5-$HT_{2A}$ antagonist properties at dosages of between about 0.001 mg/kg of patient body weight/day to about 100 mg/kg of patient body weight/day. Sustained release formulations may contain multiples of the foregoing dosages depending upon over what period the active ingredient is released. The dosage of the compounds of the present invention may be determined by administering the compound to an animal and determining the plasma level of the active ingredient.

In certain instances, it is advantageous to administer MDL 100,907 in the form of a prodrug. A prodrug is a compound that gets converted to the active drug after the compound is administered. Carr and coworkers have described ester derivatives of MDL 100,907 that function as prodrugs for MDL 100,907. See U.S. Pat. Nos. 6,028,083 and 6,063,793. The structure of the ester derivatives of MDL 100,907, as will be referred to as "Pro MDL 100,907" hereafter, is presented below:

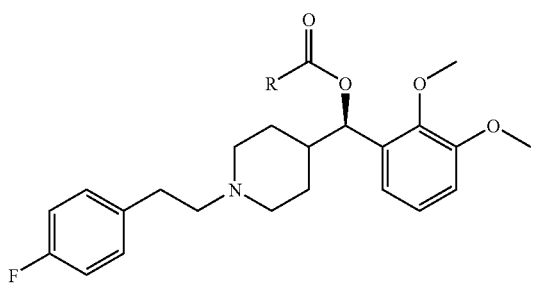

wherein, R is $C_1$-$C_{20}$ alkyl. Pro MDL 100,907 also refers to a stereoisomer or pharmaceutically acceptable salt thereof. Procedures for the preparation of Pro MDL 100,907 can be found in U.S. Pat. Nos. 6,028,083 and 6,063,793. The dosage range at which Pro MDL 100,907 exhibits its ability to block the effects of serotonin at the 5-$HT_{2A}$ receptor can vary depending upon the particular disease or condition being treated and its severity, the patient, the formulation, other underlying disease states that the patient is suffering from, and other medications that may be concurrently administered to the patient. Generally, Pro MDL 100,907 will exhibit its serotonin 5-$HT_{2A}$ modulator properties at dosages of between about 0.001 mg/kg of patient body weight/day to about 100 mg/kg of patient body weight/day. Sustained release formulations may contain multiples of the foregoing dosages depending upon over what period the active ingredient is released. The dosage of the compounds of the present invention may be determined by administering the compound to an animal and determining the plasma level of the active ingredient.

SR 46349B

SR 46349B is a highly selective antagonist of the 5-$HT_{2A}$ receptor. SR 46349B has virtually no affinity for the 5-$HT_{1A}$, 5-$HT_{1B}$, and 5-$HT_{1D}$ receptors, and has a moderate affinity for the 5-$HT_{2C}$ receptor. In studies on isolated tissues, the absence of activity of SR 46349B on rat stomach fundus indicates a 5-$HT_{2A}$ specificity versus 5-$HT_{2B}$ (M. Rinaldi-Carmona et al. *J. Pharmacol. Exp. Ther.* 1992, 759-768). In rodents, it has been shown that this compound predominantly binds to the regions of the brain containing the 5-$HT_2$ receptor (M. Rinaldi-Carmona et al. *Life Sciences* 1993, 54, 119-127). SR 46349B has the chemical name (1Z,2E)-1-(2-fluorophenyl)-3-(4-hydroxyphenyl)prop-2-en-1-one-O-(2-dimethylaminoethyl)oxime hemifumarate. SR 46349B can be prepared as described in EP 0373998 B1. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. The structure of SR 46349B is presented below:

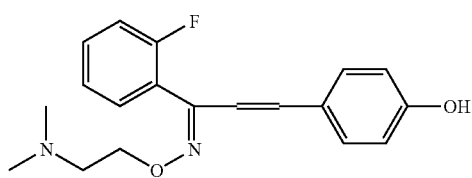

YM 992

YM 992 is an morpholine derivative described in by Takeuchi and coworkers in *Eur. J. Pharmacol.* 1997, 329, 27-35. The chemical name of YM 992 is (S)-2-[[(7-Fluoro-2,3-dihydro-1H-inden-4-yl)-oxy]methyl]morpholine hydrochloride. In general, the total daily dose ranges, for the conditions described herein, is from about 1 mg to about 900 mg. Preferably, a daily dose range should be between about 10 mg to about 200 mg. The structure of YM 992 is presented below:

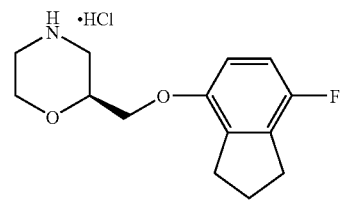

Fananserin

Fananserin is a 5-HT$_{2A}$ receptor antagonist described by Doble A. and coworkers in Br. *J. Pharmacol.* 1992, 105, 27-36. In general, the total daily dose ranges, for the conditions described herein, is from about 1 mg to about 900 mg. Preferably, a daily dose range should be between about 10 mg to about 200 mg. The structure of fananserin is presented below:

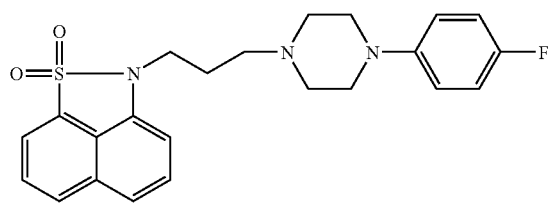

Oxazolidine Compounds A

A series of oxazolidine derivatives that have 5-HT$_{2A}$ receptor-antagonizing properties are described in WO 98/38189. Methods for preparing the oxazolidine compounds are given in WO 98/38189. In general, the total daily dose ranges, for the conditions described herein, is from about 1 mg to about 900 mg. Preferably, a daily dose range should be between about 10 mg to about 200 mg. The generic structure of the Oxazolidine Compounds A, as disclosed in WO 98/38189, is presented below. The definitions of the substituents of the generic structure can be found in WO 98/38189 which is hereby incorporated by reference.

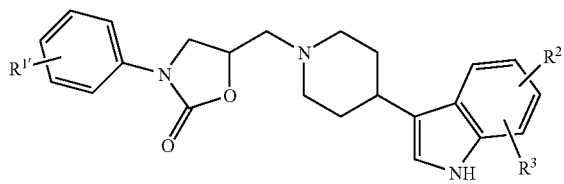

Phenylindole Compounds A

A series of phenylindole compounds that are modulators of the human 5-HT$_{2A}$ receptor have been described by Castro Pineiro and coworkers in U.S. Pat. No. 6,486,153. Methods for preparing the phenylindole compounds are presented in U.S. Pat. No. 6,486,153. In general, the total daily dose ranges, for the conditions described herein, is from about 1 mg to about 900 mg. Preferably, a daily dose range should be between about 10 mg to about 200 mg. The generic structure of the PhenylIndole Compounds A, as disclosed in U.S. Pat. No. 6,486,153, is presented below. The definitions of the substituents of the generic structure can be found in U.S. Pat. No. 6,486,153 which is hereby incorporated by reference.

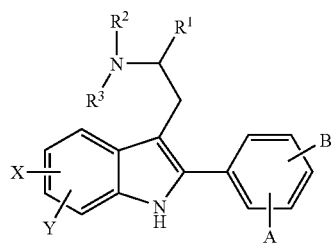

Piperidinyl Compounds B

A series of piperidinyl compounds that modulate the 5-HT$_{2A}$ receptor have been described in U.S. patent application 2004/0106600. Methods for preparing the piperidinyl compounds are presented in U.S. patent application 2004/0106600. In general, the total daily dose ranges, for the conditions described herein, is from about 1 mg to about 900 mg. Preferably, a daily dose range should be between about 10 mg to about 200 mg. The generic structure of the piperidinyl compounds A, as disclosed in U.S. patent application 2004/0106600, is presented below. The definitions of the substituents of the generic structure can be found in U.S. patent application 2004/0106600 which is hereby incorporated by reference.

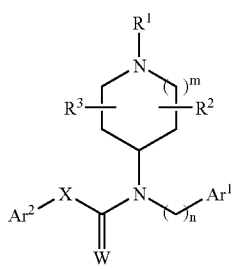

In certain embodiments, the piperidinyl compound A is N-{1-[2-(1,3-Dioxolan-2-yl)ethyl]piperidin-4-yl}-N-(4-fluorobenzyl)-N'-(4-isobutoxybenzyl)carbamide, hydrochloride; N-{1-[2-(1,3-Dioxan-2-yl)ethyl]piperidin-4-yl}-N-(4-fluorobenzyl)-2-[4-(2-hydroxy-2-methylpropoxy)phenyl]acetamide, tartrate; N-(4-Fluorobenzyl)-N-(piperidin-4-yl)-2-(4-isobutoxyphenyl)acetamide; N-{1-[3-(3,5-Dimethylpiperidin-1-yl)propyl]piperidin-4-yl}-N-(4-fluorobenzyl)-2-(4-isobutoxyphenyl)acetamide, dihydrochloride; 1-[3-(4-{(4-Fluorobenzyl)-[2-(4-isobutoxyphenyl)acetyl]amino }piperidin-1-yl)propyl]piperidin-4-carboxylic acid methyl ester, dihydrochloride; N-(4-Fluorobenzyl)-2-(4-isobutoxyphenyl)-N-{1-[2-(1-methylpyrrolidin-2-yl)ethyl]piperidin-4-yl}acetamide, dioxalate; N-{1-[3-(2,6-Dimethylmorpholin-4-yl)propyl]piperidin-4-yl}-N-(4-fluorobenzyl)-2-(4-isobutoxyphenyl)acetamide, dioxalate; N-(4-Fluorobenzyl)-N-{1-[3-(3-hydroxypiperidin-1-yl)propyl]piperidin-4-yl}-2-(4-isobutoxyphenyl)acetamide, dioxalate; N-(4-Fluorobenzyl)-2-(4-isobutoxyphenyl)-N-{1-[3-(2-methylpiperidin-1-yl)propyl]piperidin-4-yl}acetamide, dioxalate; N-(4-Fluorobenzyl)-2-(4-isobutoxyphenyl)-N-[1-(3-pyrrolidin-1-yl-propyl)piperidin-4-yl]acetamide, dioxalate; N-{1-[3-(2,5-Dimethylpyrrolidin-1-yl)propyl]piperidin-4-yl}-N-(4-fluorobenzyl)-2-(4-isobutoxyphenyl)acetamide, dioxalate; N-(4-Fluorobenzyl)-N-{1-[3-(3-hydroxymethylpiperidin-1-yl)propyl]piperidin-4-yl}-2-(4-isobutoxyphenyl)acetamide, dioxalate; N-(4-Fluorobenzyl)-2-(4-isobutoxyphenyl)-N-{1-[3-(4-(S)-isopropyl-2-oxo-oxazolidin-3-yl)propyl]piperidin-4-yl}acetamide, oxalate; N-[2-(4-Fluorophenyl)ethyl]-2-(4-isobutoxyphenyl)-N-{1-[3-(4-(S)-isopropyl-2-oxo-oxazolidin-3-yl)propyl]piperidin-4-yl}acetamide, oxalate; N-[2-(4-Fluorophenyl)ethyl]-N-{1-[3-(4-(S)-isopropyl-2-oxo-oxazolidin-3-yl)propyl]piperidin-4-yl}-2-(4-propoxyphenyl)acetamide, oxalate; N-(4-Fluorobenzyl)-N-{1-[3-(4-(S)-isopropyl-2-oxo-oxazolidin-3-yl)propyl]piperidin-4-yl}-2-(4-propoxyphenyl)acetamide, oxalate; N-{1-[2-(1,3-Dioxan-2-yl)ethyl]piperidin-4-yl}-N-(4-fluorobenzyl)-2-(4-isobutoxyphenyl)acetamide, oxalate; N-{1-

[2-(1,3-Dioxan-2-yl)ethyl]piperidin-4-yl}-N-[2-(4-fluorophenyl)ethyl]-2-(4-isobutoxyphenyl)acetamide, oxalate; N-{1-[2-(1,3-Dioxan-2-yl)ethyl]piperidin-4-yl}-N-[2-(4-fluorophenyl)ethyl]-2-(4-propoxyphenyl)acetamide, oxalate; N-{1-[2-(1,3-Dioxan-2-yl)ethyl]piperidin-4-yl}-N-(4-fluorobenzyl)-2-(4-propoxyphenyl)acetamide, tartrate; N-{1-[2-(1,3-Dioxan-2-yl)ethyl]piperidin-4-yl}-N-(4-fluorobenzyl)-N-(4-isobutoxybenzyl)carbamide, tartrate; N-{1-[2-(1,3-Dioxan-2-yl)ethyl]piperidin-4-yl}-N-(4-fluorobenzyl)-2-(4-fluorophenyl)acetamide, tartrate; N-{1-[2-(1,3-Dioxan-2-yl)ethyl]piperidin-4-yl}-N-(4-fluorobenzyl)-2-p-tolylacetamide, tartrate; 2-Benzofuran-5-yl-N-{1-[2-(1,3-dioxan-2-yl)ethyl]piperidin-4-yl}-N-(4-fluorobenzyl)acetamide, tartrate; 2-(2,3-Dihydrobenzofuran-5-yl)-N-{1-[2-(1,3-dioxan-2-yl)ethyl]piperidin-4-yl}-N-(4-fluorobenzyl)acetamide, tartrate; N-{1-[2-(2,2-Dimethyl-1,3-dioxolan-4-yl)ethyl]piperidin-4-yl}-N-(4-fluorobenzyl)-2-(4-isobutoxyphenyl)acetamide, tartrate; N-{1-[2-(1,3-Dioxan4-yl)ethyl]piperidin-4-yl}-N-(4-fluorobenzyl)amine; N-{1-[2-(1,3-Dioxan-4-yl)ethyl]piperidin-4-yl}-N (4-fluorobenzyl)-2-(4-isobutoxyphenyl)acetamide, tartrate; N-{1-[2-(1,3-Dioxan-4-yl)ethyl]piperidin-4-yl}-N-(4-fluorobenzyl)-2-(4-trifluoromethylphenyl)acetamide, tartrate; 2-(4-Cyanophenyl)-N-{1-[2-(1,3-dioxan-4-yl)ethyl]piperidin-4-yl}-N-(4-fluorobenzyl)acetamide, tartrate; N-(4-Fluorobenzyl)-2-(4-isobutoxyphenyl)-N-{1-[2-(2-oxo-imidazolidin-1-yl)ethyl]piperidin-4-yl}acetamide, hydrochloride; 2-(4-Methoxyphenyl)-N-(4-methylbenzyl)-N-{1-[2-(2-oxo-imidazolidin-1-yl)ethyl]piperidin-4-yl}acetamide, hydrochloride; N-(4-Fluorobenzyl)-2-(4-isopropoxyphenyl)-N-{1-[2-(2-oxo-imidazolidin-1-yl)ethyl]piperidin-4-yl}acetamide, hydrochloride; N-(4-Fluorobenzyl)-2-(4-isopropoxyphenyl)-N-{1-[3-(3-methyl-2-oxo-2,3-dihydro-benzoimidazol-1-yl)propyl]piperidin-4-yl}acetamide; hydrochloride; N-{1-[2-(2,4-Dioxo-1,4-dihydro-2H-quinazolin-3-yl)ethyl]piperidin-4-yl}-2-(4-methoxyphenyl)-N-(4-methylbenzyl)acetamide, hydrochloride; 2-(4-Methoxyphenyl)-N-(4-methylbenzyl)-N-1-[3-(2-oxo-2,3-dihydrobenzoimidazol-1-yl)propyl]piperidin-4-yl}-acetamide, hydrochloride; N-(4-Fluorobenzyl)-2-(4-isopropoxyphenyl)-N-{1-[4-(2-oxo-2,3-dihydrobenzoimidazol-1-yl)butyl]piperidin-4-yl}acetamide, hydrochloride; N-{1-[2-(2,4-Dioxo-1,4-dihydro-2H-quinazolin-3-yl)ethyl]piperidin-4-yl}-N-(4-fluorobenzyl)-2-(4-isopropoxyphenyl)acetamide, hydrochloride; 4-(4-Fluorobenzylamino)-piperidine-1-carboxylic acid benzyl ester; N-(1-Benzyloxycarbonylpiperidin-4-yl)-N-(4-fluorobenzyl)-N'-(4-isopropoxybenzyl)carbamide; N-(4-Fluorobenzyl)-N'-(4-isopropoxybenzyl)-N-piperidin-4-yl-carbamideoxalate; N-{1-[2-(1,3-Dioxolan-2-yl)ethyl]piperidin-4-yl}-N-(4-fluorobenzyl)-N'-(4-isopropoxybenzyl)carbamide, oxalate; N-{1-[2-(1,3-Dioxolan-2-yl)ethyl]piperidin-4-yl]-2-(4-methoxyphenyl)-N-(4-methylbenzyl)acetamide, hydrochloride; N-{1-[2-(1,3-Dioxolan-2-yl)ethyl]piperidin-4-yl}-N-(4-fluorobenzyl)-2-(4-isobutoxyphenyl)acetamide, hydrochloride; N-{1-[2-(1,3-Dioxolan-2-yl)ethyl]piperidin-4-yl}-2-(4-isopropoxyphenyl)-N-(4-methylbenzyl)acetamide, hydrochloride; N-{1-[2-(1,3-Dioxolan-2-yl)ethyl]piperidin-4-yl}-N-(4-fluorobenzyl)-2-(4-propoxyphenyl)acetamide, tartrate; N-(4-Fluorobenzyl)-N'-(4-isopropoxybenzyl)-N-{1-[2-((S)-4-methyl-1,3-dioxolane-2-yl)ethyl]piperidin-4-yl}carbamide, oxalate; N-(4-Fluorobenzyl)-N'-(4-isopropoxybenzyl)-N-[1-(3-morpholin-4-yl-propyl)piperidin-4-yl]carbamide, oxalate; 2-(4-Methoxyphenyl)-N-(4-methylbenzyl)-N-[1-(2-morpholin-4-ylethyl)piperidin-4-yl]acetamide, dihydrochloride; 2-(4-Methoxyphenyl)-N-(4-methylbenzyl)-N-[1-(3-morpholin-4-ylpropyl)piperidin-4-yl]acetamide, dihydrochloride; N-(4-Fluorobenzyl)-2-(4-isobutoxyphenyl)-N-[1-(3-morphotin-4-ylpropyl)piperidin-4-yl]acetamide, dihydrochloride; N-(4-Fluorobenzyl)-2-(4-isopropoxyphenyl)-N-[1-(3-morpholin-4-yl-propyl)piperidin-4-yl]acetamide, dihydrochloride; N-(4-Fluorobenzyl)-N'-(4-isopropoxybenzyl)-N-[1-(3-piperidin-1-yl-propyl)piperidin-4-yl]carbamide, oxalate; N-(4-Fluorobenzyl)-N'-(4-isopropoxybenzyl)-N-[1-(3-((S)-4-isopropyl-2-oxazolidinon-1-yl-propyl)piperidin-4-yl]carbamide, tartrate; N-(4-Fluorobenzyl)-N'-(4-isopropoxybenzyl)-N-{1-[2-(2,5,5-trimethyl-1,3-dioxan-2-yl)ethyl]}piperidin-4-yl]carbamide, oxalate; N-{1-[3-(1,3-Dioxolan-2-yl)propyl]piperidin-4-yl}-N-(4-fluorobenzyl)-N'-(4-isopropoxybenzyl)carbamide, oxalate; N-[1-(2,2-Dimethyl-1,3-dioxan-5-yl)piperidin-4-yl]-N-(4-fluorobenzyl)-N'-(4-isopropoxybenzyl)carbamide, oxalate; N-(4-Fluorobenzyl)-N'-(4-isopropoxybenzyl)-N-{[2-(1-methyl pyrrolidin-2-yl)ethyl]-piperidin-4-yl}carbamide, oxalate; N-[1-(2,2-Dimethyl-1,3-dioxan-5-yl)piperidin-4-yl]-N-(4-fluorobenzyl)-2-(4-isobutoxyphenyl)acetamide, oxalate; N-[1-(1,3-Dioxan-5-yl)-piperdin-4-yl)-N-(4-fluorobenzyl)-2-(4-isobutoxyphenyl)acetamide, tartrate; N-[1-(2,2-Dimethyl-1,3-dioxan-5-yl)piperidin-4-yl]-N-(4-fluorobenzyl)-2-(4-fluorophenyl)acetamide, tartrate; N-{1-[2-(1,3-Dioxan-4-yl)ethyl]piperidin-4-yl}-N-(4-fluorobenzyl)-2-(4-fluorophenyl)acetamide, tartrate; N-{1-[2-(1,3-Dioxan-4-yl)ethyl]piperidin-4-yl}-N-(4-fluorobenzyl)-2-(4-trifluoromethoxyphenyl)acetamide, tartrate; N-{1-[2-(1,3-Dioxan-4-yl)ethyl]piperidin-4-yl}-N-(4-fluorobenzyl)-2-(4-propoxyphenyl)acetamide, tartrate; N-(4-Fluorobenzyl)-2-(4-isobutoxyphenyl)-N-[1-(tetrahydropyran-4-yl)piperidin-4-yl]acetamide, tartrate; N-(4-Fluorobenzyl)-2-(4-isobutoxyphenyl)-N-[1-(tetrahydropyran-4-ylmethyl)piperidin-4-yl]acetamide, tartrate; N-(4-Fluorobenzyl)-2-(4-isobutoxyphenyl)-N-{1-[2-(tetrahydropyran-4-yl)ethyl]piperidin-4-yl]acetamide, tartrate; N-(4-Fluorobenzyl)-2-(4-fluorophenyl)-N-[1-(tetrahydropyran-4-yl)piperidin-4-yl]acetamide, tartrate; N-[1-((S)-3,5-Dihydroxypentyl)piperidine-4-yl]-N-(4-fluorobenzyl)-2-(4-isobutoxyphenyl)acetamide, tartrate; N-{1-[2-((4S)-1,3-Dioxane-4-yl)ethyl]piperidine-4-yl}-N-(4-fluorobenzyl)-2-(4-isobutoxyphenyl)acetamide, tartrate; N-{1-[2-(1,3-Dioxan-2-yl)ethyl]piperidin-4-yl}-N-(4-fluorobenzyl)amine; 2-(4-Benzyloxyphenyl)-N-{1-[2-(1,3-dioxan-2-yl)ethyl]piperidin-4-yl-}-N-(4-fluorobenzyl)acetamide, tartrate; N-{1-[2-(1,3-Dioxan-2-yl)ethyl]piperidin-4-yl}-N-(4-fluorobenzyl)-2-(4-hydroxyphenyl)-acetamide, tartrate; N-{1-[2-(1,3-Dioxan-2-yl)ethyl]piperidin-4-yl}-N-(4-fluorobenzyl)-2-(4-methoxyphenyl)-acetamide, tartrate; N-{1-[2-(1,3-Dioxan-2-yl)ethyl]piperidin-4-yl}-N-(4-fluorobenzyl)-2-(4-isopropylphenyl)-acetamide, tartrate; N-{1-[2-(1,3-Dioxan-2-yl)ethyl]piperidin-4-yl}-N-(4-fluorobenzyl)-2-(4-trifluoromethoxy-phenyl)-acetamide, tartrate; N-{1-[2-(1,3-Dioxan-2-yl)ethyl]piperidin-4-yl}-N-(4-fluorobenzyl)-2-(4-ethoxyphenyl)-acetamide, oxalate; N-{1-[2-(1,3-Dioxan-2-yl)ethyl]piperidin-4-yl}-N-(4-fluorobenzyl)-2-(4-isopropoxyphenyl)-acetamide, oxalate; N-{1-[2-(1,3-Dioxan-2-yl)ethyl]piperidin-4-yl}-N-(4-fluorobenzyl)-2-phenylacetamide, oxalate; N-{1-[2-(1,3-Dioxan-2-yl)ethyl]piperidin-4-yl}-N-(4-fluorobenzyl)-2-[4-(2-fluoroethoxy)-phenyl]acetamide, oxalate; N-{1-[2-(5,5-Dimethyl-1,3dioxan-2-yl)ethyl]piperidin-4-yl}-N-(4-fluorobenzyl)-2-(4-isobutoxyphenyl)acetamide, oxalate; N-(4-Fluorobenzyl)-2-(4-isobutoxyphenyl)-N-{1-[2-((R)-4-methyl-1,3-dioxan-2-yl)ethyl]-piperidin-4-yl}acetamide, oxalate; N-(4-Fluorobenzyl)-2-(4-isobutoxyphenyl)-N-{1-

[2-((S)-4-methyl-1,3-dioxolan-2-yl)ethyl]-piperidin-4-yl}acetamide, oxalate; N-{1-[2-(4,6-Dimethyl-1,3-dioxan-2-yl)ethyl]piperidin-4-yl}-N-(4-fluorobenzyl)-2-(4-isobutoxyphenyl)acetamide, oxalate; N-(4-Fluorobenzyl)-N-{1-[2-((S)-4-methyl-1,3-dioxolan-2-yl)ethyl]piperidin-4-yl}-2-(4-trifluoromethoxyphenyl)acetamide, oxalate; N-(4-Fluorobenzyl)-2-(4-isopropylphenyl)-N-{1-[2-((S)-4-methyl-1,3-dioxolan-2-yl)ethyl]-piperidin-4-yl}acetamide, oxalate; N-(4-Fluorobenzyl)-N-{1-[2-((R)-4-methyl-1,3-dioxan-2-yl)ethyl]piperidin-4-yl}-2-(4-trifluoromethoxyphenyl)acetamide, oxalate; N-(4-Fluorobenzyl)-2-(4-isobutoxyphenyl)-N-{1-[2-(2,5,5-trimethyl-1,3-dioxan-2-yl)ethyl]piperidin-4-yl}acetamide, oxalate; N-(4-Fluorobenzyl)-2-(4-isobutoxyphenyl)-N-{1-[2-(2-methyl-1,3-dioxolan-2-yl)ethyl]-piperidin-4-yl}acetamide, oxalate; N-(4-Fluorobenzyl)-2-(4-isobutoxyphenyl)-N-{1-[3-(1,3-dioxolan-2-yl-)propyl]piperidin-4-yl}acetamnide, tartrate; N-(4-Fluorobenzyl)-2-(4-isobutoxyphenyl)-N-{1-(3-piperidin-1-yl-propyl)piperidin-4-yl}-acetamide, dihydrochloride; N-(4-Fluorobenzyl)-2-(4-isobutoxyphenyl)-N-{1-[2-(tetrahydropyran-2-yloxy)ethyl]-piperidin-4-yl}acetamide, oxalate; N-(4-Fluorobenzyl)-2-(4-isobutoxyphenyl)-N-{1-[3-(2-oxo-piperidin-1-yl)propyl]piperidin-4-yl}acetamide; N-(4-Fluorobenzyl)-2-(4-isobutoxyphenyl)-N-{1-[3-(2-oxo-pyrrolidin-1-yl)propyl]piperidin-4-yl}acetamide, hydrochloride; N-(4-Fluorobenzyl)-2-(4-isobutoxyphenyl)-N-{1-[3-((R)-4-isopropyl-2-oxo-oxazolidin-3-yl)propyl]piperidin-4-yl}acetamide, oxalate; N-(4-Fluorobenzyl)-2-(4-isobutoxyphenyl)-N-{1-[3-(2-oxo-oxazolidin-3-yl)propyl]piperidin-4-yl}acetamide, oxalate; N-(4-Fluorobenzyl)-2-(4-isobutoxyphenyl)-N-{1-[3-((S)-4-methyl-2-oxo-oxazolidin-3-yl)propyl]piperidin-4-yl}acetamide, tartrate; N-(4-Fluorobenzyl)-2-(4-isobutoxyphenyl)-N-{1-[3-((S)-4-ethyl-2-oxo-oxazolidin-3-yl)-propyl]piperidin-4-yl}acetamide, oxalate; N-(4-Fluorobenzyl)-2-(4-isobutoxyphenyl)-N-{1-[2-(1,3-oxothiolan-2-yl)ethyl]piperidin-4-yl}acetamide, L-tartrate; 2-(4-Bromophenyl)-N-{1-[2-(1,3-dioxan-2-yl)ethyl)piperidin-4-yl}-N-(4-fluorobenzyl)-acetamide, L-tartrate; N-{1-[2-(1,3-Dioxan-2-yl)ethyl]piperidin-4-yl}-N-(4-fluorobenzyl)-2-(4-isobutylamino-phenyl)acetamide, L-tartrate; N-{1-[2-(1,3-Dioxan-2-yl)ethyl]piperidin-4-yl}-N-(4-fluorobenzyl)-2-(4-propylamino-phenyl)acetamide, L-tartrate; N-{1-[2-(1,3-Dioxan-2-yl)ethyl)piperidin-4-yl}-N-(4-fluorobenzyl)-2-(4-(1-nitropropyl)-phenyl)acetamide, L-tartrate; N-{1-[2-(1,3-Dioxan-2-yl)ethyl)piperidin-4-yl}-N-(4-fluorobenzyl)-2-[4-(2-oxopyrrolidin-1-yl)phenyl)acetamide, L-tartrate; N-{1-[2-(1,3-Dioxan-2-yl)ethyl)piperidin-4-yl}-N-(4-fluorobenzyl)-2-(4-isobutylsulfanyl-phenyl)acetamide, L-tartrate; N-{1-[2-(1,3-Dioxan-2-yl)ethyl)piperidin-4-yl}-N-(4-fluorobenzyl)-2-(4-iodophenyl)-acetamide, L-tartrate; 2-(4-Acetophenyl)-N-{1-[2-(1,3-dioxan-2-yl)ethyl)piperidin-4-yl}-N-(4-fluorobenzyl)-acetamide, L-tartrate; 2-[4-(1-Hydroxyiminoethyl)phenyl]-N-{1-[2-(1,3-dioxan-2-yl)ethyl)piperidin-4-yl}-N-(4-fluorobenzyl)acetamide, L-tartrate; N-{1-[2-(1,3-Dioxan-2-yl)ethyl)piperidin-4-yl}-N-(4-fluorobenzyl)-2-(4-morpholin-4-yl-phenyl)acetamide, L-tartrate; N-{1-[2-(1,3-Dioxan-2-yl)ethyl)piperidin-4-yl}-N-(4-fluorobenzyl)-2-(4-pyrazol-1-yl-phenyl)acetamide, L-tartrate; N-{1-[2-(1,3-Dioxan-2-yl)-1-methylethyl]piperidin-4-yl}-N-(4-fluorobenzyl)-2-(4-iso-butoxyphenyl)-acetamide, L-tartrate; N-{1-[2-(1,3-Dioxan-4-yl)ethyl]piperidin-4-yl}-N-(4-fluorobenzyl)-2-(4-pyrazol-1-yl-phenyl)acetamide, L-tartrate; N-[1-((R)-3,5-Dihydroxypentyl)piperidine-4-yl]-N-(4-fluorobenzyl)-2-(4-isobutoxyphenyl)acetamide, tartrate; N-{1-[2-((4R)-1,3-Dioxane-4-yl)ethyl]piperidine-4-yl}-N-(4-fluorobenzyl)-2-(4-isobutoxyphenyl) acetamide, tartrate; or N-{1-[2-(1,3-Dioxan-2-yl)ethyl]piperidin-4yl}-N-(4-fluorobenzyl)-2-[4-triazol-4-yl)phenyl]acetamide, L-tartrate.

Spiroazacyclic Compounds C

A series of spiroazacyclic compounds that modulate the 5-HT$_{2A}$ receptor have been described in U.S. patent application 2003/0166928. Methods for preparing the spiroazacyclic compounds are presented in U.S. patent application 2003/0166928. In general, the total daily dose ranges, for the conditions described herein, is from about 1 mg to about 900 mg. Preferably, a daily dose range should be between about 10 mg to about 200 mg. The generic structure of the spiroazacyclic compounds A, as disclosed in U.S. patent application 2003/0166928, is presented below. The definitions of the substituents of the generic structure can be found in U.S. patent application 2003/0166928 which is hereby incorporated by reference.

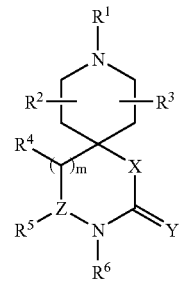

In certain instances, said spiroazacyclic compound of formula C is 1-oxa-4,9-diaza-spiro[5.5]undecan-3-one; 1-oxa-3,8-diaza-spiro[4.5]decan-2-one; 1,3,8-triaza-spiro[4.5]decan-2-one; 1,2,9-triaza-spiro[5.5]undecan-3-one; 1,2,8-triaza-spiro[4.5]decan-3-one; 1,2,8-triaza-spiro[4.5]decan-3-one; 1,2,4,8-tetraaza-spiro[4.5]decan-3-one; 2,4,9-triaza-spiro[-5.5]undecan-3-one; 2,8-diaza-spiro[4.5]decan-3-one; 2-oxa-4,9-diaza-spiro[5.5]undecan-3-one; 1-thia-3,8-diaza-spiro[4.5]-decan-2-one; 1-oxa-3,9-diaza-spiro[5.5]undecan-2-one; 4-(4-Fluorobenzyl)-3-(4-methoxybenz-yl)-8-methyl-1-oxa-3,8-diaza-spiro[4.5]decan-2-one; 3-(4-Ethoxybenzyl)-4-(4-fluorobenzyl)-8-methyl-1-oxa-3,8-diaza-spiro[4.5]-decan-2-one; 4-(4-Fluorobenzyl)-8-methyl-3-(4-propoxybenzyl)-1-oxa-3,8-diaza-spiro[4.5]decan-2-one; 3-(4-Cyclopropylmethoxybenzyl)-4-(4-fluorobenzyl)-8-methyl-1-oxa-3,8-diaza-spiro[4.5]decan-2-one; 4-(4-Fluorobenzyl)-3-(4-isopropoxybenzyl)-8-methyl-1-oxa-3,8-diaza-spiro[4.5]decan-2-one; 3-(4-Butoxybenzyl)-4-(4-fluorobenzyl)-8-methyl-1-oxa-3,8-diaza-spiro[4.5]- decan-2-one; 4-(4-Fluorobenzyl)-3-(4-isobutoxybenzyl)-8-methyl-1-oxa-3,8-diaza-spiro[4.5]decan-2-one; 3-(4-Difluoromethoxybenzyl)-4-(4-fluorobenzyl)-8-methyl-1-oxa-3,8-diaza-spiro[4.5]decan-2-one; 4-(4-Fluorobenzyl)-8-methyl-3-(4-trifluoromethoxybenzyl)-1-oxa-3,8-diaza-spiro[4.5]decan-2-one; 4-(4-Fluorobenzyl)-8-methyl-3-(4-pentoxybenzyl)-1-oxa-3,8-diaza-spiro[4.5-]decan-2-one; 8-Ethyl-4-(4-fluorobenzyl)-3-(4-isobutoxybenzyl)-1-oxa-3,8-diaza-spiro[4.5]decan-2-one; 4-(4-Fluorobenzyl)-3-(4-isobutoxybenzyl)-8-isopropyl-1-oxa-3,8-diaza-spiro [4.5]decan-2-one; 8-Cyclopropylmethyl-4-(4-fluorobenzyl)-3-(4-isobutoxybenzyl)-1-oxa-3,8-diaza-spiro[4.5]decan-2-one; 8-Cyclohexylmethyl-4-(4-fluorobenzyl)-3-(4-isobutoxybenzyl)-1-oxa-3,8-diaza-spiro[4.5]decan-2-one; 8-Cyclopentyl-4-(4-fluorobenzyl)-3-(4-isobutoxybenzyl)-1-oxa-3,8-diaza-spiro[4.5]decan-2-one; 4-(4-Fluorobenzyl)-3-(4-isobutoxybenzyl)-8-(3-morpholin-4-yl-propyl)-1-oxa-3, 8-diaza-spiro[4.5]decan-2-one; 8-(2-[1,3]Dioxolan-2-yl-ethyl)-4-(4-fluorobenzyl)-3-(4-isobutoxybenzyl)-1-oxa-3,8-diaza-spiro[4.5]decan-2-one; 4-(4-Fluorobenzyl)-3-(4-isobutoxybenzyl)-8-[2-(2-oxo-imidazolidin-1-yl)-ethyl]-1-oxa-3,8-diaza-spiro[4.5]- decan-2-one; 4-(4-Fluorobenzyl)-3-(4-isobutoxybenzyl)-8-[3-(2-oxo-2,3-dihydro-benzoimidazol-1-yl)-propyl]-1-oxa-3,8-diaza-spiro[4.5]decan-2-one; 4-(4-Fluorobenzyl)-3-(4-isobutoxybenzyl)-8-(2-methyl-thiazol-4-yl-methyl)-1-oxa-3,8-diaza-spiro [4.5]decan-2-one; 4-(4-Chlorobenzyl)-3-(4-isobutoxybenzyl)-8-methyl-1-oxa-3,8-diaza-spiro[4.5]decan-2-one; 8-Ethyl-4-(4-chlorobenzyl)-3-(4-isobutoxybenzyl)-1-oxa-3,8-diaza-spiro[4.5]decan-2-one; 4-(4-Chlorobenzyl)-3-(4-isobutoxybenzyl)-8-isopropyl-1-oxa-3,8-diaza-spiro[4.5]decan-2-one; 8-Cyclopropylmethyl-4-(4-chlorobenzyl)-3-(4-isobutoxybenzyl)-1-oxa-3,8-diaza-spiro[4.5]decan-2-one; 8-Cyclohexylmethyl-4-(4-chlorobenzyl)-3-(4-isobutoxybenzyl)-1-oxa-3,8-diaza-spiro[4.5]decan-2-one; 8-(2-[1,3]Dioxolan-2-yl-ethyl)-4-(4-chlorobenzyl)-3-(4-isobutoxybenzyl)-1-oxa-3,8-diaza-spiro[4.5]decan-2-one; 4-(4-Chlorobenzyl)-3-(4-isobutoxybenzyl)-8-[2-(2-oxo-imidazolidin-1-yl)-ethyl]-1-oxa-3,8-diaza-spiro[4.5]decan-2-one; 3-(4-Difluoromethoxybenzyl)-4-(4-fluorobenzyl)-8-methyl-1-oxa-3,8-diaza-spiro[4.5]decan-2-one; 3-(4-Difluoromethoxybenzyl)-8-ethyl-4-(4-fluorobenzyl)-1-oxa-3,8-diaza-spiro[4.5]decan-2-one; 3-(4-Difluoromethoxybenzyl)-4-(4-fluorobenzyl)-8-isopropyl-1-oxa-3,8-diaza-spiro[4.5]decan-2-one; 8-Cyclopropylmethyl-3-(4-difluoromethoxybenzyl)-4-(4-fluorobenzyl)-1-oxa-3,8-diaza-spiro[4.5]decan-2-one; 8-Cyclohexylmethyl-3-(4-difluoromethoxybenzyl)-4-(4-fluorobenzyl)-1-oxa-3,8-diaza-spiro[4.5]decan-2-one; 3-(4-Difluoromethoxybenzyl)-8-(2-[1,3]dioxolan-2-yl-ethyl)-4-(4-fluorobenzyl)-1-oxa-3,8-diaza-spiro[4.5]decan-2-one; 3-(4-Difluoromethoxybenzyl)-4-(4-fluorobenzyl)-8-[2-(2-oxo-imidazolidin-1-yl)-ethyl]-1-oxa-3,8-diaza-spiro[4.5]decan-2-one; 8-Ethyl-4-(4-fluorobenzyl-3-(4-trifluoromethoxybenzyl)-1-oxa-3,8-diaza-spiro[4.5]decan-2-one; 4-(4-Fluorobenzyl)-8-isopropyl-3-(4-trifluoromethoxybenzyl)-1-oxa-3,8-diaza-spiro[4.5]decan-2-one; 8-Cyclopropylmethyl-4-(4-fluorobenzyl)-3-(4-trifluoromethoxybenzyl)-1-oxa-3,8-diaza-spiro[4.5]decan-2-one; 8-Cyclohexylmethyl-4-(4-fluorobenzyl)-3-(4-trifluoromethoxybenzyl)-1-oxa-3,8-diaza-spiro[4.5]decan-2-one; 8-Cyclopentyl-4-(4-fluorobenzyl)-3-(4-trifluoromethoxybenzyl)-1-oxa-3,8-diaza-spiro[4.5]decan-2-one; 8-(2-[1,3]Dioxolan-2-yl-ethyl)-4-(4-fluorobenzyl)-3-(4-trifluoromethoxybenzyl)-1-oxa-3,8-diaza-spiro[4.5]decan-2-one; 4-(4-Fluorobenzyl)-8-[2-(2-oxo-imidazolidin-1-yl)-ethyl]-3-(4-trifluoromethoxybenzyl)-1-oxa-3,8-diaza-spiro[4.5]decan-2-one; 8-Ethyl-4-(4-fluorobenzyl)-3-(4-propoxybenzyl)-1-oxa- -3,8-diaza-spiro[4.5]decan-2-one; 4-(4-Fluorobenzyl)-8-isopropyl-3-(4-propoxybenzyl)-1-oxa-3,8-diaza-spiro[4.5]decan-2-one; 8-Cyclopropylmethyl-4-(4-fluorobenzyl)-3-(4-propoxybenzyl)-1-oxa-3,8-diaza-spiro[4.5]decan-2-one; 8-Cyclohexylmethyl-4-(4-fluorobenzyl)-3-(4-propoxybenzyl)-1-oxa-3,8-diaza-spiro[4.5]decan-2-one; 8-Cyclopentyl-4-(4-fluorobenzyl)-3-(4-propoxybenzyl)-1-oxa-3,8-diaza-spiro[4.5]decan-2-one; 8-(2-[1,3]Dioxolan-2-yl-ethyl)-4-(4-fluorobenzyl)-3-(4-propoxybenzyl)-1-oxa-3,8-diaza-spiro[4.5]decan-2-one; 4-(4-Fluorobenzyl)-8-[2-(2-oxo-imidazolidin-1-yl)-ethyl]-3-(4-propoxybenzyl)-1-oxa-3,8-diaza-spiro[4.5]decan-2-one; 3-(4-Cyclopropylmethoxybenzyl)-8-ethyl-4-(4-fluorobenzyl)-1-oxa-3,8-diaza-spiro[4.5]decan-2-one; 3-(4-Cyclopropylmethoxybenzyl)-4-(4-fluorobenzyl)-8-isopropyl-1-oxa-3,8-diaza-spiro[4.5]decan-2-one; 3-(4-Cyclopropylmethoxybenzyl)-8-cyclopropylmethyl-4-(4-fluorobenzyl)-1-oxa-3,8-diaza-spiro[4.5]decan-2-one; 3-(4-Cyclopropylmethoxybenzyl)-8-(2-[1,3]dioxolan-2-yl-ethyl)-4-(4-fluorobenzyl)-1-oxa-3,8-diaza-spiro[4.5]decan-2-one; 3-(4-Cyclopropylmethoxybenzyl)-4-(4-fluorobenzyl)-8-[2-(2-oxo-imidazolidin-1-yl)-ethyl]-1-oxa-3,8-diaza-spiro[4.5]decan-2-one; 8-(2-[1.3]-Dioxan-2-yl-ethyl)-4-(4-fluorobenzyl)-3-(4-isobutoxybenzyl)-1-oxa-3,8-diaza-spiro[4.5]decane-3-one; 4-(4-Fluorobenzyl)-3-(4-isobutoxybenzyl)-8-{3-[(S)-4-isopropyl-2-oxo-oxazolidin-3-yl]-propyl}-1-oxa-3,8-diaza-spiro[4.5]decane-3-one; 1-(4-Fluorobenzyl)-2-(4-methoxybenzyl)-8-methyl-1,2,8-triaza-spiro[4.5]decan-3-one; 2-(4-Ethoxybenzyl)-1-(4-fluorobenzyl)-8-methyl-1,2,8-triaza-spiro[4.5]decan-3-one; 1-(4-Fluorobenzyl)-8-methyl-2-(4-propoxybenzyl)-1,2,8-triaza-spiro[4.5]decan-3-one; 1-(4-Fluorobenzyl)-2-(4-isopropoxybenzyl)-8-methyl-1,2,8-triaza-spiro[4.5]decan-3-one; 2-(4-Butoxybenzyl)-1-(4-fluorobenzyl)-8-methyl-1,2,8-triaza-spiro[4.5]decan-3-one; 2-(4-Cyclopropylmethoxybenzyl)-1-(4-fluorobenzyl)-8-methyl-1,2,8-triaza-spiro[4.5]decan-3-one; 1-(4-Fluorobenzyl)-2-(4-isobutoxybenzyl)-8-methyl-1,2,8-triaza-spiro[4.5]decan-3-one; 2-(4-Difluoromethoxybenzyl)-1-(4-fluorobenzyl)-8-methyl-1,2,8-triaza-spiro[4.5]decan-3-one; 1-(4-Fluorobenzyl)-8-methyl-2-(4-trifluoromethoxybenzyl)-1,2,8-triaza-spiro[4.5]decan-3-one; 1-(4-Fluorobenzyl)-8-methyl-2-(4-pentoxybenzyl)-1,2,8-triaza-spiro[4.5]decan-3-one; 1-(4-Chlorobenzyl)-2-(4-ethoxybenzyl)-8-methyl-1,2,8-triaza-spiro[4.5]decan-3-one; 1-(4-Chlorobenzyl)-8-methyl-2-(4-propoxybenzyl)-1,2,8-triaza-spiro[4.5]decan-3-one; 1-(4-Chlorobenzyl)-2-(4-isobutoxybenzyl)-8-methyl-1,2,8-triaza-spiro[4.5]decan-3-one; 1-(4-Chlorobenzyl)-2-(4-cyclopropylmethoxybenzyl)-8-methyl-1,2,8-triaza-spiro[4.5]decan-3-one, 1-(4-Chlorobenzyl)-2-(4-difluoromethoxybenzyl)-8-methyl-1,2,8-triaza-spiro[4.5]decan-3-one; 1-(4-Ethylbenzyl)-2-(4-ethoxybenzyl)-8-methyl-1,2,8-triaza-spiro[4.5]decan-3-one; 1-(4-Ethylbenzyl)-2-(4-isopropoxybenzyl)-8-methyl-1,2,8-triaza-spiro[4.5]decan-3-one; I-(4-Ethylbenzyl)-2-(4-isobutoxybenzyl)-8-methyl-1,2,8-triaza-spiro[4.5]decan-3-one; 1-(4-Ethylbenzyl)-2-(4-cyclopropylmethoxybenzyl)-8-methyl-1,2,8-triaza-spiro[4.5]decan-3-one; 1-(4-Ethylbenzyl)-8-methyl-2-(4-trifluoromethoxybenzyl)-1,2,8-triaza-spiro[4.5]decan-3-one: 2-(4-Difluoromethoxybenzyl)-1-(4-fluorobenzyl)-8-ethyl-1,2,8-triaza-spiro[4.5]decan-3-one; 2-(4-Difluoromethoxybenzyl)-1-(4-fluorobenzyl)-8-isopropyl-1,2,8-triaza-spiro[4.5]decan-3-one; 2-(4-Difluoromethoxybenzyl)-1-(4-fluorobenzyl)-8-cyclopropylmethyl-1,2,8-triaza-spiro[4.5]decan-3-one; 2-(4-Difluoromethoxybenzyl)-1-(4-fluorobenzyl)-8-(2-[1,3dioxolan-2-yl-ethyl)-1,2,8-triaza-spiro[4.5]decan-3-one; 8-Ethyl-1-(4-fluorobenzyl)-2-(4-isobutoxybenzyl)-1,2,8-triaza-spiro[4.5]decan-3-one; 1-(4-Fluorobenzyl)-2-(4-isobutoxybenzyl)-8-isopropyl-1,2,8-triaza-spiro[4.5]decan-3-one; 8-Cyclopropylmethyl-1-(4-fluorobenzyl)-2-(4-isobutoxybenzyl)-1,2,8-triaza-spiro[4.5]decan-3-one; 8-(2-[1,3]dioxolan-2-ylethyl)-1-(4-fluorobenzyl)-2-(4-isobutoxybenzyl)-1,2,8-triaza-spiro[4.5]decan-3-one; 4-(4-Ethoxybenzyl)-5-(4-fluorobenzyl)-9-methyl-1-oxa-4,9-diaza-spiro[5.5]undecan-3-one; 5-(4-Fluorobenzyl)-9-methyl-4-(4-propoxybenzyl)-1-oxa-4,9-diaza-spiro[5.5]undecan-3-one; 5-(4-fluorobenzyl)-4-(4-isobutoxybenzyl)-9-methyl-1-oxa-4,9-diaza-spiro [5.5]undecan-3-one; 5-(4-fluorobenzyl)-9-methyl-4-(4-trifluoromethoxybenzyl)-1-oxa-4,9-diaza-spiro[5.5]undecan-3-one; 5-(4-Chlorobenzyl)-4-(4-isobutoxybenzyl)-9-methyl-1-oxa-4,9- diaza-spiro[5.5]undecan-3-one; 5-(4-Chlorobenzyl)-4-(4-cyclopropylmethoxybenzyl)-9-methyl-1-oxa-4,9-diaza-spiro [5.5]undecan-3-one; 9-Ethyl-5-(4-fluorobenzyl)-4-(4-propoxybenzyl)-1-oxa-4,9-diaza-spiro[5.5]undecan-3-one; 1-(4-Fluorobenzyl)-2-(4-ethoxybenzyl)-9-methyl-1,2,9-triaza-spiro[5.5]undecan-3-one; 1-(4-Fluorobenzyl)-2-(4-cyclopropylmethoxybenzyl)-9-methyl-1,2,9-triaza-spiro [5.5]undecan-3-one; 1-(4-Fluorobenzyl)-2-(4-isobutoxybenzyl)-9-methyl-1,2,9-triaza-spiro[5.5]undecan-3-one; 1-(4-Fluorobenzyl)-2-(4-propoxybenzyl)-9-methyl-1,2,9-triaza-spiro[5.5]undecan-3-one; 1-(4-Ethylbenzyl)-2-(4-isobutoxybenzyl)-9-methyl-1,2,9-triaza-spiro[5.5]undecan-3-one; 1-(4-Fluorobenzyl)-2-(4-cyclopropylmethoxybenzyl)-9-ethyl-1,2,9-triaza-spiro [5.5] undecan-3-one; 2-(4-Ethoxybenzyl)-1-(4-fluorobenzyl)-8-methyl-1,2,4,8-tetraaza-spiro[4.5]decan-3-one; 1-(4-Fluorobenzyl)-2-(4-isobutoxybenzyl)-8-methyl-1,2,4,8-tetraaza-spiro[4.5]decan-3-one; 2-(4-Difluoromethoxybenzyl)-1-(4-fluorobenzyl)-8-methyl-2,8-diaza-spiro[4.5]decan-3-one; 1-(4-Fluorobenzyl)-2-(4-isobutoxybenzyl)-8-methyl-2,8-diaza-spiro[4.5]decan-3-one; 2-(4-Cyclopropylmethoxybenzyl)-1-(4-fluorobenzyl)-8-methyl-2,8-diaza-spiro[4.5]decan-3-one; 8-Ethyl-1-(4-fluorobenzyl)-2-(4-isobutoxybenzyl)-2,8-diaza-spiro[4.5]decan-3-one; 8-(2-[1,3]Dioxolan-2-yl-ethyl)-1-(4-fluorobenzyl)-2-(4-isobutoxybenzyl)-2,8-diaza-spiro[4.5]decan-3-one; 3-(4-Difluoromethoxybenzyl)-4-(4-fluorobenzyl)-8-methyl-1,3,8-triaza-spiro[4.5]decan-2-one; 4-(4-Fluorobenzyl)-3-(4-isobutoxybenzyl)-8-methyl-1,3,8-triaza-spiro[4.5]decan-2-one; 3-(Cyclopropylmethoxybenzyl)-4-(4-fluorobenzyl)-8-methyl-1,3,8-triaza-spiro[4.5]decan-2-one; 8-Ethyl-4-(4-fluorobenzyl)-3-(4-isobutoxybenzyl)-1,3,8-triaza-spiro[4.5]decan-2-one; 8-(2-[1,3]Dioxolan-2-ylethyl)-4-(4-fluorobenzyl)-3-)4-isobutoxybenzyl)-1,3,8-triaza-spiro[4.5]decan-2-one; 1-(4-Fluorobenzyl)-2-(4-ethoxybenzyl)-9-methyl-2,4,9-triaza-spiro[5.5]undecan-3-one; 1-(4-Fluorobenzyl)-2-(4-cyclopropylmethoxybenzyl)-9-methyl-2,4,9-triaza-spiro [5.5]undecan-3-one; 1-(4-Fluorobenzyl)-2-(4-isobutoxybenzyl)-9-methyl-2,4,9-triaza-spiro[5.5]undecan-3-one; 1-(4-Fluorobenzyl)-2-(4-trifluoromethoxybenzyl)-9-methyl-2,4,9-triaza-spiro[5.5]undecan-3-one; 1-(4-Fluorobenzyl)-2-(4-isobutoxybenzyl)-9-ethyl-2,4,9-triaza-spiro[5.5]undecan-3-one; 4-(4-Ethoxybenzyl)-5-(4-fluorobenzyl)-9-methyl-1-oxa-3,9-diaza-spiro[5.5]undecan-2-one; 3-(4-Ethoxybenzyl)-5-(4-fluorobenzyl)-9-methyl- -1-oxa-3,9-diaza-spiro[5.5]undecan-2-one; 3-(4-Ethoxybenzyl)-4-(4-fluorobenzyl)-9-methyl-1-oxa-3,9-diaza-spiro[5.5]undecan-2-one; 5-(4-Fluorobenzyl)-4-(4-propoxybenzyl)-9-methyl-1-oxa-3,9-diaza-spiro[5.5]undecan-2-one; 5-(4-Fluorobenzyl)-3-(4-propoxybenzyl)-9-methyl-1-oxa-3,9-diaza-spiro[5.5]undecan-2-one; 4-(4-Fluorobenzyl)-3-(4-propoxybenzyl)-9-methyl-1-oxa-3,9-diaza-spiro[5.5]undecan-2-one; 5-(4-Fluorobenzyl)-4-(4-isobutoxybenzyl)-9-methyl-1-oxa-3,9-diaza-spiro[5.5]undecan-2-one; 4-(4-Fluorobenzyl)-3-(4-isobutoxybenzyl)-9-methyl-1-oxa-3,9-diaza-spiro[5.5]undecan-2-one; 4-(4-Ethoxybenzyl)-5-(4-fluorobenzyl)-9-methyl-2-oxa-4,9-diaza-spiro [5.5]undecan-3-one; 5-(4-Fluorobenzyl)-4-(4-methoxybenzyl)-9-methyl-2-oxa-4,9-diaza-spiro[5.5]undecan-3-one; 5-(4-Fluorobenzyl)-4-(4-propoxybenzyl)-9-methyl-2-oxa-4,9-diaza-spiro[5.5]undecan-3-one; 5-(4-Fluorobenzyl)-4-(4-isobutoxybenzyl)-9-methyl-2-oxa-4,9-diaza-spiro[5.5]undecan-3-one; 4-(4-Ethoxybenzyl)-5-(4-fluorobenzyl)-9-methyl-2-oxa-4,9-diaza-spiro[5.5]undecan-3-one; 3-(4-Ethoxybenzyl)-4-(4-fluorobenzyl)-8-methyl-1-thia-3,8-diaza-spiro[4.5]decan-2-one; 4-(4-Fluorobenzyl)-3-(4-methoxybenzyl)-8-methyl-1-thia-3,8-diaza-spiro[4.5]decan-2-one; 4-(4-Fluorobenzyl)-3-(4-propoxybenzyl)-8-methyl-1-thia-3,8-diaza-spiro[4.5]decan-2-one; or 4-(4-Fluorobenzyl)-3-(4-isobutoxybenzyl)-8-methyl-1-thia-3,8-diaza-spiro[4.5]decan-2-one.

Azacyclic Compounds D

A series of azacyclic compounds that modulate the 5-HT$_{2A}$ receptor have been described in U.S. Pat. No. 6,756,393. Methods for preparing the azacyclic compounds are presented in U.S. Pat. No. 6,756,393. In general, the total daily dose ranges, for the conditions described herein, is from about 1 mg to about 900 mg. Preferably, a daily dose range should be between about 10 mg to about 200 mg. The generic structure of the azacyclic compounds D, as disclosed in U.S. Pat. No. 6,756,393, is presented below. The definitions of the substituents of the generic structure can be found in U.S. Pat. No. 6,756,393 which is hereby incorporated by reference.

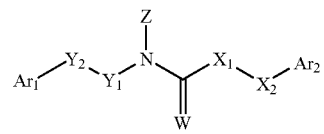

In certain instances, said azacyclic compound of formula D is N-(1-(1-methylethyl)piperidin-4-yl)-N-((4-methylphenyl)methyl)-4-methoxyphe nylacetamide, N-(1-(2,2-dimethylethyl)piperidin-4-yl)-N-((4-methylphenyl)methyl)-4-methoxyphenylacetamide, N-(1-pentylpiperidin-4-yl)-N-((4-methylphenyl)methyl)-4-methoxyphenylacetamide, N-(1-hexylpiperidin-4-yl)-N-((4-methylphenyl)methyl)-4-methoxyphenylacetamide, N-(1-cyclohexylpiperidin-4-yl)-N-((4-methylphenyl)methyl)-4-methoxyphenylacetamide, N-(1-cyclopentylpiperidin-4-yl)-N-((4-methylphenyl)methyl)-4-methoxyphenylacetamide, N-(1-cyclobutylpiperidin-4-yl)-N-((4-methylphenyl)methyl)-4-methoxyphenylacetamide, N-(1-cyclopropylpiperidin-4-yl)-N-((4-methylphenyl)methyl)-4-methoxyphenylacetamide, N-(1-(cyclopentylmethyl)piperidin-4-yl)-N-((4-methylphenyl)methyl)-4-methoxyphenylacetamide, N-(1-(cyclobutylmethyl)piperidin-4-yl)-N-((4-methylphenyl)methyl)-4-methoxy phenylacetamide, N-(1-(cyclopropylmethyl)piperidin-4-yl)-N-((4-methylphenyl)methyl)-4-methoxyphenylacetamide, N-(1-(2-hydroxyethyl)piperidin-4-yl)-N-((4-methylphenyl)methyl)-4-methoxyphenylacetamide, N-(1-(3-hydroxypropyl)piperidin-4-yl)-N-((4-methylphenyl)methyl)-4-methoxyphenylacetamide, N-((4-Methylphenyl)methyl)-N-(piperidin-4-yl)-N'-phenylmethylcarbamide, N-((4-Methylphenyl)methyl)-N-(1-(2-methylpropyl)piperidin-4-yl)-N'-phenylmethylcarbamide, N-(1-((2-Bromophenyl)methyl)piperidin-4-yl)-N-((4-methylphenyl)methyl)-N'-phenylmethylcarbamide, N-(1-((4-Hydroxy-3-methoxyphenyl)methyl)piperidin-4-yl)-N-((4-methylphenyl) methyl)-N'-phenylmethylcarbamide, N-(1-((5-Ethylthien-2-yl)methyl)piperidin-4-yl)-N-((4-methylphenyl)methyl)-N'-phenylmethylcarbamide, N-(1-(Imidazol-2-ylmethyl)piperidin-4-yl)-N-((4-methylphenyl)methyl)-N'-phenylmethylcarbamide, N-(1-(Cyclohexylmethyl)piperidin-4-yl)-N-((4-methylphenyl)methyl)-N'-phenyl methylcarbamide, N-(1-((4-Fluorophenyl)methyl)piperidin-4-yl)-N-((4-methylphenyl) methyl)-N'-phenylmethylcarbamide, N-((4-Methylphenyl)methyl)-N-(piperidin-4-yl)-4-methoxyphenylacetamide, N-((4-Methylphenyl)methyl)-N-(1-methylpiperidin-4-yl)-4- methoxyphenylacetamide, N-(1-Ethylpiperidin-4-yl)-N-((4-methylphenyl)methyl)-4-methoxyphenylacetamide, N-((4-Methylphenyl)methyl)-N-(1-propylpiperidin-4-yl)-4-methoxyphenylacetamide, N-(1-Butylpiperidin-4-yl)-N-((4-methylphenyl)methyl)-4-methoxyphenylacetamide, N-(1-(3,3-Dimethylbutyl)piperidin-4-yl)-N-((4-methylphenyl)methyl)-4-methoxyphenylacetamide, N-(1-(Cyclohexylmethyl)piperidin-4-yl)-N-((4-methylphenyl)methyl)-4-methoxy phenylacetamide, N-((4-Methylphenyl)methyl)-N-(1-(2-methylpropyl)piperidin-4-yl)-4-methoxyphenylacetamide, N-((4-Methylphenyl)methyl)-N-(1-((4-methylphenyl)methyl)piperidin-4-yl)-4-methoxyphenylacetamide, N-(1-((4-Hydroxyphenyl)methyl)piperidin-4-yl)-N-((4-methylphenyl)methyl)-4-methoxyphenylacetamide, N-(1-((2-Hydroxyphenyl)methyl)piperidin-4-yl)-N-((4-methylphenyl)methyl)-4-methoxyphenylacetamide, N-(3-Phenylpropyl)-N-(piperidin-4-yl)-4-methoxyphenylacetamide, N-(2-Phenylethyl)-N-(piperidin-4-yl)-4-methoxyphenylacetamide, N-((2-Methoxyphenyl)methyl)-N-(piperidin-4-yl)-4-methoxyphenylacetamide, N-((2-Chlorophenyl)methyl)-N-(piperidin-4-yl)-4-methoxyphenylacetamide, N-((3,4-Di-methoxyphenyl)methyl)-N-(piperidin-4-yl)-4-methoxyphenylacetamide, N-((4-Fluorophenyl)methyl)-N-(piperidin-4-yl)-4-methoxyphenylacetamide, N-((2,4-Di-chlorophenyl)methyl)-N-(piperidin-4-yl)-4-methoxyphenylacetamide, N-((3-Methylphenyl)methyl)-N-(piperidin-4-yl)-4-methoxyphenylacetamide, N-((3-Bromophenyl)methyl)-N-(piperidin-4-yl)-4-methoxyphenylacetamide, N-(1-(Phenylmethyl)piperidin-4-yl)-N-(3-phenyl-2-propen-1-yl)-4-methoxyphenylacetamide, N-((4-Methylphenyl)methyl)-N-(1-piperidin-4-yl)-phenylacetamide, N-((4-Methylphenyl)methyl)-N-(1-piperidin-4-yl)-3-phenylpropionamide, N-((4-Methylphenyl)methyl)-N-(1-piperidin-4-yl)-(phenylthio)acetamide, N-((4-Methylphenyl)methyl)-N-(1-piperidin-4-yl)-phenoxyacetamide, N-((4-Methylphenyl)methyl)-N-(1-piperidin-4-yl)-(4-chlorophenoxy) acetamide, N-((4-Methylphenyl)methyl)-N-(1-piperidin-4-yl)-3-methoxyphenylacetamide, N-((4-Methylphenyl)methyl)-N-(1-piperidin-4-yl)-4-fluorophenylacetamide, N-((4-Methylphenyl)methyl)-N-(1-piperidin-4-yl)-2,5-di-methoxyphenylacetamide, N-((4-Methylphenyl)methyl)-N-(1-piperidin-4-yl)-4-chlorophenylacetamide, N-((4-Methylphenyl)methyl)-N-(1-(phenylmethyl)pyrrolidin-3-yl)-N'-phenylmethylcarbamide, N-((4-Methylphenyl)methyl)-N-(1-(phenylmethyl)pyrrolidin-3-yl)-4-methoxyphenylacetamide, 2-(4-methoxyphenyl)-N-(4-methylbenzyl)-N-(piperidin-4-yl)acetamide, 2-(4-methoxyphenyl)-N-(4-methylbenzyl)-N-(1-methylpiperidin-4-yl)acetamide, 2-(4-methoxyphenyl)-N-(4-methylbenzyl)-N-(1-ethylpiperidin-4-yl)acetamide, 2-(4-methoxyphenyl)-N-(4-chlorbenzyl)-N-(1-ethylpiperidin-4-yl)acetamide, 2-(4-methoxyphenyl)-N-(4-chlorbenzyl)-N-(1-isopropylpiperidin-4-yl)acetamide, 2-(4-methoxyphenyl)-N-(4-chlorbenzyl)-N-(piperidin-4-yl)acetamide, 2-(4-methoxyphenyl)-N-(4-chlorbenzyl)-N-(1-cyclopentylpiperidin-4-yl)acetamide, 2-(4-methoxyphenyl)-N-(4-chlorbenzyl)-N-(1-isopropylpiperidin-4-yl)acetamide, 2-(phenyl)-N-(4-trifluoromethylbenzyl)-N-(1-methylpiperidin-4-yl)acetamide, 2-(4-fluorophenyl)-N-(4-trifluoromethylbenzyl)-N-(1-methylpiperidin-4-yl)acetamide, 2-(4-Methoxyphenyl)-N-(4-trifluoromethylbenzyl)-N-(1-methylpiperidin-4-yl)acetamide, 2-(4-Trifluoromethylphenyl)-N-(4-trifluoromethylbenzyl)-N-(1-methylpiperidin-4-yl)acetamide, 2-(4-Fluorophenyl)-N-(4-fluorobenzyl)-N-(1-methylpiperidin-4-yl)acetamide, 2-(4-Methoxyphenyl)-N-(4-fluorobenzyl)-N-(1-methylpiperidin-4-yl)acetamide, 2-(phenyl)-N-(4-fluorobenzyl)-N-(1-methylpiperidin-4-yl)acetamide, 2-(4-Trifluoromethylphenyl)-N-(4-fluorobenzyl)-N-(1-methylpiperidin-4-yl)acetamide, 2-(4-trifluoromethylphenyl)-N-[4-(methoxycarbonyl)benzyl]-N-(1-methylpiperidin-4-yl)acetamide, 2-Phenyl-N-[4-(methoxycarbonyl)benzyl]-N-(1-methylpiperidin-4-yl) acetamide, 2-(4-Chlorophenyl)-N-[4-(methoxycarbonyl)benzyl]-N-(1-methylpiperidin-4-yl)acetamide, 2-(4-Methoxyphenyl)-N-[4-(methoxycarbonyl)benzyl]-N-(1-methylpiperidin-4-yl)acetamide, 2-(4-trifluoromethylphenyl)-N-[4-(methoxycarbonyl)benzyl]-N-(1-methylpiperidin-4-yl)acetamide, 2-Phenyl-N-[4-(methoxycarbonyl)benzyl]-N-(1-methylpiperidin-4-yl) acetamide, 2-(4-Chlorophenyl)-N-[4-(methoxycarbonyl)benzyl]-N-(1-methylpiperidin-4-yl)acetamide, 2-(4-Methoxyphenyl)-N-[4-(methoxycarbonyl)benzyl]-N-(1-methylpiperidin-4-yl)acetamide, 2-(4methoxyphenyl)-N-(4-methylbenzyl)-N-[1-(4-chloromethyl-2-thiazolylmethyl)piperidin-4-yl]acetamide, 2-(4 methoxyphenyl)-N-(4-methylbenzyl)-N-{1-[3-(1,3 dihydro-2H-benzimidazol-2-on-1-yl)propyl]piperidin-4-yl}acetamide 2-(4-methoxyphenyl)-N-(2-4(fluorophenyl)ethyl)-N-(1-methylpiperidin-4-yl)acetamide, 2-(4-methoxyphenyl)-N-[2-(2,5-dimethoxyphenyl)ethyl]-N-(1-methylpiperidin-4-yl) acetamide, 2-(4-methoxyphenyl)-N-[2-(2,4-dichlorophenyl)ethyl]-N-(1-methylpiperidin-4-yl)acetamide, 2-(4-methoxyphenyl)-N-[2-(3-chlorophenyl)ethyl]-N-(1-methylpiperidin-4-yl)acetamide, 2-(4-methoxyphenyl)-N-[2-(4-methoxyphenyl)ethyl]-N-(1-methylpiperidin-4-yl) acetamide, 2-(4-methoxyphenyl)-N-[2-(3-fluorophenyl)ethyl]-N-(1-methylpiperidin-4-yl)acetamide, 2-(4-ethoxyphenyl)-N-[2-(4-fluorophenethyl]-N-(1-methylpiperidin-4-yl)acetamide, 2-(4-ethoxyphenyl)-N-(4-fluorobenzyl)-N-(1-methylpiperidin-4-yl)acetamide, 2-(4-methoxyphenyl)-N-(4-methylbenzyl)-N-{1-[2-(2-hydroxyethoxy)ethyl]piperidin-4-yl}acetamide, 2-(4-methoxyphenyl)-N-(4-methylbenzyl)-N-[ 1-((2-chloro-5-thienyl)methyl)piperidin-4-yl]acetamide, 2-(4-methoxyphenyl)-N-(4-methylbenzyl)-N-[1-2-(imidazolidinon-1-yl)ethyl]piperidin-4-yl]acetamide, 2-(4-methoxyphenyl)-N-(4-methylbenzyl)-N-{1-[2-(2,4(1H,3H) quinazolinedion-3-yl)ethyl]piperidin-4-yl}acetamide, 2-(4-methoxyphenyl)-N-(4-methylbenzyl)-N-{1-[2-(1,3-dioxolan-2-yl)ethyl]piperidin-4-yl}acetamide, 2-(4-methoxyphenyl)-N-(4-methylbenzyl)-N-{1-[2-(3-indolyl) ethyl]piperidin-4-ylacetamide, 2-(4-methoxyphenyl)-N-(4-methylbenzyl)-N-{1-[3-(1,2,4-triazol-1-yl)propyl] piperidin-4-yl}acetamide, 2-(4-methoxyphenyl)-N-(4-methylbenzyl)-N-[1-(5-benzofurazanylmethyl)piperidin-4-yl]acetamide, 2-(4-methoxyphenyl)-N-(4-methylbenzyl)-N-[1-(5-chlorobenzo[b]thien-3-ylmethyl)piperidin-4-yl] acetamide, 2-(4-methoxyphenyl)-N-(4-methylbenzyl)-N-[1-(5-phenyl-1,2,4-oxadiazol-3-ylmethyl)piperidin-4-yl] acetamide, 2-(4-Chlorophenyl)-N-(4-methylbenzyl)-N-(1-isopropylpiperidin-4-yl)-acetamide, 2-(4-Chlorophenyl)-N-(4-methylbenzyl)-N-(1-ethylpiperidin-4-yl)-acetamide, 2-Phenyl-N-(4-methylbenzyl)-N-(1-methylpiperidin-4-yl)-acetamide, 2-(4-Chlorophenyl)-N-(4-methylbenzyl)-N-(1-methylpiperidin-4-yl)-acetamide, 2-(4-Chlorophenyl)-N-(4-methylbenzyl)-N-(1-cyclopentylpiperidin-4-yl)-acetamide, 2-(4-Fluorophenyl)-N-(4-methylbenzyl)-N-(1-methylpiperidin-4-yl)-acetamide; 2-(4-Chlorophenyl)-N-(4-methylbenzyl)-N-(1-(2-hydroxyethyl)-piperidin-4-yl )-acetamide, 2-(4-Chlorophenyl)-N-(4-methylbenzyl)-N-(1-cyclobutylpiperidin-4-yl)-acetamide, 2-(4-Methoxyphenyl)-N-(4-methylbenzyl)-N-(1-cyclobutylpiperidin-4-yl)-acetamide, 2-(4-Methoxyphenyl)-N-(4-methylbenzyl)-N-(tropin-4-yl)-acetamide, N-(4-Methylbenzyl)-N-(1-methylpiperidin-4-yl)-N'-benzyl-carbamide, N-(4-Methylbenzyl)-N-(1-methylpiperidin-4-yl)-N'-phenyl-carbamide, N-Phenethyl-N-(1-methylpiperidin-4-yl)-N'-benzyl-carbamide, 2-Phenyl-N-(4-methoxybenzyl)-N-(1-methylpiperidin-4-yl)-acetamide, 2-(4-Trifluoromethylphenyl)-N-(4-methoxybenzyl)-N-(1-methylpiperidin-4-yl)-acetamide, 2-(4-Fluorophenyl)-N-(4-methoxybenzyl)-N-(1-methylpiperidin-4-yl)-acetamide 2-(4-Methoxyphenyl)-N-(4-methoxybenzyl)-N-(1-methylpiperidin-4-yl)-acetamide, 2-(4-Methylphenyl)-N-(4-chlorobenzyl)-N-(1-methylpiperidin-4-yl)-acetamide, 2-(4-Hydroxyphenyl)-N-(4-methylbenzyl)-N-(1-methylpiperidin-4-yl)-acetamide, N-Phenethyl-N-(1-methylpiperidin-4-yl)-N'-phenyl-carbamide, N-(3-Phenylpropyl)-N-(1-methylpiperidin-4-yl)-N'-benzyl-carbamide, N-(3-Phenylpropyl)-N-(1-methylpiperidin-4-yl)-N'-phenyl-carbamide, 2-(4-Methoxyphenyl)-2,2-ethylene-N-(4-methylbenzyl)-N-(1-methylpiperidin-4-yl)acetamide, 2-(4-Methoxyphenyl)-N-alpha-methylbenzyl-N-(1-methylpiperidin-4-yl)acetamide, 2-(4-Methoxyphenyl)-N-(4-methylbenzyl)-N-(3-tropen-4-yl)acetamide, 2-Phenyl-2-ethyl-N-(4-methylbenzyl)-N-(1-methylpiperidin-4-yl)acetamide, N-Phenethyl-N-(4-methylbenzyl)-N-(1-methylpiperidin-4-yl)-amine, 2-(4-Methoxyphenyl)-N-(1-indanyl)-N-(1-methylpiperidin-4-yl)acetamide, N-(4-Methylbenzyl)-N-(1-methylpiperidin-4-yl)-N'-(4-methoxybenzyl)-carbamide, 2-(3,4-dimethoxyphenyl)-N-(4-methylbenzyl)-N-(1-methylpiperidin-4-yl)acetamide, 2-(3,4-Methylenedioxyphenyl)-N-(4-methylbenzyl)-N-(1-methylpiperidin-4-yl)acetamide, 2-(4-Methoxyphenyl)-N-(4-methylbenzyl)-N-(1-t-butylpiperidin-4-yl)-acetamide, N-(4-Methylbenzyl)-N-(1-methylpiperidin-4-yl)-N'-phenethyl-carbamide, N-Phenethyl-N-(1-methylpiperidin-4-yl)-N'-phenethyl-carbamide, N-(4-Methylbenzyl)-N-(1-t-butylpiperidin-4-yl)-N'-(4-methoxybenzyl)-carbamide, 2-(4-Ethoxyphenyl)-N-(4-methylbenzyl)-N-(1-methylpiperidin-4-yl)acetamide, 2-(4-Butoxyphenyl)-N-(4-methylbenzyl)-N-(1-methylpiperidin-4-yl)acetamide, 2-(4-i-Propoxyphenyl)-N-(4-methylbenzyl)-N-(1-methylpiperidin-4-yl)acetamide, 2-(4-t-Butoxyphenyl)-N-(4-methylbenzyl)-N-(1-methylpiperidin-4-yl)acetamide, 2-(4-Butoxyphenyl)-N-(4-fluorobenzyl)-N-(1-methylpiperidin-4-yl)acetamide, 2-(4-Propoxyphenyl)-N-(4-flourobenzyl)-N-(1-methylpiperidin-4-yl)acetamide, 2-(4-i-Propoxyphenyl)-N-(4-fluorobenzyl)-N-(1-methylpiperidin-4-yl)acetamide, or 2-(4-t-Butoxyphenyl)-N-(4-fluorobenzyl)-N-(1-methylpiperidin-4-yl)acetamide.

Norepinephrine Reuptake Inhibitors (NRI)

Many compounds, including those discussed at length below, are norepinephrine reuptake inhibitors, and no doubt many more will be identified in the future. In the practice of the present invention, it is intended to include reuptake inhibitors which can be identified using the protocol described by Wong et al., Drug Development Research, 6, 397 (1985). In certain embodiments, the norepinephrine reuptake inhibitors used in the present invention are characterized in being selective for the inhibition of neurotransmitter reuptake relative to their ability to act as direct agonists or antagonists at other receptor.

The ability of compounds to inhibit the reuptake of norepinephrine may be measured by the general procedure of Wong, et al., Drug Development Research, 6, 397 (1985). Male Sprague-Dawley rats weighing 150-250 gm are decapitated and brains are immediately removed. Cerebral cortices are homogenized in 9 volumes of a medium containing 0.32 M sucrose and 10 mM glucose. Crude synaptosomal preparations are isolated after differential centrifugation at 1000 xg for 10 minutes and 17,000 xg for 28 minutes. The final pellets are suspended in the same medium and kept in ice until use within the same day.

Synaptosomal uptake of $^3$H-norepinephrine is determined as follows. Cortical synaptosomes (equivalent to 1 mg of protein) are incubated at 37° C. for 5 minutes in 1 mL Krebs-bicarbonate medium containing also 10 mM glucose, 0.1 mM iproniazide, 1 mM ascorbic acid, 0.17 mM EDTA and 50 mM $^3$H-norepinephrine. The reaction mixture is immediately diluted with 2 mL of ice-chilled Krebs-bicarbonate buffer and filtered under vacuum with a cell harvester (Brandel, Gaithersburg, Md.). Filters are rinsed twice with approximately 5 mL of ice-chilled 0.9% saline and the uptake of $^3$H-norepinephrine assessed by liquid scintillation counting. Accumulation of $^3$H-norepinephrine at 4° C. is considered to be background and is subtracted from all measurements. The concentration of the test compound required to inhibit 50% of the $^3$H-norepinephrine accumulation (IC$_{50}$ values) are determined by linear regression analysis.

In general, a suitable dose of a norepinephrine reuptake inhibitor or a pharmaceutically acceptable salt thereof for administration to a human will be in the range of 0.01 to 50 mg per kilogram body weight of the recipient per day, preferably in the range of 0.1 to 3 mg per kilogram body weight per day. Unless otherwise stated all weights of active ingredients are calculated in terms of drug per se. The desired dose is preferably presented as two, three, four, five or more sub-doses administered at appropriate intervals throughout the day. These sub-doses may be administered in unit dosage forms, for example, containing 5 to 50 mg.

Desipramine

Desipramine has the chemical name 10,11-Dihydro-N-methyl-5H-dibenz[b,f]azepine-5-propanamine and is described in U.S. Pat. No. 3,454,554. The pharmacology is described by P. D. Hrdina et al. in Prog Neuropsychopharmacol. 1980, 4, 591. Desipramine is generally administered as a hydrochloride salt marketed under the name Norpramin. Desipramine hydrochloride occurs as crystals which are soluble in water. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. The structure of desipramine is presented below.

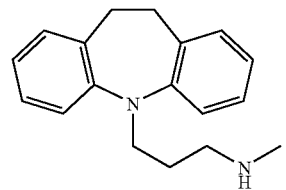

Maprotiline

Maprotiline has the chemical name N-Methyl-9,10-ethanoanthracene-9(10H)-propanamine and is described in U.S. Pat. No. 3,399,201. The pharmacology is described by R. M. Pinder et al. in Drugs 1977, 13, 321. Maprotiline is generally administered as a hydrochloride salt marketed under the name Ludiomil. Maprotiline hydrochloride occurs as crystals which are slightly soluble in water. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg. The structure of maprotiline is presented below.

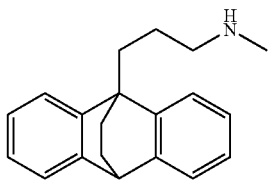

Lofepramine

Lofepramine has been found clinically effective against disorders related to the central nervous system, especially mental depressions (B. Siwers et al., *Europ. J. Clin. Pharmacol.* 1970, 3, 12-17). The synthesis and biological activity of lofepramine was described in British Pat. No. 1,177,525. A preferred method for preparing lofepramine has been reported by E. Eriksoo and O. Rohte in *Arzneimittelforschung* 1970, 20, 1561-1569. However, this known method presents difficulties of a pronounced nature, especially when used in full-scale production. Thus, slight unintentional variations in the process conditions often result in discoloured products, which are very difficult to purify. An improved procedure for the preparation of lofepramine is described in U.S. Pat. No. 4,172,074. Additional reports on the biological activity of lofepramine can be found in G. Plym Forshell et al. *Eur. J. Clin. Pharmacol.* 1976, 9, 291 and S. Wright et al. *Arzneimittel-Forsch* 1976, 26, 1167. Lofepramine has the chemical name 4'-chloro-2-{[3-(10,11-dihydro-5H-dibenz(b,f)-azepinyl-(5)-propyl]-methylamino}-acetophenone and the structure is presented below.

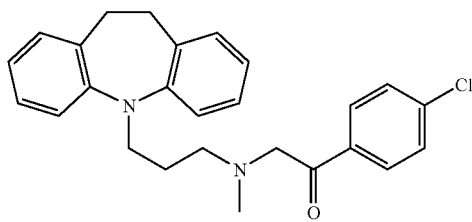

The size of a prophylactic or therapeutic dose of lofepramine in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 300 mg. Preferably, a daily dose range should be between about 10 mg to about 200 mg. Most preferably, a daily dose range should be between about 30 mg to about 120 mg. In certain embodiments, a daily dosage of 50, 75, or 100 mg may be preferred depending upon patient response. In managing the patient, the therapy may be initiated at a lower dose, perhaps about 5 mg to about 10 mg and increased up to about 20 mg or higher depending-on the patient's global response. It may be necessary to use dosages outside these ranges in some cases.

Reboxetine

Reboxetine is active on the central nervous system and has been used to treat depression, oppositional defiant disorder, attention-deficit/hyperactivity disorder, and conduct disorder. See WO 99/15163, WO 95/15176, and WO 99/15177. Reboxetine does not act like most antidepressants. Reboxetine is ineffective in the 8-OH-DPAT hypothermia test, indicating that reboxetine is not a SSRI. Brian E. Leonard, "Noradrenaline in basic models of depression." *European-Neuropsychopharmacol.*, 7 Suppl. 1 pp. S 11-6 and S71-3 (April 1997). Reboxetine is a norepinephrine reuptake inhibitor, with only marginal serotonin and no dopamine reuptake inhibitory activity. Reboxetine displays no anticholinergic binding activity in different animal models, and is substantially devoid of monoamine oxidase (MAO) inhibitory activity. Racemic reboxetine exhibits a pharmacological selectivity of serotonin ($K_i$)/norepinephrine ($K_i$) of about 80.

Reboxetine is a safe drug, and its use in ADHD, in both adults and children, is a superior treatment for that disorder because of its improved safety. The compound is particularly selective, having few if any physiological effects besides those on norepinephrine processing, and therefore is free of side effects and unwanted activities. Further, it is effective at relatively low doses, as discussed below, and may safely and effectively be administered once per day. Thus, difficulties created by the multiple dosing of patients, who are children and disorganized adults, are completely avoided.

The racemate form of reboxetine is well tolerated and has a wide safety range. The effective dose of reboxetine for ADHD is in the range from about 1 mg/day to about 100 mg/day. The preferred adult dose is in the range from about 5 to about 80 mg/day, and a more highly preferred adult dose is from about 10 to about 60 mg/day. The children's dose of course is smaller, in the range from about 1 to about 70 mg/day, more preferably from about 5 to about 60 mg/day and still more preferably from about 4 to about 10 mg/day. The optimum dose for each patient, as always, must be set by the physician in charge of the case, taking into account the patient's size, other medications which the patient requires, severity of the disorder and all of the other circumstances of the patient.

Reboxetine was first taught by U.S. Pat. No. 4,229,449 and has the chemical name 2-[α-(2-ethoxy) phenoxy-benzyl] morpholine. Reboxetine is also described in U.S. Pat. Nos. 5,068,433; 5,391,735; 6,642,235; and in GB 2,167,407. Individual stereoisomers of reboxetine can be obtained by resolution of the racemic mixture of enantiomers using conventional methods generally known by those skilled in the art. Such methods include, but are not limited to, resolution by simple crystallization and chromatographic techniques, for example, as set forth in GB 2,167,407. The structure of reboxetine is presented below.

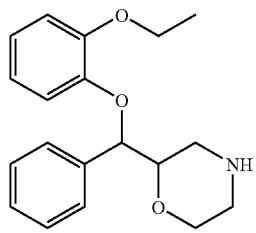

Generally, reboxetine is administered as the racemate. However, in certain instances, it may be advantageous to administer reboxetine in the form of a single enantiomer.

Specifically, it has been found that compositions containing an optically pure (S,S) reboxetine are about 5 to about 8.5 times more effective at inhibiting the reuptake of norepinephrine than compositions containing the racemic mixture of the (R,R) and (S,S) stereoisomers. Accordingly, the typical daily dosage of the racemic mixture (i.e., commercially available reboxetine) can be reduced by about 50% to about 80% when using an optically pure (S,S) reboxetine. The reduction in dosage does not lead to a reduction in efficacy, but the reduction or elimination of various adverse side effects was observed.

In particular, because an optically pure (S,S) reboxetine selectively inhibits norepinephrine reuptake compared to serotonin reuptake, adverse side effects associated with serotonin reuptake are reduced or eliminated. Such adverse side effects include, but are not limited to, gastrointestinal disturbances, anxiety, sexual dysfunction, and undesirable side effects associated with drug-drug interactions.

Oxaprotiline

Oxaprotiline has the chemical name (±)-α-[(Methylamino)-methyl]-9,10-ethanoanthracene-9(10H)-ethanol. (CAS registry number: 56433-44-4). Oxaprotiline is a promosing therapeutic agent for the treatment of depression. In an experiment where 24 patients (37 trials) with major depression where treated with oxaprotiline over 3 weeks, the patients had a significant reduction in their Hamilton Scores. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Fezolamine

Fezolamine has the chemical name N,N-dimethyl-3,4-diphenyl-1H-pyrazole-1-propanamine-(E)-2-butenedioate (CAS registry number: 80410-36-2) and shows antidepressant activity. The therapeutic affect of fezolamine is attributed to its ability to inhibit norepinephrine reuptake. In fact, fezolamine was 3 to 4 fold more selective in blocking synaptosomal uptake of norepinephrine compared to serotonin or dopamine in in vitro assays. See E. R. Baizman et al. *J. Pharmacol. Exp. Ther.* 1987 243, 40-54. Fezolamine also prevented the depressant effects of reserpine and tetrabenzine in behavioral tests conducted on monamine depleted animals. The dose, and perhaps the dose frequency, will also vary according to the age, body weight, and response of the individual patient. In general, the total daily dose ranges, for the conditions described herein, is from about 1 mg to about 900 mg. Preferably, a daily dose range should be between about 10 mg to about 200 mg.

Tomoxetine

Tomoxetine is a notably safe drug for use in adults and children for treatment of attention deficit hyperactivity disorder. It is a superior treatment for that disorder because of its improved safety. Tomoxetine is effective at relatively low doses and may safely and effectively be administered once per day. In addition, the results from animal studies indicate that tomoxetine selectively inhibits norepinephrine uptake indicating that tomoxetine would be useful in treating depression. Tomoxetine has been administered in single oral doses up to 90 mg to humans. In addition, no serious drug-related adverse effects were observed when tomoxetine was administered to humans at a dosage of 20 or 40 mg b.i.d. for 7 days.

Tomoxetine has the chemical name (R)-(−)-N-methyl-3-(2-methylphenoxy)-3-phenylpropylamine. The mechanism of tomoxetine's activity is attributed to its ability to inhibit norepinephrine reuptake. See Gehlert, et al. *Neuroscience Letters* 1993, 157, 203-06. Tomoxetine is quite active in that function, and moreover is substantially free of other central nervous system activities at the concentrations or doses at which it effectively inhibits norepinephrine reuptake. Thus, it is quite free of side effects and is properly considered to be a selective drug. Tomoxetine is usually administered as the hydrochloride salt.

The effective dose of tomoxetine for ADHD is in the range from about 5 mg/day to about 1 00 mg/day. The preferred adult dose is in the range from about 10 to about 80 mg/day, and a more highly preferred adult dose is from about 20 to about 60 mg/day. The children's dose of course is smaller, in the range from about 5 to about 70 mg/day, more preferably from about 10 to about 60 mg/day and still more preferably from about 10 to about 50 mg/day. The optimum dose for each patient, as always, must be set by the physician in charge of the case, taking into account the patient's size, other medications which the patient requires, severity of the disorder and all of the other circumstances of the patient.

Since tomoxetine is readily orally absorbed and requires only once/day administration, there is little or no reason to administer it in any other way than orally. It may be produced in the form of a clean, stable crystal, and thus is easily formulated in the usual oral pharmaceutical forms, such as tablets, capsules, suspensions, and the like. The usual methods of pharmaceutical scientists are applicable. It may usefully be administered, if there is any reason to do so in a particular circumstance, in other pharmaceutical forms, such as injectable solutions, depot injections, suppositories and the like, which are well known to and understood by pharmaceutical scientists. It will substantially always be preferred, however, to administer tomoxetine as a tablet or capsule and such pharmaceutical forms are recommended.

(S,S)-hydroxybupropion (S,S)-hydroxybupropion is a metabolite of bupropion that selectively inhibits norepinephrine reuptake and does not significantly inhibit dopamine reuptake. Methods for the preparation of (S,S)-hydroxybupropion are described in U.S. Pat. No. 6,342,496. (S,S)-hydroxybupropion has the chemical name (S,S)-2-(3-chlorophenyl)-2-hydroxy-3,5,5-trimethylmoipholinol and the structure is given below.

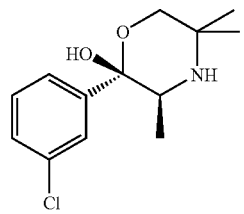

The present invention contemplates the use of norepinephrine reuptake inhibitors in general, including nortriptyline, maprotiline, protriptyline, trimipramine, venlafaxine, amitriptyline, amoxapine, doxepin, nefazodone, and lamotrigine.

Dopamine Reuptake Inhibitors

A large number of dopamine reuptake inhibitors are known in the art and are amenable to the present invention. Dopamine reuptake inhibitors can be identified using the rat corpus striatum assay described in US Patent Application 20040180857, which is hereby incorporated by reference. In general, a dose of a dopamine reuptake inhibitor or a pharmaceutically acceptable salt thereof suitable for administration to a human will be in the range of 0.01 to 50 mg per kilogram body weight of the recipient per day, preferably in the range of 0.1 to 3 mg per kilogram body weight per day.

Unless otherwise stated all weights of active ingredients are calculated in terms of drug per se. In certain embodiments, the desired dose is presented as two, three, four, five or more sub-doses administered at appropriate intervals throughout the day. These sub-doses may be administered in unit dosage forms, for example, containing about 5 to 50 mg.

Amineptine

Amineptine is a synthetic, atypical tricyclic antidepressant with central nervous system stimulating effects. It has the chemical name of 7-[(10,11-dihydro-5H-dibenzo[a,d]-cycloheptene-5-yl)amino]heptanoic acid and is available as either the free base (CAS registry number 575746-09-1; shown below) or the hydrochloride salt (CAS registry number 302724-08-3). It is also known as S-1694, Maneon and Survector. Preparation of amineptine is described in U.S. Pat. Nos. 3,758,528 and No. 3,821,249.

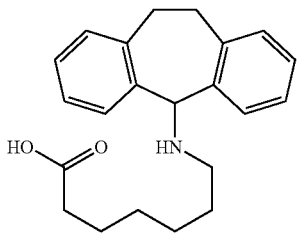

Amineptine is an indirect dopamine agonist, selectively inhibiting dopamine uptake and inducing dopamine release, with additional stimulation of the adrenergic system. Its antidepressant effects are similar to other tricyclic antidepressant drugs but it has a more rapid action, is better tolerated and has little cardiovascular, analgesic or anorectic effects. It produces a similar spectrum of pharmacological effects to psychomotor stimulants in Schedule II of the 1971 Convention on Psychotropic Substances. Recently, the use of amineptine in the treatment of depression has been described by S. M. Channabasavanna et al. in *Indian Journal of Psychiatry* 1997, 39, 147-53.

Bupropion

Bupropion is marketed under the tradename WELLBUTRIN® by GlaxoSmithKline for the treatment of depression. In certain instances, bupropion is administered as its hydrochloride salt. WELLBUTRIN® (bupropion hydrochloride), is an antidepressant of the aminoketone class, is chemically unrelated to tricyclic, tetracyclic, selective serotonin re-uptake inhibitor, or other known antidepressant agents. Its structure closely resembles that of diethylpropion; it is related to phenylethylamines. It has the chemical names 1-(3-chlorophenyl)-2-[1,1-dimethylethyl)amino]-1-propanone; (±)-2-(tert-butylamino)-3'-chloropropiophenone; m-chloro-α-(tert-butylamino)propiophenone; and amfebutamon(e). Its preparation is described in U.S. Pat. Nos. 3,819,706 and 3,885,046.

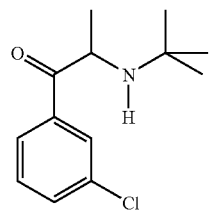

Bupropion is a novel, non-tricyclic antidepressant with a primary pharmacological action of monoamine uptake inhibition. The drug resembles a psychostimulant in terms of its neurochemical and behavioural profiles in vivo, but it does not reliably produce stimulant-like effects in humans at clinically prescribed doses. Bupropion binds with modest selectivity to the dopamine transporter, but its behavioural effects have often been attributed to its inhibition of norepinephrine uptake.

The neurochemical mechanism of the antidepressant effect of bupropion is not known. Bupropion is a relatively weak inhibitor of the neuronal uptake of norepinephrine, serotonin, and dopamine, and does not inhibit monoamine oxidase. Bupropion produces dose-related central nervous system (CNS) stimulant effects in animals, as evidenced by increased locomotor activity, increased rates of responding in various schedule-controlled operant behavior tasks, and, at high doses, induction of mild stereotyped behavior.

In humans, following oral administration, peak plasma bupropion concentrations are usually achieved 5 within 2 hours, followed by a biphasic decline. The terminal phase has a mean half-life of 14 hours, with a range of 8 to 24 hours. The distribution phase has a mean half-life of 3 to 4 hours. The mean elimination half-life (±SD) of bupropion after chronic dosing is 21 (±9) hours, and steady-state plasma concentrations of bupropion are reached within 8 days. Plasma bupropion concentrations are dose-proportional following single doses of 100 to 250 mg. Bupropion inhibits the dopamine and norepinephrine transporters with $K_i$s of 2.8 µM and 1.4 µM, respectively. It does not inhibit the serotonin transporter ($_i$=45 µM).

A recent experiment examined monoaminergic involvement in the discriminative stimulus effects of bupropion (Katz, T. P. *Psychopharmacology (Berl)* 1997, 134(2), 201-12). Rats were trained to press one lever when injected i.p. with bupropion (17.0 mg/kg), and another lever when injected with saline. The results demonstrate strong similarities with those obtained using other dopamine uptake inhibitors as training drugs, and support the view that the behavioural effects of bupropion are primarily mediated by dopaminergic mechanisms.

GBR-12935

GBR-12935 is a dopamine reuptake inhibitor described by A. R. Burkeyl and coworkers in *J. of Neuroscience* 1999, 19, 4169-4179. Its chemical name is 1-[2-(diphenylmethoxy)ethyl]-4-(3-phenylpropyl)piperazine dihydrochloride.

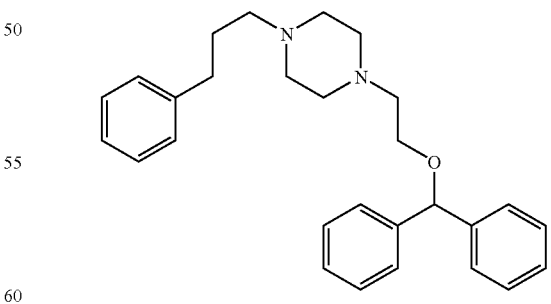

GBR-12935 inhibits the dopamine and norepinephrine transporters with $K_i$s of 21.5 nM and 225 nM, respectively. It does not inhibit the serotonin transporter ($K_i$=6.5 µM). It acts by binding to a nondopaminergic piperazine site in blood platelets and brain that has been identified as cytochrome P450.

Venlafaxine (EFFEXOR®)

Venlafaxine is dopamine reuptake inhibitor. Its hydrochloride salt is marketed under the tradename EFFEXOR® and used in the treatment of bipolar disorder. It has the chemical names (±)-1-[2-(dimethylamino)-1-(4-methyoxyphenyl) ethyl]cyclohexanol; N,N-dimethyl-2-(1-hydroxycyclohexyl)-2-(4-methoxyphenyl)ethylaminel and venlafexine. Its prepration is described in U.S. Pat. No. 4,535,186. A review of its pharmacology and clinical efficacy can be found in the Journal of Clinical Psychiatry (Montgomery, S. A. *J. Clin. Psychiatry* 1993, 54, 119-126.)

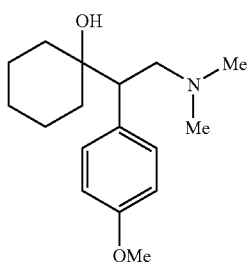

Venlafaxine is a representative of a new class of antidepressants (SNRIs) which inhibit selectively the uptake of serotonin and noradrenaline, but—in contrast to tricyclics--show no affinity for neurotransmitter receptors. 2β-Propanoyl-3β-(4-tolyl)-tropane (PTT)

2β-propanoyl-3β-(4-tolyl)-tropane or 3β-(4-(1-methylphenyl)-8-azabicyclo[3.2.1] octane are also known as PTT. PTT binds with high affinity to the dopamine transporter ($IC_{50}$ '8.2±1.6) and with lower afinity for the serotonin ($K_i$=130±10) and norepinephrine transporters ($K_i$=160±1.6).

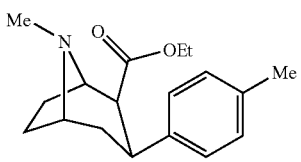

The preparation of PTT can be found in U.S. Pat. No. 5,763, 455. The dopamine reuptake inhibitory properties of 2β-propanoyl-3β-(4-tolyl)-tropane have been described by J. A. Lile and coworkers in *J. Pharmacol. Exp. Ther.* 2002, 303, 640-8.

Sedative Agent: GABA Receptor Modulating Agents

γ-Aminobutyric acid (GABA) is the major inhibitory neurotransmitter in the mammalian central nervous system. Receptors for GABA have traditionally been divided into $GABA_A$ and $GABA_B$ receptor subtypes. The $GABA_A$ receptor is the more prominent GABA receptor subtype, and is a ligand-gated chloride ion channel that is opened after release of GABA from presynaptic neurons. The $GABA_B$ receptor is a member of the G protein-coupled receptor family coupled both to biochemical pathways and to regulation of ion channels. See Goodman and Gilman's The Pharmacological Basis of Therapeutics, McGraw-Hill, New York, N.Y., 9th Edition, (1996) and Kerr, D. I. B. and Ong, *J. Pharmac. Ther.* 1995, 67, 187-246.

By gating negative chloride ions into the interior of cells, GABA inhibits the presynaptic release of neurotransmitter due to a positive voltage polarization pulse. This form of inhibition is extremely common. For example, GABA receptors can be found in 60-80% of central nervous system neurons. Subtypes of GABA receptors can be activated by the mushroom toxin muscimol (at $GABA_A$) as well as the antispasmodic amino acid baclofen ($GABA_B$). These compounds directly mimic the action of GABA at the receptor. Allosteric facilitation of GABA receptors occurs at several distinct sites; compounds that bind there are used as sedatives and anxiolytics.

A characteristic property of $GABA_A$ receptors is the presence of a number of modulatory sites, one of which is the benzodiazepine (BZ) binding site. The BZ binding site is the most explored of the $GABA_A$-receptor modulatory sites, and is the site through which anxiolytic drugs such as temazepam exert their effect. Before the cloning of the $GABA_A$-receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$-receptor comprising the α1-subunit in combination with a β-subunit and γ2. This is the most abundant $GABA_A$-receptor subtype, and is believed to represent almost half of all $GABA_A$ receptors in the brain.

In general, a dose of the GABA-receptor modulating agent or a pharmaceutically acceptable salt thereof suitable for administration to a human will be in the range of 0.01 to 50 mg per kilogram body weight of the recipient per day, preferably in the range of 0.1 to 3 mg per kilogram body weight per day. Unless otherwise stated all weights of active ingredients are calculated in terms of drug per se. In certain embodiments, the desired dose is presented as two, three, four, five or more sub-doses administered at appropriate intervals throughout the day. These sub-doses may be administered in unit dosage forms, for example, containing about 5 to 50 mg.

GABA Binding Assay

The affinity of a compound to bind to a GABA receptor can be measured using procedures known in the art. In addition, assay kits for determining GABA-receptor binding affinity can be purchased from MDS Pharma Services. For representative examples of procedures to determine GABA-receptor binding affinity see Enna, S. J.; Snyder, S. H. *Mol. Pharmacol.* 1976, 13, 442; C. Martini et al. *J. Neurochem.* 1983, 41, 1183; Lewin, A. H. et al. *Mol. Pharmacol.* 1989, 35, 189; Schwartz, R. D.; Mindlin, M. C. *J. Pharmacol. Exp. Ther.* 1988, 244, 963; Facklam, M.; Bowery, N. G. Br. *J. Pharmacol.* 1993, 110, 1291; P. Mathivet et al. *Eur. J. Pharmacol.* 1992, 321, 67; A. Green et al. *Br. J. Pharmacol.* 2000, 131(8), 1766; K. Kaupmann et al. *Nature* 1997, 386, 239; H. W. Damm et al. *Res. Comm. Chem. Pathol. Pharmacol.* 1978, 22, 597; and R. C. Speth et al. *Life Sci.* 1979, 24, 351. Furthermore, a representative procedure for determining the binding affinity of a compound to a GABA receptor is described below. For additional details pertaining to the following procedure see U.S. Pat. No. 6,743,789.

The affinity of a compound at $GABA_A$-receptor subtypes can be measured by competition for [$^3$H]flumazenil (85 Ci/mmol; Amersham) binding to SF9 cells expressing rat receptors of composition α1β3γ2, α2β3γ2, α3β3γ2 and α5β3γ2.

Cellpellets are suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 15 sec on ice and centrifuged in UZ for 30 min at 4° C. (100000 g; rotor: TFT 4594=300000 rpm). The cellpellets were resuspended in Krebs-tris buffer and homogenized by polytron for ca. 15 sec on ice. Aliquots of 1 mL are prepared, protein is measured (Bradford method) and the resulting membrane aliquots were stored at −70° C.

Radioligand binding assays are carried out in a volume of 200 μL (96-well plates) which contained 100 μL of cells, [$^3$H]flumazenil at a concentration of 1 nM for α1α2α3 subunits and 0.5 nM for α5 subunits and the test compound in the range of $10^{-10}$ to $3\times10^{-6}$ M. In certain instances, nonspecific binding is defined by $10^{-5}$ M diazepam. Assays are incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. $K_i$ values are calculated using Excel-Fit (Microsoft) and are the means of two determinations.

GABA Receptor Modulating Compounds or Agents

A large number of compounds are known to bind to the GABA receptor and modulate the activity of the receptor. Modulation of the GABA receptor can be agonistic or antagonistic. The compound can bind to any part of the GABA receptor sufficient to modulate the activity of the receptor. In certain instances, the GABA-receptor modulating compound binds to a $GABA_A$ receptor. In certain instances, the GABA-receptor modulating compound binds to a $GABA_B$ receptor. In certain embodiments, the GABA-receptor modulating compound has a $K_i$ of less than about 750 nM in a GABA-receptor binding assay. In certain embodiments, the GABA-receptor modulating compound has a $K_i$ of less than about 500 nM in a GABA-receptor binding assay. In certain embodiments, the GABA-receptor modulating compound has a $K_i$ of less than about 250 nM in a GABA-receptor binding assay. In certain embodiments, the GABA-receptor modulating compound has a $K_i$ of less than about 100 nM in a GABA-receptor binding assay. In certain embodiments, the GABA-receptor modulating compound has a $K_i$ of less than about 75 nM in a GABA-receptor binding assay. In certain embodiments, the GABA-receptor modulating compound has a $K_i$ of less than about 50 nM in a GABA-receptor binding assay. In certain embodiments, the GABA-receptor modulating compound has a $K_i$ of less than about 25 nM in a GABA-receptor binding assay. In certain embodiments, the GABA-receptor modulating compound has a $K_i$ of less than about 15 nM in a GABA-receptor binding assay. In certain embodiments, said GABA-receptor binding assay is a $GABA_A$-receptor binding assay. In certain embodiments, said GABA-receptor binding assay is a $GABA_A$-agonist receptor binding assay. In certain embodiments, said GABA-receptor binding assay is a $GABA_A$-antagonist receptor binding assay. In certain embodiments, said GABA-receptor binding assay is a $GABA_A$-benzodiazepine receptor binding assay. In certain embodiments, said GABA-receptor binding assay is a $GABA_B$-receptor binding assay. In certain embodiments, said GABA-receptor binding assay is a $GABA_B$-agonist receptor binding assay.

Importantly, compounds known in the art that modulate the activity of the GABA receptor are amenable to the present invention. Accordingly, GABA analogs with pharmaceutical activity have been synthesized and described in U.S. Pat. Nos. 4,024,175; 5,563,175; 6,020,370; 6,028,214; 6,103,932; and 6,117,906; and International Patent Applications WO 92/09560, WO 93/23383, WO 97/29101, WO 97/33858, WO 97/33859, WO 98/17627, WO 99/08671, WO 99/21824, WO 99/31057, WO 99/31074, WO 99/31075, WO 99/61424, WO 00/15611, WO 00/31020, and WO 00/50027, each of which is hereby incorporated by reference. In addition, GABAB receptor agonists are disclosed in EP 0356128; EP 0181833, EP 0399949, EP 0463969, and FR 2,722,192, each of which is hereby incorporated by reference.

Racemic Zopiclone

Zopiclone is the first of a chemically distinct class of hypnotic and anxiolytic compounds that offers a psychotherapeutic profile of efficacy and side effects similar to the benzodiazepines. This class of compounds, the cyclopyrrolones, appears to cause less residual sedation and slowing of reaction times than the benzodiazepines, and it offers the promise of an improved therapeutic index over benzodiazepines.

The pharmacology of zopiclone has been shown both preclinically and clinically to be characterized by five distinct elements. It is predominantly a hypnotic-sedative, offering significant activity on first treatment in the absence of respiratory or cardiac depression. Additionally, zopiclone is an anticonvulsant, and it further exhibits muscle relaxant, anti-aggressive, and anxiolytic activities.

The compound binds to the benzodiazepine receptor complex, or to a site linked closely to this receptor complex. (See Goa, K. L. and Heel, R. C. Drugs, 32:48-65, (1986); Brun, J. P., Pharmacology, Biochemistry and Behavior, 29:831-832, (1988); Julou, L. et al., Pharmacology, Biochemistry and Behavior, 23:653-659, (1985); Verma, A. and Snyder S. H., Annu. Rev. Pharmacol. Toxicol, 29:307-322, (1989). The central benzodiazepine receptor is a macromolecular complex that includes a site for the binding of gamma-aminobutyric acid (GABA), the inhibitory neurotransmitter, suggesting that benzodiazepines and chemically unrelated agonists including zopiclone may exert their effects by facilitating the synaptic effects of GABA. While it interacts with the benzodiazepine receptor, zopiclone apparently has minimal effects on memory, no interaction with alcohol, and little or no abuse or dependence potential.

The pharmacologic activity of zopiclone is predominantly that of a sedative or hypnotic, particularly at low doses. Accordingly, the drug may improve sleep in adults and geriatric patients with several types of sleep disorders, and situational, transient, primary, and secondary insomnia. Following a bedtime dose of zopiclone, there is minimal impairment of psychomotor skills and mental acuity the following morning. The drug is well absorbed from the stomach, and it is not highly bound to plasma proteins.

The racemic mixture of zopiclone is presently used outside the United States primarily as an hypnotic, improving sleep patterns in chronic insomniacs and providing sleep induction before surgical procedures in hospitalized patients.

Insomnia is characterized by difficulty in sleeping or disturbed sleep patterns. Insomnia may be of a primary nature with little apparent relationship to immediate somatic or psychic events, or secondary to some acquired pain, anxiety or depression. Where possible, treatment is directed to the underlying cause of the condition; hypnotic medication such as zopiclone is generally reserved for insomnia of emotional disturbances and for refractory cases due to more common causes. In these cases, zopiclone provides sedative-hypnotic effects from the first day of treatment, an activity that is maintained following subsequent doses over long treatment periods. There appears to be no diminution or potentiation of activity in adult or geriatric patients, and little or no effect on alertness and performance some ten hours following the bedtime dose. (Brun, J. P. *Pharmacology, Biochemistry and Behavior* 1988, 29, 831-832).

In addition, the racemic mixture of zopiclone may be useful in treating other disorders such as convulsive states like epilepsy. Seizure disorder or epilepsy represents a broad group of central nervous system disorders of function that are characterized by recurrent, sudden, often brief attacks, which may alter consciousness, motor activity, sensory phenomena, and autonomic responses, and which may prompt inappropriate behavior. Recurrent seizure patterns of either an idiopathic or symptomatic etiology are termed epilepsy. The most common form of these recurrent but transient episodes are convulsive seizures, which may include loss of consciousness, motor function and control, and which may produce tonic or clonic jerking of the extremities. Pharmacological treatment of epilepsy has been directed to control based on seizure type, rather than etiology. Accordingly, the convulsions have been grouped in broad but rather distinct types including Tonic-clonic (Grand Mal), Partial (Focal) seizures, psychomotor (Complex partial) seizures, pyknoepileptic or Absence (Petit Mal) and the less frequent Myoclonic seizures.

The binding of zopiclone at or near the benzodiazepine receptor complex suggests that the compound may facilitate the inhibitory action of the neurotransmitter GABA and therefore its synaptic effects. As stated above, benzodiazepine receptors, which can be located both within the central nervous system and peripherally (e.g., in the endocrine system), are comprised of macromolecular complexes characterized by sites for binding of the benzodiazepines, GABA, and zopiclone. The benzodiazepine receptor complex is further associated with, and interacts with, a transmembrane channel for chloride ion transport. The effect of zopiclone's interaction with the benzodiazepine receptor/GABA receptor/chloride channel complex is to cause GABA to inhibit cerebral neuronal discharge, presumably by increasing membrane conductance of chloride ion, thus stabilizing membrane potentials and dampening excitatory input. (See Meldrum, B. S., Brit. J. Clin. Pharm., 27 (suppl. 1): 3S- 11S, (1989)). It is believed that through mediation of this process zopiclone may be useful in treating epilepsy and a number of other conditions in which GABA is believed to exert a physiologic role.

While the racemic mixture of zopiclone may be useful in the treatment of the above-described disorders, it has a low therapeutic index and also causes adverse effects. These adverse effects include, but are not limited to, the development of a bitter taste due to the salivary secretion of the drug, dry mouth, drowsiness, morning tiredness, headache, dizziness, impairment of psychomotor skills and related effects.

It has recently been discovered that by using optically pure or substantially optically pure (+) zopiclone yields an increase in the potency of therapeutic effect as compared to that found in the racemic mixture. In addition, utilizing the optically pure isomer of (+) zopiclone results in clearer dose-related definitions of efficacy, diminished adverse effects, and accordingly, an improved therapeutic index. Hence, it is generally more desirable to use the (+) isomer of zopiclone.

Eszopiclone

Eszopiclone (or (+)-Zopiclone or (S)-zopiclone) is a potent drug useful for the treatment of sleep disorders, convulsive disorders, and disorders that are affected by the binding of agonists to central nervous system or peripheral benzodiazepine receptors. Administration of isomerically pure or substantially isomerically pure (e.g., 90%, 95%, or 99% isomeric purity) (+)-zopiclone is generally preferred because this isomer possesses potent activity in treating sleep disorders while avoiding adverse effects including but not limited to drowsiness, next day effects, such as tiredness in the morning, inability to concentrate and headache.

Eszopiclone is a cyclopyrrolone that has the chemical name (+) 6-(5-chloro-pyri-2-dyl)-5-(4-methylpiperazin-1-yl) carbonyloxy-7-oxo-6,7-dihydro-5H-pyrrolo[3-4b] pyrazin or (+) 6-(5-chloro-2-pyridinyl)-6,7-dihydro-7-oxo-5H-pyrrolo[3,4b]pyrazin-5-yl 4-methylpiperazine-1-carboxylate. The chemical structure of zopiclone is shown below:

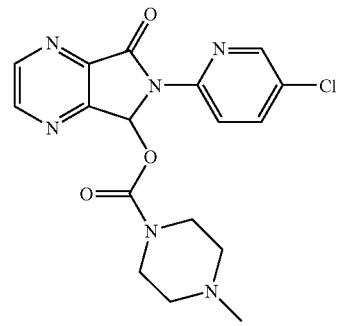

Eszopiclone is an optical isomer, the (+)-isomer, of the compound zopiclone, which is described in U.S. Pat. Nos. 6,319,926 and 6,444,673, and in Goa and Heel, [Drugs, 32:48-65 (1986)] and in U.S. Pat. Nos. 3,862,149 and 4,220,646. This isomer, which will hereinafter be referred to as eszopiclone, includes optically pure and the substantially optically pure (e.g., 90%, 95% or 99% optical purity) (+)-zopiclone isomer.

Racemic zopiclone is commercially available and can be made using various methods, such as those disclosed in U.S. Pat. Nos. 3,862,149 and 4,220,646. Eszopiclone may be prepared from racemic zopiclone using standard methods, such as chiral-phase chromatography, resolution of an optically active salt, stereoselective enzymatic catalysis by means of an appropriate microorganism, or asymmetric synthesis. U.S. Pat. No. 6,319,926 discloses methods for making eszopiclone, including resolution from racemic zopiclone by means of an optically active acid, such as D(+)-O,O'-dibenzoyltartaric acid.

Another method for making eszopiclone (or (S)-zopiclone) is by synthesis from racemic zopiclone (or (RS)-zopiclone) by chemical resolution via the D-malate salt as shown in the following synthesis schematic.

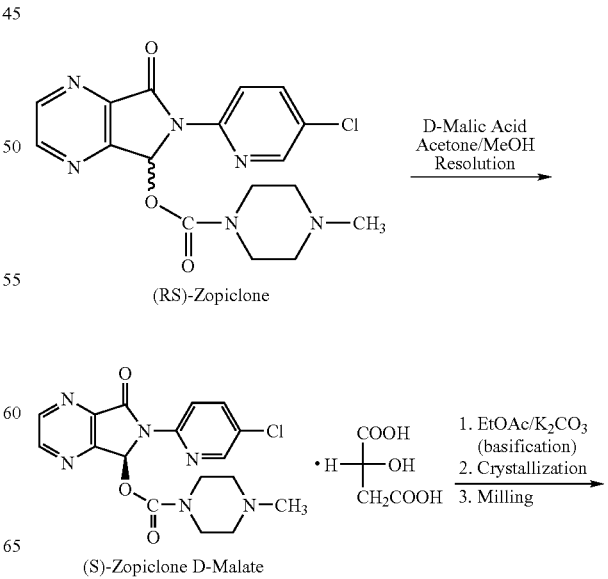

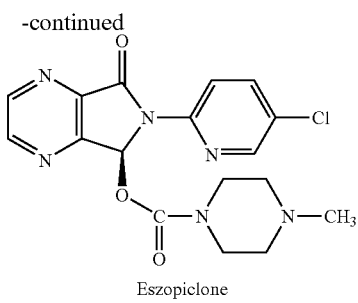
Eszopiclone

In the synthetic route shown above, (RS)-Zopiclone and D-malic acid are dissolved in a mixture of acetone and methanol to form (S)-zopiclone D-malate and (R)-zopiclone D-malate. The two diastereomeric salts are resolved in-situ by selective crystallization, filtration and rinsing to produce highly (S)-enriched zopiclone D-malate salt. In this process, the majority of (R)-zopiclone D-malate remains in the mother liquors. In this method, the use of an acetone/methanol co-solvent system results in a highly diastereoselective salt crystallization, and preferably, the co-solvent ratio used should be in the range of approximately 1.9/1 to 2.3/1 w/w acetone in methanol. Preferably, this stage of the process may also include cooling the reaction mixture during the isolation step to a temperature in the inclusive range of about 10° C. to 15° C., and washing or rinsing the wet cake obtained after filtration with cold solvent, such as cold methanol.

The resulting (S)-zopiclone D-malate salt is converted to optically pure eszopiclone free base by treatment with aqueous potassium carbonate and ethyl acetate, followed by phase separation and crystallization. In this process, once a solution of eszopiclone free-base is obtained, additional enantiomeric enrichment (typically 1 to 4%) can be achieved by crystallization from ethyl acetate of low water content. The water content can be controlled, e.g., by azeotropic distillation, and incorporating an in-process control of water content into the crystallization process can further improve the robustness of enantiomeric purity. Preferably, the water level during this step is 2% or less, more preferably 1% or less, and most preferably 0.6% or less.

Figure 2:
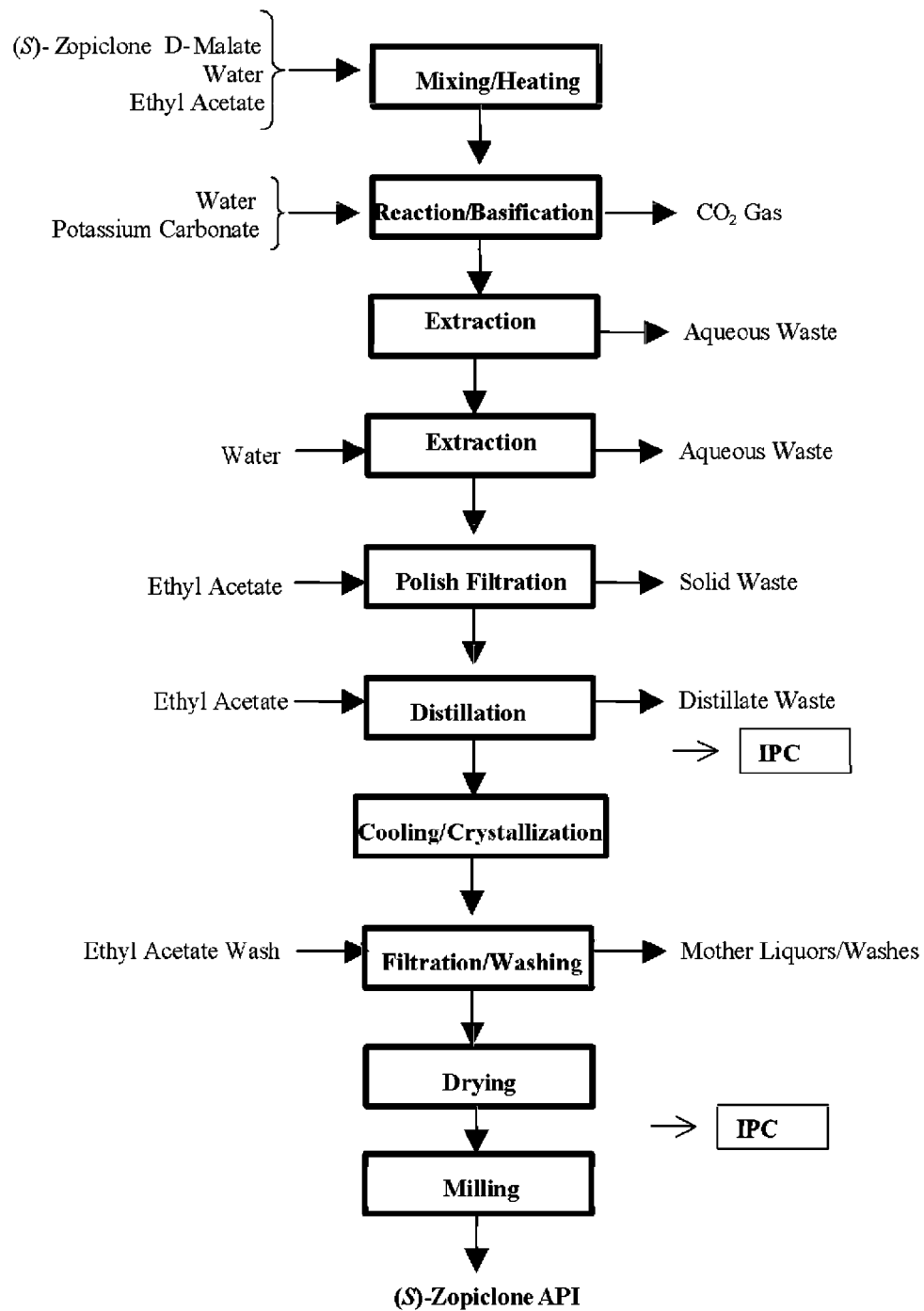
FIG. 2 depicts a schematic diagram of a method for preparing (S)-zopiclone as the free base (IPC=in-process control testing).
Figure 3:
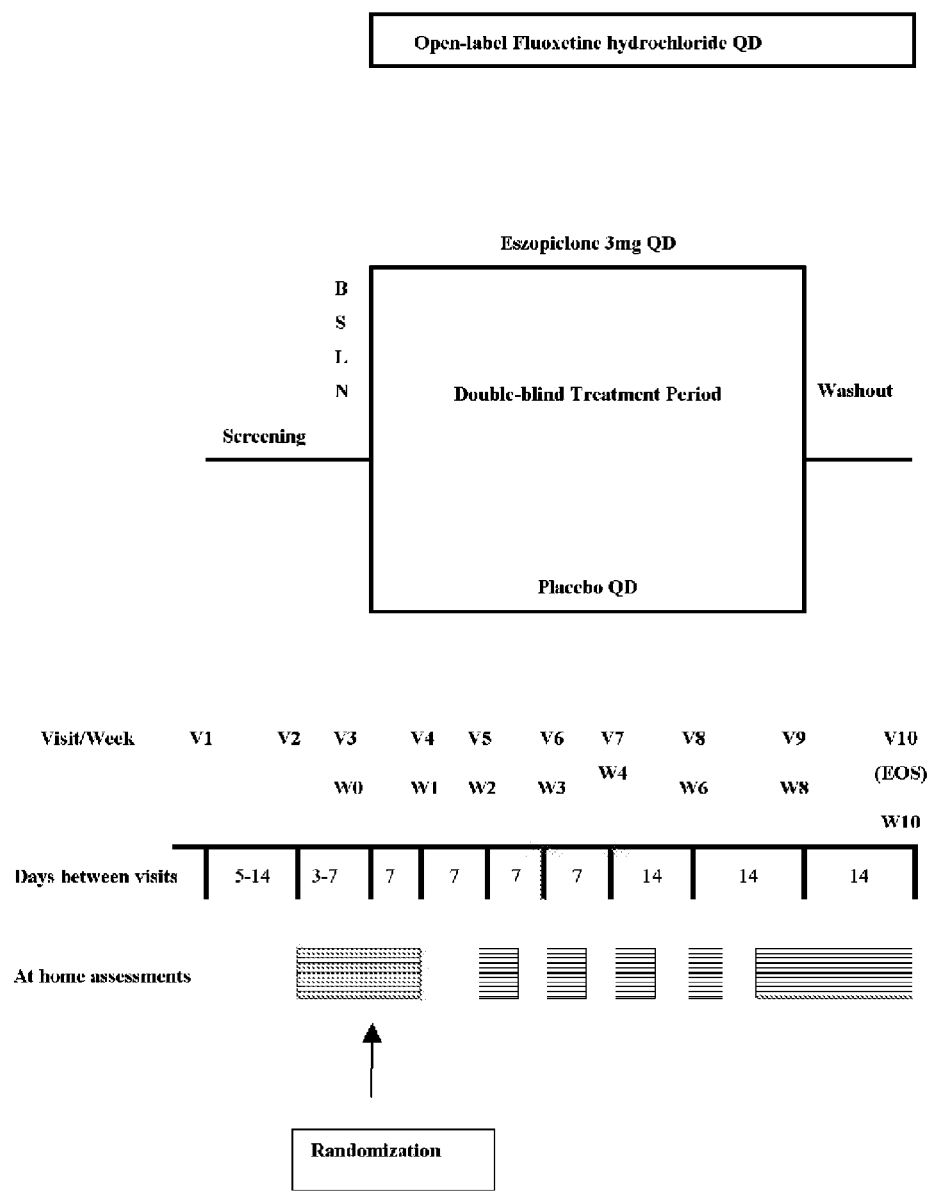
FIG. 3 depicts a schematic diagram of a clinical-study protocol used to assess the safety and efficacy of compositions and methods of the present invention.
Figure 4:
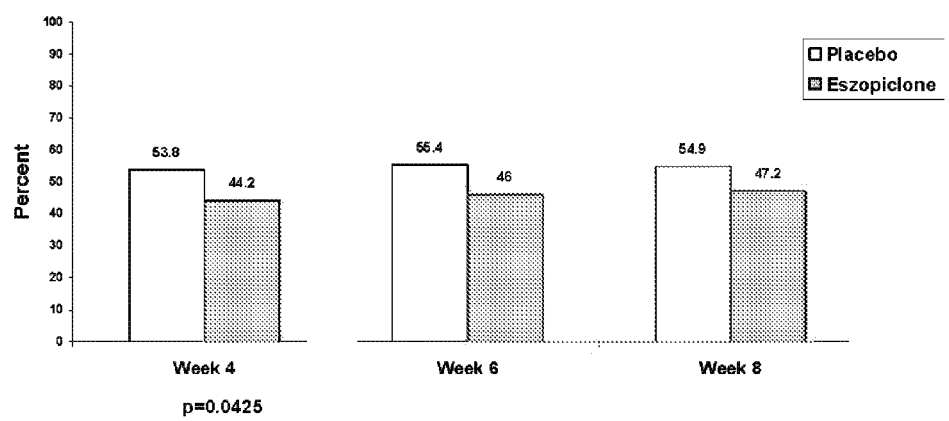
FIG. 4 depicts graphically fluoxetine titration as a function of length of treatment and co-administration with a placebo or eszopiclone.
Figure 5:
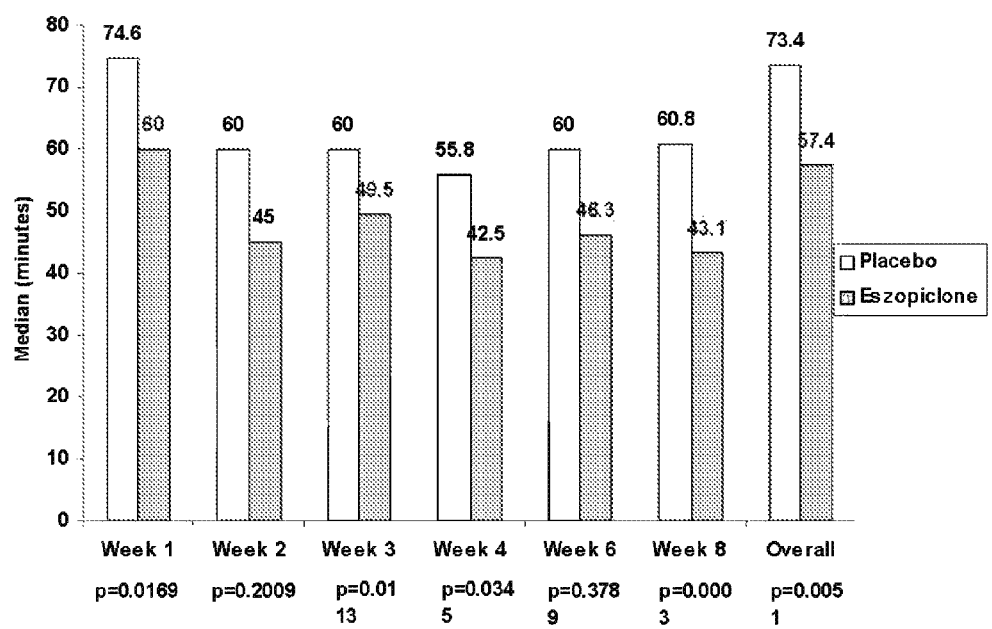
FIG. 5 depicts graphically Subjective Wake Time After Sleep Onset (WASO) as a function of length of treatment with a placebo or eszopiclone.
Figure 6:
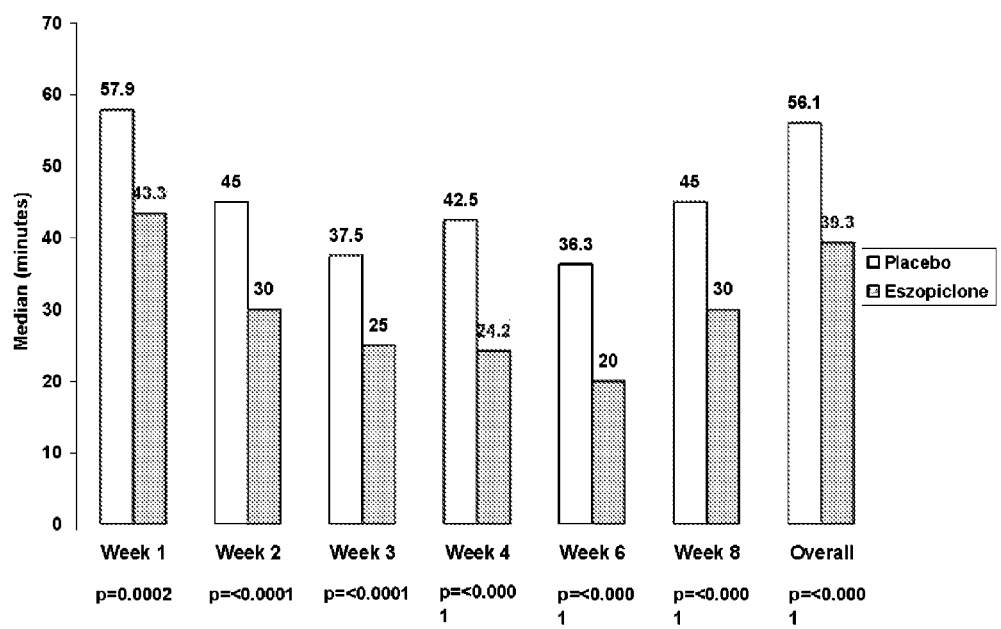
FIG. 6 depicts a chart of Subjective Sleep Latency (SL) as a function of length of treatment with a placebo or eszopiclone.
Figure 7:
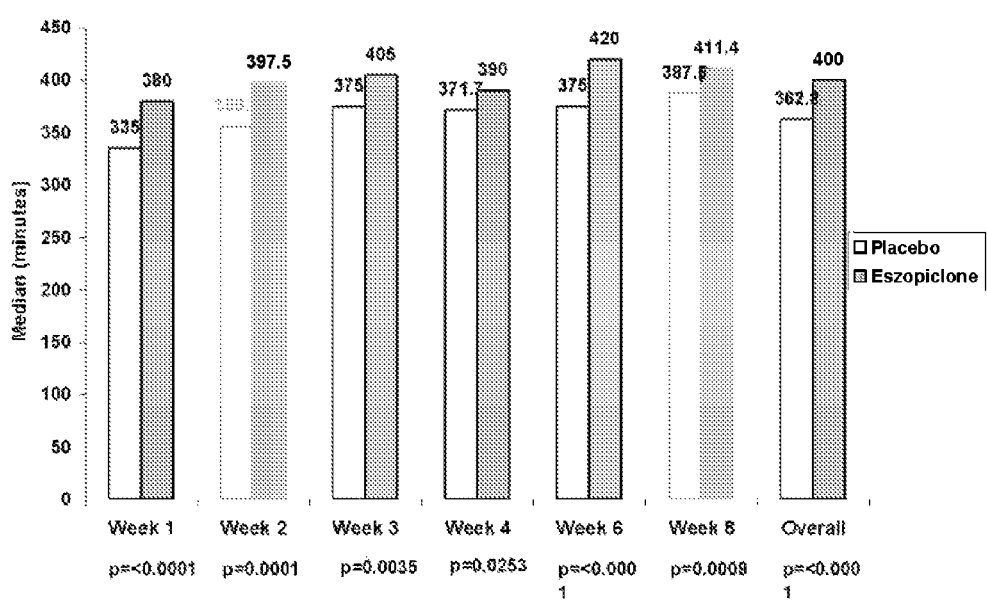
FIG. 7 depicts a chart of Subjective Total Sleep Time (TST) as a function of length of treatment with a placebo or eszopiclone.
Figure 8:
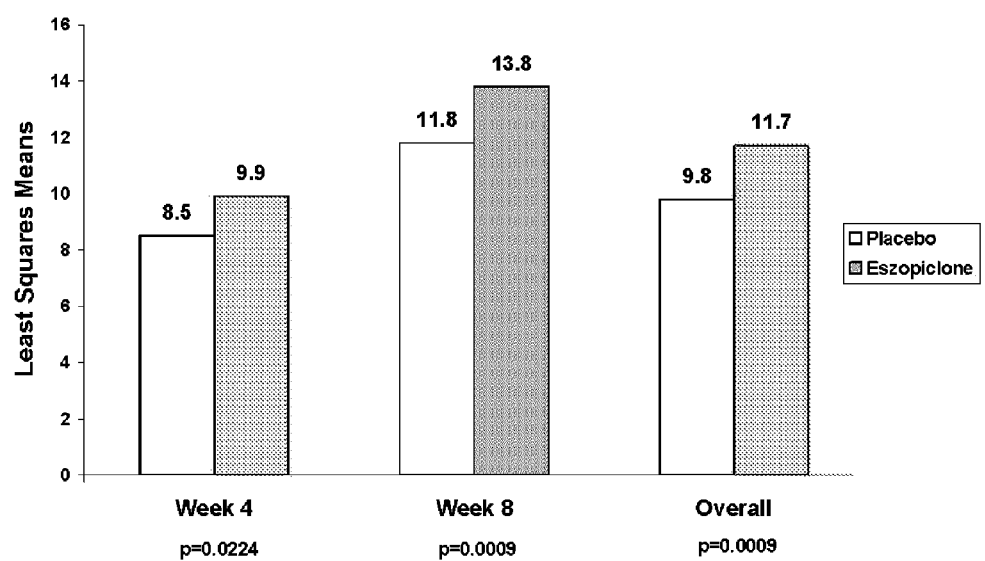
FIG. 8 depicts a chart of improvement from baseline in Ham-D-17 as a function of length of treatment with a placebo or eszopiclone.
Figure 9:
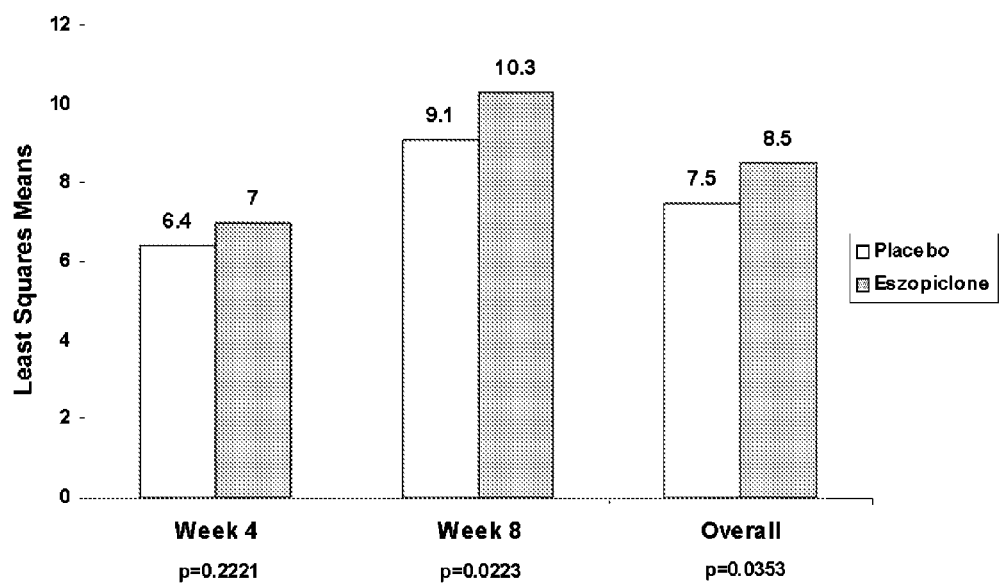
FIG. 9 depicts a chart of improvement from baseline in Ham-D-17
(excluding questions related to insomnia) as a function of length of treatment with a placebo or eszopiclone.
Figure 10:
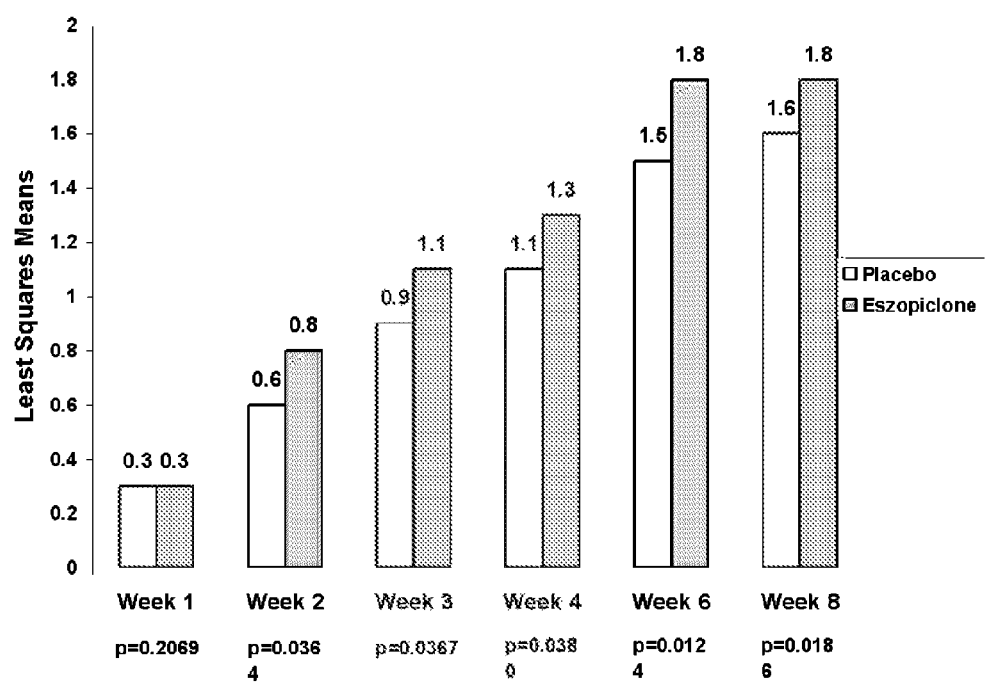
FIG. 10 depicts a chart of improvement from baseline in Clinical Global Impression (severity) as a function of length of treatment with a placebo or eszopiclone.
Figure 11:
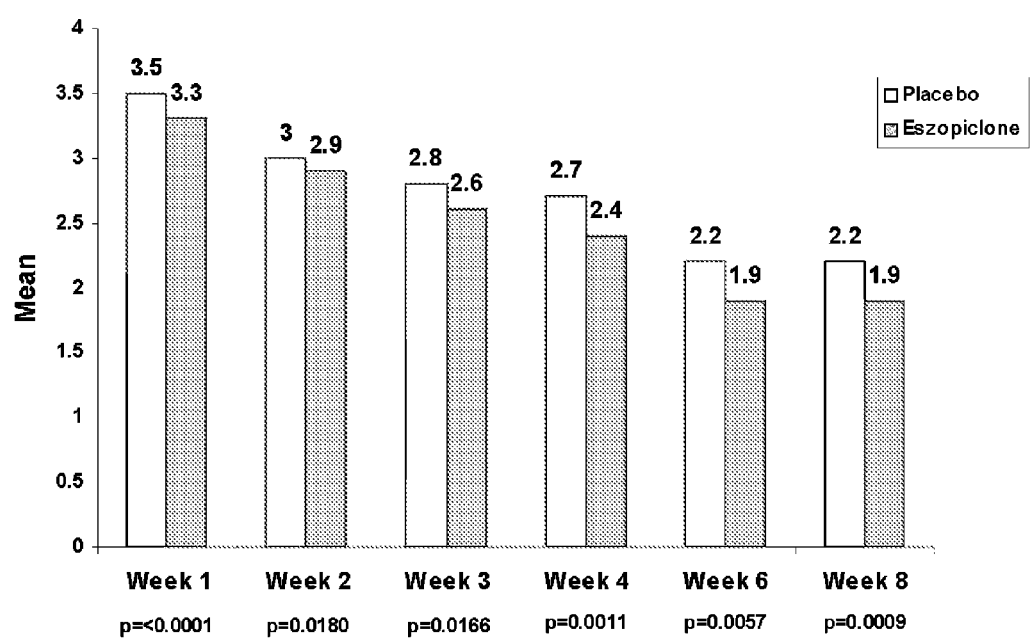
FIG. 11 depicts a chart of Clinical Global Impression (Global Improvement) as a function of length of treatment with a placebo or eszopiclone.
Figure 12:
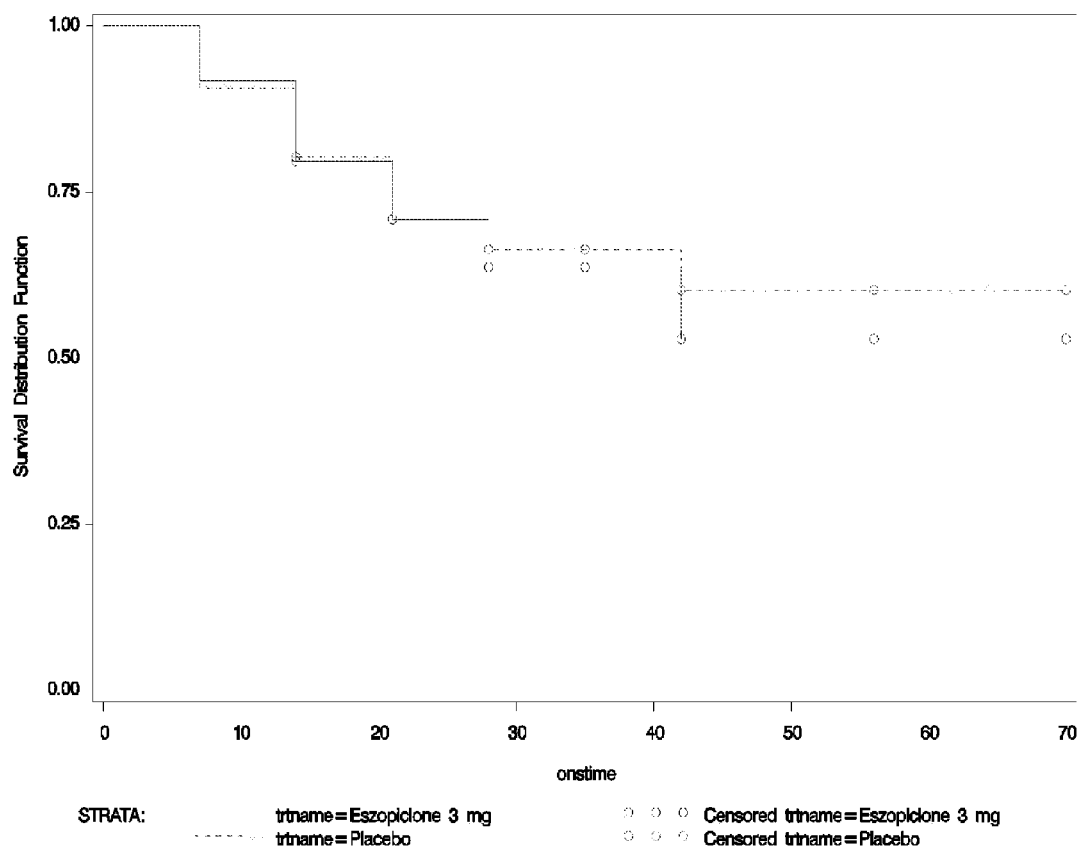
FIG. 12 depicts a graph of Time to Onset of 50% Antidepressant Response on HAM-D6 (Maier) Scores as a function of treatment with a placebo or eszopiclone.
Figure 13:
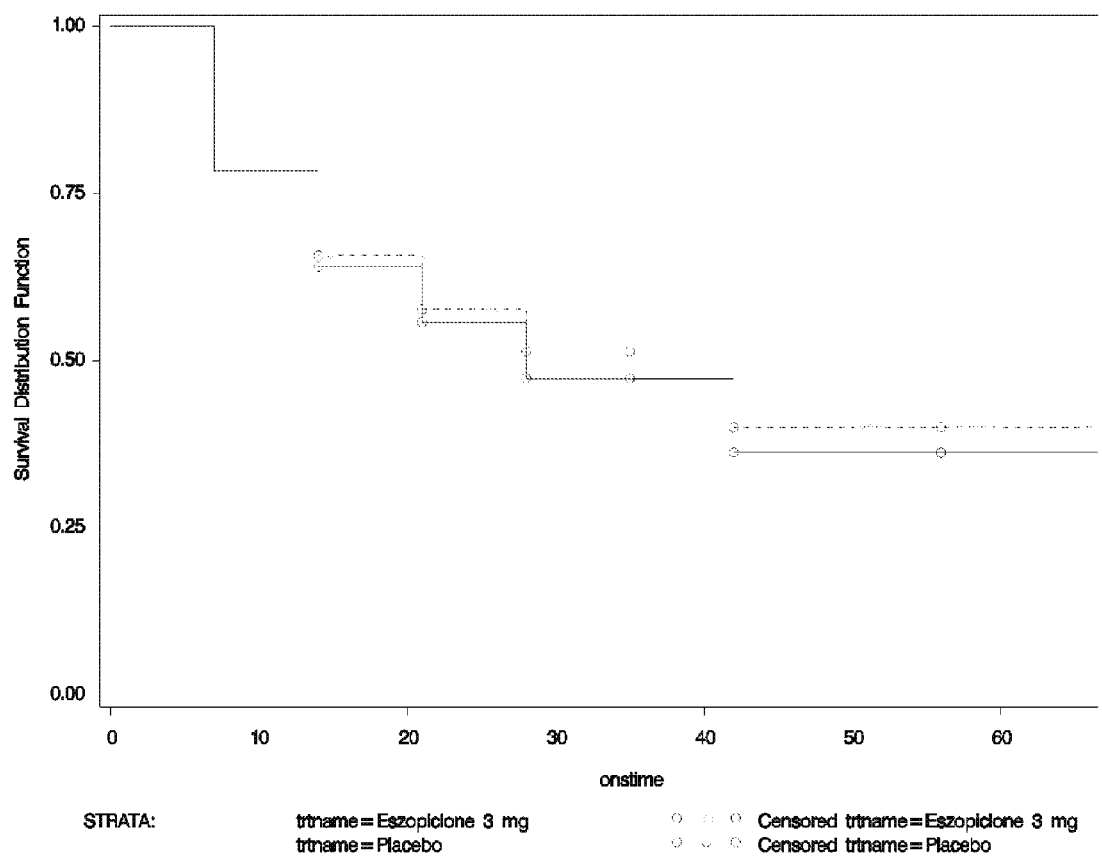
FIG. 13 depicts a graph of Time to Onset of 30% Antidepressant Response on HAM-D6 (Maier) Scores as a function of treatment with a placebo or eszopiclone.

The resulting optically pure eszopiclone free base can then be milled to a desired size for use as an active ingredient in a pharmaceutical composition according to or for use in methods of the present invention. This two-stage process is depicted in the diagrams of FIGS. 1 and 2.

Eszopiclone possess potent activity in treating sleep disorders such as insomnia. Eszopiclone also possess potent activity in treating sleep disorders while avoiding the usual adverse effects including but not limited to drowsiness, next day effects tiredness in the morning, inability to concentrate and headache, which are associated with the administration of the racemic mixture of zopiclone. Eszopiclone also possess potent activity in treating convulsive disorders such as epilepsy while avoiding the adverse effects which are associated with the administration of the racemic mixture of zopiclone.

Additionally, compositions containing optically pure eszopiclone are useful in treating disorders that are affected by the binding of agonists to central nervous system and peripheral benzodiazepine receptors. Such disorders include but are not limited to aggressive behavior, muscle tension, behavioral disorders, depression, schizophrenia, and disorders associated with abnormal plasma hormone levels such as endocrine disorders. These compositions are useful in treating disorders that are affected by the binding of agonists to central nervous system and peripheral benzodiazepine receptors.

The size of a prophylactic or therapeutic dose of eszopiclone in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.25 mg to about 15 mg. Preferably, a daily dose range should be between about 0.5 mg to about 10 mg. Most preferably, a daily dose range should be between about 1.0 mg to about 5.0 mg. In managing the patient, the therapy may be initiated at a lower dose, perhaps about 0.5 mg to about 3 mg and increased up to about 5 mg or higher depending-on the patient's global response. It is further recommended that children and patients over 65 years, and those with impaired renal or hepatic function, initially receive low doses, and that they be titrated based on global response and blood level. It may be necessary to use dosages outside these ranges in some cases.

In the case where an oral composition is employed, a suitable dosage range for use is from about 0.25 mg to about 15.0 mg with, in the usual case, the lower doses serving more common insomnia, and the higher doses, presented in divided dosing, reserved for control of psychiatric disorders. Preferably, a dose range of between about 0.5 mg to about 10 mg is given as a once daily administration or in divided doses if required; most preferably, a dose range of from about 1.0 mg to about 5 mg is given, either as a once daily administration or in divided doses if required. Patients may be upward titrated from below to within this dose range to a satisfactory control of symptoms as appropriate.

The pharmacologic profile of hypnotic-sedative agents of the benzodiazepine class has been rather well established (Goodman and Gilman: The Pharmacological Basis of Therapeutics, 7th. Edition, Chapt. 17, 340-351, (1985), MacMillan Publishing Co., N.Y.) and has been extended to non-benzodiazepine agents of the cyclopyrrolone class (Bardone, M. C. et al., Abstract No. 2319, 7th. Int. Congr. Pharm. Paris, July, 1978, Pergamon Press, London; Julou, L. et al., Pharmacology, Biochemistry and Behavior, 23:653-659 (1985)). Accordingly, a variety of experimental models, which are rather well characterized (Julou, L. et al., ibid, 1985) can be used to characterize the various activities of zopiclone, its anticonvulsant, myorelaxant, anti-aggressive, and sedative-hypnotic activities. In an examination of each element of the pharmacologic profile, the activity of a pharmaceutical composition comprising zopiclone can be compared and contrasted with such pharmacologic standards as nitrazepam and diazepam, two benzodiazepine agents, in a variety of animal models. The dose (mg/kg) of each agent that is capable of inhibiting by 50% (the $ID_{50}$ or $ED_{50}$) an induced response in rodents, for example, provides the basis for comparison. Thus, pentylenetetrazole-induced convulsions, picrotoxin convulsions, and electrically-induced convulsions can be used to demonstrate the anti-convulsant activity of zopiclone (Haefely, W., Psychotropic Agents, eds. Hofmeister, F. and Stille, G., Springer Verlag, Berlin, Part 11, 12-262, (1981)). Further, in the rat, in the amygdala kindled model of epilepsy, daily electrical stimulation of the amygdala induces a progressive increase of epileptic afterdischarge duration, with increasing epileptic behavioral symptoms, producing in some two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myorelaxant, anti-aggressive, and sedative-hypnotic activities of pharmaceutical compositions comprising zopiclone and its optically pure enantiomers in both mice and rats. (For review see Julou, L. et al., ibid, 1985.)

The acute toxicity of a pharmaceutical composition comprising zopiclone or eszopiclone can be determined in studies in which rats are administered at progressively higher doses (mg/kg) of pharmaceutical composition. That lethal dose which, when administered orally, causes death of 50% of the test animals, is reported as the $LD_{50}$.

The effects of a pharmaceutical composition on Psychomotor Behavior can be determined by measuring ten parameters (pinna reflex, spontaneous activity, palpebral size, startle response, touch response, reactivity, placing, righting reflex, exploration, and ataxia). Each parameter scores 2 points for normalcy for a total of 20 points×3 mice=60 points possible. Scores below 40 (<40) denote behavioral deprsesion. Scores are determined before and after dosing with test sample. See Irwin, S., Psychopharrmacologia, 13:222-257 (1968).

REFERENCE AGENTS ($ED_{100}$, mg/kg)

| | |
|---|---|
| chlordiazepoxide | 100 |
| chlorpromazine | 25 |
| clozapine | 25 |
| diazepam | 50 |
| glutethimide | 300 |
| haloperidol | 10 |
| meprobamate | 300 |
| pentobarbital | 100 |
| phenobarbital | 150 |
| reserpine | 50 |
| thioridazine | 50 |

Indiplon

Indiplon is a potent sedative, anxiolytic and anti-convulsant agent, and possesses an improved profile of side effects, as compared to other benzodiazepine agents. Indiplon shows a reduced tolerance to sedation, a lowered potential for abuse and a reduced tendency to potentiate the deleterious effects of ethanol. In addition, Indiplon appears to be substantially devoid of next-day hangover effects and to have a considerably reduced amnesic potential compared to currently marketed sedative-hypnotic agents. The half-life of indiplon in vivio is approximately 1.3 hours. Indiplon has the chemical name N-methyl-N-(3-{3-[2-thienylcarbonyl]-pyrazolo-[1,5-a]-pyrimidin-7-yl}-phenyl)acetamide and is represented by the formula below:

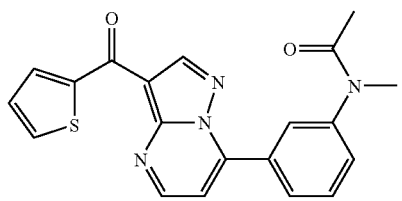

Indiplon occurs as an off-white to yellow, non-free flowing powder with little static charge. The compound is lipid soluble (log D partition coefficient=1.73), and is soluble in water at approximately 20-30.mu.g/mL with a resulting pH of approximately 8.0. Indiplon may be prepared using chemical synthesis techniques known to those skilled in this field. For example, Indiplon may generally be made by the synthetic procedures disclosed in U.S. Pat. Nos. 4,521,422 and 4,900,836. These patents, particularly U.S. Pat. No. 4,521,422, disclose a genus encompassing certain aryl and heteroaryl[7-(aryl and heteroaryl)-pyrazolo[1,5-a]pyrimidin-3-yl] methanones.

The size of a prophylactic or therapeutic dose of Indiplon in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 75 mg. Preferably, a daily dose range should be between about 5 mg to about 50 mg. Most preferably, a daily dose range should be between about 10 mg to about 35 mg. In certain embodiments, the daily dose range should be about 10, 25, 30, or 35 mg. In managing the patient, the therapy may be initiated at a lower dose, perhaps about 2 mg to about 5 mg and increased up to about 10 mg or higher depending-on the patient's global response.

The mean plasma half-life of a sedative-hypnotic compound may be determined using well known techniques. Terminal half-life may be determined using standard pharmacokinetic calculations, such as those presented by Rolland and Tozer (Clinical Pharmacokinetics Concepts and Applications, $3^{rd}$ Ed., Chap. 3, 1995). in addition, software is commercially available which performs this calculation, such as the product sold under the tradename "WinNinlin™"(Prof. Ver. 1.5). This software calculates terminal plasma half-life ($t_{1/2}$) from the following relationship: "$t_{1/2}=\ln(2)/\text{lambda}$.", wherein "ln(2)" is the natural log of 2 and "lambda." is the first order rate constant associated with the terminal (log-linear) portion of the plasma test compound concentration: time profile. This is estimated by linear regression analysis of the time vs. log concentration of the test compound.

The sedative-hypnotic effect of a compound may be readily established using, for example, standard tests that monitor the effects of a drug on motor activity, muscle relaxation and motor coordination (see, e.g., Beer et al., CNS Drug Reviews 3:207-224, 1997; Sanger et al., Eur. J. Pharmacol. 313:35-42, 1996, and references cited therein). In general, a sedative-hypnotic compound should have a statistically significant sedative effect within at least one, and preferably all, of the following assays: (a) assays to detect a reduction in locomotor activity, as described by Sanger et al., European J Pharmacol. 313:35-42, 1996 and Beer et al., CNS Drug Reviews 3:207-224, 1997; (b) assays to detect an increase in total sleep time, as determined by electroencephalographic (EEG) measures, as described in Beer et al., CNS Drug Reviews 3:207-224, 1997; and (c) assays to detect a reduction in motor coordination, as defined by a reduced latency to remain on a rotating rod and/or a reduction in alertness, or vigilance (both assays as described by Sanger et al., European J Pharmacol. 313:35-42, 1996 and Beer et al., CNS Drug Reviews 3:207-224, 1997).

Zolpidem

Zolpidem is a hypnotic agent that is known to induce or maintain sleep. Zolpidem is an imidazopyridine having IUPAC chemical nomenclature N,N,6-trimethyl-2-(4-methylphenyl)-imidazo [1,2-s]pyridine-3-acetamide. The structure of zolpidem is presented below.

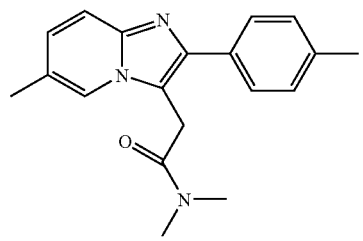

The zolpidem free base was disclosed generically in EP 50563 of Synthelabo. Zolpidem tartrate was subsequently disclosed in EP 251859 (U.S. Pat. No. 4,794,185). More recently, zolpidem has been suggested as useful in treating Parkinson's disease, parkinsonian symptoms, obsessive-compulsive disorder and certain forms of dementia in U.S. Pat. No. 5,891,891.

Zolpidem has been marketed as an immediate release tablet for oral application under the trade marks AMBIEN® and STILNOX®. In these commercial pharmaceutical dosage forms, zolpidem is present as a salt with L(+)tartaric acid wherein the molar ratio of zolpidem to tartaric acid is 2:1. This salt is conventionally called zolpidem hemitartrate but a more correct denomination thereof, which will be used hereinafter, is zolpidem tartrate. The European Pharmacopoeia, Monograph No. 1999:1280, states that zolpidem tartrate is characterized as a white or almost white crystalline powder, hygroscopic, slightly soluble in water, sparingly soluble in methanol, and practically insoluble in methylene chloride. Commercially available zolpidem tablets are conventional film coated tablets for immediate release of the active substance after ingestion and they contain 5 or 10 mg of zolpidem tartrate. The inactive ingredients are: lactose, microcrystalline cellulose, sodium starch glycolate, hydroxypropylmethylcellulose and magnesium stearate. The film coating layer consists of hydroxypropylmethylcellulose, polyethylene glycol and colorants.

Zolpidem is generally administrated orally by means of a tablet or other solid dosage form. Indeed pharmacokinetic and pharmacodynamic data show that zolpidem has both a rapid absorption and onset of hypnotic action. Its bioavailability is 70% following oral administration and demonstrates linear kinetics in the therapeutical dose range, which lies between 5 and 10 mg in conventional forms, peak plasma concentration is reached at between 0.5 and 3 hours, the elimination half-life is short, with a mean of 2.4 hours and a duration of action of up to 6 hours. Generally, the dosage of zolpidem is between 1 and 50 mg.

Traditionally, only immediate release dosage forms were developed which disintegrated rapidly in the gastrointestinal tract, dissolved in the fluid of the gastrointestinal tract and underwent systemic absorption, where zolpidem, can exert its pharmacological effect and induce sleep of the patient. More recently, new dosage forms have been developed which sustain release of zolpidem over a period compatible with the desired time of sleep and the time needed for elimination of the drug from the human body to a sufficiently low level. See U.S. Pat. Nos. 6,638,535 and 6,514,531.

The pharmacological effect of the zolpidem can be evaluated using the biological assays described in U.S. Pat. No. 4,382,938. For example, the toxicity of a compound can be determined on mice by intraperitoneal administration using LD 50 ranges from 500 to 1,000 mg/kg. In addition, the anxiolytic activity can be determined according to the eating test (R. J. Stephens, (1973), Brit. J. Pharmac., 49, 146 P). In this test, the doses which increases the food consumption of the mice vary from 0.1 to 10 mg/kg, administered intraperitoneally.

The activity of the compounds in the area of cerebral circulation can be determined in the test for the hypoxia caused by pressure reduction. Mice of the CD I strain are kept in an oxygen-depleted atmosphere produced by creating a partial vacuum (190 mm of mercury, corresponding to 5.25% of oxygen). The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically.

The anticonvulsant activity can be determined in accordance with the test for the antagonism towards the mortality induced by bicuculline in mice (P. Worms, H. Depoortere and K. G. Lloyd, (1979) Life Sci., 25, 607-614). The products to be studied are injected intraperitoneally, 30 minutes before the bicuculline (0.9 mg/kg, administered intravenously). With death being the criterion selected for this test, the percentage mortalities are noted for each batch, 2 hours after administration of the bicuculline (control batch: 100% mortality). For each product, the 50% active dose (AD 50 or the dose which protects 50% of the animals from the lethal effects of the bicuculline) is determined graphically.

The sedative or hypnotic activity can be determined by observing the action of the compounds on the EEG of curarised rats and also on the wake-sleep states in freely moving, implanted rats and cats (H. Depoortere, Rev. E. E. G. Neurophysiol., (1980) 10, 3, 207-214; L. M. Da Costa, H. Depoortere and R. Naquet, Rev. E. E. G. Neurophysiol., (1977), 7, 2, 158-164). In curarised rats, the products to be studied are injected intraperitoneally or orally at doses increasing from 0.1 to 30 mg/kg. In freely moving, implanted rats, the products to be studied were injected intraperitoneally or orally at a single dose ranging from 1 to 10 mg/kg. In freely moving, implanted cats, the products to be studied were injected intraperitoneally or orally at a single dose of 10 mg/kg.

The results of these various tests can be used to determine the anti-anoxic, sleep-inducing, hypnotic and anticonvulsant properties of a pharmaceutical composition.

Zaleplon

Zaleplon (Wyeth-Ayerst), also known as "Sonata", is a nonbenzodiazipine recently approved by the FDA as sedative-hypnotic (see U.S. Pat. No. 4,626,538). Zaleplon is a pyrazolopyrimidine that has the chemical name N-[3-(3-cyanopyrazolo[1,5-a]pyrimidin-7-yl)phenyl]-N-ethylacetamide. Zaleplon is a white powder that has very low solubility in water and limited solubility in alcohol or propylene glycol.

The structure of Zaleplon is given below.

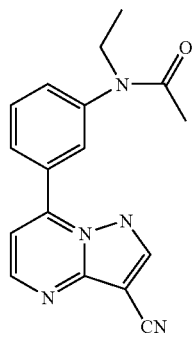

Zaleplon binds to the gamma-aminobutyric acid benzodiazepine (GABA-BZ) receptor complex. Binding studies have revealed that Zaleplon binds selectively to the brain omega-1 receptor located on alpha subunit of the GABAA/chloride ion channel receptor complex. This interaction modulates the binding of t-butylbicyclophosphorothionate binding. Importantly, the pharmacological properties of benzodiazepines, e.g. sedative, anxiolytic, muscle relaxant, and anticonvulsive effects in animals, are linked to modulation of the GABA-BZ receptor chloride channel complex.

The pharmacokinetic profile of Zaleplon has been investigated in trials using a 60 mg single dose and once-daily administration of a 15 or 30 mg dose for up to 10 days. The data indicate that pharmacokinetics are proportional to the dose throughout the therapeutic range. In addition, Zaleplon does not accumulate in once-daily administration treatment regimes. Zaleplon is rapidly absorbed when administered orally; however, Zaleplon is subject to substantial presystemic metabolism resulting in only 30% bioavailability. The majority of the metabolism is attributed to an aldehyde oxidase which converts Zaleplon to 5-oxo-Zaleplon. Consequently, peak plasma concentrations following oral administration typically occur 1 hour after administration.

The size of a prophylactic or therapeutic dose of Zaleplon in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 50 mg. Preferably, a daily dose range should be between about 1 mg to about 25 mg. Most preferably, a daily dose range should be between about 5 mg to about 20 mg. In certain embodiments, the daily dose range should be about 5, 10, 15, or 20 mg. In managing the patient, the therapy may be initiated at a lower dose, perhaps about 2 mg to about 5 mg and increased up to about 10 mg or higher depending-on the patient's global response.

Generally, Zaleplon should be taken just prior to bedtime or immediately if a patient the patient has already gone to bed is having diffuculty falling asleep. In certain instances the dose of Zaleplon should be adjusted in accord with diet or special needs of the patient. For example, the dosage of Zaleplon should be approximately 5 mg for elderly or debilitated patients whom are likely to be particularly sensitive to hypnotic medications. In addition, patients suffering from mild to moderate hepatic impairment should be administered only a 5 mg dose because systemic removal of drug is reduced in such patients.

Gaboxadol

Gaboxadol is a GABA-receptor agonist that has been shown to improve sleep-quality in both human and animal studies. Procedures for the preparation of gaboxadol have been described. U.S. Pat. No. 4,278,676; and P. Krogsgaard-Larsen, *Acta. Chem. Scand.* 1977, 31, 584. Gaboxadol, also known as THIP, is a crystalline, colorless solid that is soluble in water and methanol. The chemical name for gaboxadol is 4,5,6,7-tetrahydroisoxazolo[5,4-c]pyridin-3-ol. Gaboxadol is known to exist in two isomeric forms (Form A and Form B, shown below) and the term "gaboxadol" as used herein encompasses both forms separately, a mixture comprising both isomeric forms, and the pharmaceutically acceptable salts of any of them.

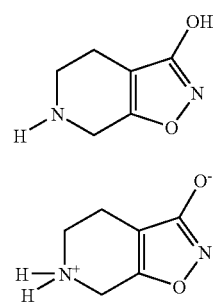

The GABA-receptor binding affinity and pharmacological properties of gaboxadol have been described. U.S. Pat. No. 4,278,676. In order to study the interactions of gaboxadol with the central GABA receptors in vitro, gaboxadol was tested in affinity binding experiments. See S. J. Enna and S. H. Snyder, *Brain Res.* 1975, 100, 81-97. The $IC_{50}$ value of gaboxadol was determined to be 0.13±0.005 μM based on experiments using five different concentrations of gaboxadol. Each experiment was conducted in triplicate and the $IC_{50}$ value was determined by logprobit analysis.

In order to study the interactions of gaboxadol with the central GABA receptors in vivo, gaboxadol was tested in microelectrophoretic experiments. See U.S. Pat. No. 4,278,676. Experiments were performed on lumbar dorsal horn interneurones and Renshaw cells of cats anaesthetized with pentobarbitone sodium. Gaboxadol was found to be relatively more potent than GABA on the basis of electrophoretic currents required to produce equal and submaximal inhibitions of the firing of the central neurones. The inhibitory action of gaboxadol on central neurones was reversibly antagonized by the specific GABA antagonist bicuculline methochloride (BMC). Interestingly, gaboxadol did not interact with the GABA uptake system at concentrations of $5 \times 10^4$ M, and it did not interact with the GABA metabolizing enzymes GABA: 2-oxo-glutarate aminotransferase and L-glutamate 1-carboxylase at concentrations of $10^{-3}$ M. Based on the above-mentioned experiments, gaboxadol is a specific and very potent GABA agonist. For additional information regarding the GABA receptor binding properties of gaboxadol, see: P. Krogsgaard-Larsen et al. *Nature* 1977, 268, 53.

The results from toxicity tests indicate that gaboxadol is less toxic than muscimol. The hydrobromide salt of gaboxadol has a $LD_{50}$ (mg/kg) of 80 (i.v.), 145 (i.p.), and >320 (p.o.) in mice. In comparison, muscimol has a $LD_{50}$ (mg/kg) of 7 (i.v.), 12 (i.p.), and 22 (p.o.) in mice. See U.S. Pat. No. 4,278,676.

Several studies have verified that gaboxadol can improve sleep quality. Lancel and coworkers conducted a double-blind, placebo-controlled study in healthy, elderly patients which revealed that oral administration of gaboxadol can increase sleep consolidation and the intensity of non-REM sleep. See Lancel, M.; Wetter, T. C.; Steiger, A.; Mathias, S. *Am. J Physiol. Endocrinol. Metab.* 2001, 281, E130. In a post-nap sleep study, Mathias and coworkers found that gaboxadol facilitates falling asleep while increasing the total sleep time and promoting deep sleep. Mathias, S.; Steiger, A.; Lancel, M. *Psychopharmacology (Berl.)* 2001, 157, 299. For additional studies relating to therapeutic uses for gaboxadol see U.S. Pat. No. 5,929,065; Christensen et al. *Pharm. Weekbl, Scie. Ed.* 1982, 4, 145; and S. Korsgaard et al. *Arch. Gen. Psychiatry* 1982, 39, 1017.

The size of a prophylactic or therapeutic dose of gaboxadol will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 90 mg. Preferably, a daily dose range should be between about 2 mg to about 40 mg. Most preferably, a daily dose range should be between about 5 mg to about 30 mg. In certain embodiments, the daily dose range should be about 10, 15, 20, or 25 mg. In managing the patient, the therapy may be initiated at a lower dose, perhaps about 2 mg to about 4 mg and increased up to about 10 mg or higher depending-on the patient's global response.

Baclofen

Baclofen is a GABA-receptor agonist that has the chemical name β-(aminomethyl)-4-chlorobenzenepropanoic acid. Procedures for the preparation of baclofen are described in U.S. Pat. No. 3,471,548. The pharmacological properties are described in Hudgson, Weightman *Brit. Med. J* 1971, 4, 15 and S. Ahuja in *Analytical Profiles of Drug Substances* vol. 14, K. Florey, Ed. (Academic Press, New York, 1985) pp 527-548. The structure of baclofen is presented below.

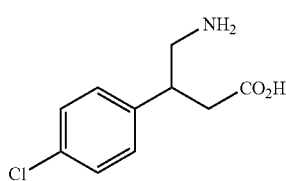

The size of a prophylactic or therapeutic dose of baclofen, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 250 mg. Preferably, a daily dose range should be between about 20 mg to about 150 mg. Most preferably, a daily dose range should be between about 30 mg to about 100 mg. In certain embodiments, the daily dose range should be about 40, 50, 60, 70, or 80 mg. In managing the patient, the therapy may be initiated at a lower dose, perhaps about 5 mg to about 15 mg and increased up to about 35 mg or higher depending on the patient's global response. In general, children are administered a dosage in the range of about 40, 50 or 60 mg per day, often times in divided dosages.

Bicuculline

Bicuculline is a naturally occurring GABA antagonist. Procedures for the preparation of bicuculline are described in Groenewoud, Robinson *J. Chem. Soc.* 1936, 199 and Haworth et al. *Nature* 1950, 165, 529. The pharmacological properties are described in Curtis et al. *Nature* 1970, 226, 1222. In general, the total daily dose range is from about 1 mg to about 2000 mg. Preferably, a daily dose range should be between about 5 mg to about 1000 mg. More preferably, a daily dose range should be between about 10 mg to about 250 mg. Bicuculline has the chemical name (6R)-6-[(5S)-5,6,7,8-tetahydro-6-methyl-1,3-dioxolo[4,5-g]isoquinolin-5-yl]furo[3,4-e]1,3-benzodioxol-8(6H)-one and the structure is presented below.

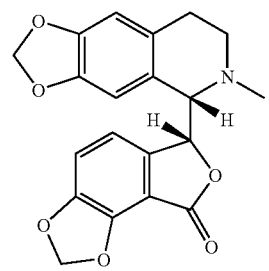

CACA

CACA is a GABA receptor agonist that has the chemical name cis-4-aminocrotonic acid. CACA can be purchased from Tocris Cookson Inc. in Ellisville, Mo. The pharmacological properties are described in J. Ulloor et al. *J. Neurophysiol.* 2004, 91(4), 1822-31. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CACA is presented below.

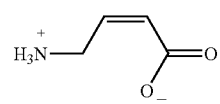

β-CCP

β-CCP is an inverse agonist of the GABA receptor. β-CCP can be purchased from Tocris Cookson Inc. in Ellisville, Mo. The pharmacological properties are described in P. Polc et al. *Epilepsia* 1996, 37(10), 1007-14. In general, the total daily dose range is from about 1 mg to about 2000 mg. Preferably, a daily dose range should be between about 5 mg to about 1000 mg. More preferably, a daily dose range should be between about 10 mg to about 250 mg. The structure of P-CCP is presented below.

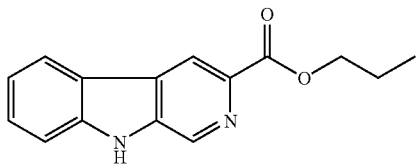

CGP 35348

CGP 35348 is a GABA-receptor antagonist that has the chemical name 3-(aminopropyl)(diethoxymethyl)phosphinic acid. CGP 35348 can be purchased from Tocris Cookson Inc. in Ellisville, Mo. The pharmacological properties are described in Olpe et al. *Eur. J. Pharmacol.* 1990, 187, 27; Hao et al. *Neurosci. Lett.* 1994, 182, 299; and Froestl et al. *Pharmacol. Rev. Comm.* 1996, 8, 127. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CGP 35348 is presented below.

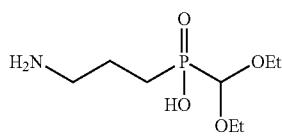

CGP 46381

CGP 46381 is a GABA-receptor antagonist that has the chemical name (3-aminopropyl) (cyclohexylmethyl)phosphinic acid. CGP 46381 can be purchased from KOMA Biotech, Inc. The pharmacological properties are described in Lingenhoehl, Olpe *Pharmacol. Comm.* 1993, 3, 49. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CGP 46381 is presented below.

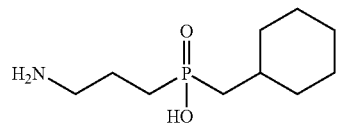

CGP 52432

CGP 52432 is a GABA-receptor antagonist that has the chemical name 3-[[(3,4-dichlorophenyl)methyl]amino]propyl]diethoxymethyl)phosphinic acid. CGP 52432 can be purchased from KOMA Biotech, Inc. The pharmacological properties are described in Lanza et al. *Eur. J. Pharmacol.* 1993, 237, 191; Froestl et al. *Pharmacol. Rev. Comm.* 1996, 8, 127; Bonanno et al. *Eur. J. Pharmacol.* 1998, 362, 143; and Libri et al. *Naunyn-Schmied. Arch. Pharmacol.* 1998, 358, 168. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CGP 52432 is presented below.

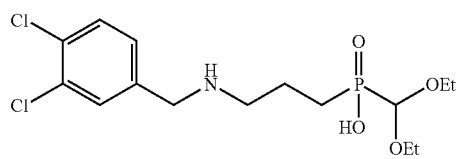

CGP 54626

CGP 54626 is a GABA-receptor antagonist that has the chemical name [S-(R*,R*)]-[3-[[1-(3,4-dichlorophenyl)ethyl]amino]-2-hydroxypropyl](cyclohexylmethyl)phosphinic acid. CGP 52432 can be purchased from KOMA Biotech, Inc. The pharmacological properties are described in Brugger et al. *Eur. J. Pharmacol.* 1993, 235, 153; Froestl et al. *Pharmacol. Rev. Comm.* 1996, 8, 127; and Kaupmann et al. *Nature* 1998, 396, 683. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CGP 54626 is presented below.

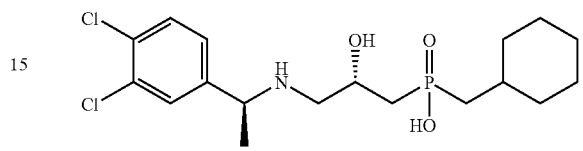

CGP 55845

CGP 55845 is a GABA-receptor antagonist that has the chemical name (2S)-3-[[(1S)-1-(3,4-dichlorophenyl)ethyl]amino-2-hydroxypropyl](phenylmethyl)phosphinic acid. CGP 55845 can be purchased from KOMA Biotech, Inc. The pharmacological properties are described in Davies et al. *Neuropharmacology* 1993, 32, 1071; Froestl et al. *Pharmacol. Rev. Comm.* 1996, 8, 127; and Deisz *Neuroscience* 1999, 93, 1241. In general, the total daily dose range is from about 1 mg to about 2000 mg. Preferably, a daily dose range should be between about 5 mg to about 1000 mg. More preferably, a daily dose range should be between about 10 mg to about 250 mg. The structure of CGP 55845 is presented below.

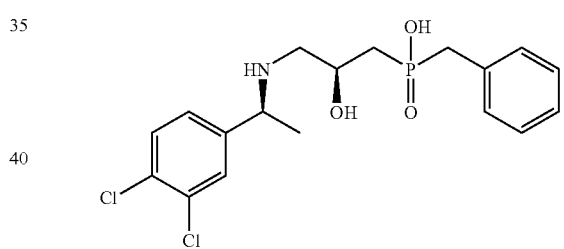

Clonazepam

Clonazepam is an antianxiety agent marketed under the tradename KLONOPIN®. Procedures for the preparation of clonazepam are described in U.S. Pat. Nos. 3,121,076 and 3,116,203. The pharmacological properties are described in Guerrero-Figueroa et al. *Curr. Ther. Res. Clin. Exp.* 1969, 11, 40 and W. C. Winslow *Anal. Profiles Drug Subs.* 1977, 6, 61-81. Clonazepam has the chemical name 5-(2-chlorophenyl)-1,3-dihydro-7-nitro-2H-1,4-benzodiazepin-2-one and the structure is presented below.

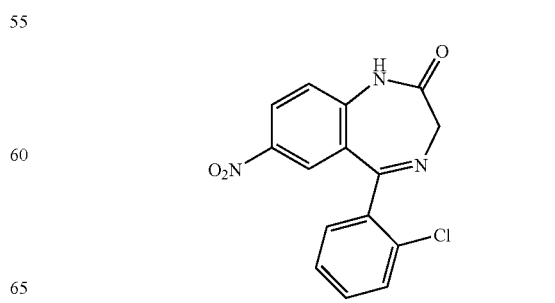

The size of a prophylactic or therapeutic dose of clonazepam, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 1 mg to about 40 mg. Preferably, a daily dose range should be between about 2 mg to about 30 mg. Most preferably, a daily dose range should be between about 4 mg to about 20 mg. In certain embodiments, the daily dose range should be about 8, 12, or 16 mg. In managing the patient, the therapy may be initiated at a lower dose, perhaps about 1.5 mg to about 3.0 mg and increased up to about 6 mg or higher depending on the patient's global response.

Diazepam

Diazepam is a benzodiazepine used to relieve anxiety, nervousness, and tension associated with anxiety disorders. In addition, diazepam is used to treat certain seizure disorders and muscle spasms. Procedures for the preparation of diazepam are described in U.S. Pat. Nos. 3,371,085; 3,109,843; and 3,136,815. The pharmacological properties are described in Hudson, Wolpert *Arch. Int. Pharmacodyn. Ther.* 1970, 186, 388; M. Mandelli et al. *Clin. Pharmacokinet.* 1978, 3, 72; and A. MacDonald et al. *Anal. Profiles Drug Subs.* 1972, 1, 79-99. Diazepam has the chemical name 7-chloro-1,3-dihydro-1-methyl-5-phenyl-2H-1,4-benzodiazepin-2-one and the structure is presented below.

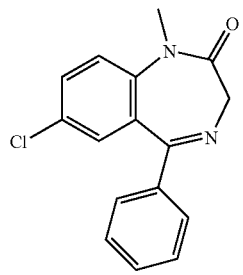

The size of a prophylactic or therapeutic dose of diazepam, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 200 mg. Preferably, a daily dose range should be between about 1 mg to about 100 mg. Most preferably, a daily dose range should be between about 5 mg to about 40 mg. In certain embodiments, the daily dose range should be about 10, 15, 20, 25, 30 or 35 mg. In managing the patient, the therapy may be initiated at a lower dose, perhaps about 3 mg to about 4 mg and increased up to about 12 mg or higher depending on the patient's global response.

Flumazenil

Flumazenil is a imidazodiazepine marketed under the tradename ROMAZICON®. Procedures for the preparation of flumazenil are described in U.S. Pat. No. 4,316,839. The pharmacological properties are described in W. Hunkeler et al. *Nature* 1981, 290, 514; S. E. File et al. *Psychopharmacol.* 1986, 89, 113; and A. Darragh et al. *Lancet* 1981, 2, 8.

Flumazenil has the chemical name 8-fluoro-5,6-dihydro-5-methyl-6-oxo-4H-imidazo[1,5-a][1,4]benzodiazepine-3-carboxylic acid ethyl ester and the structure is presented below.

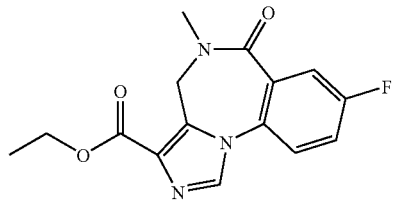

The size of a prophylactic or therapeutic dose of flumazenil, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.01 mg to about 4.0 mg. Preferably, a daily dose range should be between about 0.1 mg to about 2.0 mg. Most preferably, a daily dose range should be between about 0.2 mg to about 1.0 mg. In certain embodiments, the daily dose range should be about 0.4, 0.6, or 0.8 mg. In managing the patient, the therapy may be initiated at a lower dose, perhaps about 0.15 mg to about 0.17 mg and increased up to about 0.5 mg or higher depending on the patient's global response.

Gabapentin (NEURONTIN®)

Gabapentin is a GABA-receptor agonist marketed under the tradename NEURONTIN®. Procedures for the preparation of gabapentin are described in U.S. Pat. No. 4,024,175. The pharmacological properties are described in K.O. Vollmer et al. *Arzneimittel-Forsch.* 1986, 36, 830 and The US Gabapentin Study Group No. 5 *Neurology* 1993, 43, 2292. Gabapentin has the chemical name 1-(aminomethyl)cyclohexaneacetic acid and the structure is presented below.

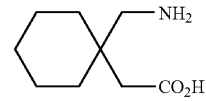

The size of a prophylactic or therapeutic dose of gabapentin, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 100 mg to about 3000 mg. Preferably, a daily dose range should be between about 450 mg to about 2400 mg. Most preferably, a daily dose range should be between about 900 mg to about 1800 mg. In certain embodiments, the daily dose range should be about 1100, 1300, 1500, or 1700 mg. In managing the patient, the therapy may be initiated at a lower dose, perhaps about 500 mg to about 700 mg and increased up to about 1400 mg or higher depending on the patient's global response. In general, children ages 3-12 years old are given a smaller dosage. For example, a child between the age of 3-12 years old may be given a dose in the range of about 10-15 mg/kg/day up to about 25-35 mg/kg/day. 2-Hydroxysaclofen 2-Hydroxysaclofen is a GABA-receptor antagonist that has the chemical name (RS)-3-amino-2-(4-chlorophenyl)-2-hydroxypropyl-sulphonic acid. 2-Hydroxysaclofen can be purchased from KOMA Biotech, Inc. The pharmacological properties are described in Kerr et al. *Neurosci. Lett.* 1988, 92, 92; Curtis et al. *Neurosci. Lett.* 1988, 92, 97. In general, the total daily dose range is from about 1 mg to about 2000 mg. Preferably, a daily dose range should be between about 5 mg to about 1000 mg. More preferably, a daily dose range should be between about 10 mg to about 250 mg. The structure of 2-hydroxysaclofen is presented below.

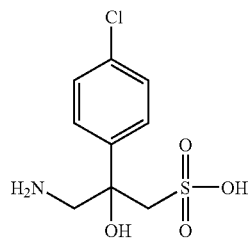

Isoguvacine

Isoguvacine is a GABA receptor agonist. The pharmacological properties of isoguvacine are described in Chebib, M.; Johnston, G. A. *Clin. Exp. Pharamacol Physiol.* 1999, 26, 937-940; X. Leinekugel et al. *J. Physiol.* 1995, 487, 319-29; and White, W. F.; Snodgrass, S. R. *J. Neurochem.* 1983, 40(6), 1701-8. In general, the total daily dose range is from about 1 mg to about 2000 mg. Preferably, a daily dose range should be between about 5 mg to about 1000 mg. More preferably, a daily dose range should be between about 10 mg to about 250 mg. The structure of isoguvacine is presented below.

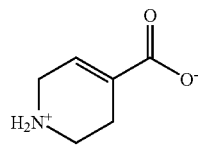

Lamotrigine (LAMICTAL®)

Lamotrigine is a GABA-receptor agonist marketed under the tradename LAMICTAL®. Procedures for the preparation of lamotrigine are described in U.S. Pat. No. 4,602,017 and EP 21,121. The pharmacological properties are described in A. F. Cohen et al. *Clin. Pharmacol. Ther.* 1987, 42, 535; *Epilepsia* 1991, 32(*Supp.* 2), S9-S21; and K. L. Goa et al. *Drugs* 1993, 46, 152-157. Lamotrigine has the chemical name 6-(2,3-dichlorophenyl)-l,2,4-triazine-3,5-diamine and the structure is presented below.

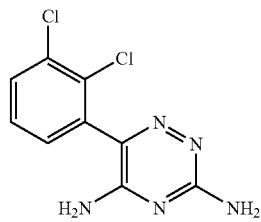

The size of a prophylactic or therapeutic dose of lamotrigine, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 1000 mg. Preferably, a daily dose range should be between about 25 mg to about 750 mg. Most preferably, a daily dose range should be between about 50 mg to about 500 mg. In certain embodiments, the daily dose range should be about 100, 200, 300 or 400 mg. In managing the patient, the therapy may be initiated at a lower dose, perhaps about 40 mg to about 75 mg and increased up to about 250 mg or higher depending on the patient's global response.

Lorazepam

Lorazepam is an antianxiety agent marketed under the tradename ATIVAN®. Procedures for the preparation of lorazepam are described in U.S. Pat. No. 3,296,249. The pharmacological properties are described in *Arzneimittel-Forsch.* 1971, 21, 1047-1102 and Ameer, B.; Greenblatt, D. J. *Drugs* 1981, 21, 161-200. Lorazepam has the chemical name 7-chloro-5-(2-chlorophenyl)-1,3-dihydro-3-hydroxy-2H-1,4-benzodiazepin-2-one and the structure is presented below.

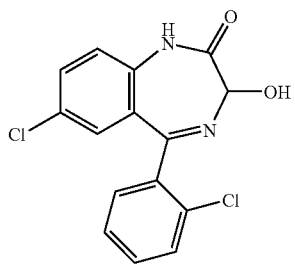

The size of a prophylactic or therapeutic dose of lorazepam, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.1 mg to about 20 mg. Preferably, a daily dose range should be between about 0.5 mg to about 13 mg. Most preferably, a daily dose range should be between about 1 mg to about 6 mg. In certain embodiments, the daily dose range should be about 2, 3, 4, or 5 mg. In managing the patient, the therapy may be initiated at a lower dose, perhaps about 0.6 mg to about 0.8 mg and increased up to about 1.5 mg or higher depending on the patient's global response.

L-655708

L-655708 is a benzodiazepine that binds selectively to the GABAA receptor. L-655708 has the chemical name 11,12,13,13a-tetrahydro-7-methoxy-9-oxo-9H-imidazo[1,5-a]pyrrolo[2,1-c] [1,4]benzodiazepine-1-carboxylic acid, ethyl ester. L-655708 can be purchased from KOMA Biotech, Inc. The pharmacological properties are described in Quirk et al. *Neuropharmacology* 1996, 35, 1331; Sur et al. *Mol. Pharmacol.* 1998, 54, 928; and Sur et al. *Brain Res.* 1999, 822, 265. In general, the total daily dose range is from about 1 mg to about 2000 mg. Preferably, a daily dose range should be between about 5 mg to about 1000 mg. More preferably, a daily dose range should be between about 10 mg to about 250 mg. The structure of L-655708 is presented below.

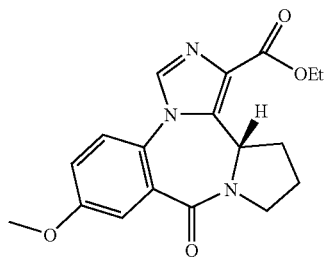

Midazolam

Midazolam is a short-acting derivative of diazepam. Procedures for the preparation of midazolam are described in U.S. Pat. No. 4,280,957. The pharmacological properties are described in *Brit. J Clin. Pharmacol.* 1983, 16 (*Supp.* 1), 1S-199S; J. W. Dundee et al. .Drugs 1984, 28, 519-543; and E. Lahat et al. *Brit. Med. J.* 2000, 321, 83. Midazolam has the chemical name 8-chloro-6-(2-fluorophenyl)-1-methyl-4H-imidazo[1,5-a] [1,4]benzodiazepine and the structure is presented below.

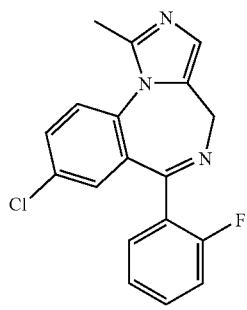

The size of a prophylactic or therapeutic dose of midazolam, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 0.5 mg to about 100 mg. Preferably, a daily dose range should be between about 1 mg to about 40 mg. Most preferably, a daily dose range should be between about 4 mg to about 20 mg. In certain embodiments, the daily dose range should be about 8, 12, or 16 mg. In managing the patient, the therapy may be initiated at a lower dose, perhaps about 2 mg to about 3 mg and increased up to about 6 mg or higher depending on the patient's global response.

Muscimol

Muscimol is a GABA-receptor agonist that has the chemical name 5-(aminomethyl)-3(2H)-isoxazolone. Procedures for the preparation of muscimol are described in Nakamura *Chem. Pharm. Bull.* 1971, 19, 46 and McCarry, B. E.; Savard, M. *Tetrahedron Letters* 1981, 22, 5153. The pharmacological properties are described in Theobald et al. *Arzneimittel-Forsch.* 1968, 18, 311 and F. V. DeFeudis *Neurochem. Res.* 1980, 5, 1047-1068. For additional information see U.S. Pat. Nos. 3,242,190 and 3,397,209. In general, the total daily dose range is from about 1 mg to about 2000 mg. Preferably, a daily dose range should be between about 5 mg to about 1000 mg. More preferably, a daily dose range should be between about 10 mg to about 250 mg. The structure of muscimol is presented below.

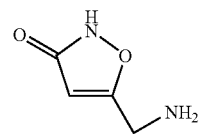

Phaclofen

Phaclofen is a GABA-receptor antagonist that has the chemical name 3-amino-2-(4-chlorophenyl)propylphosphonic acid. Phaclofen can be purchased from KOMA Biotech, Inc. The pharmacological properties are described in Kerr et al. *Brain Res.* 1987, 405, 150; Karlsson et al. *Eur. J. Pharmacol.* 1988, 148, 485; and Hasuo, Gallagher *Neurosci. Lett.* 1988, 86, 77. In general, the total daily dose range is from about 1 mg to about 2000 mg. Preferably, a daily dose range should be between about 5 mg to about 1000 mg. More preferably, a daily dose range should be between about 10 mg to about 250 mg. The structure of phaclofen is presented below.

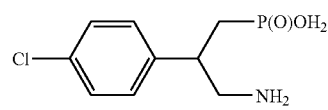

Phenytoin (DILANTIN®)

Phenytoin is a GABA-receptor agonist marketed under the tradename DILANTIN®. Procedures for the preparation of phenytoin are described in U.S. Pat. No. 2,409,754. The pharmacological properties are described in Gillis et al. *J Pharmacol. Exp. Ther.* 1971, 179, 599 and J. Philip et al. *Anal. Profiles Drug Subs.* 1984, 13, 417-445. In certain instances, the sodium salt of phenytoin is preferred. Phenytoin has the chemical name 5,5-diphenyl-2,4-imidazolidinedione and the structure is presented below.

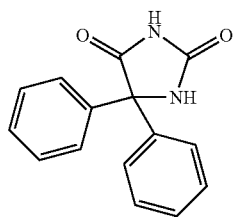

The size of a prophylactic or therapeutic dose of phenytoin, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 600 mg. Preferably, a daily dose range should be between about 15 mg to about 450 mg. Most preferably, a daily dose range should be between about 25 mg to about 300 mg. In certain embodiments, the daily dose range should be about 50, 100, 150, 200, or 250 mg. In managing the patient, the therapy may be initiated at a lower dose, perhaps about 10 mg to about 20 mg and increased up to about 75 mg or higher depending on the patient's global response.

Pregabalin

Pregabalin is an isobutyl analog of GABA developed by Pfizer in collaboration with researchers at Northwestern University. Pregabalin has a more linear relationship between drug plasma levels and the dosage of the drug compared to gabapentin. Procedures for the preparation of pregabalin are described in M. J. Burk et al. *J. Org Chem.* 2003, 68, 5731-5734. The pharmacological properties are described in Bayes, M.; Rabasseda, X.; Prous, J. R. *Methods Find Exp. Clin. Pharmacol.* 2004, 26(3), 211-44 and A. C. Pande et al. *J. Clin. Psychopharmacol.* 2004, 24(2), 141-9. For additional information see U.S. Pat. No. 6,028,214. Pregabalin has the chemical name (S)-(+)-3-aminomethyl-5-methylhexanoic acid and the structure is presented below.

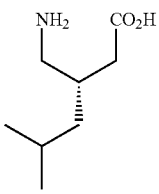

The size of a prophylactic or therapeutic dose of pregabalin, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 1200 mg. Preferably, a daily dose range should be between about 30 mg to about 800 mg. Most preferably, a daily dose range should be between about 75 mg to about 600 mg. In certain embodiments, the daily dose range should be about 100, 150, 250, 400, or 500 mg. In managing the patient, the therapy may be initiated at a lower dose, perhaps about 50 mg to about 65 mg and increased up to about 125 mg or higher depending on the patient's global response.

Progabide (GABRENE®)

Progabide is a GABA receptor antagonist marketed under the tradename GABRENE®. Procedures for the preparation of progabide are described in U.S. Pat. No. 4,094,992. The pharmacological properties are described in I. Johno et al. *J. Pharm. Sci.* 1982, 71, 633 and U.S. Pat. No. 4,361,583. Progabide has the chemical name 4-[[(4-chlorophenyl)-(5-fluoro-2-hydroxyphenyl)methylene]amino]butanamide and the structure is presented below.

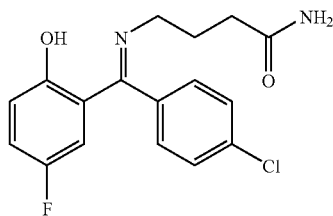

The size of a prophylactic or therapeutic dose of progabide, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg/kg/day to about 75 mg/kg/day. Preferably, a daily dose range should be between about 15 mg/kg/day to about 55 mg/kg/day. Most preferably, a daily dose range should be between about 25 mg/kg/day to about 45 mg/kg/day. In certain embodiments, the daily dose range should be about about 30, 35, or 40 mg/kg/day. In managing the patient, the therapy may be initiated at a lower dose, perhaps about 10 mg/kg/day to about 15 mg/kg/day and increased up to about 30 mg/kg/day or higher depending on the patient's global response.

Riluzole

Riluzole is a benzothiazole derivative marketed by Rhone Poulenc Rorer. Procedures for the preparation of riluzole are described in U.S. Pat. No. 4,370,338 and EP 50,551. The pharmacological properties are described in J. Mizoule et al. *Neuropharmacology* 1985, 24, 767 amd M. W. Debono et al. *Eur. J. Pharmacol.* 1993, 235, 283. Riluzole has the chemical name 6-(trifluoromethoxy)benzothiazolamine and the structure is presented below.

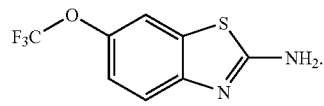

The size of a prophylactic or therapeutic dose of riluzole, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 250 mg. Preferably, a daily dose range should be between about 50 mg to about 175 mg. Most preferably, a daily dose range should be between about 80 mg to about 120 mg. In certain embodiments, the daily dose range should be about 90, 100, or 110 mg. In managing the patient, the therapy may be initiated at a lower dose, perhaps about 60 mg to about 70 mg and increased up to about 100 mg or higher depending on the patient's global response.

Saclofen

Saclofen is a GABA-receptor antagonist that has the chemical name (RS)-3-amino-2-(4-chlorophenyl)propylsulphonic acid. Saclofen can be purchased from KOMA Biotech, Inc. The pharmacological properties are described in Bowery TiPS. 1989, 10, 401; Kerr et al. *Neurosci. Lett.* 1989, 107, 239; and Jane et al. in *GABA$_B$ Receptors in Mammalian Function.* Eds. Bowery et al., p 42b, John Wiley & Sons, 1990, Chichester, U. K. In general, the total daily dose range is from about 1 mg to about 2000 mg. Preferably, a daily dose range should be between about 5 mg to about 1000 mg. More preferably, a daily dose range should be between about 10 mg to about 250 mg. The structure of saclofen is presented below.

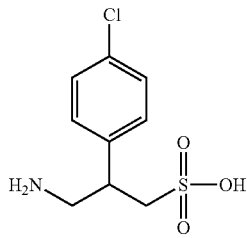

SCH 50911

SCH 50911 is a GABA-receptor antagonist that has the chemical name (2S)-5,5-dimethyl-2-morpholineacetic acid. SCH 50911 can be purchased from KOMA Biotech, Inc. The pharmacological properties are described in Bolser et al. *J. Pharmacol. Exp. Ther.* 1996, 274, 1393; Hosford et al. *J. Pharmacol. Exp. Ther.* 1996, 274, 1399; and Ong et al. *Eur. J. Pharmacol.* 1998, 362, 35. In general, the total daily dose range is from about 1 mg to about 2000 mg. Preferably, a daily dose range should be between about 5 mg to about 1000 mg. More preferably, a daily dose range should be between about 10 mg to about 250 mg. The structure of SCH 50911 is presented below.

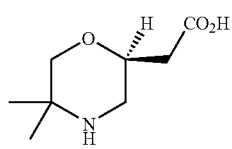

SKF 97541

SKF 97541 is a GABA-receptor agonist with the chemical name 3-aminopropyl(methyl)phosphinic acid. SKF 97541 is a white solid that is readily soluble in sater and dilute aqueous base. SKF 97541 can be purchased from A. G. Scientific, Inc. located in San Diego, Calif. The pharmacological properties are described in Hoskison, M. M.; Connor, J. A.; Shuttleworth, C. W. *Neurosci. Lett.* 2004, 365(1), 48-53 and Hue, B.; Amat, C. *J. Insect Physiol.* 1997, 43(12), 1125-1131. In certain instances, the hydrochloride salt is preferred. In general, the total daily dose range is from about 1 mg to about 2000 mg. Preferably, a daily dose range should be between about 5 mg to about 1000 mg. More preferably, a daily dose range should be between about 10 mg to about 250 mg. The structure of SKF 97541 is presented below.

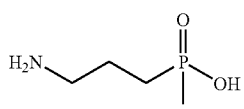

SR 95531

SR 95531 is a GABA-receptor antagonist. SR 95531 can be purchased from Tocris Cookson Inc. in Ellisville, MO. The pharmacological properties are described in B. M. Stell et al. *J. Neurosci.* 2002, 22(10), RC223. In general, the total daily dose range is from about I mg to about 2000 mg. Preferably, a daily dose range should be between about 5 mg to about 1000 mg. More preferably, a daily dose range should be between about 10 mg to about 250 mg. The structure of SR 95531 is presented below.

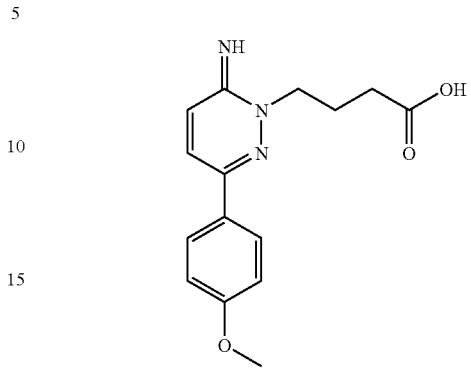

Tiagabine (GABITIRIL®)

Tiagabine is a GABA uptake inhibitor marketed under the tradename GABITIRIL®. Procedures for the preparation of tiagabine are described in U.S. Pat. No. 5,010,090 and K. E. Andersen et al. *J. Med. Chem.* 1993, 36, 1716. The pharmacological properties are described in C. L. Faingold et al. *Exp. Neurology* 1994, 126, 225 and W. J. Giardina *J. Epilepsy* 1994, 7, 161-166. Tiagabine has the chemical name (R)-1-[4,4-bis(3-methyl-2-thienyl)-3-butenyl]-3-piperidinecarboxylic acid and the structure is presented below.

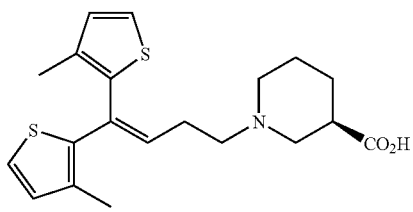

The size of a prophylactic or therapeutic dose of tiagabine, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about I mg to about 100 mg. Preferably, a daily dose range should be between about 15 mg to about 50 mg. Most preferably, a daily dose range should be between about 30 mg to about 35 mg. In certain embodiments, the daily dose range should be about 32 or 34 mg. In managing the patient, the therapy may be initiated at a lower dose, perhaps about 5 mg to about 10 mg and increased up to about 20 mg or higher depending on the patient's global response.

TPMPA

TPMPA is a GABA-receptor antagonist. TPMPA can be purchased from Tocris Cookson Inc. in Ellisville, Mo. The pharmacological properties of TPMPA are described in K. Schlicker et al. *Brain Res. Bull.* 2004, 63(2), 91-7. In general, the total daily dose range is from about 1 mg to about 2000 mg. Preferably, a daily dose range should be between about 5 mg to about 1000 mg. More preferably, a daily dose range should be between about 10 mg to about 250 mg. The structure of isoguvacine is presented below.

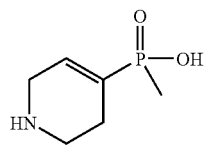

Topiramate (TOPAMAX®)

Topiramate is a fructopyranose derivative marketed under the tradename TOPAMAX®. Procedures for the preparation of topiramate are described in U.S. Pat. No. 4,513,006. The pharmacological properties are described in M. Bialer Clin. Pharmacokinet. 1993, 24, 441 and B. E. Maryanoff et al J. Med. Chem. 1987, 30, 880. Topiramate has the chemical name 2,3:4,5-bis-O-(1-methylethylidene)-β-D-fructopyranose sulfamate and the structure is presented below.

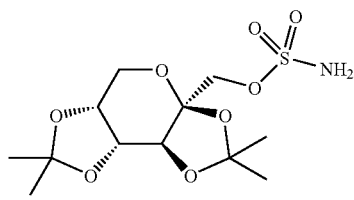

The size of a prophylactic or therapeutic dose of topiramate, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 400 mg. Preferably, a daily dose range should be between about 100 mg to about 300 mg. Most preferably, a daily dose range should be between about 170 mg to about 230 mg. In certain embodiments, the daily dose range should be about 180, 190, 200, 210, or 220 mg. In managing the patient, the therapy may be initiated at a lower dose, perhaps about 125 mg to about 150 mg and increased up to about 175 mg or higher depending on the patient's global response. In general, children a given a smaller dosage.

Valproic Acid

Valproic acid has the chemical name 2-propylpentanoic acid and is used to treat migraine headaches and prevent seizures in people suffering from epilepsy. Procedures for the preparation of valproic acid are described in Weimann, Thuan Bull. Soc. Chim. France 1958, 199. The pharmacological properties are described in Rimmer, E. M.; Richens, A. Pharmacother. 1985, 5, 171-184 and Z. L. Chang in Analytical Profiles of Drug Substances vol. 8, K. Florey, Ed. (Academic Press, New York, 1979) pp 529-556. The structure of valproic acid is presented below.

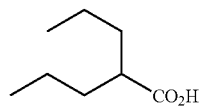

The size of a prophylactic or therapeutic dose of valproic acid, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 5 mg to about 900 mg. Preferably, a daily dose range should be between about 25 mg to about 700 mg. Most preferably, a daily dose range should be between about 50 mg to about 500 mg. In certain embodiments, the daily dose range should be about 100, 200, 300 or 400 mg. In managing the patient, the therapy may be initiated at a lower dose, perhaps about 20 mg to about 40 mg and increased up to about 75 mg or higher depending on the patient's global response.

Vigabatrin

Vigabatrin has the chemical name 4-amino-5-hexenoic acid and is used to prevent seizures in people suffering from epilepsy. Procedures for the preparation of vigabatrin are described in U.S. Pat. No. 3,960,927. The pharmacological properties are described in K. D. Haegele et al. Clin. Pharmacol. Ther. 1986, 40, 581 and Grant, S. M.; Heel, R. C. Drugs 1991, 41, 889-926. The structure of vigabatrin is presented below.

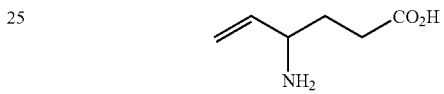

The size of a prophylactic or therapeutic dose of vigabatrin, or one of its salts, in the acute or chronic management of disease will vary with the severity of the condition to be treated and the route of administration. The dose, and perhaps the dose frequency, will also vary according to the age, body weight, and response of the individual patient. In general, the total daily dose ranges, for the conditions described herein, is from about 100 mg to about 5000 mg. Preferably, a daily dose range should be between about 500 mg to about 4000 mg. Most preferably, a daily dose range should be between about 1000 mg to about 3000 mg. In certain embodiments, the daily dose range should be about 1200, 1500, 2000, or 2500 mg. In managing the patient, the therapy may be initiated at a lower dose, perhaps about 700 mg to about 900 mg and increased up to about 1300 mg or higher depending on the patient's global response.

Additional GABA receptor modulating compounds amenable to the present invention include the GABA receptor agonists described in U.S. Patent Application 20030162754 and WO 02/06786, which are hereby incorporated by reference. For example, compounds amenable to the present invention include 4-amino-3-phenylbutanoic acid, 4-amino-3-hydroxybutanoic acid, 4-amino-3-(4-chlorophenyl)-3-hydroxyphenylbutanoic acid, 4-amino-3-(thien-2-yl)butanoic acid, 4-amino-3-(5-chlorothien-2-yl)butanoic acid, 4-amino-3-(5-bromothien-2-yl)butanoic acid, 4-amino-3-(5-methylthien-2-yl)butanoic acid, 4-amino-3-(2-imidazolyl)butanoic acid, 4-guanidino-3-(4-chlorophenyl) butanoic acid, 3-amino-2-(4-chlorophenyl)-1-nitropropane, (3-aminopropyl)phosphonous acid, (4-aminobut-2-yl)phosphonous acid, (3-amino-2-methylpropyl)phosphonous acid, (3-aminobutyl)phosphonous acid, (3-amino-2-(4-chlorophenyl)propyl) phosphonous acid, (3-amino-2-(4-chlorophenyl)-2-hydroxypropyl)phosphonous acid, (3-amino-2-(4-fluorophenyl) propyl) phosphonous acid, (3-amino-2-phenylpropyl) phosphonous acid, (3-amino-2-hydroxypropyl )phosphonous acid, (E)-(3-aminopropen-1-yl)phosphonous acid, (3-amino-2-cyclohexylpropyl) phosphonous acid, (3-amino-2-benzylpropyl)phosphonous acid, [3-amino-2-(4-methylphenyl)propyl]phosphonous acid, [3-amino-2-(4-trifluoromethylphenyl)propyl]phosphonous acid, [3-amino-2-(4-methoxyphenyl)propyl]phosphonous acid, [3-amino-2-(4-chlorophenyl)-2-hydroxypropyl]phosphonous acid, (3-aminopropyl)methylphosphinic acid, (3-amino-2-hydroxypropyl)methylphosphinic acid, (3-aminopropyl)(difluoromethyl)phosphinic acid, (4-aminobut-2-yl)methylphosphinic acid, (3-amino-1-hydroxypropyl)methylphosphinic acid, (3-amino-2-hydroxypropyl)(difluoromethyl)phosphinic acid, (E)-(3-aminopropen-1-yl)methylphosphinic acid, (3-amino-2-oxo-propyl)methyl phosphinic acid, (3-aminopropyl) hydroxymethylphosphinic acid, (5-aminopent-3-yl)methylphosphinic acid, (4-amino-1,1,1-trifluorobut-2-yl)methylphosphinic acid, (3-amino-2-(4-chlorophenyl)propyl)sulfinic acid, and 3-aminopropylsulfinic acid.

Additional GABA receptor modulating compounds amenable to the present invention include the GABA receptors agonsits described in U.S. Pat. No. 6,399,608; which is hereby incorporated by reference. For example, compounds amenable to the present invention include 3,7-diphenyl-6-(2-pyridyl)methyloxy-1,2,4-triazolo[4,3-b]pyridazine; 7,8-dimethyl-3-phenyl-6-(2-pyridyl)methyloxy-1,2,4-triazolo [4,3-b]pyridazine; 7-methyl-3-phenyl-6-(2-pyridyl) methyloxy-1,2,4-triazolo[4,3-b]pyridazine; b 7-ethyl-3-phenyl-6-(2-pyridyl)methyloxy-1,2,4-triazolo[4,3-b] pyridazine; 8-methyl-3,7-diphenyl-6-(2-pyridyl)methyloxy-1,2,4-triazolo[4,3-b]pyridazine; 3-phenyl-7-(piperidin-1-yl)-6-(pyridin-2-ylmethoxy)-1,2,4-triazolo[4,3-b] pyridazine; 3-phenyl-7-(pyridin-4-yl)-6-(pyridin-2-ylmethoxy)-1,2,4-triazolo[4,3-b]pyridazine; 3-phenyl-6-(pyridin-2-ylmethoxy)-7-(thiophen-2-yl)-1,2,4-triazolo[4,3-b]pyridazine; 3-phenyl-6-(pyridin-2-ylmethoxy)-7-(thiophen-3-yl)-1,2,4-triazolo[4,3b]pyridazine; 6-(1-methyl-1H-1,2,4-triazol-3-ylmethoxy)-3,7-diphenyl-1,2,4-triazolo [4,3-b ]pyridazine; 6-(2-methyl-2H-1,2,4-triazol-3-ylmethoxy)-3,7-diphenyl-1,2,4-triazolo [4,3-b ]pyridazine; 3,7-diphenyl-6-(2H-1,2,4-triazol-3-ylmethoxy)-1,2,4-triazolo[4,3-b]pyridazine; 6-(2-methyl-2H-tetrazol-5-yl-methoxy)-3,7-diphenyl-1,2,4-triazolo[4,3-b]-pyr idazine; 3,7-diphenyl-6-(2-propyl-2H-1,2,4-triazol-3-ylmethoxy)-1, 2,4-triazolo[4,3-b ]pyridazine; 3,7-diphenyl-6-(1-propyl-1H-1,2,4-triazol-3-ylmethoxy)-1,2,4-triazolo [4,3-b ]pyridazine; 6-(1-methyl-1H-imidazol-4-ylmethoxy)-3,7-diphenyl-1,2,4-triazolo[4,3-b]pyridazine; 6-(3-methyl-3H-imidazol-4-ylmethoxy)-3,7-diphenyl-1,2,4-triazolo[4,3-b] pyridazine; 6-(4-methyl-4H-1,2,4-triazol-3-ylmethoxy)-3,7-diphenyl-1,2,4-triazolo[4,3-b]pyridazine; 6-(5-methyl-2H-1, 2,4-triazol-3-ylmethoxy)-3,7-diphenyl-1,2,4-triazolo[4,3-b] pyridazine; 6-(3-methyl-3H-1,2,3-triazol-4-ylmethoxy)-3,7-diphenyl-1,2,4-triazolo [4,3-b]pyridazine; 3-(4-methoxyphenyl)-6-(1-methyl-1H-1,2,4-triazol-3-ylmethoxy)-7-phenyl-1,2, 4-triazolo[4,3-b]pyridazine; 6-(3-methylpyridin-2-ylmethoxy)-3-phenyl-7-(piperidin-1-yl)-1, 2,4-triazolo[4,3-b]pyridazine; 7-(morpholin-4-yl)-3-phenyl-6-(pyridin-2-ylmethoxy)-1,2,4-triazolo [4,3-b]pyridazine; 3-phenyl-7-(pyridin-3-yl)-6-(pyridin-2-ylmethoxy)-1,2,4-triazolo[4,3-b]pyridazine; 8-methyl-6-(2-methyl-2H-1,2,4-triazol-3-ylmethoxy)-3,7-diphenyl-1,2,4-triazolo[4,3-b]pyridazine; 6-(1-methyl-1H-1,2,4-triazol-3-ylmethoxy)-7-(morpholin-4-yl)-3-phenyl-1,2,4-triazolo[4,3-b]pyridazine; 6-(2-methyl-2H-1,2,4-triazol-3-ylmethoxy)-7-(morpholin-4-yl)-3-phenyl-1,2,4-triazolo[4,3-b]pyridazine; 7-cyclohexyl-6-(2-methyl-2H-1,2,4-triazol-3-ylmethoxy)-3-phenyl-1,2,4-triazolo[4,3-b]pyridazine; 7-cyclohexyl-6-(1-methyl-1H-1,2,4-triazol-3-ylmethoxy)-3-phenyl-1,2,4-triaz olo [4,3-b]pyridazine; 7-cyclopentyl-6-(2-methyl-2H-1,2,4-triazol-3-ylmethoxy)-3-phenyl-1,2,4-triazolo[4,3-b]pyridazine; 8-methyl-6-(1-methyl-1H-1,2,4-triazol-3-ylmethoxy)-3,7-diphenyl-1,2,4-triazolo[4,3-b]pyridazine; 7-cyclobutyl-6-(1-methyl-1H-1,2,4-triazol-3-ylmethoxy)-3-phenyl-1,2,4-triaz olo[4,3-b]pyridazine; 7-tert-butyl-6-(2-methyl-2H-1,2,4-triazol-3-ylmethoxy)-3-phenyl-1,2,4-triazolo[4,3-b]pyridazine; 7-cyclobutyl-6-(2-methyl-2H-1,2,4-triazol-3-ylmethoxy)-3-phenyl-1,2,4-triazolo [4,3-b] pyridazine; 7-ethyl-6-(2-methyl-2H-1,2,4-triazol-3-ylmethoxy)-3-phenyl-1,2,4-triazolo [4,3-b]pyridazine; 7-tert-butyl-6-(1-methyl-1H-1,2,4-triazol-3-ylmethoxy)-3-phenyl-1,2,4-triazolo[4,3-b]pyridazine; 7-ethyl-6-(1-methyl-1H-1,2,4-triazol-3-ylmethoxy)-3-phenyl-1,2,4-triazolo [4,3-b]pyridazine; 7-methyl-6-(2-methyl-2H-1,2,4-triazol-3-ylmethoxy)-3-phenyl-1,2,4-triazolo [4,3-b]pyridazine; 7-(1-methylcyclobutyl)-6-(2-methyl-2H-1,2,4-triazol-3-ylmethoxy)-3-phenyl-1,2,4-triazolo[4,3-b]pyridazine; 7-methyl-6-(1-methyl-1H-1,2,4-triazol-3-ylmethoxy)-3-phenyl-1,2,4-triazolo[4,3-b]pyridazine; 7-cyclobutyl-3-phenyl-6-(2H-1,2,4-triazol-3-ylmethoxy)-1,2,4-triazolo[4,3-b ] pyridazine; 7-cyclopentyl-6-(pyridin-2-ylmethoxy)-3-(thiophen-2-yl)-1,2,4-triazolo[4,3-b]pyridazine; 7-cyclopentyl-3-(2,4-difluorophenyl)-6-(1-methyl-1H-1,2,4-triazol-3-ylmethoxy)-1,2,4-triazolo[4,3-b)pyridazine; 7-cyclopentyl-6-(1-methyl-1H-1,2,4-triazol-3-ylmethoxy)-3-(thiophen-2-yl)-1,2,4-triazolo[4,3-b]pyridazine; 7-cyclopentyl-6-(2-methyl-2H-1,2,4-triazol -3-ylmethoxy)-3-(thiophen-2-yl)-1, 2,4-triazolo [4,3-b]pyridazine; 7-cyclopentyl-6-(2-methyl-2H-1,2,4-triazol-3-ylmethoxy)-3-(pyridin-4-yl)-1,2,4-triazolo[4,3-b]pyridazine; 7-cyclopentyl-3-(2-fluorophenyl)-6-(1-methyl-1H-1,2,4-triazol-3-ylmethoxy)-1,2,4-triazolo[4,3-b]pyridazine; 7-cyclopentyl-3-(2-fluorophenyl)-6-(2-methyl-2H-1,2,4-triazol-3-ylmethoxy)-1,2,4-triazolo[4,3-b]pyridazine; 7-cyclopentyl-3-(2-fluorophenyl)-6-(pyridin-2-ylmethoxy)-1,2,4-triazolo[4,3-b]pyridazine; 7-cyclopentyl-3-(2,4-difluorophenyl)-6-(2-methyl-2H-1,2,4-triazol-3-ylmethoxy)-1,2,4-triazolo[4,3-b] pyridazine; 7-cyclopentyl-3-phenyl-6-(pyridin-2-ylmethoxy)-1,2,4-triazolo(4,3-b)pyridazine; 7-cyclopentyl-8-methyl-6-(2-methyl-2H-1,2,4-triazol-3-ylmethoxy)-3-phenyl-1,2,4-triazolo[4,3b]pyridazine; 7-cyclopentyl-3-phenyl-6-(2H-1,2,4-triazol-3-ylmethoxy)-1,2,4-triazolo[4, 3-b]pyridazine; 3-(4-methylphenyl)-7-phenyl-6-(pyridin-2-ylmethoxy)-1,2,4-triazolo[4,3-b]pyridazine; 3-(4-methylphenyl)-6-(3-methylpyridin-2-ylmethoxy)-7-phenyl-1,2,4-triazolo[4,3-b]pyridazine; 6-(1-ethyl-1H-imidazol-2-ylmethoxy)-3-(4-methylphenyl)-7-phenyl-1,2,4-triazolo [4,3-b]pyridazine; 3-phenyl-6-(pyridin-2-ylmethoxy)-7-(thiomorpholin-4-yl)-1,2,4-triazolo[4,3-b]pyridazine; 6-[2-(4-methylthiazol-5-yl)ethoxy]-3,7-diphenyl-1,2,4-triazolo [4,3-b]pyridazine; (±)-7-(2-methylpyrrolidin-1-yl)-3-phenyl-6-(pyridin-2-ylmethoxy)-1,2,4-triazolo [4,3-b] pyridazine; 6-(1-methyl-1H-1,2,4-triazol-3-ylmethoxy)-3-phenyl-7-(pyridin-4-yl)-1,2,4-triazolo[4,3-b]pyridazine; 7-cyclopentyl-6-(1-methyl-1H-1,2,4-triazol-3-ylmethoxy)-3-phenyl-1,2,4-tria zolo[4,3-b]pyridazine; 7-isopropyl-6-(1-methyl-1H-1,2,4-triazol-3-ylmethoxy)-3-phenyl-1,2,4-triazolo[4,3b]pyridazine; 3-cyclopropyl-6-(1-methyl-1H-1,2,4-triazol-3-ylmethoxy)-7-phenyl-1,2,4-triazolo[4,3-b] pyridazine; 3-(2-fluorophenyl)-6-(2-methyl-2H-1,2,4-triazol-3-ylmethoxy)-7-phenyl-1,2,4-triazolo[4,3-b] pyridazine; 3-(2-fluorophenyl)-6-(1-methyl-1H-1,2,4-triazol-3-ylmethoxy)-7-phenyl-1,2,4-triazolo[4,3-b] pyridazine; 6-(1-methyl-1H-1,2,4-triazol-3-ylmethoxy)-7-phenyl-3-(thiophen-2-yl)-1,2,4-triazolo[4,3-b]pyridazine; 6-(1-methyl-1H-1,2,4-triazol-3-ylmethoxy)-7-phenyl-3-

(pyridin-3-yl)-1,2,4-triazolo[4,3-b]pyridazine; 6-(2-methyl-2H-1,2,4-triazol-3-ylmethoxy)-7-phenyl-3-(thiophen-2-yl)-1,2,4-triazolo[4,3-b]pyridazine; 6-(2-methyl-2H-1,2,4-triazol-3-ylmethoxy)-7-phenyl-3-(pyridin-3-yl)-1,2,4-triazolo [4,3-b]pyridazine; 3-(furan-3-yl)-6-(1-methyl-1 H-1,2,4-triazol-3-ylmethoxy)-7-phenyl-1,2,4-triazolo[4,3-b]pyridazine; 6-(1-methyl-1H-1,2,4-triazol-3-ylmethoxy)-7-phenyl-3-(thiophen-2-yl)-1,2,4-triazolo[4,3-b]pyridazine; 6-(5-methyl-1,2,4-oxadiazol-3-ylmethoxy)-3,7-diphenyl-1,2,4-triazolo[4,3-b]pyridazine; 7-phenyl-3-(thiophen-2-yl)-6-(2H-1,2,4-triazol-3-ylmethoxy)-1,2,4-triazolo[4,3-b] pyridazine; 3-(furan-2-yl)-6-(1-methyl-1H-1,2,4-triazol-3-ylmethoxy)-7-phenyl-1,2,4-triazolo [4,3-b]pyridazine; 6-(1-methyl-1H-1,2,4-triazol-3-ylmethoxy)-3-phenyl-7-(thiophen-3-yl)-1,2,4-triazolo[4,3-b]pyridazine; 6-(2-methyl-2H-1,2,4-triazol-3-ylmethoxy)-7-(thiophen-3-yl)-1,2,4-triazolo [4,3b]pyridazine; 3-phenyl-7-(thiophen-3-yl)-6-(2H-1,2,4-triazol-3-ylmethoxy)-1,2,4-triazolo[4,3-b]pyridazine; 6-(2-methyl-2H-1,2,4-triazol-3-ylmethoxy)-3-phenyl-7-(thiophen-2-yl)-1,2,4-triazolo[4,3-b]pyridazine; 6-(1-methyl-1H-1,2,4-triazol-3-ylmethoxy)-3-phenyl-7-(thiophen-2-yl)-1,2,4-triazolo[4,3-b]pyridazine; 7-(furan-2-yl)-6-(2-methyl-2H-1,2,4-triazol-3-ylmethoxy)-3-phenyl-1,2,4-triazolo[4,3-b]pyridazine; 7-(furan-2-yl)-6-(1-methyl-1H-1,2,4-triazol-3-ylmethoxy)-3-phenyl-1,2,4-triazolo[4,3-b]pyridazine; 6-(3-methyl-1,2,4-oxadiazol-5-ylmethoxy)-3,7-diphenyl-1,2,4-triazolo[4,3-b]pyridazine; 3-(4-fluorophenyl)-6-(1-methyl-1H-1,2,4-triazol-3-ylmethoxy)-7-phenyl-1,2,4-triazolo[4,3-b]pyridazine; 3,7-diphenyl-6-(2H-1,2,3-triazol-4-ylmethoxy)-1,2,4-triazolo [4,3-b] pyridazine; 3,7-diphenyl-6-(pyrazin-2-ylmethoxy)-1,2,4-triazolo[4,3-b]pyridazine; 3-(4-methylphenyl)-6-(1-1H-1,2,4-triazol-3-ylmethoxy)-7-phenyl-1,2,4-triazolo[4,3-b]pyridazine; 6-(4-methylthiazol-2-ylmethoxy)-3,7-diphenyl-1,2,4-triazolo[4,3-b]pyridazine; 6-(5-methylthiazol-2-ylmethoxy)-3,7-diphenyl-1,2,4-triazolo[4,3-b]pyridazine; 3,7-diphenyl-6-(pyrimidin-4-ylmethoxy)-1,2,4-triazolo[4,3-b]pyridazine; 3,7-diphenyl-6-(pyridazin-3-ylmethoxy)-1,2,4-triazolo[4,3-b]pyridazine; 6-(1-methyl-1H-1,2,4-triazol-3-ylmethoxy)-7-(morpholin-4-yl)-3-(thiophen-2-yl)-1,2,4-triazolo [4,3-b]pyridazine; 3,7-diphenyl-6-(thiazol-4-ylmethoxy)-1,2,4-triazolo[4,3-b] pyridazine; 6-(5-methylisoxazol-3-ylmethoxy)-3,7-diphenyl-1,2,4-triazolo[4,3-b]pyridazine; 3-(3-fluorophenyl)-6-(1-methyl-1H-1,2,4-triazol-3-ylmethoxy)-7-(morpholin-4-yl)-1,2,4-triazolo[4,3-b]pyridazine; 3,7-diphenyl-6-(pyrimidin-2-ylmethoxy)-1,2,4-triazolo[4,3-b]pyridazine; 6-(2-methyl-2H-1,2,3-triazol-4-ylmethoxy)-3,7-diphenyl-1,2,4-triazolo[4,3-b]pyridazine; 7-(1-methylcyclobutyl)-6-(1-methyl-1H-1,2,4-triazol-3-ylmethoxy)-3-phenyl-1,2,4-triazolo[4,3-b]pyridazine; 7-isopropyl-6-(2-methyl-2H-1,2,4-triazol-3-ylmethoxy)-3-phenyl-1,2,4-triazolo[4,3-b]pyridazine; 7-tert-butyl-3-(2-fluorophenyl)-6-(1-methyl-1H-1,2,4-triazol-3-ylmethoxy)-1,2,4-triazolo[4,3-b]pyridazine; 7-cyclopentyl-3-(4-methoxyphenyl)-6-(2-methyl-2H-1,2,4-triazol-3-ylmethoxy)-1,2,4-triazolo[4,3-b]pyridazine; 7-(1-methylcyclopentyl)-6-(1-methyl-1H-1,2,4-triazol-3-ylmethoxy)-3-phenyl-1,2,4-triazolo[4,3-b]pyridazine; 7-(1-methylcyclopentyl)-6-(2-methyl-2H-1,2,4-triazol-3-ylmethoxy)-3-phenyl-1,2,4-triazolo[4,3-b]pyridazine; 7-cyclopentyl-3-(furan-2-yl)-6-(2-methyl-2H-1,2,4-triazol-3-ylmethoxy)-1,2,4-triazolo[4,3-b]pyridazine; 7-cyclopentyl-3-(furan-2-yl)-6-(1-methyl-1H-1,2,4-triazol-3-yl-methoxy)-1,2,4-triazolo[4,3-b]pyridazine; 3-(3,7-diphenyl-1,2,4-triazolo[4,3-b]pyridazin-6-yloxymethyl)-1,2,4-triazol-1-ylacetonitrile; 7-(1-methylcyclopropyl)-6-(2-methyl-2H-1,2,4-triazol-3-ylmethoxy)-3-phenyl-1,2,4-triazolo[4,3-b]pyridazine; 7-(1-methylcyclopropyl)-6-(1-methyl-1H-1,2,4-triazol-3-ylmethoxy)-3-phenyl-1,2,4-triazolo[4,3-b]pyridazine; 3-(3-fluorophenyl)-6-(1-methyl-1H-1,2,4-triazol-3-ylmethoxy)-7-phenyl-1,2,4-triazolo[4,3-b]pyridazine; 7-(1-methylcyclopentyl)-6-(3-methylpyridin-2-ylmethoxy)-3-phenyl-1,2,4-triazolo[4,3-b]pyridazine; 6-(1-methyl-1H-1,2,3-triazol-4-ylmethoxy)-3,7-diphenyl-1,2,4-triazolo[4,3-b ]pyridazine; 3-(5-methylthiophen-2-yl)-6-(1-methyl-1H-1,2,4-triazol-3-ylmethoxy)-7-phenyl-1,2,4-triazolo[4,3-b]pyridazine; 2-[3-(3,7-diphenyl-1,2,4-triazolo[4,3-b]pyridazin-6-yloxymethyl)-1,2,4-triazol-1-yl]-N,N-dimethylacetamide; 3,7-diphenyl-6-[1-(pyridin-2-ylmethyl)-1 H-1,2,4-triazol-3-ylmethoxy]-1,2,4-triazolo [4,3-b] pyridazine; 6-(1-benzyl-1H-1,2,4-triazol-3-ylmethoxy)-3,7-diphenyl-1,2,4-triazolo[4,3-b ]pyridazine; 2-[5-(3,7-diphenyl-1,2,4-triazolo[4,3-b]pyridazin-6-yloxymethyl)-1,2,4-triazol-1-yl]acetamide; N-[2-[3-(3,7-diphenyl-1,2,4-triazolo [4,3-b]pyridazin-6-yloxymethyl)-1,2,4-triazol-1-yl]ethyl]-N,N-dimethylamine; 3,7-diphenyl-6-(pyrimidin-5-ylmethoxy)-1,2,4-triazolo[4,3-b]pyridazine; 6-[1-(2-(morpholin-4-yl)-ethyl)-1H-1,2,4-triazol-3-ylmethoxy]-3,7-diphenyl-1,2,4-triazolo[4,3-b]pyridazine; 6-(2-methyl-2H-1,2,4-triazolo[4,3-b]pyridazine; 6-(2-methyl-2H-1,2,4-triazol-3-ylmethoxy)-3-phenyl-7-(pyrrolidin-1-yl)-1,2,4-triazolo[4,3-b]pyridazine; 7-(5-chlorothiophen-2-yl)-6-(2-methyl-2H-1,2,4-triazol-3-ylmethoxy)-3-phenyl-1,2,4-triazolo[4,3-b]pyridazine; 7-(5-chlorothiophen-2-yl)-6-(1-methyl-1H-1,2,4-triazol-3-ylmethoxy)-3-phenyl-1,2,4-triazolo[4,3-b]pyridazine; 6-(1H-benzimidazol-2-ylmethoxy)-3-(2,4-difluorophenyl)-7-(1-methylcyclopentyl)-1,2,4-triazolo [4,3-b]pyridazine; 2-[3-(3,7-diphenyl-1,2,4-triazolo [4,3-b]pyridazin-6-yloxymethyl)-1,2,4-triazol-1-yl]ethylamine; 3,7-diphenyl-6-[1-(2-(pyrrolidin-1-yl)ethyl)-1H-1,2,4-triazol-3-ylmethoxy]-1,2,4-triazolo[4,3-b]pyridazine; 6-[1-(1-methylpiperidin-4-yl)-1 H-1,2,4-triazol-3-ylmethoxy]-3,7-diphenyl-1,2,4-triazolo[4,3-b]pyridazine; 3,7-diphenyl-6-[1-(2-(piperazin-1-yl)ethyl)-1H-1,2,4-triazol-3-ylmethoxy]-1,2,4-triazolo[4,3-b]pyridazine; 7-(1-methylcyclopentyl)-6-(2-methyl-2H-1,2,4-triazol-3-ylmethoxy)-3-(2,4-difluorophenyl)-1,2,4-triazolo[4,3-b]pyridazine; 7-(cyclobut-1-enyl)-6-(2-methyl-2H-1,2,4-triazol-3-ylmethoxy)-3-phenyl-1,2,4-triazolo[4,3-b]pyridazine; 7-(furan-3-yl)-6-(1-methyl-1H-1,2,4-triazol-3-ylmethoxy)-3-phenyl-1,2,4-triazolo [4,3-b]pyridazine; N,N-diethyl-N-[6-(1-methyl-1H-1,2,4-triazol-3-ylmethoxy)-3-phenyl-1,2,4-triazolo [4,3-b] pyridazin-7-yl]amine; 7-(1-methylcyclopentyl)-6-(1-methyl-1H-1,2,4-triazol-3-ylmethoxy)-3-(2,4-difluorophenyl)-1,2,4-triazolo[4,3-b]pyridazine; 7-(1,1-dimethylpropyl)-6-(1-methyl-1H-1,2,4-triazol-3-ylmethoxy)-3-phenyl-1,2,4-triazolo[4,3-b]pyridazine; 6-(2-methyl-2H-1,2,4-triazol-3-ylmethoxy)-3-(4-fluorophenyl)-7-(thiophen-3-yl)-1,2,4-triazolo[4,3-b]pyridazine; 6-(1-methyl-1H-1,2,4-triazol-3-ylmethoxy)-3-(4-fluorophenyl)-7-(thiophen-3-yl)-1,2,4-triazolo[4,3-b]pyridazine; 6-(2-methyl-2H-1,2,4-triazol-3-ylmethoxy)-3-(2-fluorophenyl)-7-(thiophen-3-yl)1,2,4-triazolo[4,3-b]pyridazine; 3-(2-fluorophenyl)-7-(1-methylcyclobutyl)-6-(2-methyl-2H-1,2,4-triazol-3-yl methoxy)-1,2,4-triazolo[4,3-b]pyridazine; 3-(2-fluorophenyl)-7-(1-methylcyclobutyl)-6-(1-methyl-1H-1,2,4-triazol-3-yl methoxy)-1,2,4-triazolo[4,3-b]pyridazine; 6-(1-methyl-1H-1,2,4-triazol-3-ylmethoxy)-3(2-fluorophenyl)-7-(thiophen-3-yl)-1,2,4-triazolo[4,3-b]pyridazine; 8-methyl-7-(1-methylcyclobutyl)-6-(1-methyl-1H-1,2,4-triazol-3-ylmethoxy)-3-phenyl-1,2,4-triazolo[4,3-b]pyridazine; 8-methyl-7-(1-methylcyclobutyl)-6-(2-methyl-2H-1,2,4-triazol-3-ylmethoxy)-3-phenyl-1,2,4- triazolo [4,3-b]pyridazine; 6-(1-methyl-1H-1,2,4-triazol-3-ylmethoxy)-3-phenyl-7-(pyrrolidin-1-yl)-1,2,4-triazolo[4,3-b]pyridazine; 7-cyclobutyl-8-methyl-6-(2-methyl-2H-1,2,4-triazol-3-ylmethoxy)-3-phenyl-1,2,4-triazolo[4,3-b]pyridazine; 7-cyclobutyl-8-methyl-6-(1-methyl-1H-1,2,4-triazol-3-ylmethoxy)-3-phenyl-1, 2,4-triazolo[4,3-b]pyridazine; 7-(1-methylcyclopentyl)-6-(2-methyl-2H-1,2,4-triazol-3-ylmethoxy)-3-(2-fluorophenyl)-1,2,4-triazolo[4,3-b]pyridazine; and 7-(1-methylcyclopentyl)-6-(1-methyl 1H-1,2,4-triazol-3-ylmethoxy)-3-(2-fluorophenyl)-1,2,4-triazolo[4,3-b]pyridazine.

Additional GABA modulating agents for use in the present invention are 3-amino-propyl phosphinic acid and (1S,2R)-(+)-2-(aminomethyl)-cyclopropane-1-carboxylate. The structure of 3-amino-propyl phosphinic acid is presented below.

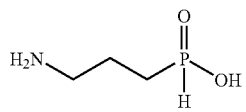

The structure of (1S,2R)-(+)-2-(aminomethyl)-cyclopropane-1-carboxylate is presented below.

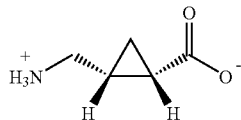

Combination Therapy

One aspect of the present invention relates to combination therapy. This type of therapy is advantageous because the co-administration of active ingredients achieves a therapeutic effect that is greater than the therapeutic effect achieved by administration of only a single therapeutic agent. In one embodiment, the co-administration of two or more therapeutic agents achieves a synergistic effect, i.e., a therapeutic affect that is greater than the sum of the therapeutic effects of the individual components of the combination. In another embodiment, the co-administration of two or more therapeutic agents achieves an augmentation effect.

The active ingredients that comprise a combination therapy may be administered together via a single dosage form or by separate administration of each active agent. In certain embodiments, the first and second therapeutic agents are administered in a single dosage form. The agents may be formulated into a single tablet, pill, capsule, or solution for parenteral administration and the like.

Alternatively, the first therapeutic agent and the second therapeutic agents may be administered as separate compositions, e.g., as separate tablets or solutions. The first active agent may be administered at the same time as the second active agent or the first active agent may be administered intermittently with the second active agent. The length of time between administration of the first and second therapeutic agent may be adjusted to achieve the desired therapeutic effect. In certain instances, the second therapeutic agent may be administered only a few minutes (e.g., 1, 2, 5, 10, 30, or 60 min) after administration of the first therapeutic agent. Alternatively, the second therapeutic agent may be administered several hours (e.g., 2,4, 6, 10, 12, 24, or 36 hr) after administration of the first therapeutic agent. In certain embodiments, it may be advantageous to administer more than one dosage of the second therapeutic agent between administrations of the first therapeutic agent. For example, the second therapeutic agent may be administered at 2 hours and then again at 10 hours following administration of the first therapeutic agent. Alternatively, it may be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For example, for a normal adult having a body weight of about 70 kg, a dosage in the range of from about 0.1 to about 25 mg/kg body weight is typically preferred. However, some variability in this general dosage range may be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

In certain embodiments, it may be advantageous for the pharmaceutical combination to have a relatively large amount of the first component compared to the second component. In certain instances, the ratio of the first active agent to second active agent is 30:1, 20:1, 15:1, 10:1, 9:1, 8:1, 7:1, 6:1, or 5:1. In certain embodiments, it may be preferable to have a more equal distribution of pharmaceutical agents. In certain instances, the ratio of the first active agent to the second active agent is 4:1, 3:1, 2:1, 1:1, 1:2, 1:3, or 1:4. In certain embodiments, it may be advantageous for the pharmaceutical combination to have a relatively large amount of the second component compared to the first component. In certain instances, the ratio of the second active agent to the first active agent is 30:1, 20:1, 15:1, 10:1, 9:1, 8:1, 7:1, 6:1, or 5:1. Importantly, a composition comprising any of the above-identified combinations of first therapeutic agent and second therapeutic agent may be administered in divided doses 1, 2, 3, 4, 5, 6, or more times per day or in a form that will provide a rate of release effective to attain the desired results. In a preferred embodiment, the dosage form contains both the first and second active agents. In a more preferred embodiment, the dosage form only has to be administered one time per day and the dosage form contains both the first and second active agents.

For example, a formulation intended for oral administration to humans may contain from 0.1 mg to 5 g of the first therapeutic agent and 0.1 mg to 5 g of the second therapeutic agent, both of which are compounded with an appropriate and convenient amount of carrier material varying from about 5 to about 95 percent of the total composition. Unit dosages will generally contain between from about 0.5 mg to about 1500 mg of the first therapeutic agent and 0.5 mg to about 1500 mg of the second therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the first therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the second therapeutic agent.

The optimal ratios of the first and second therapeutic agent can be determined by standard assays known in the art. For example, the phenyl-p-benzoquinone test may be used to establish analgesic effectiveness. The phenyl-p-benzoquinone induced writhing test in mice (H. Blumberg et al., 1965, Proc. Soc. Exp. Med. 118:763-766) and known modifications thereof is a standard procedure which may be used for detecting and comparing the analgesic activity of different classes of analgesic drugs with a good correlation with human analgesic activity. Data for the mouse, as presented in an isobologram, can be translated to other species where the orally effective analgesic dose of the individual compounds are known or can be estimated. The method consists of reading the percent $ED_{50}$ dose for each dose ratio on the best fit regression analysis curve from the mouse isobologram, multiplying each component by its effective species dose, and then forming the ratio of the amount of COX-2 inhibitor and opioid analgesic. This basic correlation for analgesic properties enables estimation of the range of human effectiveness (E. W. Pelikan, 1959, The Pharmacologist 1:73). Thus, application of an equieffective dose substitution model and a curvilinear regression analysis utilizing all the data for the individual compounds and various dose ratios for the combinations can be used to establish the existence of unexpectedly enhanced analgesic activity of combinations of active agents, i.e., the resulting activity is greater than the activity expected from the sum of the activities of the individual components.

The toxicity and therapeutic efficacy of such compounds can be determined by standard pharmacological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of RT production from infected cells compared to untreated control as determined in cell culture. Such information can be used to more accurately determine useful doses in humans. Levels in plasma may be measured, for example, by high performance liquid chromatography (HPLC).

Synergism and Augmentation

The term "synergistic" refers to a combination which is more effective than the additive effects of any two or more single agents. A synergistic effect permits the effective treatment of a disease using lower amounts (doses) of either individual therapy. The lower doses result in lower toxicity without reduced efficacy. In addition, a synergistic effect can result in improved efficacy, e.g., improved antiviral activity. Finally, synergy may result in an improved avoidance or reduction of disease as compared to any single therapy.

Combination therapy can allow for the use of lower doses of the first therapeutic or the second therapeutic agent (referred to as "apparent one-way synergy" herein), or lower doses F both therapeutic agents (referred to as "two-way synergy" herein) than would normally be required when either drug is used alone.

In certain embodiments, the synergism exhibited between the second therapeutic agent and the first therapeutic agent is such that the dosage of the first therapeutic agent would be sub-therapeutic if administered without the dosage of the second therapeutic agent. Alternatively, the synergism exhibited between the second therapeutic agent and the first therapeutic agent is such that the dosage of the second therapeutic agent would be sub-therapeutic if administered without the dosage of the first therapeutic agent.

The terms "augmentation" or "augment" refer to combination where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the present invention relates to a pharmaceutical composition comprising a therapeutically effective dose of a first therapeutic agent together with a dose of a second therapeutic agent effective to augment the therapeutic effect of the first therapeutic agent. In other embodiments, the present invention relates to methods of augmenting the therapeutic effect in a patient of a first therapeutic agent by administering the second therapeutic agent to the patient. In other embodiments, the present invention relates to a pharmaceutical composition comprising an therapeutically effective dose of a second therapeutic agent together with a dose of a first therapeutic agent effective to augment the therapeutic effect of the second therapeutic agent. In other embodiments, the present invention relates to methods of augmenting the therapeutic effect in a patient of a second therapeutic agent by administering the first therapeutic agent to the patient.

In certain preferred embodiments, the invention is directed in part to synergistic combinations of the first therapeutic agent in an amount sufficient to render a therapeutic effect together with a second therapeutic agent. For example, in certain embodiments a therapeutic effect is attained which is at least about 2 (or at least about 4, 6, 8, or 10) times greater than that obtained with the dose of the first therapeutic agent alone. In certain embodiments, the synergistic combination provides a therapeutic effect which is up to about 20, 30 or 40 times greater than that obtained with the dose of first therapeutic agent alone. In such embodiments, the synergistic combinations display what is referred to herein as an "apparent one-way synergy", meaning that the dose of second therapeutic agent synergistically potentiates the effect of the first therapeutic agent, but the dose of first therapeutic agent does not appear to significantly potentiate the effect of the second therapeutic agent.

In certain embodiments, the combination of active agents exhibit two-way synergism, meaning that the second therapeutic agent potentiates the effect of the first therapeutic agent, and the first therapeutic agent potentiates the effect of the second therapeutic agent. Thus, other embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy may be evaluated by biological activity assays. For example, the therapeutic agents are be mixed at molar ratios designed to give approximately equipotent therapeutic effects based on the $EC_{90}$ values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic and/or additive effects provided by the inventive combination of the first and second therapeutic agent, it may be possible to use reduced dosages of each of therapeutic agent. By using lesser amounts of other or both drugs, the side effects associated with each may be reduced in number and degree. Moreover, the inventive combination avoids side effects to which some patients are particularly sensitive. Compositions & Methods of the Invention One aspect of the present invention relates to a pharmaceutical composition comprising eszopiclone, or a pharmaceutically acceptable salt, solvate, clathrate, polymorph, or co-crystal thereof, and a serotonin reuptake inhibitor.

Another aspect of the present invention relates to a pharmaceutical composition comprising eszopiclone, or a pharmaceutically acceptable salt, solvate, clathrate, polymorph, or co-crystal thereof, and a serotonin reuptake inhibitor, wherein said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them.

In certain embodiments, the present invention relates to the aforementioned pharmaceutical composition, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned pharmaceutical composition, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned pharmaceutical composition, wherein said serotonin reuptake inhibitor is fluoxetine, or a pharmaceutically acceptable salt, solvate, clathrate, polymorph, or co-crystal thereof.

In certain embodiments, the present invention relates to the aforementioned pharmaceutical composition, wherein said fluoxetine is fluoxetine hydrochloride, or a pharmaceutically acceptable solvate, clathrate, polymorph, or co-crystal thereof.

Another aspect of the present invention relates to a pharmaceutical composition consisting essentially of eszopiclone, or a pharmaceutically acceptable salt, solvate, clathrate, polymorph, or co-crystal thereof; a serotonin reuptake inhibitor; and at least one pharmaceutically acceptable carrier.

Another aspect of the present invention relates to a pharmaceutical composition consisting essentially of eszopiclone, or a pharmaceutically acceptable salt, solvate, clathrate, polymorph, or co-crystal thereof; a serotonin reuptake inhibitor, wherein said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them; and at least one pharmaceutically acceptable carrier.

In certain embodiments, the present invention relates to the aforementioned pharmaceutical composition, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned pharmaceutical composition, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned pharmaceutical composition, wherein said serotonin reuptake inhibitor is fluoxetine, or a pharmaceutically acceptable salt, solvate, clathrate, polymorph, or co-crystal thereof.

In certain embodiments, the present invention relates to the aforementioned pharmaceutical composition, wherein said fluoxetine is fluoxetine hydrochloride, or a pharmaceutically acceptable solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor; and at least one pharmaceutically acceptable carrier.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

In certain embodiments, the present invention relates to the aforementioned method, wherein said sleep abnormality is difficulty falling asleep, difficulty staying asleep, or waking up too early.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor; and at least one pharmaceutically acceptable carrier.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

In certain embodiments, the present invention relates to the aforementioned method, wherein said insomnia is transient insomnia.

In certain embodiments, the present invention relates to the aforementioned method, wherein said insomnia is short-term insomnia.

In certain embodiments, the present invention relates to the aforementioned method, wherein said insomnia is chronic insomnia.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor; and at least one pharmaceutically acceptable carrier.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a serotonin reuptake inhibitor, wherein said serotonin reuptake inibitor is citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said serotonin reuptake inhibitor is fluoxetine, fluvoxamine, milnacipran, or paroxetine, or a pharmaceutically acceptable salt, solvate, clathrate, polymorph, or co-crystal of any one of them.

In certain embodiments, the present invention relates to the aforementioned method, wherein said serotonin reuptake inhibitor is fluoxetine, paroxetine, or a pharmaceutically acceptable salt, solvate, clathrate, polymorph, or co-crystal of either of them.

In certain embodiments, the present invention relates to the aforementioned method, wherein said serotonin reuptake inhibitor is fluoxetine, or a pharmaceutically acceptable salt, solvate, clathrate, polymorph, or co-crystal thereof.

In certain embodiments, the present invention relates to the aforementioned method, wherein said fluoxetine is fluoxetine hydrochloride, or a pharmaceutically acceptable solvate, clathrate, polymorph, or co-crystal thereof.

In certain embodiments, the present invention relates to the aforementioned method, wherein said depression is a major depressive disorder.

Another aspect of the present invention relates to a pharmaceutical composition comprising eszopiclone, or a pharmaceutically acceptable salt, solvate, clathrate, polymorph, or co-crystal thereof, and a norepinephrine reuptake inhibitor.

Another aspect of the present invention relates to a pharmaceutical composition comprising eszopiclone, or a pharmaceutically acceptable salt, solvate, clathrate, polymorph, or co-crystal thereof, and a norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said norepinephrine reuptake inhibitor is (S,S)-hydroxybupropion, or a pharmaceutically acceptable salt, solvate, clathrate, polymorph, or co-crystal thereof.

Another aspect of the present invention relates to a pharmaceutical composition consisting essentially of eszopiclone, or a pharmaceutically acceptable salt, solvate, clathrate, polymorph, or co-crystal thereof; a norepinephrine reuptake inhibitor; and at least one pharmaceutically acceptable carrier.

Another aspect of the present invention relates to a pharmaceutical composition consisting essentially of eszopiclone, or a pharmaceutically acceptable salt, solvate, clathrate, polymorph, or co-crystal thereof, a norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them; and at least one pharmaceutically acceptable carrier.

In certain embodiments, the present invention relates to the aforementioned pharmaceutical composition, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said norepinephrine reuptake inhibitor is (S,S)-hydroxybupropion, or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of norepinephrine reuptake inhibitor; and at least one pharmaceutically acceptable carrier.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal thereof.

In certain embodiments, the present invention relates to the aforementioned method, wherein said sleep abnormality is difficulty falling asleep, difficulty staying asleep, or waking up too early.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of norepinephrine reuptake inhibitor; and at least one pharmaceutically acceptable carrier.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal of any one of them.

In certain embodiments, the present invention relates to the aforementioned method, wherein said insomnia is transient insomnia.

In certain embodiments, the present invention relates to the aforementioned method, wherein said insomnia is short-term insomnia.

In certain embodiments, the present invention relates to the aforementioned method, wherein said insomnia is chronic insomnia.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, a therapeutically effective amount of norepinephrine reuptake inhibitor; and at least one pharmaceutically acceptable carrier.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, a therapeutically effective amount of norepinephrine reuptake inhibitor, wherein said norepinephrine reuptake inhibitor is desipramine, maprotiline, lofepramine, reboxetine, oxaprotiline, fezolamine, tomoxetine, or (S,S)-hydroxybupropion, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said norepinephrine reuptake inhibitor is desipramine, reboxetine, oxaprotiline, or (S,S)-hydroxybupropion, or a pharmaceutically acceptable salt, solvate, clathrate, polymorph, or co-crystal of any one of them.

In certain embodiments, the present invention relates to the aforementioned method, wherein said norepinephrine reuptake inhibitor is (S,S)-hydroxybupropion, or a pharmaceutically acceptable salt, solvate, clathrate, polymorph, or co-crystal of any one of them.

In certain embodiments, the present invention relates to the aforementioned method, wherein said depression is a major depressive disorder.

Another aspect of the present invention relates to a pharmaceutical composition comprising eszopiclone, or a pharmaceutically acceptable salt, solvate, clathrate, polymorph, or co-crystal thereof, and a dopamine reuptake inhibitor.

Another aspect of the present invention relates to a pharmaceutical composition comprising eszopiclone, or a pharmaceutically acceptable salt, solvate, clathrate, polymorph, or co-crystal thereof, and a dopamine reuptake inhibitor, said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned pharmaceutical composition, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned pharmaceutical composition, wherein said dopamine reuptake inhibitor is bupropion, or a pharmaceutically acceptable salt, solvate, clathrate, polymorph, or co-crystal thereof.

In certain embodiments, the present invention relates to the aforementioned pharmaceutical composition, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned pharmaceutical composition, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

Another aspect of the present invention relates to a pharmaceutical composition consisting essentially of eszopiclone, or a pharmaceutically acceptable salt, solvate, clathrate, polymorph, or co-crystal thereof; a dopamine reuptake inhibitor; and at least one pharmaceutically acceptable carrier.

Another aspect of the present invention relates to a pharmaceutical composition consisting essentially of eszopiclone, or a pharmaceutically acceptable salt, solvate, clathrate, polymorph, or co-crystal thereof; a dopamine reuptake inhibitor, said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them; and at least one pharmaceutically acceptable carrier.

In certain embodiments, the present invention relates to the aforementioned pharmaceutical composition, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned pharmaceutical composition, wherein said dopamine reuptake inhibitor is bupropion, or a pharmaceutically acceptable salt, solvate, clathrate, polymorph, or co-crystal thereof.

In certain embodiments, the present invention relates to the aforementioned pharmaceutical composition, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned pharmaceutical composition, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor; and at least one pharmaceutically acceptable carrier.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

In certain embodiments, the present invention relates to the aforementioned method, wherein said sleep abnormality is difficulty falling asleep, difficulty staying asleep, or waking up too early.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said doparnine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor; and at least one pharmaceutically acceptable carrier.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

In certain embodiments, the present invention relates to the aforementioned method, wherein said insomnia is transient insomnia.

In certain embodiments, the present invention relates to the aforementioned method, wherein said insomnia is short-term insomnia.

In certain embodiments, the present invention relates to the aforementioned method, wherein said insomnia is chronic insomnia.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor; and at least one pharmaceutically acceptable carrier.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a dopamine reuptake inhibitor, wherein said dopamine reuptake inhibitor is amineptine, bupropion, GBR-12935, venlafaxine, desmethylvenlafaxine, or 2β-propanoyl-3β-(4-tolyl)-tropane, or a pharmaceutically acceptable salt, solvate, clathrate, polymorph, or co-crystal of any one of them; and at least one pharmaceutically acceptable carrier.

In certain embodiments, the present invention relates to the aforementioned method, wherein said dopamine reuptake inhibitor is bupropion, or GBR-12935, or a pharmaceutically acceptable salt, solvate, clathrate, polymorph, or co-crystal of either of them.

In certain embodiments, the present invention relates to the aforementioned method, wherein said dopamine reuptake inhibitor is bupropion, or a pharmaceutically acceptable salt, solvate, clathrate, polymorph, or co-crystal thereof.

In certain embodiments, the present invention relates to the aforementioned method, wherein said dopamine reuptake inhibitor is venlafaxine, desmethylvenlafaxine, or a pharmaceutically acceptable salt, solvate, clathrate, polymorph, or co-crystal of either of them.

In certain embodiments, the present invention relates to the aforementioned method, wherein said desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

In certain embodiments, the present invention relates to the aforementioned method, wherein said depression is a major depressive disorder.

Another aspect of the present invention relates to a pharmaceutical composition comprising eszopiclone, or a pharmaceutically acceptable salt, solvate, clathrate, polymorph, or co-crystal thereof, and a 5-HT$_{2A}$ modulator.

In certain embodiments, the present invention relates to the aforementioned pharmaceutical composition, wherein the 5-HT$_{2A}$ modulator is a 5-HT$_{2A}$ antagonist.

In certain embodiments, the present invention relates to the aforementioned pharmaceutical composition, wherein the 5-HT$_{2A}$ modulator is a 5-HT$_{2A}$ inverse agonist.

Another aspect of the present invention relates to a pharmaceutical composition comprising eszopiclone, or a pharmaceutically acceptable salt, solvate, clathrate, polymorph, or co-crystal thereof, and a 5-HT$_{2A}$ modulator, wherein said 5 HT$_{2A}$ modulator is MDL 100907, SR 46349B, YM 992, fananserin, oxazolidine compounds A, phenylindole compounds A, piperidinyl compounds B, spiroazacyclic compounds C, or azacyclic compounds D, or a pharmaceutically acceptable salt, solvate, clathrate, polymorph, or co-crystal of any one of them.

In certain embodiments, the present invention relates to the aforementioned pharmaceutical composition, wherein said 5-HT$_{2A}$ modulator is MDL 100907, SR 46349B, YM 992, fananserin, oxazolidine compounds A, or phenylindole compounds A, or a pharmaceutically acceptable salt, solvate, clathrate, polymorph, or co crystal of any one of them.

In certain embodiments, the present invention relates to the aforementioned pharmaceutical composition, wherein said 5-HT$_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned pharmaceutical composition, wherein said 5-HT$_{2A}$ modulator, wherein said 5-HT$_{2A}$ modulator is piperidinyl compounds B, spiroazacyclic compounds C, or azacyclic compounds D, or a pharmaceutically acceptable salt, solvate, clathrate, polymorph, or co-crystal of any one of them.

Another aspect of the present invention relates to a pharmaceutical composition consisting essentially of eszopiclone, or a pharmaceutically acceptable salt, solvate, clathrate, polymorph, or co-crystal thereof; a 5-HT$_{2A}$ modulator; and at least one pharmaceutically acceptable carrier.

In certain embodiments, the present invention relates to the aforementioned pharmaceutical composition, wherein the 5-HT$_{2A}$ modulator is a 5-HT$_{2A}$ antagonist.

In certain embodiments, the present invention relates to the aforementioned pharmaceutical composition, wherein the 5-HT$_{2A}$ modulator is a 5-HT$_{2A}$ inverse agonist.

Another aspect of the present invention relates to a pharmaceutical composition consisting essentially of eszopiclone, or a pharmaceutically acceptable salt, solvate, clathrate, polymorph, or co-crystal thereof; a 5-HT$_{2A}$ modulator, wherein said 5 HT$_{2A}$ modulator is MDL 100907, SR 46349B, YM 992, fananserin, oxazolidine compounds A, phenylindole compounds A, piperidinyl compounds B, spiroazacyclic compounds C, or azacyclic compounds D, or a pharmaceutically acceptable salt, solvate, clathrate, polymorph, or co-crystal of any one of them; and at least one pharmaceutically acceptable carrier.

In certain embodiments, the present invention relates to the aforementioned pharmaceutical composition, wherein said 5-HT$_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned pharmaceutical composition, wherein said 5-HT$_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned pharmaceutical composition, wherein said 5-HT$_{2A}$ modulator, wherein said 5 HT$_{2A}$ modulator is piperidinyl compounds B, spiroazacyclic compounds C, or azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-HT$_{2A}$ modulator.

In certain embodiments, the present invention relates to the aforementioned method, wherein the 5-HT$_{2A}$ modulator is a 5-HT$_{2A}$ antagonist.

In certain embodiments, the present invention relates to the aforementioned method, wherein the 5-HT$_{2A}$ modulator is a 5-HT$_{2A}$ inverse agonist.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-HT$_{2A}$ modulator, wherein said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein the 5-HT$_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-HT$_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-HT$_{2A}$ modulator is piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-HT$_{2A}$ modulator; and at least one pharmaceutically acceptable carrier.

In certain embodiments, the present invention relates to the aforementioned method, wherein the 5-$HT_{2A}$ modulator is a 5-$HT_{2A}$ antagonist.

In certain embodiments, the present invention relates to the aforementioned method, wherein the 5-$HT_{2A}$ modulator is a 5-$HT_{2A}$ inverse agonist.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-$HT_{2A}$ modulator, wherein said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them; and at least one pharmaceutically acceptable carrier.

In certain embodiments, the present invention relates to the aforementioned method, wherein the 5-$HT_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-$HT_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-$HT_{2A}$ modulator is piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein said sleep abnormality is difficulty falling asleep, difficulty staying asleep, or waking up too early.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-$HT_{2A}$ modulator.

In certain embodiments, the present invention relates to the aforementioned method, wherein the 5-$HT_{2A}$ modulator is a 5-$HT_{2A}$ antagonist.

In certain embodiments, the present invention relates to the aforementioned method, wherein the 5-$HT_{2A}$ modulator is a 5-$HT_{2A}$ inverse agonist.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-$HT_{2A}$ modulator, wherein said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein the 5-$HT_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-$HT_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-$HT_{2A}$ modulator is piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-$HT_{2A}$ modulator; and at least one pharmaceutically acceptable carrier.

In certain embodiments, the present invention relates to the aforementioned method, wherein the 5-$HT_{2A}$ modulator is a 5-$HT_{2A}$ antagonist.

In certain embodiments, the present invention relates to the aforementioned method, wherein the 5-$HT_{2A}$ modulator is a 5-$HT_{2A}$ inverse agonist.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-$HT_{2A}$ modulator, wherein said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them; and at least one pharmaceutically acceptable carrier.

In certain embodiments, the present invention relates to the aforementioned method, wherein the 5-$HT_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-$HT_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-$HT_{2A}$ modulator is piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein said insomnia is transient insomnia.

In certain embodiments, the present invention relates to the aforementioned method, wherein said insomnia is short-term insomnia.

In certain embodiments, the present invention relates to the aforementioned method, wherein said insomnia is chronic insomnia.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-HT$_{2A}$ modulator.

In certain embodiments, the present invention relates to the aforementioned method, wherein the 5-HT$_{2A}$ modulator is a 5-HT$_{2A}$ antagonist.

In certain embodiments, the present invention relates to the aforementioned method, wherein the 5-HT$_{2A}$ modulator is a 5-HT$_{2A}$ inverse agonist.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof, and a therapeutically effective amount of a 5-HT$_{2A}$ modulator, wherein said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein the 5-HT$_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-HT$_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-HT$_{2A}$ modulator is piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-HT$_{2A}$ modulator; and at least one pharmaceutically acceptable carrier.

In certain embodiments, the present invention relates to the aforementioned method, wherein the 5-HT$_{2A}$ modulator is a 5-HT$_{2A}$ antagonist.

In certain embodiments, the present invention relates to the aforementioned method, wherein the 5-HT$_{2A}$ modulator is a 5-HT$_{2A}$ inverse agonist.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal thereof; a therapeutically effective amount of a 5-HT$_{2A}$ modulator, wherein said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them; and at least one pharmaceutically acceptable carrier.

In certain embodiments, the present invention relates to the aforementioned method, wherein the 5-HT$_{2A}$ modulator is MDL 100907, SR 46349B, YM 992, fananserin, oxazolidine compounds A, or phenylindole compounds A, or a pharmaceutically acceptable salt, solvate, clathrate, polymorph, or co-crystal of any one of them.

In certain embodiments, the present invention relates to the aforementioned method, wherein the 5-HT$_{2A}$ modulator is MDL 100907, SR 46349B, YM 992, or fananserin, or a pharmaceutically acceptable salt, solvate, clathrate, polymorph, or co-crystal of any one of them.

In certain embodiments, the present invention relates to the aforementioned method, wherein the 5-HT$_{2A}$ modulator is piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned method, wherein said depression is a major depressive disorder.

Another aspect of the present invention relates to a method for augmentation of antidepressant therapy in a patient comprising administering to the patient in need thereof, undergoing antidepressant therapy, a therapeutically effective amount of eszopiclone, or a pharmaceutically acceptable salt, solvate, clathrate, polymorph, or co-crystal thereof.

Another aspect of the present invention relates to a method for eliciting a dose sparing effect in a patient undergoing treatment with an antidepressant, comprising administering to the patient in need thereof, undergoing antidepressant therapy, a therapeutically effective amount of eszopiclone, or a pharmaceutically acceptable salt, solvate, clathrate, polymorph, or co-crystal thereof.

Another aspect of the present invention relates to a method for reducing depression relapse in a patient who received antidepressant treatment, comprising administering to the patient in need thereof a therapeutically effective amount of eszopiclone, or a pharmaceutically acceptable salt, solvate, clathrate, polymorph, or co-crystal thereof.

In certain embodiments, the present invention relates to the aforementioned method, wherein the eszopiclone is administered chronically or long-term.

Another aspect of the present invention relates to a method for improving the tolerability of antidepressant therapy in a patient suffering from depression, comprising administering to the patient in need thereof, undergoing antidepressant therapy, a therapeutically effective amount of eszopiclone, or a pharmaceutically acceptable salt, solvate, clathrate, polymorph, or co-crystal thereof.

In certain embodiments, the present invention relates to the aforementioned method, wherein the antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned method, wherein the antidepressant is desipramine, maprotiline, lofepramine, reboxetine, oxaprotiline, fezolamine, tomoxetine, (S,S)hydroxybupropion, or a pharmaceutically acceptable salt, solvate, clathrate, polymorph, or co-crystal of any one of them.

In certain embodiments, the present invention relates to the aforementioned method, wherein the antidepressant is bupropion, venlafaxine, or desmethylvenlafaxine, or a pharmaceutically acceptable salt, solvate, clathrate, polymorph, or co-crystal of any one of them.

In certain embodiments, the present invention relates to the aforementioned method, wherein the desmethylvenlafaxine is racemic desmethylvenlafaxine, (+)-desmethylvenlafaxine, or (−)-desmethylvenlafaxine, or a pharmaceutically acceptable salt, solvate, clathrate, polymorph, or co-crystal of any one of them.

In certain embodiments, the present invention relates to the aforementioned method, wherein the antidepressant is a dopamine reuptake inhibitor or an atypical antidepressant.

One aspect of the present invention relates to a pharmaceutical composition, comprising a sedative agent and an antidepressant. In certain embodiments, the antidepressant is a serotonin reuptake inhibitor, including without limitation selective serotonin reuptake inhibitors, a norepinephrine reuptake inhibitor, including without limitation a selective norepinephrine reuptake inhibitor, a dopamine reuptake inhibitor, or an atypical antidepressant. In other embodiments, the antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a pharmaceutical composition, comprising a sedative agent and a serotonin reuptake inhibitor; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, comprising a sedative agent and a serotonin reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned pharmaceutical composition, wherein said sedative agent is racemic zopiclone, eszopiclone, indiplon, or a pharmaceutically acceptable salt, solvate, clathrate, polymorph, or co-crystal of any one of them.

In certain embodiments, the present invention relates to the aforementioned pharmaceutical composition, wherein said sedative agent is eszopiclone, or a pharmaceutically acceptable salt, solvate, clathrate, polymorph, or co-crystal thereof.

In certain embodiments, the present invention relates to the aforementioned pharmaceutical composition, wherein said serotonin reuptake inhibitor is fluoxetine, fluvoxamine, milnacipran, paroxetine, or a pharmaceutically acceptable salt, solvate, clathrate, polymorph, or co-crystal of any one of them.

Another aspect of the present invention relates to a pharmaceutical composition, comprising a sedative agent and a serotonin reuptake inhibitor; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a pharmaceutical composition, comprising a sedative agent and a serotonin reuptake inhibitor; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a pharmaceutical composition, comprising eszopiclone or a pharmaceutically acceptable salt, solvate, clathrate, polymorph, or co-crystal thereof and fluoxetine hydrochloride or a pharmaceutically acceptable salt, solvate, clathrate, polymorph, or co-crystal thereof.

Another aspect of the present invention relates to a pharmaceutical composition, comprising a sedative agent and a norepinephrine reuptake inhibitor; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, comprising a sedative agent and a norepinephrine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a pharmaceutical composition, comprising a sedative agent and a norepinephrine reuptake inhibitor; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a pharmaceutical composition, comprising eszopiclone or a pharmaceutically acceptable salt, solvate, clathrate, polymorph, or co-crystal thereof, and a norepinephrine reuptake inhibitor; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a pharmaceutical composition, comprising a sedative agent and a 5-$HT_2$ receptor modulator. In certain embodiments, the 5-$HT_2$ receptor modulator is a 5-$HT_{2A}$ receptor antagonist or a 5-$HT_{2A}$ inverse agonist.

In one embodiment, the pharmaceutical composition comprises a sedative agent and a 5-$HT_2$ receptor modulator, wherein said sedative agent is a compound that modulates the activity of a GABA receptor and has a $K_i$ less than about 300 nM in a GABA-receptor binding assay; and said said 5-$HT_2$ receptor modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, comprising a sedative agent and a 5-$HT_{2A}$ modulator; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a pharmaceutical composition, comprising a sedative agent and a 5-$HT_{2A}$ modulator; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a pharmaceutical composition, comprising eszopiclone and a 5-$HT_{2A}$ modulator; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a pharmaceutical composition, comprising eszopiclone, or a pharmaceutically acceptable salt, solvate, clathrate, polymorph, or co-crystal thereof; and a 5-$HT_{2A}$ inverse agonist. In certain embodiments, the 5-$HT_{2A}$ inverse agonist is piperidinyl compounds B, spiroazacyclic compounds C, azacyclic compounds D, or a pharmaceutically acceptable salt, solvate, clathrate, polymorph, or co-crystal of any one of them Another aspect of the present invention relates to a pharmaceutical composition, comprising a sedative agent and a dopamine reuptake inhibitor; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, comprising a sedative agent and a dopamine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a pharmaceutical composition, comprising a sedative agent and a dopamine reuptake inhibitor; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned pharmaceutical composition, wherein said dopamine reuptake inhibitor is bupropion, GBR-12935, or a pharmaceutically acceptable salt, solvate, clathrate, polymorph, or co-crystal of either of them.

Another aspect of the present invention relates to a pharmaceutical composition, comprising eszopiclone and bupropion, or a pharmaceutically acceptable salt, solvate, clathrate, polymorph, or co-crystal of either of them.

Another aspect of the present invention relates to a pharmaceutical composition, consisting essentially of a sedative agent, a serotonin reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, consisting essentially of a sedative agent, a serotonin reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned pharmaceutical composition, wherein said sedative agent is racemic zopiclone, eszopiclone, indiplon, or a pharmaceutically acceptable salt, solvate, clathrate, polymorph, or co-crystal of any one of them.

In certain embodiments, the present invention relates to the aforementioned pharmaceutical composition, wherein said serotonin reuptake inhibitor is fluoxetine, fluvoxamine, milnacipran, paroxetine, or a pharmaceutically acceptable salt, solvate, clathrate, polymorph, or co-crystal of any one of them.

Another aspect of the present invention relates to a pharmaceutical composition, consisting essentially of a sedative agent, a serotonin reuptake inhibitor, and at least one pharmaceutically acceptable carrier; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a pharmaceutical composition, consisting essentially of a sedative agent, a serotonin reuptake inhibitor, and at least one pharmaceutically acceptable carrier; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a pharmaceutical composition, consisting essentially of eszopiclone or a pharmaceutically acceptable salt, solvate, clathrate, polymorph, or co-crystal thereof, fluoxetine hydrochloride or a pharmaceutically acceptable salt, solvate, clathrate, polymorph, or co-crystal thereof, and at least one pharmaceutically acceptable carrier.

Another aspect of the present invention relates to a pharmaceutical composition, consisting essentially of a sedative agent, a norepinephrine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, consisting essentially of a sedative agent, a norepinephrine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a pharmaceutical composition, consisting essentially of a sedative agent, a norepinephrine reuptake inhibitor, and at least one pharmaceutically acceptable carrier; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

In certain embodiments, the present invention relates to the aforementioned pharmaceutical composition, wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a pharmaceutical composition, consisting essentially of eszopiclone or a pharmaceutically acceptable salt, solvate, clathrate, polymorph, or co-crystal thereof, a norepinephrine reuptake inhibitor, and at least one pharmaceutically acceptable carrier; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a pharmaceutical composition, consisting essentially of a sedative agent, a 5-$HT_{2A}$ modulator, and at least one pharmaceutically acceptable carrier; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, consisting essentially of a sedative agent, a 5-$HT_{2A}$ modulator, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a pharmaceutical composition, consisting essentially of a sedative agent, a 5-$HT_{2A}$ modulator, and at least one pharmaceutically acceptable carrier; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

In certain embodiments, the present invention relates to the aforementioned pharmaceutical composition, wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a pharmaceutical composition, consisting essentially of eszopiclone, or a pharmaceutically acceptable salt, solvate, clathrate, polymorph, or co-crystal of any one of them, a 5-$HT_{2A}$ modulator, and at least one pharmaceutically acceptable carrier; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a pharmaceutical composition, consisting essentially of a sedative agent, a dopamine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned pharmaceutical composition, wherein said $K_i$ is less than about 150 nM.

In certain embodiments, the present invention relates to the aforementioned pharmaceutical composition, wherein said $K_i$ is less than about 75 nM.

In certain embodiments, the present invention relates to the aforementioned pharmaceutical composition, wherein said $K_i$ is less than about 30 nM.

Another aspect of the present invention relates to a pharmaceutical composition, consisting essentially of a sedative agent, a dopamine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a pharmaceutical composition, consisting essentially of a sedative agent, a dopamine reuptake inhibitor, and at least one pharmaceutically acceptable carrier; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

In certain embodiments, the present invention relates to the aforementioned pharmaceutical composition, wherein said dopamine reuptake inhibitor is bupropion, GBR-12935, or a pharmaceutically acceptable salt, solvate, clathrate, polymorph, or co-crystal of either of them.

Another aspect of the present invention relates to a pharmaceutical composition, consisting essentially of eszopiclone and bupropion, or a pharmaceutically acceptable salt, solvate, clathrate, polymorph, or co-crystal of either of them, and at least one pharmaceutically acceptable carrier.

Another aspect of the present invention relates to a method of treating a patient suffering from a sleep abnormality, comprising the step of co-administering to a patient in need thereof a therapeutically effective amount of a sedative and a therapeutically effective amount of an antidepressant; wherein said sedative agent is a compound that modulates the activity of a GABA receptor and has a $K_i$ less than about 300 nM in a GABA-receptor binding assay; and said antidepressant is a serotonin reuptake inhibitor, norepinephrine reuptake inhibitor, 5$HT_{2A}$ modulator, or dopamine reuptake inhibitor.

In certain embodiments, the present invention relates to the aforementioned method, wherein said sedative is racemic zopiclone, (S)-zopiclone, indiplon, zolpidem, zaleplon, gaboxadol, or a pharmaceutically acceptable salt, solvate, or hydrate of any one of them; and said antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, desipramine, maprotiline, lofepramine, reboxetine, oxaprotiline, fezolamine, tomoxetine, (S,S)-hydroxybupropion, MDL 100907, SR 46349B, YM 992, fananserin, oxazolidine compounds A, phenylindole compounds A, piperidinyl compounds B, spiroazacyclic compounds C, azacyclic compounds D, aminephtine, bupropion, GBR-12935, venlafaxine, or 2β-propanoyl-3β-(4-tolyl)-tropane, or a pharmaceutically acceptable salt, solvate, or hydrate of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a serotonin reuptake inhibitor; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from a sleep abnormality, comprising the step of co-administering to a patient in need thereof a therapeutically effective amount of a sedative agent and a therapeutically effective amount of a serotonin reuptake inhibitor; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone or a pharmaceutically acceptable salt, solvate, clathrate, polymorph, or co-crystal thereof; and a therapeutically effective amount of fluoxetine hydrochloride or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of a sedative agent and a therapeutically effective amount of a norepinephrine reuptake inhibitor; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a norepinephrine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a norepinephrine reuptake inhibitor; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal; and a therapeutically effective amount of a norepinephrine reuptake inhibitor; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a 5-HT$_{2A}$ modulator; wherein said sedative agent is a compound that modulates the activity of a GABA receptor and has a $K_i$ less than about 300 nM in a GABA-receptor binding assay; and said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a 5-HT$_{2A}$ modulator; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a 5-HT$_{2A}$ modulator; wherein said sedative agent is eszopiclone or a pharmaceutically acceptable salt, solvate, clathrate, polymorph, or co-crystal thereof; and said 5-HT$_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone and a therapeutically effective amount of a 5-HT$_{2A}$ modulator; wherein said 5-HT$_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a dopamine reuptake inhibitor; wherein said sedative agent is a compound that modulates the activity of a GABA receptor and has a K$_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a dopamine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent and a therapeutically effective amount of a dopamine reuptake inhibitor; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is a compound that modulates the activity of a GABA receptor and has a K$_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from a sleep abnormality, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from a sleep abnormality, comprising the step of co-administering to a patient in need thereof a therapeutically effective amount of eszopiclone or a pharmaceutically acceptable salt, solvate, clathrate, polymorph, or co-crystal thereof; a therapeutically effective amount of fluoxetine hydrochloride or a pharmaceutically acceptable salt, solvate, clathrate, polymorph, or co-crystal thereof; and at least one pharmaceutically acceptable carrier.

Another aspect of the present invention relates to a method of treating a patient suffering from a sleep abnormality, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone or a pharmaceutically acceptable salt, solvate, clathrate, polymorph, or co-crystal thereof; a therapeutically effective amount of a norepinephrine reuptake inhibitor; and at least one pharmaceutically acceptable carrier; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone, or a pharmaceutically acceptable salt, solvate, clathrate, polymorph, or co-crystal of any one of them; a therapeutically effective amount of a 5-$HT_{2A}$ modulator; and at least one pharmaceutically acceptable carrier; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from a sleep abnormality, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof, and at least one pharmaceutically acceptable carrier.

In certain embodiments, the present invention relates to the aforementioned methods, wherein said sleep disturbance is difficulty falling asleep, difficulty staying asleep, or waking up too early.

Another aspect of the present invention relates generally to a method of treating a patient suffering from insomnia, comprising the step of co-administering to a patient in need thereof a therapeutically effective amount of a sedative and a therapeutically effective amount of an antidepressant; wherein said sedative agent is a compound that modulates the activity of a GABA receptor and has a $K_i$ less than about 300 nM in a GABA-receptor binding assay; and said antidepressant is a serotonin reuptake inhibitor, norepinephrine reuptake inhibitor, $5HT_{2A}$ modulator, or dopamine reuptake inhibitor.

In certain embodiments, the present invention relates to the aforementioned method, wherein said sedative is racemic zopiclone, (S)-zopiclone, indiplon, zolpidem, zaleplon, gaboxadol, or a pharmaceutically acceptable salt, solvate, or hydrate of any one of them; and said antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, desipramine, maprotiline, lofepramine, reboxetine, oxaprotiline, fezolamine, tomoxetine, (S,S)-hydroxybupropion, MDL 100907, SR 46349B, YM 992, fananserin, oxazolidine compounds A, phenylindole compounds A, piperidinyl compounds B, spiroazacyclic compounds C, azacyclic compounds D, amineptine, bupropion, GBR-12935, venlafaxine, or 2β-propanoyl-3β-(4-tolyl)-tropane, or a pharmaceutically acceptable salt, solvate, or hydrate of any one of them.

Another aspect of the present invention relates to a method of treating a patient suffering from insomnia, comprising the step of co-administering to a patient in need thereof a therapeutically effective amount of a sedative agent and a therapeutically effective amount of a serotonin reuptake inhibitor; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from insomnia, comprising the step of co-administering to a patient in need thereof a therapeutically effective amount of a sedative agent and a therapeutically effective amount of a serotonin reuptake inhibitor; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from insomnia, comprising the step of co-administering to a patient in need thereof a therapeutically effective amount of eszopiclone or a pharmaceutically acceptable salt, solvate, clathrate, polymorph, or co-crystal thereof; and a therapeutically effective amount of fluoxetine hydrochloride or a pharmaceutically acceptable salt, solvate, clathrate, polymorph, or co-crystal thereof.

Another aspect of the present invention relates to a method of treating a patient suffering from insomnia, comprising the step of co-administering to a patient in need thereof a therapeutically effective amount of a sedative agent and a therapeutically effective amount of a norepinephrine reuptake inhibitor; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a norepinephrine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a norepinephrine reuptake inhibitor; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal; and a therapeutically effective amount of a norepinephrine reuptake inhibitor; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a 5-$HT_{2A}$ modulator; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a 5-$HT_{2A}$ modulator; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a 5-$HT_{2A}$ modulator; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone and a therapeutically effective amount of a 5-$HT_{2A}$ modulator; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a dopamine reuptake inhibitor; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a dopamine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent and a therapeutically effective amount of a dopamine reuptake inhibitor; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof.

Another aspect of the present invention relates to a method of treating a patient suffering from insomnia, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from insomnia, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from insomnia, comprising the step of co-administering to a patient in need thereof a therapeutically effective amount of eszopiclone or a pharmaceutically acceptable salt, solvate, clathrate, polymorph, or co-crystal thereof, a therapeutically effective amount of fluoxetine hydrochloride or a pharmaceutically acceptable salt, solvate, clathrate, polymorph, or co-crystal thereof; and at least one pharmaceutically acceptable carrier.

Another aspect of the present invention relates to a method of treating a patient suffering from insomnia, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone or a pharmaceutically acceptable salt, solvate, clathrate, polymorph, or co-crystal thereof; a therapeutically effective amount of a norepinephrine reuptake inhibitor; and at least one pharmaceutically acceptable carrier; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone, or a pharmaceutically acceptable salt, solvate, clathrate, polymorph, or co-crystal of any one of them; a therapeutically effective amount of a 5-HT$_{2A}$ modulator; and at least one pharmaceutically acceptable carrier; wherein said 5-HT$_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is a compound that modulates the activity of a GABA receptor and has a K$_i$ less than about 300 nM in a GABA-receptor binding assay; and said dopamine reuptake inhibitor is aminoptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is aminoptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is eszopiclone or a pharmaceutically acceptable salt, solvate, clathrate, polymorph, or co-crystal thereof; and said dopamine reuptake inhibitor is aminoptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from insomnia, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof, and at least one pharmaceutically acceptable carrier.

In certain embodiments, the present invention relates to the aforementioned methods, wherein said insomnia is transient insomnia.

In certain embodiments, the present invention relates to the aforementioned methods, wherein said insomnia is short-term insomnia.

In certain embodiments, the present invention relates to the aforementioned methods, wherein said insomnia is chronic insomnia.

Another aspect of the present invention relates generally to a method of treating a patient suffering from depression, comprising the step of co-administering to a patient in need thereof a therapeutically effective amount of a sedative and a therapeutically effective amount of an antidepressant; wherein said sedative agent is a compound that modulates the activity of a GABA receptor and has a K$_i$ less than about 300 nM in a GABA-receptor binding assay; and said antidepressant is a serotonin reuptake inhibitor, norepinephrine reuptake inhibitor, 5HT$_{2A}$ modulator, or dopamine reuptake inhibitor.

In certain embodiments, the present invention relates to the aforementioned method, wherein said sedative is racemic zopiclone, (S)-zopiclone, indiplon, zolpidem, zaleplon, gaboxadol, or a pharmaceutically acceptable salt, solvate, or hydrate of any one of them; and said antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, desipramine, maprotiline, lofepramine, reboxetine, oxaprotiline, fezolamine, tomoxetine, (S,S)-hydroxybupropion, MDL 100907, SR 46349B, YM 992, fananserin, oxazolidine compounds A, phenylindole compounds A, piperidinyl compounds B, spiroazacyclic compounds C, azacyclic compounds D, aminoptine, bupropion, GBR-12935, venlafaxine, or 2β-propanoyl-3β-(4-tolyl)-tropane, or a pharmaceutically acceptable salt, solvate, or hydrate of any one of them.

Another aspect of the present invention relates to a method of treating a patient suffering from depression, comprising the step of co-administering to a patient in need thereof a therapeutically effective amount of a sedative agent and a therapeutically effective amount of a serotonin reuptake inhibitor; wherein said sedative agent is a compound that modulates the activity of a GABA receptor and has a K$_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a serotonin reuptake inhibitor; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from depression, comprising the step of co-administering to a patient in need thereof a therapeutically effective amount of a sedative agent and a therapeutically effective amount of a serotonin reuptake inhibitor; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from depression, comprising the step of co-administering to a patient in need thereof a therapeutically effective amount of eszopiclone or a pharmaceutically acceptable salt, solvate, clathrate, polymorph, or co-crystal thereof; and a therapeutically effective amount of fluoxetine hydrochloride or a pharmaceutically acceptable salt, solvate, clathrate, polymorph, or co-crystal thereof.

Another aspect of the present invention relates to a method of treating a patient suffering from depression, comprising the step of co-administering to a patient in need thereof a therapeutically effective amount of a sedative agent and a therapeutically effective amount of a norepinephrine reuptake inhibitor; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a norepinephrine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a norepinephrine reuptake inhibitor; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal; and a therapeutically effective amount of a norepinephrine reuptake inhibitor; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a 5-$HT_{2A}$ modulator; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a 5-$HT_{2A}$ modulator; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a 5-$HT_{2A}$ modulator; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone and a therapeutically effective amount of a 5-$HT_{2A}$ modulator; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a dopamine reuptake inhibitor; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a dopamine reuptake inhibitor; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent and a therapeutically effective amount of a dopamine reuptake inhibitor; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof.

Another aspect of the present invention relates to a method of treating a patient suffering from depression, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said serotonin reuptake inhibitor is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is racemic zopiclone, eszopiclone, or a pharmaceutically acceptable salt, solvate, clathrate, polymorph, or co-crystal of either of them; and said serotonin reuptake inhibitor is fluoxetine, paroxetine, or a pharmaceutically acceptable salt, solvate, clathrate, polymorph, or co-crystal of either of them.

Another aspect of the present invention relates to a method of treating a patient suffering from depression, comprising the step of co-administering to a patient in need thereof a therapeutically effective amount of a sedative agent, a therapeutically effective amount of a serotonin reuptake inhibitor, and at least one pharmaceutically acceptable carrier; wherein said sedative agent is eszopiclone or a pharmaceutically acceptable salt, solvate, clathrate, polymorph, or co-crystal thereof; and said serotonin reuptake inhibitor is fluoxetine or a pharmaceutically acceptable salt, solvate, clathrate, polymorph, or co-crystal thereof.

Another aspect of the present invention relates to a method of treating a patient suffering from depression, comprising the step of co-administering to a patient in need thereof a therapeutically effective amount of eszopiclone or a pharmaceutically acceptable salt, solvate, clathrate, polymorph, or co-crystal thereof; a therapeutically effective amount of fluoxetine hydrochloride or a pharmaceutically acceptable salt, solvate, clathrate, polymorph, or co-crystal thereof; and at least one pharmaceutically acceptable carrier.

Another aspect of the present invention relates to a method of treating a patient suffering from depression, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a norepinephrine reuptake inhibitor, and at least one pharmaceutically acceptable carrier; wherein said sedative agent is eszopiclone or a pharmaceutically acceptable salt, solvate, clathrate, polymorph, or co-crystal thereof; and said norepinephrine reuptake inhibitor is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone or a pharmaceutically acceptable salt, solvate, clathrate, polymorph, or co-crystal thereof; a therapeutically effective amount of a norepinephrine reuptake inhibitor; and at least one pharmaceutically acceptable carrier; wherein said norepinephrine reuptake inhibitor is desipramine, reboxetine, oxaprotiline, (S,S)-hydroxybupropion, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is a compound that modulates the activity of a GABA receptor and has a $K_i$ less than about 300 nM in a GABA-receptor binding assay; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a 5-$HT_{2A}$ modulator, and at least one pharmaceutically acceptable carrier; wherein said sedative agent is eszopiclone or a pharmaceutically acceptable salt, solvate, clathrate, polymorph, or co-crystal thereof; and said 5-$HT_{2A}$ modulator is MDL 100907, SR 46349B, YM 992, fananserin, oxazolidine compounds A, phenylindole compounds A, piperidinyl compounds B, spiroazacyclic compounds C, azacyclic compounds D, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone, or a pharmaceutically acceptable salt, solvate, clathrate, polymorph, or co-crystal of any one of them; a therapeutically effective amount of a 5-$HT_{2A}$ modulator; and at least one pharmaceutically acceptable carrier; wherein said 5-$HT_{2A}$ modulator is MDL 100907, SR 46349B, YM 992, fananserin, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is a compound that modulates the activity of a GABA receptor and has a $K_i$ less than about 300 nM in a GABA-receptor binding assay; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of a sedative agent, a therapeutically effective amount of a dopamine reuptake inhibitor, and at least one pharmaceutically acceptable carrier; wherein said sedative agent is eszopiclone or a pharmaceutically acceptable salt, solvate, clathrate, polymorph, or co-crystal thereof; and said dopamine reuptake inhibitor is amineptine, bupropion, GBR-12935, venlafaxine, 2β-propanoyl-3β-(4-tolyl)-tropane, or a pharmaceutically acceptable salt, solvate, clathrate, polymorph, or co-crystal of any one of them.

Another aspect of the present invention relates to a method of treating a patient suffering from depression, comprising the step of co-administering to a patient in need thereof a therapeutically effective amount of eszopiclone or a pharmaceutically acceptable salt, solvate, clathrate, polymorph, or co-crystal thereof; and a therapeutically effective amount of bupropion or a pharmaceutically acceptable salt, solvate, clathrate, polymorph, or co-crystal thereof, and at least one pharmaceutically acceptable carrier.

Another aspect of the present invention relates to a method of augmentation of antidepressant therapy in a patient, comprising the step of administering to a patient in need thereof, undergoing antidepressant therapy, a therapeutically effective amount of a sedative agent; wherein said sedative agent is a compound that modulates the activity of a GABA receptor and has a $K_i$ less than about 300 nM in a GABA-receptor binding assay.

Another aspect of the present invention relates to a method of augmentation of antidepressant therapy in a patient, comprising the step of administering to a patient in need thereof, undergoing antidepressant therapy, a therapeutically effective amount of a sedative agent; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them.

Another aspect of the present invention relates to a method for augmentation of antidepressant therapy in a patient comprising administering to the patient in need thereof, undergoing antidepressant therapy, a therapeutically effective amount of eszopiclone, or a pharmaceutically acceptable salt, solvate, clathrate, polymorph, or co-crystal thereof.

Another aspect of the present invention relates to a method for eliciting a dose sparing effect in a patient undergoing treatment with an antidepressant, comprising the step of administering to a patient in need thereof, undergoing antidepressant therapy, a therapeutically effective amount of a sedative agent; wherein said sedative agent is a compound that modulates the activity of a GABA receptor and has a $K_i$ less than about 300 nM in a GABA-receptor binding assay.

Another aspect of the present invention relates to a method for eliciting a dose sparing effect in a patient undergoing treatment with an antidepressant, comprising the step of administering to a patient in need thereof, undergoing antidepressant therapy, a therapeutically effective amount of a sedative agent; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them.

Another aspect of the present invention relates to a method for eliciting a dose sparing effect in a patient undergoing treatment with an antidepressant, comprising administering to the patient in need thereof, undergoing antidepressant therapy, a therapeutically effective amount of eszopiclone, or a pharmaceutically acceptable salt, solvate, clathrate, polymorph, or co-crystal thereof.

Another aspect of the present invention relates to a method for reducing depression relapse in a patient who received antidepressant treatment, comprising the step of administering to a patient in need thereof, receiving antidepressant treatment, a therapeutically effective amount of a sedative agent; wherein said sedative agent is a compound that modulates the activity of a GABA receptor and has a $K_i$ less than about 300 nM in a GABA-receptor binding assay.

Another aspect of the present invention relates to a method for reducing depression relapse in a patient who received antidepressant treatment, comprising the step of administering to a patient in need thereof, receiving antidepressant treatment, a therapeutically effective amount of a sedative agent; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them.

Another aspect of the present invention relates to a method for reducing depression relapse in a patient who received antidepressant treatment, comprising administering to the patient in need thereof receiving antidepressant treatment, a therapeutically effective amount of eszopiclone, or a pharmaceutically acceptable salt, solvate, clathrate, polymorph, or co-crystal thereof.

In certain embodiments, the present invention relates to the aforementioned method, wherein the eszopiclone is administered chronically or long-term.

Another aspect of the present invention relates to a method for improving the efficacy of antidepressant therapy in a patient suffering from depression, comprising the step of administering to a patient in need thereof, undergoing antidepressant therapy, a therapeutically effective amount of a sedative agent; wherein said sedative agent is a compound that modulates the activity of a GABA receptor and has a $K_i$ less than about 300 nM in a GABA-receptor binding assay.

Another aspect of the present invention relates to a method for improving the efficacy of antidepressant therapy in a patient suffering from depression, comprising the step of administering to a patient in need thereof, undergoing antidepressant therapy, a therapeutically effective amount of a sedative agent; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them.

Another aspect of the present invention relates to a method for improving the tolerability of antidepressant therapy in a patient suffering from depression, comprising administering to the patient in need thereof, undergoing antidepressant therapy, a therapeutically effective amount of eszopiclone, or a pharmaceutically acceptable salt, solvate, clathrate, polymorph, or co-crystal thereof.

Another aspect of the present invention relates to a method for improving the tolerability of antidepressant therapy in a patient suffering from depression, comprising the step of administering to a patient in need thereof, undergoing antidepressant therapy, a therapeutically effective amount of a sedative agent; wherein said sedative agent is racemic zopiclone, eszopiclone, indiplon, zolpidem, zaleplon, gaboxadol, or a pharmaceutically acceptable salt, solvate, clathrate, polymorph, or co-crystal of any one of them.

Another aspect of the present invention relates to a method for improving the tolerability of antidepressant therapy in a patient suffering from depression, comprising administering to the patient in need thereof, undergoing antidepressant therapy, a therapeutically effective amount of eszopiclone, or a pharmaceutically acceptable salt, solvate, clathrate, polymorph, or co-crystal thereof.

In certain embodiments, the present invention relates to the aforementioned methods, wherein the antidepressant is citalopram, duloxetine, escitalopram, fluoxetine, fluvoxamine, milnacipran, paroxetine, sertraline, clominpramine, femoxetine, indapline, alaprolclate, cericlamine, ifoxetine, or a pharmaceutically acceptable salt, solvate, clathrate, polymorph, or co-crystal of any one of them.

In certain embodiments, the present invention relates to the aforementioned methods, wherein the antidepressant is desipramine, maprotiline, lofepramine, reboxetine, oxaprotiline, fezolamine, tomoxetine, (S,S)-hydroxybupropion, or a pharmaceutically acceptable salt, solvate, clathrate, polymorph, or co-crystal of any one of them.

In certain embodiments, the present invention relates to the aforementioned methods, wherein the antidepressant is a dopamine reuptake inhibitor or an atypical antidepressant.

Immediate/Sustained Release Combination Therapy Dosage Forms

The combination therapy may be formulated in an immediate release dosage form or a sustained release dosage form. In certain embodiments, the present invention relates to immediate release dosage forms of the first and second therapeutic agents. An immediate release dosage form may be formulated as a tablet or multiparticulate which may be encapsulated. Other immediate release dosage forms known in the art can be employed. In certain embodiments, the combination of therapeutic agents may be formulated to provide for an increased duration (sustained release) of therapeutic action. These formulations, at comparable daily dosages of conventional immediate release drug, are often associated with a lower incidence or severity of adverse drug reactions; and they can also be administered at a lower daily dose than conventional oral medication while maintaining therapeutic activity.

In certain embodiments, the combination therapy can be formulated to delivery the therapeutic agents at the same time or at separate times. In certain embodiments, the first and second therapeutic agents are administered via an oral solid dosage form that includes a sustained release carrier causing the sustained release of the first therapeutic agent, or both the first therapeutic agent and the second therapeutic agent when the dosage form contacts gastrointestinal fluid. The sustained release dosage form may comprise a plurality of substrates which include the drugs. The substrates may comprise matrix spheroids or may comprise inert pharmaceutically acceptable beads which are coated with the drugs. The coated beads are then preferably overcoated with a sustained release coating comprising the sustained release carrier. The matrix spheroid may include the sustained release carrier in the matrix itself; or the matrix may comprise a normal release matrix containing the drugs, the matrix having a coating applied thereon which comprises the sustained release carrier. In other embodiments, the oral solid dosage form comprises a tablet core containing the drugs within a normal release matrix, with the tablet core being coated with a sustained release coating comprising the sustained release carrier. In further embodiments, the tablet contains the drugs within a sustained release matrix comprising the sustained release carrier. In additional embodiments, the tablet contains the first therapeutic agent within a sustained release matrix and the second therapeutic agent coated into the tablet as an immediate release layer.

The term "sustained release" is defined for purposes of the present invention as the release of the therapeutic agent from the formulation at such a rate that blood (e.g., plasma) concentrations (levels) are maintained within the therapeutic range (above the minimum effective analgesic concentration or "MEAC") but below toxic levels over a period of time of about 12 hours or longer.

The first and second therapeutic agents can be formulated as a controlled or sustained release oral formulation in any suitable tablet, coated tablet or multiparticulate formulation known to those skilled in the art. The sustained release dosage form may optionally include a sustained released carrier which is incorporated into a matrix along with the active agents, or which is applied as a sustained release coating.

The sustained release dosage form may include the first therapeutic agent in sustained release form and second therapeutic agent in the sustained release form or in immediate release form. The first therapeutic agent may be incorporated into the sustained release matrix along with the second therapeutic agent; incorporated into the sustained release coating; incorporated as a separated sustained release layer or immediate release layer; or may be incorporated as a powder, granulation, etc., in a gelatin capsule with the substrates of the present invention. Alternatively, the sustained release dosage form may have the first therapeutic agent in the sustained release form and the second therapeutic agent in the sustained release form or immediate release form.

An oral dosage form according to the invention may be provided as, for example, granules, spheroids, beads, pellets (hereinafter collectively referred to as "multiparticulates") and/or particles. An amount of the multiparticulates which is effective to provide the desired dose of the therapeutic agents over time may be placed in a capsule or may be incorporated in any other suitable oral solid form. In one certain embodiments of the present invention, the sustained release dosage form comprises such particles containing or comprising the active ingredient, wherein the particles have diameter from about 0.1 mm to about 2.5 mm, preferably from about 0.5 mm to about 2 mm.

In certain embodiments, the particles comprise normal release matrixes containing the first therapeutic agent with the second therapeutic agent. These particles are then coated with the sustained release carrier in embodiments where the first therapeutic agent is immediately released, the first therapeutic agent may be included in separate normal release matrix particles, or may be co-administered in a different immediate release composition which is either enveloped within a gelatin capsule or is administered separately. In other embodiments, the particles comprise inert beads which are coated with the second therapeutic agent with the first therapeutic agents. Thereafter, a coating comprising the sustained release carrier is applied onto the beads as an overcoat.

The particles are preferably film coated with a material that permits release of the active agents at a sustained rate in an aqueous medium. The film coat is chosen so as to achieve, in combination with the other stated properties, a desired in vitro release rate. The sustained release coating formulations of the present invention should be capable of producing a strong, continuous film that is smooth and elegant, capable of supporting pigments and other coating additives, non-toxic, inert, and tack-free.

Coatings

The dosage forms of the present invention may optionally be coated with one or more materials suitable for the regulation of release or for the protection of the formulation. In one embodiment, coatings are provided to permit either pH-dependent or pH-independent release, e.g., when exposed to gastrointestinal fluid. A pH-dependent coating serves to release the first active agent, second active agent, or both in the desired areas of the gastro-intestinal (GI) tract, e.g., the stomach or small intestine, such that an absorption profile is provided which is capable of providing at least about twelve hours and preferably up to twenty-four hours of therapeutic benefit to a patient. When a pH-independent coating is desired, the coating is designed to achieve optimal release regardless of pH-changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine. In certain embodiments, the first therapeutic agent is released in one area of the GI tract and the second therapeutic agent is released in a second area of the GI tract. In certain embodiments, the first and second therapeutic agents are released in nearly equal amounts at the same location in the GI tract.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like. Thus, one aspect of the present invention relates to a formulation wherein the first therapeutic agent is coated over the enteric coat and released into the stomach while the second therapeutic agent is protected by the enteric coating and is released further down the GI tract. Alternatively, one aspect of the present invention relates to a formulation wherein the second therapeutic agent is coated over the enteric coat and released into the stomach while the first therapeutic agent is protected by the enteric coating and is released further down the GI tract.

In certain preferred embodiments, the substrate (e.g., tablet core bead, matrix particle) containing the first therapeutic agent (with or without the second therapeutic agent) is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2 to about 25% of the substrate in order to obtain a desired sustained release profile. Alternatively, the invention relates to instances wherein the substrate (e.g., tablet core bead, matrix particle) containing the second therapeutic agent (with or without the first therapeutic agent) is coated with a hydrophobic material. Such formulations are described, e.g., in detail in U.S. Pat. Nos. 5,273,760 and 5,286,493. Other examples of sustained release formulations and coatings which may be used in accordance with the present invention include U.S. Pat. Nos. 5,324,351; 5,356,467, and 5,472,712.

Alkylcellulose Polymers

Cellulosic materials and polymers, including alkylcelluloses, provide hydrophobic materials well suited for coating the formulations according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are copolymers of acrylic and methacrylic acid esters with a low content of quaternary ammonium groups. In order to obtain a desirable dissolution profile, it may be necessary to incorporate in a coating two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit® from Rohm Tech, Inc. There are several different types of Eudragit®. For example, Eudragit® E is an example of a methacrylic acid copolymer which swells and dissolves in acidic media. Eudragit® L is a methacrylic acid copolymer which does not swell at about pH<5.7 and is soluble at about pH>6. Eudragit® S does not swell at about pH<6.5 and is soluble at about pH>7. Eudragit® RL and Eudragit® RS are water swellable, and the amount of water absorbed by these polymers is pH-dependent, however, dosage forms coated with Eudragit® RL and RS are pH-independent.

In certain preferred embodiments, the acrylic coating comprises a mixture of two acrylic resin lacquers commercially available from Rohm Pharma under the Tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When the aqueous dispersion of hydrophobic material is used to coat inert pharmaceutical beads such as nu pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the active agents to the beads, and/or to color the solution, etc. For example, a product which includes hydroxypropylmethylcellulose, etc. with or without colorant (e.g., Opadry®, commercially available from Colorcon, Inc.) may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, preformulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic material. For example, color be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic material may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agent when said coated substrate is exposed to aqueous solutions, e.g., gastric fluid, is preferably applied, taking into account the physical characteristics of the therapeutically active agent, the manner of incorporation of the plasticizer, etc. After coating with the hydrophobic material, a further overcoat of a film-former, such as Opadry®, is optionally applied to the beads. This overcoat is provided, if at all, in order to substantially reduce agglomeration of the beads.

The release of the therapeutically active agent from the controlled release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents which function as poreformers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain. The release-modifying agent may also comprise a semi-permeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864. The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in-vitro dissolution rates of the active agent within the preferred ranges and that releases the active agent in a pH-dependent or pH-independent manner. The materials suitable for inclusion in a controlled release matrix will depend on the method used to form the matrix.

For example, a matrix in addition to the first active agent and (optionally) the second active agent may include: (1) Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts (or softens to the extent necessary to be extruded) may be used in accordance with the present invention. (2) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly(methacrylic acid)(anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30 to about 200 C., preferably from about 45 to about 90 C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material which is normally solid at room temperature and has a melting point of from about 30 to about 100 C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25 and 90 C. are preferred. Of the long chain hydrocarbon materials, fatty (aliphatic) alcohols are preferred in certain embodiments. The oral dosage form may contain up to 60% (by weight) of at least one digestible, long chain hydrocarbon.

In certain instances, a combination of two or more hydrophobic materials are included in the matrix formulations. If an additional hydrophobic material is included, it may be selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of release desired for the therapeutic agent. The at least one aliphatic alcohol may be, for example, lauryl alcohol, myristyl alcohol or stearyl alcohol. In certain embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of release desired for the therapeutic agent. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the active agent from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000. Another suitable controlled release matrix would comprise an alkylcellulose (especially ethyl cellulose), a $C_{12}$ to $C_{36}$ aliphatic alcohol and, optionally, a polyalkylene glycol. In another preferred embodiment, the matrix includes a pharmaceutically acceptable combination of at least two hydrophobic materials. In addition to the above ingredients, a controlled release matrix may also contain suitable quantities of other materials, e.g. diluents, lubricants, binders, granulating aids, colorants, flavorants and glidants that are conventional in the pharmaceutical art.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The therapeutic agent alone or on combination with other therapeutic agents can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. Ampoules are convenient unit dosages. For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions contain the above-identified combination of drugs and that mixture has one or more excipients suitable as suspending agents, for example pharmaceutically acceptable synthetic gums such as hydroxypropylmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

One aspect of combination therapy pertains to a method for providing effective therapeutic treatment in humans, comprising administering an effective or sub-therapeutic amount of a first therapeutic agent; and administering an effective amount of a second therapeutic agent in an amount effective to augment the therapeutic effect provided by said first therapeutic agent. The second therapeutic agent can be administered before, simultaneously with, or after administration of the first therapeutic agent, as long as the dosing interval of the second therapeutic agent overlaps with the dosing interval of the first therapeutic agent (or its therapeutic effect). In other words, according to the method of the present invention, in certain preferred embodiments the second therapeutic agent need not be administered in the same dosage form or even by the same route of administration as the first therapeutic agent. Rather, the method is directed to the surprising synergistic and/or additive benefits obtained in humans, when therapeutically effective levels of a first therapeutic agent have been administered to a human, and, prior to or during the dosage interval for the second therapeutic agent or while the human is experiencing the therapeutic effect, an effective amount of a second therapeutic agent to augment the therapeutic effect of the first therapeutic agent is administered. If the second therapeutic agent is administered prior to the administration of the first therapeutic agent, it is preferred that the dosage intervals for the two drugs overlap, i.e., such that the therapeutic effect over at least a portion of the dosage interval of the first therapeutic agent is at least partly attributable to the second therapeutic agent.

In an additional method of the invention, the surprising synergistic and/or additive benefits obtained in the patient are achieved when therapeutically effective levels of the second therapeutic agent have been administered to the patient, and, during the dosage interval for the second therapeutic agent or while the patient is experiencing the therapeutic effect by virtue of the administration of a second therapeutic agent, an effective amount of a first therapeutic agent to augment the therapeutic effect of the second therapeutic agent is administered.

Another aspect of combination therapy relates to an oral solid dosage form comprising an therapeutically effective amount of a first therapeutic agent together with an amount of a second therapeutic agent or pharmaceutically acceptable salt thereof which augments the effect of the first therapeutic agent.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy, management and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-, di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha., .beta. or gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459, 731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426, 011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Processes for Preparing Matrix-Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and the active agent; (b) mixing the hydroxyalkyl cellulose containing granules with at least one $C_{12}$-$C_{36}$ aliphatic alcohol; and (c) optionally, compressing and shaping the granules. Preferably, the granules are formed by wet granulating the hydroxyalkyl cellulose/active agent with water. In a particularly preferred embodiment of this process, the amount of water added during tie wet granulation step is preferably between 1.5 and 5 times, especially between 1.75 and 3.5 times, the dry weight of the active agent.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropylcellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colorants, flavorants and glidants that are conventional in the pharmaceutical art. The quantities of these additional materials will be sufficient to provide the desired effect to the desired formulation. In addition to the above ingredients, a sustained release matrix incorporating melt-extruded multiparticulates may also contain suitable quantities of other materials, e.g. diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the active agent, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets (compressed and molded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681 (Klimesch, et. al.).

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular active agent utilized and the desired release rate, among other things.

The melt-extruded unit dosage forms of the present invention may further include combinations of melt-extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated, e.g., as separate pellets within a gelatin capsule, or may be coated on the surface of the multiparticulates after preparation of the dosage forms (e.g., controlled release coating or matrix-based). The unit dosage forms of the present invention may also contain a combination of controlled release beads and matrix multiparticulates to achieve a desired effect.

The sustained release formulations of the present invention preferably slowly release the therapeutically active agent, e.g., when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticizer relative to hydrophobic material, by the inclusion of additional ingredients or excipients, by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

Definitions

Many of the sedative agents, antidepressants, including without limitation, serotonin reuptake inhibitors, norepinephrine reuptake inhibitors, and $5\text{-HT}_{2A}$ modulators are chiral compounds that can exist as a racemic mixture, a non-equal mixture of enantiomers, or as a single enantiomer. Importantly, the recitation of a compound that can exist as a racemic mixture, a non-equal mixture of enantiomers, or a single enantiomer is meant to encompass all three aforementioned forms, unless stated otherwise. The term "enantiomeric excess" is well known in the art and is defined for a resolution of ab 6 a+b as:

$$ee_a = \left(\frac{conc.\ of\ a - conc.\ of\ b}{conc.\ of\ a + conc.\ of\ b}\right) \times 100$$

The term "enantiomeric excess" is related to the older term "optical purity" in that both are measures of the same phenomenon. The value of e.e. will be a number from 0 to 100, zero being racemic and 100 being pure, single enantiomer. A compound which in the past might have been called 98% optically pure is now more precisely described as 96% e.e.; in other words, a 90% e.e. reflects the presence of 95% of one enantiomer and 5% of the other in the material in question. In instances when a specific enantiomer is recited (e.g., eszopiclone) for use in the compositions or methods of the present invention, this indicates that the composition contains a significantly greater proportion of the specified enantiomer in relation to the non-specified enantiomer. In a preferred embodiment, compositions comprising a specified enantiomer contain the specified enantiomer in at least 90% e.e. More preferably, such compositions comprising a specified enantiomer contain the specified enantiomer in at least 95% e.e. Even more preferably, such compositions comprising a specified enantiomer contain the specified enantiomer in at least 98% e.e. Most preferably, such compositions comprising a specified enantiomer contain the specified enantiomer in at least 99% e.e.

For example, compositions comprising eszopiclone contain the S-enantiomer of zopiclone in at least 90% e.e. More preferably, compositions comprising eszopiclone contain the S-enantiomer of zopiclone in at least 95% e.e. Even more preferably, such compositions comprising eszopiclone contain the S-enantiomer of zopiclone in at least 98% e.e. Most preferably, such compositions comprising eszopiclone contain the S-enantiomer of zopiclone in at least 99% e.e.

The term "serotonin reuptake inhibitor" refers to a compound that at least partially inhibits the reuptake of serotonin. In a preferred embodiment, the serotonin reuptake inhibitor is a selective serotonin reuptake inhibitor.

The term "selective serotonin reuptake inhibitor" refers to a compound that preferentially inhibits serotonin reuptake relative to its ability to modulate the activity of other receptors.

The term "norepinephrine reuptake inhibitor" refers to a compound that at least partially inhibits the reuptake of norepinephrine. In a preferred embodiment, the norepinephrine reuptake inhibitor is a selective norepinephrine reuptake inhibitor.

The term "selective norepinephrine reuptake inhibitor" refers to a compound that preferentially inhibits norepinephrine reuptake relative to its ability to modulate the activity of other receptors.

The term "$5-HT_{2A}$ modulator" refers to a compound that modulates the activity of $5-HT_{2A}$ receptor. The term "$5-HT_{2A}$ modulator" includes $5-HT_{2A}$ antagonists and $5-HT_{2A}$ inverse agonists and $5-HT_{2A}$ partial agonists.

The term "antagonist" refers to a compound that binds to a receptor site, but does not cause any physiological changes.

The terms "inverse agonist" and "negative antagonist" and "neutral antagonist" refer to compounds that inhibit an unoccupied, but active receptor.

The term "patient" refers to a mammal in need of a particular treatment. In a preferred embodiment, a patient is a primate, canine, feline, or equine. In another preferred embodiment, a patient is a human.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "solvate" refers to a pharmaceutically acceptable form of a specified compound, with one or more solvent molecules, that retains the biological effectiveness of such compound. Examples of solvates include compounds of the invention in combination with solvents such, for example, water (to form the hydrate), isopropanol, ethanol, methanol, dimethyl sulfoxide, ethyl acetate, acetic acid, ethanolamine, or acetone. Also included are formulations of solvate mixtures such as a compound of the invention in combination with two or more solvents.

The term "screened subject" refers to any subject who signs the Informed Consent and completes at least one study related procedure.

The term "screen failure subject" refers to any subject who has signed the informed consent and completed at least one study related procedure and discontinues for any reason prior to receiving any study medication.

The term "randomized subject" refers to any subject who receives a randomization number.

The term "completed subject" refers to any subject who completes all study visits.

The term "early termination subject" refers to any subject who is assigned a randomization number but does not complete all study visits.

The phrases "sleep disorders" or "sleep abnormality" refers to primary insomnia; secondary insomnia; situational insomnia; transient insomnia; short-term insomnia; chronic insomnia; acute insomnia; prolonged latency to sleep onset; difficulty falling asleep; difficulty staying asleep; sleep maintenance problems, including without limitation, frequent awakenings, an increase in time spent awake after initially falling asleep (wake time after sleep onset, or WASO), sleep fragmentation, transient microarousals, and unrefreshing sleep; increased time awake during the sleep period; waking up too early; and reduced total sleep time.

The term "depression" refers to major depression, major depressive disorder, mild depression, moderate depression, severe depression without psychosis, severe depression with psychosis, dysthymia, bipolar disorder, or manic depression.

The term "antidepressant" refers to compounds used to treat depression, including without limitation: tricyclic antidepressants, such as clomipramine, amoxapine, nortriptyline, moprotilene, trimipramine, imipramine, or protriptyline; monoamine oxidase inhibitors; serotonin reuptake inhibitors, including selective serotonin reuptake inhibitors, such as citalopram, escitalopram, duloxetine, fluoxetine, sertraline, norsertraline, paroxetine, mirtrazepine, fluvoxamine, milnacipran, clominpramine, femoxetine, indapline, alaproiclate, cericlamine, or ifoxetine; norepinephrine reuptake inhibitors, including selective norepinephrine reuptake inhibitors, such as desipramine, maprotiline, lofepramine, reboxetine, oxaprotiline, fezolamine, tomoxetine, or (S,S)-hydroxybupropion; and atypical antidepressants, such as venlafaxine, desmethylvenlafaxine, nefazadone, or trazodone; therapeutically active isomers or metabolites of any of the foregoing; and pharmaceutically acceptable salts, solvates, clathrates, polymorphs, or co-crystals of any one of the foregoing.

For purposes of this invention, the chemical elements are identified in accordance with the Periodic Table of the Elements, CAS version, Handbook of Chemistry and Physics, 67th Ed., 1986-87, inside cover.

Exemplification

The invention now being generally described, it will be more readily understood by reference to the following examples, which are included merely for purposes of illustration of certain aspects and embodiments of the present invention, and are not intended to limit the invention.

EXAMPLE 1

Depression Response to Eszopiclone in Adults With Major Depressive Disorder (DREAMDD): A Randomized, Double-Blind, Placebo-Controlled, Parallel-Group, 8-Week, Safety and Efficacy Study of Eszopiclone 3 mg Compared to Placebo in Subjects with Insomnia Related to Major Depressive Disorder Rationale & Objectives Insomnia often occurs simultaneously with the onset of major depression, and may negatively impact the depressed subject's quality of life (QoL) and functional abilities. In fact, in some patients, insomnia is the most disabling of the depressive symptom complex. In addition, many subjects are treated with selective serotonin re-uptake inhibitors (SSRIs) that may accentuate insomnia initially following treatment with these agents. This study aims to establish that the early addition of continuous eszopiclone 3 mg at bedtime to a standard antidepressant treatment with fluoxetine hydrochloride (20 or 40 mg) daily in the morning for 8 weeks is safe and provides improved sleep to depressed subjects. Beyond direct impact on sleep efficacy measures, differences in time to onset and amplitude of antidepressant effects, and improvements in quality of life and functional restoration are investigated A primary objective of the present study was to evaluate subjective sleep efficacy during eight weeks of treatment with eszopiclone 3 mg nightly (at bed time) in subjects with insomnia related to major depressive disorder and treated concurrently with fluoxetine hydrochloride. A secondary objective of the study was to evaluate the potential for eszopiclone 3 mg to augment the antidepressant effect of fluoxetine hydrochloride by investigating the differences in time to onset and amplitude of antidepressant responses over an 8-week treatment period.

Study Design

This study was a double-blind randomized, placebo-controlled, parallel group study. The study consisted of subjects with major depression disorder treated for ten weeks with a common antidepressant regimen, 20-40 mg of fluoxetine hydrochloride per day, and randomized to receive (in addition) either eszopiclone 3 mg or placebo for eight weeks. All subjects must satisfy DSM-IV criteria for insomnia related to major depression.

Visit 1 (Screening): After signing the Informed Consent, subjects were screened with the following assessments: administration of the Hamilton Depression Rating Scale (17 item; HAM-D-17) via interactive voice response system, medical and sleep history, physical examination including vital signs, clinical laboratory assessments, and standard 12-lead electrocardiogram (ECG). Subjects returned for Visit 2 within 5 to 14 days.

Visit 2 (Week 0; Baseline): Subjects meeting inclusion and exclusion criteria begin a 3-7 day baseline period. At this visit safety assessments and evaluation of adverse events (AEs) were performed. In addition, subjects were trained on use of the interactive voice response system (IVRS) system for collection of sleep and depression endpoints and the frequency of assessments. Subjects completed 7 selected items of the HAM-D-17 via IVRS the morning after this visit. During this 3-7 day period, subjects made daily IVRS calls to evaluate sleep parameters, and depression symptoms [Daily Telephone Assessment (DTA) and Symptoms Questionnaire (SQ; 23-item Depression subscale)].

Visit 3 (End of Week 0; Randomization): Subjects with a minimum of three complete IVRS assessments during the baseline week were randomized to eszopiclone 3 mg or matching placebo nightly (at bedtime) for eight weeks in addition to taking open-label fluoxetine hydrochloride administered in the morning. On the morning of this visit (prior to the visit), subjects completed the Hamilton Depression Rating Scale (7 selected items of the HAM-D-17) via IVRS in addition to the daily sleep diary. At this visit, the HAM-D-17 was administered by a clinician; safety assessments and evaluation of adverse effects (AEs) were performed; and the study drug was dispensed. Following this visit, subjects continued to make daily IVRS calls to evaluate sleep and depression symptoms until the morning of Visit 4.

Visits 4 (Week 1), 5 (Week 2), 6 (Week 3), 7 (Week 4), 8 (Week 6); and Visit 9 (Week 8; End of Double-blind): On the morning of each visit, subjects completed the 7 selected items of the HAM-D-17 and sleep diary via IVRS. In clinic, the subject completed sleep and quality of life questionnaires. In addition, the HAM-D-17 was administered by a clinician (at Visits 7 and 9 only); safety assessments and an evaluation of AEs were performed; and study drug and supplies were dispensed. On the morning following each office visit, subjects completed the sleep diary and depression symptoms questionnaires via IVRS. Beginning one week prior to Visit 9 until Visit 10, subjects resumed daily IVRS for completion of the sleep diary. Subjects completed randomized double-blind (DB) study drug the night prior to Visit 9 but remained on fluoxetine hydrochloride for the two-week wash-out period.

At Visit 9, the end of treatment assessments were performed (ECG, clinical laboratory assessments, physical exam, vital sign).

Visit 10 (Week 10; End of Study): Subjects completed their last dose of fluoxetine hydrochloride for this study on the day of this visit. On the morning of the day prior to Visit 10, subjects completed the IVRS sleep diary and HAM-D-7. On the morning of Visit 10, prior to the visit, subjects completed their final IVRS call during which the sleep diary and depression symptoms (DTA/SQ) questionnaires were administered. At the clinic visit, the HAM-D-17 was administered by a clinician. Final safety assessments [physical examination, ECG, clinical laboratory assessments] and an evaluation of AEs were performed and study drug and supplies are collected. At this time, subjects were referred for follow-up to their primary physicians.

Sample Population: Approximately 600 subjects were randomized in order to complete 360. Subjects are males and females between the ages of 21 and 64, inclusive. All subjects were required to meet the DSM IV criteria for insomnia related to a major depressive disorder. Subjects must have reported all of the following: sleep onset time>30 minutes, wake time after sleep onset>45 minutes and total sleep time of<6.5 hours. Subjects must also have had a minimum HAM-D-17 score of 14, not including scores for sleep items, at Visit 1.

Dose Description: All subjects received fluoxetine hydrochloride 20 mg daily until Week 4 (Visit 7). At Week 4 (Visit 7), the dose of fluoxetine hydrochloride was permitted to 40 mg if the investigator's clinical global impression of the subject's depression symptoms was rated at >3 compared symptoms at baseline (Visit 3). In addition, subjects were randomized at Visit 3 (end of baseline) to treatment with one of the following nightly (at bedtime): eszopiclone (3 mg) or matching placebo.

Study Methods

Primary Efficacy Endpoint: The primary endpoint was the mean subjective wake time after sleep onset (WASO) during Week 1.

Key Secondary Endpoints: Time to onset of 30% antidepressant response, defined as the time from Visit 3 to the first of two successive clinic assessment time points at which the subject achieved a≧30% reduction from baseline, on the HAM-D-6 (Bech) was a key secondary endpoint. 30% antidepressant response, defined as a≧30% reduction from baseline for at least two successive clinic assessment time points, on the HAM-D-6 (Bech) score was also a key secondary endpoint.

Secondary Endpoints: Secondary sleep endpoints were the following:

Mean wake time after sleep onset (WASO) at weeks 2, 3, 4, 6 and 8 post randomization.

Mean subjective total sleep time (TST) at weeks 1, 2, 3, 4, 6 and 8 post randomization.

Mean subjective sleep latency (SL) at weeks 1, 2, 3, 4, 6 and 8 post randomization.

Mean number of awakenings at weeks 1, 2, 3, 4, 6 and 8 post randomization.

Quality and depth of sleep at weeks 1, 2, 3, 4, 6 and 8 post randomization.

Daytime alertness at weeks 1, 2, 3, 4, 6 and 8 post randomization.

Ability to concentrate at weeks 1, 2, 3, 4, 6 and 8 post randomization.

Physical well-being at weeks 1, 2, 3, 4, 6 and 8 post randomization.

Ability to function at weeks 1, 2, 3, 4, 6, and 8 post randomization.

In addition, the double-blind average (average of weeks 1, 2, 3, 4, 6, and 8) and the rebound and withdrawal effects were analyzed for each of the subjective sleep endpoints. Other secondary efficacy endpoints were the following:

Time to onset of 50% antidepressant response, defined as the time from Visit 3 to the first of two successive clinic assessment time points at which the subject achieved a≧50% reduction from baseline, on the HAM-D-6 (Bech).

50% antidepressant response, defined as a≧50% reduction from baseline for at least two successive clinic assessment time points, on the HAM-D-6 (Bech) score.

Time to onset of 30% antidepressant response on HAM-D-6 (Maier) for at least two successive clinic assessment time points.

30% antidepressant response on HAM-D-6 (Maier) score for at least two successive clinic assessment time points.

Time to onset of 50% antidepressant response on HAM-D-6 (Maier) for at least two successive clinic assessment time points.

50% antidepressant response on HAM-D-6 (Maier) score for at least two successive clinic assessment time points.

The change in the HAM-D-6 (Bech) and HAM-D-6 (Maier) from baseline to each visit.

The change in the HAM-D-17 from baseline to weeks 4 and 8.

SQ score (Depression Subscale) during weeks 1, 2, 3, 4, 6, and 8.

DTA score during weeks 1, 2, 3, 4, 6, and 8.

The change in HAM-D-6 (Bech), HAM-D-6 (Maier), HAM-D-17, SQ, and DTA during the wash-out phase until end of study (Week 8 minus Week 10).

SF-36 score at weeks 4, 8, and 10.

WLQ score at weeks 2, 4, 8, and 10.

ESS at weeks 1, 2, 3, 4, 6, 8, and 10.

ISI score at weeks 2, 4, 8, and 10.

Clinical Global Impression (CGI) at weeks 1, 2, 3, 4, 6, 8, and 10.

Safety Assessments

Safety was assessed by physical examinations, a standard 12-lead ECG, vital signs, clinical laboratory assessments and AE reporting.

Subjective Assessments

IVRS questionnaire: Subjective sleep assessments, depression symptoms and quality of life were evaluated via an IVRS. At Visit 1, subjects were trained on the use of the system and received a unique user ID and password.

Sleep Diary: This questionnaire asked the subjects to report information about the previous night's sleep.

Daily Telephone Assessment: This questionnaire rated the subjects depressive symptoms over the past day on a scale of 0 to 9.

The Symptoms Questionnaire (Depression Subscale): This questionnaire asked if subjects have experienced a number of depressive symptoms over the previous day.

The Hamilton-Depression-7: Depression symptoms and general well being over the previous 2 weeks were assessed by 7 selected items of the Hamilton-Depression Rating Scale-17. The items included in the 7 item scale are mood (Item 1), feelings of guilt (Item 2); work activities (Item 7); retardation (Item 8), agitation (Item 9); anxiety psychic (Item 10); and somatic symptoms (Item 13). For data analysis, two 6 item sub scales were evaluated: the Bech HAM-D-6 (9) which includes Items 1, 2, 7, 8, 10 and 13; and the Maier HAM-D-7 (10) which includes Items 1, 2, 7, 8, 9, and 10.

Subject compliance with the use of the IVRS was tracked. Sites were notified of non-compliance and were required to follow-up with the subject.

Sleep, Depression, and Productivity Questionnaires and Clinical Global Impression: The following questionnaires were administered as listed below.

Epworth Sleepiness Scale (ESS): ESS was completed by the subject at Visits 2-10. The ESS is a subjective assessment of the likelihood of falling asleep in various situations.

Insomnia Severity Index (ISI): ISI was completed by the subject at Visits 3, 5, 7, 9 and 10. The ISI is a subjective assessment of sleep quality, restedness/refreshness upon arising, daytime fatigue, attention/concentration and relationship and mood disturbances.

Work Limitations Questionnaire (WLQ): WLQ was completed by the subject at Visits 3, 5, 7, 9, and 10. The WLQ is a validated self-report instrument for measuring the degree to which chronic health problems interfere with ability to perform job roles, addressing the content of the job through a demand-level methodology.

Hamilton Depression-17: HAM-D-17 was administered via IVRS at screening and rated by a trained clinician at Visits 3, 7, 9, and 10.

SF-36: SF-36 was completed by the subject at Visits 3, 7, 9 and 10. The SF-36 represents multiple operational definitions of health, including function and dysfunction, distress and well-being, objective reports and subjective ratings, and both favorable and unfavorable self-evaluations of general health status.

Clinical Global Impression (CGI): CGI was completed by the investigator at Visits 3-10 The CGI is the investigator's subjective assessment of improvement in the subject's depressive symptoms. The response on the CGI at Visit 7 (Week 4 of double-blind treatment) was used by the investigator to assess the need for increasing the dose of fluoxetine to 40 mg daily (in the morning). If in the opinion of the investigator the subject's condition has not improved on the Global Improvement question of the CGI to a score of 1 (very much improved) or 2 (much improved), the investigator was permitted to increase the dose of fluoxetine hydrochloride to 40 mg.

Study Conduct

Inclusion Criteria:

1. Subject must give appropriate written informed consent and privacy authorization prior to participation in the study. A female subject must also sign the Women of Childbearing Potential Informed Consent Addendum.
2. Subject must understand the purpose of the study and be willing to adhere to the study schedule and procedures described in this protocol.
3. Subject must be 21 to 64 years of age (inclusive) on the day of signing consent.
4. Subject must meet DSM IV criteria for a primary and principal diagnosis of Major Depressive Disorder (MDD; 296.XX), moderate (296.X2) or severe depression without psychotic features (296.X3) with the presences of either a single episode (296.2X) or recurrent episode (296.3X) based on a clinical interview with the primary investigator or sub-investigator (see below for definitions).
5. Subject's current depressive episode is at least 2 weeks but not longer than 6 months in duration.
6. Subject must score a minimum of 14 on the Hamilton-D-17 (not including sleep items).

7. Subject must meet DSM IV criteria for insomnia related to MDD and the symptoms of insomnia must not pre-date the symptoms of MDD by more than 10 weeks (see below for definitions).
8. Subject must report a sleep onset time of ≧30 minutes, and wake time after sleep onset of ≧45 minutes, and ≦6.5 hours of total sleep time at least three times a week over the previous month.
9. Subject physical examination must show no clinically significant abnormal findings (other than MDD) at screening.
10. Subject must have no known clinically significant abnormal laboratory findings at screening.
11. Subject must have no clinically significant ECG abnormalities at screening.
12. Subject must meet one of the following conditions:
   Subject is not taking antidepressant medications at the time of Visit 1.
   Subject is taking a sub-therapeutic dose of antidepressant or other disallowed psychotropic medication and with the approval of the investigator agrees to taper off of this medication, prior to completion of screening assessments at Visit 1.

Exclusion Criteria

1. Female subject is pregnant, lactating or within 6 months post partum.
2. Subject has known sensitivity to any selective SSRI, zopiclone, or eszopiclone.
3. Subject is, in the opinion of the investigator, at significant suicide risk as determined by a clinical interview by the investigator or sub-investigator.
4. Subject has history of major depressive disorder that was refractory to treatment with SSRIs as determined by the Antidepressant Treatment History Questionnaire.
5. Subject has a current primary DSM-IV Axis I psychiatric diagnosis of any of the following disorders: dementia, delirium, schizophrenia, psychosis, other psychotic disorders, dysthymic disorder; bipolar disorders; cyclothymic disorder, other mood disorders, nocturnal panic disorder, primary anxiety disorders, primary panic disorders or any other psychiatric disorder that would compromise the investigator's ability to evaluate the safety and efficacy of the study medication.
Note: Subjects with Sexual and Gender Identity Disorders or other non-psychotic Axis I disorders were considered on a case-by-case basis (see below for DSM-IV criteria for disallowed psychiatric diagnoses). Subjects with MDD and a secondary diagnosis of generalized anxiety disorder, panic disorders other than nocturnal panic disorder or seasonal affective disorder were allowed.
6. Subject has any of the following DSM IV Axis II Personality Disorders diagnoses: schizotypal, schizoid, borderline personality disorder; mental retardation or any other personality disorder that would compromise the investigator's ability to evaluate the safety and efficacy of the study medication.
7. Subject has difficulties in sleep initiation or maintenance associated with known medical diagnosis [e.g. sleep apnea, restless leg syndrome (RLS), or periodic leg movement syndrome (PLMS)], or has any condition that has or may affect sleep [(e.g., chronic pain, benign prostatic hypertrophy (BPH)].
8. Subject has any clinically significant unstable medical or neurologic abnormality, unstable chronic disease, or a history of a clinically significant abnormality of the cardiovascular, respiratory, hepatic, or renal systems.
9. Subject has a disorder or history of a condition (e.g., malabsorption, gastrointestinal surgery) that may interfere with drug absorption, distribution, metabolism, or excretion.
10. Subject has a history of malignancy within 5 years, or current malignancy, except for non-melanoma skin cancer.
11. Subject is using any of the disallowed medications, or has not met the required wash-out period for disallowed medications listed below.
12. Subject has a history of drug or alcohol abuse or dependence in the past 6 months or positive urine drug and alcohol test at screening.
13. Subject is participating in, has participated in, or plans to participate in any investigational drug study within 30 days prior to screening until the end of this study.
14. Subject has history of circadian rhythm disorder, or travels across ≧3 time zones on a regular basis.
15. Subject is known to be seropositive for Human Immunodeficiency Virus (HIV).
16. Subject has used any drugs known or suspected to affect hepatic or renal clearance capacity within a period of 30 days prior to screening.
17. Subject is unwilling to refrain from drinking alcoholic beverages during study participation.
18. Subject is a rotating or third/night shift worker.
19. Subject is a staff member or relative of a staff member.

Randomization Criteria

To be eligible for randomization, the subject must have completed a minimum of 3 daily diary assessments via IVRS during the baseline period.

Concurrent Medications and Restrictions

Disallowed Medications

The following medications were disallowed during study participation and must have been discontinued for minimum periods as listed below:

| Drug Class | Wash-out Periods* |
| --- | --- |
| Any antipsychotic medications | 30 days prior to Visit 2 |
| Fluoxetine | 35 days prior to completion of screening assessments |
| Any other SSRI | 14 days prior to completion of screening assessments |
| Any monoamine oxidase inhibitors | 14 days prior to completion of screening assessments |
| Any tricyclic antidepressant (TCA) | 14 days prior to completion of screening assessments |
| Any serotonin-norepinephrine re-uptake inhibitors (NSRIs) | 14 days prior to completion of screening assessments |
| Other antidepressants (trazadone, nefazadone, bupropion, mirtazapine) | 14 days prior to completion of screening assessments |
| Benzodiazepine sedative hypnotics or anxiolytics | 14 days prior to Visit 2 |
| Any drugs including over-the-counter drugs and herbal supplements known to affect sleep wake function | 14 days prior to Visit 2 |

*The wash-out period begins after the subject has successfully tapered from prior therapy and is no longer taking any of the disallowed medication.

Concurrent Medications for the Duration of the Study: Chronic medications other than those listed above taken at a stable dose for at least 30 days prior to clinical assessment screening (Visit 2) were allowed. Standard over the counter medications other than those listed above (analgesics, topical ointments, etc) were also allowed. All females on oral contraceptives and hormonal therapy were encouraged to dose at the same time of day each day while on study.

Additional Instructions: Subjects were to be instructed not to consume alcohol during this study. Subjects were to eat dinner at least 2 hours prior to their scheduled double-blind study medication dosing time. Subjects were to refrain from driving or using heavy machinery within 7 hours after taking double-blind study medication.

Drugs and Dosage

Study Medication Description

Eszopiclone was supplied as 3 mg tablets. Subjects received a 3 mg dose as one tablet. In addition to eszopiclone, the active ingredient, each tablet contained: microcrystalline cellulose, USP; calcium phosphate anhydrous, USP; croscarmellose sodium, USP; colloidal silicon dioxide, USP and magnesium stearate, USP. The tablets were coated with opadry II. The matching placebo contains all ingredients, except the active eszopiclone.

Fluoxetine hydrochloride is a white to off-white crystalline solid with a solubility of 14 mg/mL in water. Each capsule contained fluoxetine hydrochloride equivalent to 20 mg or 40 mg of fluoxetine. The capsules also contained starch, gelatin, silicone, titanium dioxide, iron oxide, and other inactive ingredients.

Administration of Study Medication

Randomized Double-Blind Kits: Eligible subjects were randomized and assigned a numbered double-blind kit containing 6 blister packs. Kits were dispensed in ascending order (lowest to highest) from the sites double-blind drug supply. Each kit contained the following:

Four blister packs clearly labeled with the visit number (Visits 3, 4, 5, and 6). Each Visit 3, 4, 5, and 6 blister pack will contain a 7 (±2) day supply of double-blind study medication and fluoxetine hydrochloride capsules.

Four blister packs clearly labeled with the visit number (Visits 7—20 mg fluoxetine hydrochloride; Visit 7—40 mg fluoxetine hydrochloride; Visit 8—20 mg fluoxetine hydrochloride and Visit 8—40 mg fluoxetine hydrochloride). Each Visit 7 and Visit 8 blister pack will contain a 14 (±2) day supply of double-blind study drug and fluoxetine hydrochloride capsules. At the investigator's discretion based on lack of improvement or minimal improvement on the Clinical Global Impression (rating of ≧3), the dose of fluoxetine may be increased to 40 mg at Visit 7. If the subject requires the 40 mg dose of fluoxetine hydrochloride, the Visit 7—a 40 mg fluoxetine hydrochloride blister pack will be dispensed. Choose only one Visit 7 and one Visit 8 card. The Visit 7 and Visit 8 card that is not used will remain in the kit and will be returned.

Single-Blind Wash-out: Subjects who completed the 8-week double-blind treatment period were entered into a two-week single-blind wash-out period. At Visit 9, subjects were provided with a blister pack containing a 14 (±2) day supply of single blind placebo tablets and open-label fluoxetine hydrochloride capsules.

Dosing Instructions

Subjects were instructed to take one double- or single-blind tablet each night (at bedtime) beginning the evening of each office visit. Subject were instructed to take one fluoxetine hydrochloride capsule each morning beginning at Visit 3. Subjects were to return each blister pack at the next office visit. The morning dose of fluoxetine hydrochloride on the day of Visits 4-10 was to be taken prior to coming into clinic (from the previous visit's blister pack).

Treatment Plan

Standardization of Data Capture

Vital signs: For each visit, vital signs consist of ≧5 minutes resting, seated blood pressure, respiration rate, heart rate, and oral or auricular body temperature.

ECG: An ECG was performed at Visits 1, 9 and Visit 10. Collection was started after 5 minutes of supine rest. When possible, this ECG was obtained prior to drawing blood samples for clinical laboratory evaluations.

Clinical laboratory: Blood and urine samples for clinical laboratory assessments were obtained at Visits 1, 3, 7, 9, and 10 and analyzed accordingly. The analysis included Hematology: 1) Total WBC Count; 2) Differential: neutrophils, lymphocytes, monocytes, eosinophils, basophils; 3) Hemoglobin; 4) Hematocrit; 5) Platelet Count; and 6) RBC Count. Qualitative Urinalysis: 1) glucose, 2) ketones, 3) protein, and 4) blood. Other Urine Laboratory Tests: urine drug and alcohol screen. Blood chemistry tests included tests for electrolytes, certain enzymes, and certain other tests as described herein. Electrolytes: carbon dioxide, calcium, chloride, phosphorus (inorganic), potassium, sodium, and magnesium. Enzymes: alkaline phosphatase, SGOT (AST), and SGPT (ALT). Other: albumin, bilirubin (total), creatinine, glucose, protein (total), blood urea nitrogen, uric acid, and T4. Other tests: serum β-hCG pregnancy test (all females) and serum cortisol.

IVRS: All subjects were instructed on the use of the IVRS for the collection of sleep and depressive symptom endpoints at Visit 2. A brief review was conducted at subsequent visits, as needed. The following assessments were completed via IVRS:

Sleep Diary: Daily in the morning beginning the morning after Visit 2 until the morning after Visit 4; Morning of and morning after Visits 5, 6, 7, 8; Beginning on the first morning of the last week on DB (start of week 8) until the morning of Visit 10.

7 selected items of the HAM-D-17: Once on the morning after Visit 2; once on the morning of clinic visits 3 through 9; and once in between Visit 9 and 10 at approximately 7 days post visit 9 (on the first day of the daily diary at Week 9 on DB) and on the morning to prior to Visit 10.

Daily Telephone Assessment (DTA) and Symptoms Questionnaire (SQ): Daily in the morning beginning the morning after Visit 2 until the morning after Visit 4; Morning after Visits 5, 6, 7, 8, 9; Eight days post Visit 9; Morning of Visit 10.

QoL Measurements: All subjects completed the sleep and quality of life questionnaires in the clinic as described above. The questionnaires were reviewed by study staff with the subjects for completeness only. Patients were not questioned about any of their responses or given suggestions on how to answer any of the questions.

Medical Events Calendar (MEC): All subjects were given a Medical Event Calender (MEC) to be completed throughout their time on study. The MED simply provided a place for patients to record the medications taken each day and any illnesses, symptoms or medical conditions they experience each day. At each return visit, the MEC was reviewed, collected, and a new MEC was dispensed.

Adverse Events (AEs): Subjects were queried in a non-leading manner, without specific prompting (e.g., "How are you feeling?") to assess whether they are suffering from any adverse events.

Concomitant Medications and Medical History: Subject-self report was acceptable for listing all concomitant medication use, medical history and evaluation for inclusion/exclusion except where specific protocols procedures are mandated to ensure appropriate enrollment (e.g. certain baseline lab values).

Screening (Visit 1)

No protocol-related procedures were performed prior to obtaining written informed consent. Subjects were evaluated at screening to determine their eligibility for study participation. All clinical assessments (clinical laboratory, physical examination, ECG, etc.) was completed and reviewed by the Investigator prior to Visit 2.

Subject informed consent was obtained prior to initiation of study specific tapering of any disallowed medications. Investigators discussed the process of tapering antidepressant medications with subjects prior to signing consent and should note the discussion in progress notes in the source documentation. Tapering of antidepressant or other disallowed psychotropic medications was approached cautiously taking into consideration the subjects current depression symptoms and medical history and the manufacturer's package insert instructions for withdrawing therapy. Under no circumstances did the Investigators withdraw antidepressant or other disallowed psychotropic therapy:
1) prior to obtaining informed consent;
2) improperly/abruptly to adhere to the protocol specified wash-out periods.

If a tapering period was required, the screening visit was completed on multiple dates. At the first office visit, subjects were seen for the signing of the informed consent, collection of medical history and concomitant medications. The investigator performed a brief examination to assess the subject's status and to evaluate the potential for the subject to safely taper off of antidepressant or other disallowed psychotropic medication. The investigator documented rationale for enrolling a subject currently on antidepressant or other psychotropic therapy and the plan for tapering this medication in the source documents. Subjects did not complete the sleep history questionnaire or the Ham-D-17 via IVRS until the end of the wash-out period. If all screening procedures were not completed within 30 days from the date of signed Informed Consent, the subject returned to the clinic to sign a new Informed Consent.

The following study-related procedures were performed at screening:
1. Signed informed consent (including women of child-bearing potential addendum, if applicable) and privacy authorization from the subject before conducting any other visit procedures were obtained
2. A medical history (including psychiatric history), sleep history, demographic information, and alcohol use and any prior treatments for insomnia was obtained. NOTE: If tapering from antidepressant or other disallowed psychotropic medication was required, the sleep history questionnaire was not completed until the subject had completed the wash-out period.
3. The subject was registered on the IVRS and trained in its use. The subject completed the Hamilton-D-17 via IVRS to assess depression symptoms. NOTE: If tapering from antidepressant or other disallowed psychotropic medication was required, the Ham-D-17 should was not completed until the subject had completed the wash-out period.
4. All concurrent medications were recorded, including OTC and health and dietary supplements, taken within the previous 30 days; the Antidepressant Treatment History Questionnaire to evaluate prior response to antidepressants was completed.
5. A physical examination was performed, including a brief neurological examination (excluding genitourinary, breast and rectal).
6. Vital signs (seated), height and weight were obtained.
7. A 12-lead ECG was obtained
8. A blood sample for clinical laboratory tests (including hematology, chemistry and a serum pregnancy test for all women), and urine samples for urinalysis and urine alcohol and drug screen was obtained.
9. All inclusion and exclusion criteria were reviewed.
10. Issued MEC to all subjects and instructed subject on their use.
11. Scheduled Visit 2 in 5-14 days.

Visit 2 (Start of Baseline Period)

Visit 2 occurred 5-14 days after Visit 1. Subjects begin using the IVRS daily until Visit 4 following this visit. The following study-related procedures were performed:
1. Reviewed all inclusion and exclusion criteria including clinical laboratory assessments, and the IVRS HAM-D-17 score.
2. Subjects meeting all inclusion and exclusion criteria completed the ESS questionnaire prior to performing any other study related procedures. The questionnaire was reviewed for completeness by study staff. Any items left blank were returned to the subject for completion.
3. Collected and reviewed the MEC. Recorded all changes in concurrent medications, including OTC and health and dietary supplements, and AEs that may have occurred between Visit 1 and Visit 2.
4. Obtained vital signs (seated) and weight.
5. Instructed subjects on the use of the IVRS. Subjects will begin IVRS calls in the morning following Visit 2 and will continue daily calls for two-weeks until Visit 4.
6. Issued MEC and instruct the subject on its use.
7. Scheduled Visit 3 in 3-7 days.

Visit 3 (Randomization; Beginning of Double-blind Treatment Period)

Visit 3 occurred 3-7 days after Visit 2. The first dose of fluoxetine hydrochloride 20 mg was administered in clinic at Visit 3. Open-label fluoxetine hydrochloride dosing (in the morning) continued daily through Visit 10. The first dose of double-blind study medication was administered at bedtime on the day of Visit 3. Double-blind dosing (at bedtime) continued nightly through Visit 9.
1. Collected and reviewed the MEC. Recorded all changes in concurrent medications, including OTC and health and dietary supplements, and AEs that may have occurred between Visit 2 and Visit 3.
2. Reviewed randomization criteria.
3. Subjects meeting all randomization criteria completed the ESS, ISI, WLQ, and SF-36 questionnaires prior to performing any other study related procedures. Questionnaires were reviewed for completeness by study staff. Any items left blank were returned to the subject for completion.
4. A trained clinician administered the Hamilton-D-17 to assess depression symptoms.
5. The investigator completed the Clinical Global Impression of the subject's depression symptoms.
6. Obtained vital signs (seated) and weight.
7. Obtained blood and urine samples for clinical laboratory assessments including urinalysis, urine drug and alcohol screen, and serum pregnancy tests for all women.
8. Assigned a randomization number and dispensed the Visit 3 double-blind blister pack from the randomization kit. Instructed the subject to begin taking one double-blind tablet nightly at bedtime and one fluoxetine hydrochloride 20 mg capsule daily (in the morning). The first dose of fluoxetine hydrochloride was taken in clinic. The first dose of double-blind study medication was administered at bedtime on the day of Visit 3.

9. Reviewed use of IVRS and the schedule for calling. Subjects continued daily IVRS calls in the morning until Visit 4.
10. Issued MEC and instruct the subject on its use.
11. Scheduled Visit 4 in 7 (±2) days.

Visit 4 (Double-Blind Treatment Week 1)

Visit 4 occurred 7 (±2) days after Visit 3. Open-label fluoxetine hydrochloride dosing (in the morning) continued daily through Visit 10. Double-blind dosing (at bedtime) continued nightly through Visit 9.

1. Collected and reviewed the MEC. Recorded all changes in concurrent medications, including OTC and health and dietary supplements, and AEs that may have occurred between Visit 3 and Visit 4.
2. Collected the Visit 3 study-drug blister pack (fluoxetine hydrochloride and double-blind) and reviewed subject compliance.
3. Subjects completed the ESS questionnaire prior to performing any other study related procedures. The questionnaire was reviewed for completeness by study staff. Any items left blank were returned to the subject for completion.
4. The investigator completed the Clinical Global Impression of the subject's depression symptoms.
5. Obtained vital signs (seated) and weight.
6. Dispensed the Visit 4 double-blind blister pack. Instructed the subject to take one double-blind tablet nightly (at bedtime) and one open-label fluoxetine hydrochloride 20 mg capsule daily (in the morning).
7. Reviewed use of IVRS and the schedule for calling. Subjects called the IVRS on morning of Visit 5 (prior to coming to the visit).
8. Issued MEC and instructed the subject on its use.
9. Scheduled Visit 5 in 7 (±2) days.

Visit 5 (Double-Blind Treatment Week 2)

Visit 5 occurred 7 (±2) days after Visit 4. Open-label fluoxetine hydrochloride dosing (in the morning) continued daily through Visit 10. Double-blind dosing (at bedtime) continued nightly through Visit 9.

1. Collected and reviewed the MEC. Recorded all changes in concurrent medications, including OTC and health and dietary supplements, and AEs that may have occurred between Visit 4 and Visit 5.
2. Collected the Visit 4 study-drug blister pack (fluoxetine hydrochloride and double-blind) and reviewed subject compliance.
3. Subjects completed the ESS, ISI, and WLQ questionnaires prior to performing any other study related procedures. The questionnaires were reviewed for completeness by study staff. Any items left blank were returned to the subject for completion.
4. The investigator completed the Clinical Global Impression of the subject's depression symptoms.
5. Obtained vital signs (seated) and weight.
6. Dispensed the Visit 5 double-blind blister pack. Instructed the subject to take one tablet nightly (at bedtime) and one open-label fluoxetine hydrochloride 20 mg capsule daily (in the morning).
7. Reviewed use of IVRS and the schedule for calling. Subjects called the IVRS the morning following this visit and on the morning of Visit 6 (prior to the visit).
8. Issued MEC and instructed the subject on its use.
9. Scheduled Visit 6 in 7 (±2) days.

Visit 6 (Double-Blind Treatment Week 3)

Visit 6 occurred 7 (±2) days after Visit 5. Open-label fluoxetine hydrochloride dosing (in the morning) continued daily through Visit 10. Double-blind dosing (at bedtime) continued nightly through Visit 9.

1. Collected and reviewed the MEC. Recorded all changes in concurrent medications, including OTC and health and dietary supplements, and AEs that may have occurred between Visit 5 and Visit 6.
2. Collected the Visit 5 study-drug blister pack (fluoxetine hydrochloride and double-blind) and reviewed subject compliance.
3. Subjects completed the ESS questionnaire prior to performing any other study related procedures. The questionnaire was reviewed for completeness by study staff. Any items left blank were returned to the subject for completion.
4. The investigator completed the Clinical Global Impression of the subject's depression symptoms.
5. Obtained vital signs (seated) and weight.
6. Dispensed the Visit 6 double-blind blister pack. Instructed the subject to take one double-blind tablet nightly (at bedtime) and one open-label fluoxetine hydrochloride 20 mg capsule daily (in the morning).
7. Reviewed use of IVRS and the schedule for calling. Subjects called the IVRS the morning following this visit and on the morning of Visit 7 (prior to the visit).
8. Issued MEC and instruct the subject on its use.
9. Scheduled Visit 7 in 7 (±2) days.

Visit 7 (Double-Blind Treatment Week 4)

Visit 7 occurred 7 (±2) days after Visit 6. Open-label fluoxetine hydrochloride dosing (in the morning) continued daily through Visit 10. Double-blind dosing (at bedtime) continued nightly through Visit 9.

1. Collected and reviewed the MEC. Recorded all changes in concurrent medications, including OTC and health and dietary supplements, and AEs that may have occurred between Visit 6 and Visit 7.
2. Collected Visit 6 study-drug blister pack (fluoxetine hydrochloride and double-blind) and review subject compliance.
3. Subjects completed the ESS, 1SI, WLQ, and SF-36 questionnaires prior to performing any other study related procedures. The questionnaires were reviewed for completeness by study staff. Any items left blank were returned to the subject for completion.
4. A trained clinician administered the Hamilton-D-17 to assess depression symptoms.
5. The investigator completed the Clinical Global Impression. If in the investigators opinion the subject's depressive symptoms had not improved beyond minimal improvement (rating of $\geq 3$), the investigator could increase the dose of fluoxetine hydrochloride to 40 mg daily (in the morning). If an increased dose of fluoxetine was required, the investigator dispensed the double-blind blister pack containing the 40 mg dose of fluoxetine.
6. Dispensed the appropriate Visit 7 double-blind blister pack. Instructed the subject to take one double-blind tablet nightly (at bedtime) and one open-label fluoxetine hydrochloride 20 mg or 40 mg capsule daily (in the morning). Note: only one Visit 7 blister card was dispensed.
7. Obtained vital signs (seated) and weight.
8. Obtained blood and urine samples for clinical laboratory assessments including urinalysis, urine drug and alcohol screen, and a serum pregnancy tests on all women.
9. Reviewed use of IVRS and the schedule for calling. Subjects call the IVRS the morning following this visit and on the morning of Visit 8 (prior to the visit).

10. Issued MEC and instruct the subject on its use.
11. Scheduled Visit 8 in 14 (±2) days.

Visit 8 (Double-Blind Treatment Week 6)

Visit 8 occurred 14 (±2) days after Visit 7. Open-label fluoxetine hydrochloride dosing (in the morning) continued daily through Visit 10. Double-blind dosing (at bedtime) continued nightly through Visit 9.

1. Collected and reviewed the MEC. Recorded all changes in concurrent medications, including OTC and health and dietary supplements, and AEs that may have occurred between Visit 7 and Visit 8.
2. Collected Visit 7 study-drug blister pack (fluoxetine hydrochloride and double-blind) and reviewed subject compliance.
3. Subjects completed the ESS questionnaire prior to performing any other study related procedures. The questionnaire was reviewed for completeness by study staff. Any items left blank were returned to the subject for completion.
4. The investigator completed the Clinical Global Impression of the subject's depression symptoms.
5. Obtained vital signs (seated) and weight.
6. Dispensed one Visit 8 double-blind blister pack (20 mg or 40 mg fluoxetine hydrochloride). Instructed the subject to take one double-blind tablet nightly (at bedtime) and one open-label fluoxetine hydrochloride 20 or 40 mg capsule daily (in the morning).
7. Reviewed use of IVRS and the schedule for calling. Subjects called the IVRS the morning following this visit and resumed daily calls one week following Visit 8 until the morning of Visit 10 (prior to the visit).
8. Issued MEC and instruct the subject on its use.
9. Scheduled Visit 9 in 14 (±2) days.

Visit 9 (End of Double-Blind Treatment Week 8)

Visit 9 occurred 14 (±2) days after Visit 8. Open-label fluoxetine hydrochloride dosing (in the morning) continued daily through Visit 10. Double-blind dosing (at bedtime) continued nightly through the night prior to Visit 9.

1. Collected and reviewed the MEC. Recorded all changes in concurrent medications, including OTC and health and dietary supplements, and AEs that may have occurred between Visit 7 and Visit 8.
2. Collected Visit 8 the study-drug blister pack (fluoxetine hydrochloride and double-blind) and review subject compliance.
3. Subjects completed the ESS, ISI, WLQ, and SF-36 questionnaires prior to performing any other study related procedures. The questionnaire were reviewed for completeness by study staff. Any items left blank were returned to the subject for completion
4. A trained clinician administered the Hamilton-D-17 to assess depression symptoms.
5. The investigator completed the Clinical Global Impression of the subject's depression symptoms
6. Obtained vital signs (seated) and weight
7. Obtained standard 12-lead ECG
8. Obtained blood and urine samples for clinical laboratory assessments including urinalysis, urine drug and alcohol screen, serum pregnancy test on all women.
9. Performed the end of treatment physical exam to assess changes that have occurred since Visit 1.
10. Dispensed one Visit 9 single-blind placebo blister pack (Blister pack contains 20 mg or 40 mg fluoxetine hydrochloride) and instructed the subject to continue taking one single-blind tablet nightly (at bedtime) and one open-label fluoxetine hydrochloride 20 mg or 40 mg capsule daily (in the morning).
11. Reviewed use of IVRS and the schedule for calling. Subjects called the IVRS daily until the morning of Visit 10.
12. Issued MEC and instruct the subject on its use.
13. Scheduled Visit 10 in 14 (±2) days.

Visit 10 (End of Study)

Visit 10 occurred 14 (±2) days after Visit 9. Open-label fluoxetine hydrochloride dosing (in the morning) continued daily through Visit 10. Double-blind dosing (at bedtime) continued nightly through Visit 9. Subject completed the final IVRS assessment on the morning of Visit 10.

1. Collected and reviewed the MEC. Recorded all changes in concurrent medications, including OTC and health and dietary supplements, and AEs that may have occurred between Visit 9 and Visit 10.
2. Collected the Visit 9 blister pack and review subject compliance.
3. Subjects completed the ESS, ISI, WLQ, and SF-36 questionnaires prior to performing any other study related procedures. The questionnaires were reviewed for completeness by study staff. Any items left blank were returned to the subject for completion.
4. A trained clinician administered the Hamilton-D-17 to assess depression symptoms.
5. The investigator completed the Clinical Global Impression of the subject's depression symptoms
6. Obtained vital signs (seated) and weight.
7. Obtained a standard 12-lead ECG.
8. Obtained blood and urine samples for clinical laboratory assessments including urinalysis, urine drug and alcohol screen, serum pregnancy tests on all women.

Discontinuation and Replacement of Subjects

Subjects in this study were discontinued for any of the following reasons: 1) adverse reactions; 2) protocol violations; 3) withdrawal of consent; 4) lost to follow-up; 5) treatment failure; 6) does not meet inclusion/exclusion/randomization criteria; 7) other. All subjects prematurely discontinuing from the trial during the double-blind period, regardless of cause, were seen for an End of Study evaluation, at which time Visit 9 procedures 1-9 were performed. Subjects who discontinued early for any reason were replaced.

Statistics

General Design

This is a randomized, double-blind, multi-center, placebo-controlled, parallel group study of the efficacy and safety of Eszopiclone in the treatment of subjects diagnosed with major depressive disorder associated with insomnia. Approximately 600 subjects were randomized in a 1:1 ratio to receive one of the two treatments, eszopiclone 3 mg or placebo, for eight weeks in a double-blind fashion.

Analysis Variables

Primary and Secondary Efficacy Endpoints are described above.

Analysis Populations

The Intent-To-Treat (ITT) population included all randomized subjects who received at least one dose of study medication. All analyses were conducted using this population.

Data Analysis

Continuous variables were summarized using descriptive statistics, including number of subjects, mean, standard deviation, minimum, $25^{th}$ percentile, median, $75^{th}$ percentile, and maximum. For categorical variables, summaries included counts of subjects and percentages. Baseline was defined as the last non-missing value prior to the first dose of study medication. All statistical tests were two-sided and were conducted at the 5% significance level, unless otherwise specified.

To facilitate assessment of site effects and treatment by site interactions for analysis of efficacy data, all sites with fewer than 3 subjects per treatment group were ranked according to the number of subjects randomized. These sites were sequentially pooled together, starting with the site that has the fewest number of subjects (lowest rank), until a pseudo-site was formed that meets the 3 subjects per treatment group criterion. Then a second pseudo-site was formed by combining the next lowest ranking sites until the 3 subjects per treatment group criteria is met, and so on. If the final pseudo-site created did not meet the 3 subjects per treatment group criterion, then it was combined with the previous pseudo-site created.

All statistical procedures were performed using SAS Version 8.2 or higher. All p-values were reported to four decimal points with p-values less than 0.0001 reported at<0.0001.

Subject Disposition and Drug Exposure: Subject disposition was summarized and presented for the number and percentage of subjects, who were screened, randomized, received treatment, completed the study, and discontinued early (including reasons for discontinuations). For each subject, the number of doses taken was computed from the study drug dispensation and accountability CRF records obtained at each visit, assuming that subjects took their study drug medication evenly throughout the between-visits periods. The extent of exposure to the double-blind medication as well as the number of doses taken during the double-blind treatment period was summarized with descriptive statistics and presented by treatment group.

Important Protocol Deviations: Important protocol deviations (IPDs) which were reviewed include, but are not limited to, subjects who:
Did not meet inclusion/exclusion criteria or eligibility was not adequately verified
Did not meet baseline eligibility criteria
Received any disallowed concomitant medication post-baseline
Developed withdrawal criteria but were not withdrawn
Received less than 80% or more than 120% of the prescribed dose or had another dosing error that would be likely to impact efficacy outcome measures The potentially important protocol deviations were identified shortly before database lock and treatment unblinding either programmatically (e.g., inclusion/exclusion criteria violations, compliance assessment) or through review of treatment-blinded data listings (e.g., investigator comments, concomitant medications). Appropriate personnel (including, at a minimum, an M.D. and a biostatistician) reviewed the list of potential IPDs to identify which protocol deviations will be considered IPDs. The final list of IPDs was documented and used to generate a data listing.

Demographic and Baseline Characteristics: Demographic and baseline characteristics, including age, gender, race, height, weight, as well as sleep history parameters, was summarized using descriptive statistics. Continuous variables were compared across treatment groups using an ANOVA model with fixed effects for treatment and site, while categorical variables were compared using Cochran-Mantel-Haenszel (CMH) test for general association controlling for site. Sleep history was summarized by treatment group.

Efficacy Analysis: Efficacy analyses were conducted using ITT population. All subjective sleep parameters assessed via the IVRS were summarized descriptively (n, mean, SD, minimum, $25^{th}$ percentile, median, $75^{th}$ percentile and maximum) at each week and were presented by treatment group.

Primary Analysis: The primary analysis was conducted using the ITT population for the primary efficacy variable, mean WASO during the first week of double-blind medication. This endpoint was computed by averaging the daily WASO values obtained via IVRS from Visit 3 to Visit 4. The analysis was conducted using an analysis of variance model (ANOVA) with treatment and site as fixed effects. The analysis was performed on rank-transformed data, using the SAS MIXED procedure. The cumulative distribution function by treatment was plotted.

Key Secondary Analyses: An analysis of the time to onset of 30% antidepressant response, defined as the time from Visit 3 to the first of two successive clinic assessment time points at which the subject achieved a ≧30% reduction from baseline on the HAM-D-6 (Bech) score was analyzed using PROC LIFETEST within SAS. The number of subjects with antidepressant response, and the number of subjects censored were presented for each treatment along with one minus the Kaplan-Meier estimates. Subjects without an antidepressant response of ≧30% reduction in HAM-D-6 (Bech) score for at least two successive assessment time points were censored at the minimum of the end of study or the end of double-blind treatment+14 days. Additionally, the p-value from the log-rank test for equality of survival curves across treatments was reported and a time-to-onset plot (one minus Kaplan-Meier estimate) was produced. The percentage of subjects achieving antidepressant response, defined as a≧30% reduction from baseline in HAM-D-6 (Bech) score for at least two successive clinic assessments was also analyzed using a logistic regression model with treatment and site as fixed effects.

Other Secondary Analyses: Analysis of the secondary subjective sleep parameters, the 1, 2, 3, 4, 6, and 8 week post-randomization and double-blind averages of WASO (except week 1 average, which is the primary efficacy endpoint), TST, SL, mean number of awakenings, depth and quality of sleep, daytime alertness, ability to concentrate, physical well-being and ability to function was conducted on rank-transformed data using the same method as for the primary analysis.

Analysis of the time to onset of 50% antidepressant response, defined as the time from Visit 3 to the first of two successive clinic assessment time points at which the subject achieved a≧50% reduction from baseline on the HAM-D-6 (Bech) score was analyzed using the same method as for the key secondary analysis based on 30% antidepressant response. A 50% antidepressant response, defined as ≧50% reduction from baseline in on the HAM-D-6 (Bech) score for at least two successive clinic assessments was also analyzed using a logistic regression model with treatment and site as fixed effects. These analyses were repeated using both ≧30% reduction from baseline on the HAM-D-6 (Maier) and≧50% reduction from baseline on the HAM-D-6 (Maier) as the criteria used to define antidepressant response.

The change from baseline to each double-blind, post-treatment visit in the HAM-D-17 score as well as the change from baseline to each double-blind, weekly, post-treatment assessments in the HAM-D-6 (Bech) scores and HAM-D-6 (Maier) scores was presented descriptively (n, mean, median, standard deviation, minimum, $25^{th}$ percentile, median, $75^{th}$ percentile, and maximum) by treatment. Treatment comparisons were performed at each assessed time point. The analysis compared the eszopiclone 3 mg group to placebo using an analysis of variance model (ANOVA) with treatment and site as fixed effects. The analysis was performed using the SAS MIXED procedure.

Treatment comparisons were performed on the Mean Symptoms Questionnaire (SQ) Score during Week 1, defined as the average of the daily SQ scores obtained via IVRS from Visit 3 to Visit 4 using an analysis of variance model (ANOVA) with treatment and site as fixed effects. Mean Daily Telephone Assessment (DTA) Scores during Week 1, defined as the average of the daily DTA scores obtained via IVRS from Visit 3 to Visit 4 were analyzed using the same method as for the Week 1 SQ score. SQ and DTA scores were also summarized descriptively at each assessed time point, with treatment comparisons performed at Weeks 2, 3, 4, 6 and 8, using the same method as for the Week 1 SQ score.

All quality of life and productivity parameters were summarized descriptively at each assessed time point for the double-blind treatment period and were presented by treatment. Treatment comparisons were performed at each assessed time point using an analysis of variance model (ANOVA) with treatment and site as fixed effects.

Analyses of Rebound and Withdrawal Effects: The occurrence of rebound insomnia and withdrawal effects was assessed for WASO, TST, and SL. For each sleep parameter, the baseline value was computed by averaging the values obtained from IVRS for the SB period (i.e., Visit 2 to Visit 3). The change from baseline to each post-treatment IVRS assessment obtained during the single-blind washout period (Visit 9 to Visit 10), as well as to the average of the washout period assessments, was computed. Descriptive statistics (mean, standard deviation, minimum, $25^{th}$ percentile, median, $75^{th}$ percentile and maximum) were presented by treatment at each time point. A Wilcoxon signed-rank test was performed for each treatment group to assess whether the distribution of changes from baseline are centered at zero. In addition, between-group comparisons were performed for these change-from-baseline variables using the same method as for the primary analysis.

The same analyses were performed for the change from the end of treatment (i.e., mean value during the last week of double-blind treatment) to each night of the washout period, as well as for the change from the end of treatment to the average over the washout period.

Assessment of rebound and withdrawal was also performed for the depression measures, HAM-D-17, HAM-D-6 (Bech), HAM-D-6 (Maier), SQ and DTA. Baseline will be defined as the Visit 3 value for the HAM-D-17, the single-blind average scores from Visit 2 and Visit 3 for HAM-D-6 (Bech) and HAM-D-6 (Maier) and the average of daily values obtained via IVRS during the single-blind period (from Visit 2 to Visit 3) for SQ and DTA. The change from baseline to Visit 10 in HAM-D-17 score, and the change from baseline to each post-treatment assessment obtained during the single-blind washout period (Visit 9 to Visit 10) was computed for all the other depression measures. Descriptive statistics (mean, standard deviation, minimum, $25^{th}$ percentile, median, $75^{th}$ percentile and maximum) was presented by treatment at each time point. A Wilcoxon signed-rank test was performed for each treatment group to assess whether the distribution of changes from baseline are centered at zero. In addition, between-group comparisons will be performed for these change-from-baseline variables using an analysis of variance model (ANOVA) with treatment and site as fixed effects.

The same analyses were performed for the change from the end of treatment (i.e., value obtained during the last week of double-blind treatment) to the washout period (Visit 10).

Exploratory analyses: The full ANOVA model including treatment by site interaction was used for exploratory analysis of the homogeneity of response by investigative sites using the primary and the secondary subjective sleep variables for the intent-to-treat population. If the interaction is statistically significant at the 0.10 significance level, additional analyses will be completed to more thoroughly explore this interaction.

Treatment comparisons (eszopiclone 3 mg versus placebo) were also performed, using an ANOVA model with treatment, site, and baseline as fixed effects for Week 1 average of WASO, TST, and SL. Baseline is defined as the average of daily IVRS values obtained between Visit 2 and Visit 3. WASO and SL, the values were log transformed prior to averaging.

An analysis exploring the time to onset of antidepressant response was performed on a subset of those subjects who had a 30%n antidepressant response, defined as the time from Visit 3 to the first of two successive clinic assessment time points at which the subject achieved a $\geq 30\%$ reduction from baseline on the HAM-D-6 (Bech) score. The number of subjects with antidepressant response was presented along with one minus the Kaplan-Meier estimate (which in this case, would be the sample proportions of subjects with response times greater than t). Additionally, the p-value from the log rank test for equality of survival curves across treatments was reported and a time to onset plot (one minus Kaplan-Meier estimate) was produced. This analysis was repeated for a 50% antidepressant response on the using a $\geq 50\%$ reduction in the HAM-D-6 (Bech), and a 30% and 50% antidepressant response on the HAM-D-6 (Maier) as the criteria used to define antidepressant response.

Adverse Events: All adverse experiences were coded using the COSTART dictionary (Coding Symbols for a thesaurus of Adverse Event Terms; version 5.0, 1995). Treatment emergent adverse experiences was defined as 1) AEs that occurred or worsened (increased in severity and/or frequency) on or after the first dose of study medication, 2) AEs with a missing start data and a stop date on or after the first dose of study medication, or 3) AEs with both a missing start and stop date. Treatment emergent AEs was summarized by treatment and by COSTART body system and preferred term. AEs that occurred within 14 days after treatment discontinuation was considered treatment-emergent AEs.

The following treatment emergent adverse experience summaries were summarized and presented by treatment group and by COSTART body system and preferred term:
  All AEs (including number of events and subject incidence)
  AEs by Severity (mild, moderate, severe)
  AEs by Relationship to Treatment (not related, unknown, possible, probable, or definite)

The following conventions were followed in summarizing AEs:
  For subject incidence summaries, each subject will be counted only once within each body system and within each preferred term.
  If a subject reports more than one adverse event within a preferred term and/or a body system, the adverse event with the highest known severity within each body system and within each preferred term will be included in the summaries by severity.
  For summaries by relationship to study medication, adverse event will be reported by the strongest relationship within each body system and within each preferred term (AEs with unknown relationship will be considered "more related" than events not related to study drug).

Appearance of all new adverse events following discontinuation of treatment or occurring the day after the last dose of study drug through the end of the study were summarized and presented by treatment group. For each subject, an adverse event is considered a new event if the subject does not experience that event during treatment or the event worsens in severity after the end of the treatment.

Subjective Assessments and Questionnaires

Epworth Sleepiness Scale: The Epworth Sleepiness Scale test asks patients to how likely they are to doze off or fall asleep, in contrast to feeling just tired, in the the following situations: a) sitting and reading, b) watching TV, c) sitting inactive in a public place, e.g, theatre or meeting, d) as a passenger in a car for 1 hour without a break, e) lying down to rest in the afternoon, f) sitting and talking to someone, g) sitting quietly after lunch (when you've had no alcohol), and h) in a car while stopped in traffic for a few minutes. Patients rate their likelihood of dozing off or fall asleep according to by selecting one of the following: 1) would never doze, 2) slight chance of dozing, 3) moderate chance of dozing, or 4) high chance of dozing.

Insomnia Severity Index: The insomnia severity index test is a series of thirteen questions (See FIG. 14) used to evaluate insomnia.

Work Limitations Questionnaire: The work limitations questionnaire is a series of questions used to evaluate how the patient's health has affected his or her work. In part I of the questionnaire, patients are asked to indicate how satisfied they are with a) their local schools, and b) their local police department. Patients indicate that they are 1) not at all satisfied, 2) moderately satisfied, or 3) very satisfied. In Part II of the questionnaire, patients are asked 25 questions related to work performance. First, patients are asked how much of the time in the last two weeks did their physical health or emotional problems make it difficult for them to do the following: a) work the required number of hours, b) get going easily at the beginning of the workday, c) start on your job as soon as you arrived at work, d) do your work without stopping to take breaks or rests, or e) stick to a routine or schedule. Second, patients are asked how much of the time in the past two weeks were they able to do the following without difficulty caused by physical health or emotional problems: a) walk or move around different work locations (for example, go to meetings) b) lift, carry, or move objects at work weighing more than 10 lbs., c) sit, stand, or stay in one position for longer than 15 minutes while working, d) repeat the same motions over and over again while working, e) bend, twist, or reach while working, or f) use hand-held tools or equipment (for example, a phone, pen, keyboard, computer mouse, drill, hairdryer, or sander). Third, patients were asked how much of the time in the past two weeks did their physical health or emotional problems make it difficult to do the following: a) keep your mind on your work, b) think clearly when working, c) do work carefully, d) concentrate on your work, e) work without losing your train of thought, or f) easily read or use your eyes when working. Fourth, patients were asked how much of the time in the past two weeks did their physical health or emotional problems make it difficult to do the following: a) speak with people in-person, in meetings or on the phone, b) control your temper around people when working, or c) help other people to get work done. Fifth, patients were asked how much of the time in the past two weeks did their physical health or emotional problems make it difficult to do the following: a) handle the workload, b) work fast enough, c) finish work on time, d) do your work without making mistakes, or e) feel you've done what you are capable of doing. Patients respond to the aforementioned questions by indicating one of the following responses: 1) All of the time (100%), 2) most of the time, 3) some of the time (about 50%), 4) a slight bit of the time, 5) none of the time (0%), or 6) does not apply to my job.

Acute Health Survey: The Acute Health Survey is a series of eleven questions (See FIGS. 15 and 16) answered by the patient to evaluate how they perceive their health.

Hamilton Depression Rating Scale (HAM-D17): During this analysis, a medical professional evaluates the patient according to seventeen criteria by selecting the response that best characterizes the patient's behavior during the past week. The criteria and responses are based on that described in Br. J. Soc. Clin. Psychol. 6: 278-296 (1967) and are reproduced below. Question 1: Depressed mood (Sadness, hopeless, helpless, worthless); Response: 0—Absent, 1—These feeling states indicated only on questioning, 2—These feeling states spontaneously reported verbally, 3—Communicates feeling states non-verbally i.e., through facial expression, posture, voice, and tendency to weep, or 4—Patient report virtually only these feeling states in his spontaneous verbal and non-verbal communication. Question 2: Feeling of guilt; Response: 0—Absent, 1—Self reproach, feels he has let people down, 2—Ideas of guilt or rumination over past errors or sinful deeds, 3—Present illness is a punishment and/or has delusions of guilt, or 4—Hears accusatory or denunciatory voices and/or experiences threatening visual hallucinations. Question 3: Suicide; Response: 0—Absent, 1—Feels life is not worth living, 2—Wishes he were dead or any thoughts of possible death to self, 3—Suicide ideas or gesture, 4-Attempts at suicide (any serious attempt rates 4). Question 4: Insomnia early; Response: 0—No difficulty falling asleep; 1—Complains of occasional difficulty falling asleep—i.e., more than ½ hour; or 2—complains of nightly difficulty falling asleep. Question 5: Insomnia middle; Response: 0—No difficulty, 1—patient complains of being restless and disturbed during the night, or 2—Waking during the night—any getting out of bed rates 2 (except for purposes of voiding). Question 6: Insomnia Late; Response: 0—No difficulty, 1—Waking in early hours of the morning but goes back to sleep, or 2—Unable to fall asleep again if he gets out of bed. Question 7: Work and activities; Response: 0—No difficulty, 1—Thoughts and feelings of incapacity, fatigue or weakness related to activities, work or hobbies; 2—Loss of interest in activity, hobbies or work—either directly reported by patient, or indirect in listlessness, indecision and vacillation (feels he has to push self to work or activities); 3—Decrease in actual time spent in activities or decrease in productivity (In hospital, rate 3 if patient does not spend at least three hours a day in activities (hospital job or hobbies) exclusive of ward chores); or 4—Stopped working because of present illness (In hospital, rate 4 if patient engages in no activities except ward chores, or if patient fails to perform ward chores unassisted). Question 8: Retardation (Slowness of thought and speech; impaired ability to concentrate; decreased motor activity); Response: 0—Normal speech and thought, 1—Slight retardation at interview, 2—Obvious retardation at interview, 3—Interview difficult, or 4—Complete stupor. Question 9: Agitation; Response: 0—None; 1—Fidgetiness; 2—Playing with hands, hair, etc.; 3—Moving about, can't sit still; or 4—Hand wringing, nail biting, hair-pulling, biting of lips. Question 10: Anxiety psychic: 0—No difficulty, 1—Subjective tension and irritability, 2—Worrying about minor matters, 3—Apprehensive attitude apparent in face or speech, or 4—Fears expressed without questioning. Question 11: Anxiety somatic (Physiological concomitants of anxiety, such as:—Gastro-intestinal: dry mouth, wind, indigestion, diarrhea, cramps, belching.—Cardio-vascular: palpitations, headaches.—Respiratory: hyperventilation, sighing.—Urinary frequency—Sweating); Response: 0—Absent, 1—Mild, 2—Moderate, 3—Severe, or 4—Incapacitating. Question 12: Somatic symptoms gastro-intestinal; Response: 0—None, 1—Loss of appetite but eating without staff encouragement and/or heavy feelings in abdomen; or 2—Difficulty eating without staff urging and/or requests or requires laxatives or medication for bowels or medication for gastro-intestinal symptoms. Question 13: Somatic symptoms general; Response: 0—None; 1—Heaviness in limbs, back or head; backaches, headache, or muscle aches; or loss of energy and fatigability; or 2—Any clear-cut symptom rates 2. Question 14: Genital symptoms (Symptoms such as loss of libido, menstrual disturbances); Response: 0—Absent, 1—Mild, or 2—Severe. Question 15: Hypochondriasis; Response: 0—Not present, 1—Self-absorption (bodily); 2—Preoccupation with health; 3—Frequent complaints, requests for help, etc.; or 4—Hypochondriacal delusions. Question 16: Loss of Weight; Response: A) When rating by history: 0—No weight loss, 1—Probable weight loss associated with present illness, or 2—Definite (according to patient) weight loss. B) On weekly rating by ward psychiatrist, when actual weight changes are measured: 0—Less than 1 lb (500 g), weight loss in week; 1—Greater than 1 lb (500 g), weight loss in week; or 2—Greater than 2 lb (1000 g), weight loss in week. Question 17: Insight: 0—Acknowledges being depressed and ill; 1—Acknowledges illness but attributes cause to bad food, climate, overwork, virus, need for rest, etc.; or 2—Denies being ill at all.

Clinical Global Impression: In this test, a medical professional rates the patient's depression and whether the improvement in depression is due to the drug treatment. Question 1) Severity: Considering your total clinical experience with this particular population, how depressed is the patient at this time? Respond by indicating 1=normal, not at all depressed, 2=borderline depressed, 3=mildly depressed, 4=moderately depressed, 5=markedly depressed, 6=severely depressed, or 7=among the most extremely depressed patients. Question 2) Global Improvement: Rate total improvement whether or not, in your judgment, it is due entirely to drug treatment. Compared to his/her condition at Visit 3, how much has he/she changed? Respond by indicating 1=very much improved, 2=much improved, 3=minimally improved, 4=no change, 5=minimally worse, 6=much worse, or 7=very much worse.

Sleep Diary Test: Patients are to call between 6 a.m. and 10 a.m. and answer the following questions. 1) Did you take study medication last night? 2) What time did you go to bed to go to sleep last night? 3) Did you fall asleep last night? (If No, go to question 10) 4) How long did it take you to fall asleep last night? Hours+Minutes? 5) Last night, did you wake up during the night, after falling asleep? 5a) How many times, did you wake up after falling asleep? 5b) After falling asleep for the first time, how much total time did you spend awake during the night? Hours+Minutes? 6) How long did you sleep last night? Hours+Minutes? 7) What time did you get out of bed to rise for the day? 8) What number best describes the quality of your sleep last night? (0=poor and 10=excellent) 9) How would you describe the depth of your sleep last night? (0=very light and 10=very deep) 10) What number best describes how you generally felt yesterday during the day? (0=very sleepy and 10=wide awake and alert) 11) What number best describes your ability to concentrate or think clearly during the day yesterday (0=poor, 10=excellent) 12) What number best describes your sense of physical well being yesterday? (0=poor, 10=excellent) 13) How would you describe your ability to function during the day yesterday? (0=poor and 10=excellent)

Daily Telephone Assessment (DTA): In this test, patients call in to and indicate their condition relating to the following: Question 1) Sadness: On a scale from 0 to 9, how sad or depressed have you felt in the last 24-hours? 0 means you have not felt sad or depressed at all in the last 24 hours and 9 means you've been extremely depressed or sad. Press a number from 0 to 9 that best describes your feelings of sadness. Question 2) Nervousness: On a scale from 0 to 9, how nervous or anxious have you felt in the last 24-hours? 0 means you've not felt nervous or anxious at all in the last 24-hours and 9 means you've been extremely nervous or anxious. Press a number from 0 to 9 that best describes your feelings of nervousness or anxiety. Question 3) Irritability: On a scale from 0 to 9, how easily annoyed, irritated or upset have you been in the last 24-hours? 0 means you've not become annoyed, irritated or upset at all in the last 24-hours and 9 means you've been extremely easily annoyed, irritated or upset. Press a number from 0 to 9 that best describes your irritability. Question 4) Lack of energy: On a scale from 0 to 9, how much has your energy level been a problem for you in the last 24-hours? 0 means you've had plenty of energy and have not felt tired at all in the last 24-hours and 9 means you've been extremely tired, sluggish, or lacking in energy. Press a number from 0 to 9 that best describes your lack of energy. Question 5) Difficulty thinking: On a scale from 0 to 9, how difficult has it been for you to think about or concentrate on things in the last 24-hours? 0 means you've had no trouble thinking or concentrating at all in the last 24-hours and 9 means it's been extremely difficult for you to think or concentrate. Press a number from 0 to 9 that best describes your difficulty in thinking or concentrating. Question 6) Aches, pains or other discomforts: On a scale from 0 to 9, rate how much aches, pains, or other physical discomforts in your head, back, chest, belly, arms, or legs have bothered you in the last 24-hours. 0 means you've had no problems with aches, pains, or other discomforts at all in the last 24-hours and 9 means your aches, pains, or other discomforts have been extremely bothersome. Press a number from 0 to 9 that best describes how much your aches, pains, or other discomforts have been bothering you. Question 7) Problems with sleep: On a scale from 0 to 9, rate how much of a problem you had getting the sleep you wanted last night. 0 means you had no sleep problems at all. That is, you were able to go to sleep easily, you slept well, and you woke up feeling refreshed. 9 means you had great difficulty in getting to sleep, slept extremely poorly, or woke up feeling exhausted as if you had not slept. Press a number from 0 to 9 that best describes your problems with sleep. Question 8) Difficulty enjoying things: On a scale of 0 to 9, rate how hard it has been for you to enjoy things in the last 24-hours. Press 0 if you have had no trouble enjoying things. Press 9 if you have not been able to enjoy anything. Or press the number from 0 and 9 that best describes how much difficulty you have enjoying things in the last 24-hours. Question 9) Overall change since your last call, if you've not changed, press 1; if you're feeling better, press 2; if you're feeling worse, press 3. 9a)<<If better>> If you're a little better, press 1; if you're much better, press 2; if you're very much better, press 3. 9b)<<If worse>> If you're a little worse, press 1; if you're much worse, press 2; if you're very much worse, press 3.

The Symptom Questionnaire (23-Item Depression Subscale): This test asks patients to describe how they have felt in the last 24-hours regarding twenty-three criteria. Patients are asked to answer yes or no to the criteria. Criteria: weary, cheerful, sad or blue, happy, feeling unworthy, cannot enjoy yourself, feeling guilty, feeling well, contented, feeling desperate or terrible, thinking death or dying, enjoying yourself, depressed, feeling a failure, not interested in things, blaming yourself, thoughts of ending your life, looking forward toward the future, feeling that life is bad, feeling inferior to others, feeling useless, feel like crying, and feeling hopelessness.

DSM-IV: Criteria for Major Depressive Disorder

Diagnostic criteria for 296.2x Major Depressive Disorder, Single Episode: A) Presence of a single Major Depressive Episode. B) The Major Depressive Episode is not better accounted for by Schizoaffective Disorder and is not superimposed on Schizophrenia, Schizophreniform Disorder, Delusional Disorder, or Psychotic Disorder Not Otherwise Specified. C) There has never been a Manic Episode, a Mixed Episode, or a Hypomanic Episode. Note: This exclusion does not apply if all of the manic-like, mixed-like, or hypomanic-like episodes are substance or treatment-induced or are due to the direct physiological effects of a general medical condition.

Diagnostic criteria for 296.3x Major Depressive Disorder, Recurrent: A) Presence of two or more Major Depressive Episodes. Note: To be considered separate episodes, there must be an interval of at least 2 consecutive months in which criteria are not met for a Major Depressive Episode. B) The Major Depressive Episodes are not better accounted for by Schizoaffective Disorder and are not superimposed on Schizophrenia, Schizophreniform Disorder, Delusional Disorder, or Psychotic Disorder Not Otherwise Specified. C) There has never been a Manic Episode, a Mixed Episode, or a Hypomanic Episode. Note: This exclusion does not apply if all of the manic-like, mixed-like, or hypomanic-like episodes are substance or treatment-induced or are due to the direct physiological effects of a general medical condition.

DSM-IV Diagnostic Criteria for Insomnia Related to Major Depressive Disorder: A) The predominant complaint is difficulty initiating or maintaining sleep, or nonrestorative sleep, for a least 1 month that is associated with daytime fatigue or impaired daytime functioning. B) The sleep disturbance (or daytime sequelae) causes clinically significant distress or impairment in social, occupational, or other important areas of functioning. C) The insomnia is judged to be related to Major Depressive Disorder, but is sufficiently severe to warrant independent clinical attention. D) The disturbance is not better accounted for by another Sleep Disorder (e.g., Narcolepsy, Breathing-Related Sleep Disorder, a Parasomnia). E) The disturbance is not due to the direct physiological effects of a substance (e.g., a drug of abuse, a medication) or a general medical condition.

Results of Study:

TABLE 1

Summary of Fluoxetine Titration During Double-Blind Treatment Period
(Intent-to-Treat Population)

| | Placebo (N = 274) | | | Eszopiclone 3 mg (N = 269) | | |
|---|---|---|---|---|---|---|
| Assessment | Total Subjects on Study n | Fluoxetine Hydrochloride 20 mg n (%) | Fluoxetine Hydrochloride 40 mg n (%) | Total Subjects on Study n | Fluoxetine Hydrochloride 20 mg n (%) | Fluoxetine Hydrochloride 40 mg n (%) |
| Visit 3 | 274 | 274 (100.0%) | 0 (0.0%) | 269 | 269 (100.0%) | 0 (0.0%) |
| Visit 4 | 274 | 274 (100.0%) | 0 (0.0%) | 268 | 268 (100.0%) | 0 (0.0%) |
| Visit 5 | 274 | 274 (100.0%) | 0 (0.0%) | 268 | 268 (100.0%) | 0 (0.0%) |
| Visit 6 | 274 | 274 (100.0%) | 0 (0.0%) | 268 | 268 (100.0%) | 0 (0.0%) |
| Visit 7 [1] | 225 | 104 (46.2%) | 121 (53.8%) | 224 | 125 (55.8%) | 99 (44.2%) |
| Visit 8 | 204 | 91 (44.6%) | 113 (55.4%) | 213 | 115 (54.0%) | 98 (46.0%) |
| Visit 9 | 195 | 88 (45.1%) | 107 (54.9%) | 195 | 103 (52.8%) | 92 (47.2%) |

[1] If the subject's depressive symptoms had not improved in the investigator's opinion, then fluoxetine dose was increased to 40 mg at Visit 7.

Note(s):

Percentages are computed based on the total number of subjects on study within each double-blind treatment group at each visit. All subjects were administered single-blind placebo and fluoxetine during the single-blind wash-out period.

TABLE 2

Subjective Wake Time After Sleep Onset (WASO) (Minutes)
(Intent-to-Treat Population)

| Week [1] | Statistic | Placebo (N = 274) | Eszopiclone 3 mg (N = 269) |
|---|---|---|---|
| 4 | N | 129 | 138 |
|   | Mean (SD) | 73.5 (69.5) | 71.4 (80.3) |
|   | 25th Percentile | 30.0 | 20.0 |
|   | Median | 55.8 | 42.5 |
|   | 75th Percentile | 90.0 | 90.0 |
|   | Minimum, Maximum | 0, 420 | 0, 420 |
|   | p-value vs. placebo [2] |  | 0.0345 |
| 6 | N | 117 | 116 |
|   | Mean (SD) | 73.5 (83.4) | 76.5 (88.1) |
|   | 25th Percentile | 30.0 | 15.0 |
|   | Median | 60.0 | 46.3 |
|   | 75th Percentile | 90.0 | 111.5 |
|   | Minimum, Maximum | 0, 600 | 0, 605 |
|   | p-value vs. placebo [2] |  | 0.3789 |
| 8 | N | 164 | 160 |
|   | Mean (SD) | 82.0 (73.2) | 63.8 (74.1) |
|   | 25th Percentile | 36.3 | 21.9 |
|   | Median | 60.8 | 43.1 |
|   | 75th Percentile | 105.0 | 80.1 |
|   | Minimum, Maximum | 0, 480 | 0, 600 |
|   | p-value vs. placebo [2] |  | 0.0003 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 3

Subjective Wake Time After Sleep Onset (WASO) (Minutes)
(Intent-to-Treat Population)

| Week [1] | Statistic | Placebo (N = 274) | Eszopiclone 3 mg (N = 269) |
|---|---|---|---|
| Double-Blind Average | N | 242 | 242 |
|   | Mean (SD) | 84.1 (63.2) | 72.6 (58.7) |
|   | 25th Percentile | 42.9 | 28.4 |
|   | Median | 73.4 | 57.4 |
|   | 75th Percentile | 110.8 | 100.0 |
|   | Minimum, Maximum | 0, 490 | 2, 350 |
|   | p-value vs. placebo [2] |  | 0.0051 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 4

Subjective Sleep Latency (Minutes)
(Intent-to-Treat Population)

| Week [1] | Statistic | Placebo (N = 274) | Eszopiclone 3 mg (N = 269) |
|---|---|---|---|
| 1 | N | 236 | 238 |
|   | Mean (SD) | 79.2 (82.8) | 62.6 (61.0) |
|   | 25th Percentile | 33.3 | 23.6 |
|   | Median | 57.9 | 43.3 |
|   | 75th Percentile | 94.0 | 75.0 |
|   | Minimum, Maximum | 6, 668 | 0, 435 |
|   | p-value vs. placebo [2] |  | 0.0002 |
| 2 | N | 217 | 224 |
|   | Mean (SD) | 64.4 (78.3) | 45.0 (52.2) |
|   | 25th Percentile | 30.0 | 15.0 |
|   | Median | 45.0 | 30.0 |
|   | 75th Percentile | 75.0 | 58.8 |
|   | Minimum, Maximum | 1, 720 | 0, 458 |
|   | p-value vs. placebo [2] |  | <.0001 |
| 3 | N | 205 | 217 |
|   | Mean (SD) | 62.9 (74.3) | 54.1 (100.9) |
|   | 25th Percentile | 25.0 | 15.0 |
|   | Median | 37.5 | 25.0 |
|   | 75th Percentile | 75.0 | 60.0 |
|   | Minimum, Maximum | 0, 611 | 0, 1058 |
|   | p-value vs. placebo [2] |  | <.0001 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 5

Subjective Sleep Latency (Minutes)
(Intent-to-Treat Population)

| Week [1] | Statistic | Placebo (N = 274) | Eszopiclone 3 mg (N = 269) |
|---|---|---|---|
| 4 | N | 191 | 207 |
|   | Mean (SD) | 60.0 (68.8) | 40.5 (50.5) |
|   | 25th Percentile | 22.5 | 15.0 |
|   | Median | 42.5 | 24.2 |
|   | 75th Percentile | 75.0 | 45.0 |
|   | Minimum, Maximum | 0, 665 | 0, 330 |
|   | p-value vs. placebo [2] |  | <.0001 |
| 6 | N | 176 | 189 |
|   | Mean (SD) | 71.4 (122.1) | 43.8 (77.3) |
|   | 25th Percentile | 20.0 | 12.5 |
|   | Median | 36.3 | 20.0 |
|   | 75th Percentile | 69.6 | 45.0 |
|   | Minimum, Maximum | 0, 1200 | 0, 630 |
|   | p-value vs. placebo [2] |  | <.0001 |
| 8 | N | 205 | 209 |
|   | Mean (SD) | 61.4 (56.1) | 42.4 (42.3) |
|   | 25th Percentile | 25.0 | 15.5 |
|   | Median | 45.0 | 30.0 |
|   | 75th Percentile | 78.0 | 54.0 |
|   | Minimum, Maximum | 0, 326 | 1, 254 |
|   | p-value vs. placebo [2] |  | <.0001 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 6

Subjective Sleep Latency (Minutes)
(Intent-to-Treat Population)

| Week [1] | Statistic | Placebo (N = 274) | Eszopiclone 3 mg (N = 269) |
|---|---|---|---|
| Double-Blind Average | N | 257 | 257 |
|   | Mean (SD) | 73.8 (65.4) | 53.0 (52.6) |
|   | 25th Percentile | 33.1 | 22.5 |
|   | Median | 56.1 | 39.3 |
|   | 75th Percentile | 92.6 | 65.0 |

TABLE 6-continued

Subjective Sleep Latency (Minutes)
(Intent-to-Treat Population)

| Week [1] | Statistic | Placebo (N = 274) | Eszopiclone 3 mg (N = 269) |
|---|---|---|---|
| | Minimum, Maximum | 6, 668 | 4, 465 |
| | p-value vs. placebo [2] | | <.0001 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 7

Subjective Total Sleep Time (Minutes)
(Intent-to-Treat Population)

| Week [1] | Statistic | Placebo (N = 274) | Eszopiclone 3 mg (N = 269) |
|---|---|---|---|
| 1 | N | 236 | 238 |
| | Mean (SD) | 340.3 (86.3) | 375.9 (76.5) |
| | 25th Percentile | 281.7 | 330.0 |
| | Median | 335.0 | 380.0 |
| | 75th Percentile | 391.8 | 423.8 |
| | Minimum, Maximum | 120, 780 | 80, 565 |
| | p-value vs. placebo [2] | | <.0001 |
| 2 | N | 217 | 224 |
| | Mean (SD) | 360.1 (91.6) | 393.6 (103.0) |
| | 25th Percentile | 300.0 | 333.1 |
| | Median | 356.3 | 397.5 |
| | 75th Percentile | 420.0 | 450.0 |
| | Minimum, Maximum | 150, 720 | 140, 1200 |
| | p-value vs. placebo [2] | | 0.0001 |
| 3 | N | 205 | 217 |
| | Mean (SD) | 373.8 (88.4) | 397.3 (88.1) |
| | 25th Percentile | 315.0 | 345.0 |
| | Median | 375.0 | 405.0 |
| | 75th Percentile | 425.0 | 450.0 |
| | Minimum, Maximum | 135, 793 | 0, 660 |
| | p-value vs. placebo [2] | | 0.0035 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 8

Subjective Total Sleep Time (Minutes)
(Intent-to-Treat Population)

| Week [1] | Statistic | Placebo (N = 274) | Eszopiclone 3 mg (N = 269) |
|---|---|---|---|
| 4 | N | 191 | 207 |
| | Mean (SD) | 370.4 (95.5) | 395.6 (87.3) |
| | 25th Percentile | 300.0 | 337.5 |
| | Median | 371.7 | 390.0 |
| | 75th Percentile | 450.0 | 450.0 |
| | Minimum, Maximum | 60, 600 | 165, 653 |
| | p-value vs. placebo [2] | | 0.0253 |
| 6 | N | 176 | 189 |
| | Mean (SD) | 369.9 (95.9) | 408.5 (84.3) |
| | 25th Percentile | 315.0 | 360.0 |
| | Median | 375.0 | 420.0 |
| | 75th Percentile | 428.8 | 472.5 |
| | Minimum, Maximum | 0, 720 | 150, 600 |
| | p-value vs. placebo [2] | | <.0001 |

TABLE 8-continued

Subjective Total Sleep Time (Minutes)
(Intent-to-Treat Population)

| Week [1] | Statistic | Placebo (N = 274) | Eszopiclone 3 mg (N = 269) |
|---|---|---|---|
| 8 | N | 205 | 209 |
| | Mean (SD) | 375.9 (87.2) | 405.9 (80.6) |
| | 25th Percentile | 321.4 | 365.0 |
| | Median | 387.5 | 411.4 |
| | 75th Percentile | 439.3 | 462.1 |
| | Minimum, Maximum | 0, 554 | 60, 630 |
| | p-value vs. placebo [2] | | 0.0009 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 9

Subjective Total Sleep Time (Minutes)
(Intent-to-Treat Population)

| Week [1] | Statistic | Placebo (N = 274) | Eszopiclone 3 mg (N = 269) |
|---|---|---|---|
| Double-Blind Average | N | 257 | 257 |
| | Mean (SD) | 358.8 (75.4) | 395.5 (66.9) |
| | 25th Percentile | 310.4 | 353.7 |
| | Median | 362.8 | 400.0 |
| | 75th Percentile | 405.0 | 441.2 |
| | Minimum, Maximum | 23, 556 | 210, 630 |
| | p-value vs. placebo [2] | | <.0001 |

[1] For each subject, Week 1 = average of all post randomization assessments obtained between Visit 3 and Visit 4, Week 2 = average of all post randomization assessments obtained between Visit 4 and Visit 5. Double-Blind Average includes all assessments obtained from Visits 3, 4, 5, 6, 7, and 8.
[2] The analysis is conducted using an analysis of variance model (ANOVA) on the rank-transformed data with treatment and site as fixed effects. The analysis is performed using the SAS MIXED procedure.

TABLE 10

Summary of Change from Baseline in Clinical Global Impression
(CGI) - Severity (Intent-to-Treat Population)

| | | Placebo | | Eszopiclone 3 mg | |
|---|---|---|---|---|---|
| Visit [1] | Statistic | Observed Value | Change from Baseline | Observed Value | Change from Baseline |
| 3 (Baseline) | N | 274 | | 269 | |
| | Mean (SD) | 4.3 (0.6) | | 4.3 (0.6) | |
| | 25th Percentile | 4.0 | | 4.0 | |
| | Median | 4.0 | | 4.0 | |
| | 75th Percentile | 5.0 | | 5.0 | |
| | Minimum, Maximum | 2, 6 | | 3, 6 | |
| 4 | N | 251 | 251 | 245 | 245 |
| | Mean (SD) | 4.0 (0.7) | −0.3 (0.6) | 4.0 (0.7) | −0.3 (0.7) |
| | 25th Percentile | 4.0 | 0.0 | 4.0 | −1.0 |
| | Median | 4.0 | 0.0 | 4.0 | 0.0 |
| | 75th Percentile | 4.0 | 0.0 | 4.0 | 0.0 |
| | Minimum, Maximum | 1, 6 | −3, 1 | 1, 6 | −4, 1 |
| | Least Squares Mean (SE) | | −0.3 (0.0) | | −0.3 (0.0) |
| | p-value vs. placebo [2] | | | | 0.2069 |

[1] For each subject, Baseline = Average of Daily IVRS values obtained prior to or on the first dose of double-blind treatment.
[2] The pairwise comparison of the placebo treatment mean to the eszopiclone treatment mean is performed using the analysis of covariance model (ANCOVA) with treatment and site as fixed effects and the baseline as a covariate. The analysis is performed using the SAS MIXED procedure.

TABLE 11

Summary of Change from Baseline in Clinical Global Impression (CGI) - Severity (Intent-to-Treat Population)

|  |  | Placebo | | Eszopiclone 3 mg | |
| --- | --- | --- | --- | --- | --- |
| Visit [1] | Statistic | Observed Value | Change from Baseline | Observed Value | Change from Baseline |
| 5 | N | 243 | 243 | 241 | 241 |
|  | Mean (SD) | 3.7 (0.8) | −0.6 (0.8) | 3.6 (0.9) | −0.8 (0.9) |
|  | 25th Percentile | 3.0 | −1.0 | 3.0 | −1.0 |
|  | Median | 4.0 | 0.0 | 4.0 | −1.0 |
|  | 75th Percentile | 4.0 | 0.0 | 4.0 | 0.0 |
|  | Minimum, Maximum | 1, 6 | −3, 2 | 1, 6 | −4, 0 |
|  | Least Squares Mean (SE) |  | −0.6 (0.1) |  | −0.8 (0.1) |
|  | p-value vs. placebo [2] |  |  |  | 0.0364 |
| 6 | N | 233 | 233 | 233 | 233 |
|  | Mean (SD) | 3.4 (1.0) | −0.9 (0.9) | 3.2 (1.0) | −1.1 (1.0) |
|  | 25th Percentile | 3.0 | −1.0 | 3.0 | −2.0 |
|  | Median | 4.0 | −1.0 | 3.0 | −1.0 |
|  | 75th Percentile | 4.0 | 0.0 | 4.0 | 0.0 |
|  | Minimum, Maximum | 1, 6 | −4, 2 | 1, 6 | −5, 1 |
|  | Least Squares Mean (SE) |  | −0.9 (0.1) |  | −1.1 (0.1) |
|  | p-value vs. placebo [2] |  |  |  | 0.0367 |

[1] For each subject, Baseline = Average of Daily IVRS values obtained prior to or on the first dose of double-blind treatment.
[2] The pairwise comparison of the placebo treatment mean to the eszopiclone treatment mean is performed using the analysis of covariance model (ANCOVA) with treatment and site as fixed effects and the baseline as a covariate. The analysis is performed using the SAS MIXED procedure.

TABLE 12

Summary of Change from Baseline in Clinical Global Impression (CGI) - Severity (Intent-to-Treat Population)

|  |  | Placebo | | Eszopiclone 3 mg | |
| --- | --- | --- | --- | --- | --- |
| Visit [1] | Statistic | Observed Value | Change from Baseline | Observed Value | Change from Baseline |
| 7 | N | 223 | 223 | 222 | 222 |
|  | Mean (SD) | 3.2 (1.1) | −1.1 (1.2) | 3.0 (1.1) | −1.4 (1.1) |
|  | 25th Percentile | 3.0 | −2.0 | 2.0 | −2.0 |
|  | Median | 3.0 | −1.0 | 3.0 | −1.0 |
|  | 75th Percentile | 4.0 | 0.0 | 4.0 | 0.0 |
|  | Minimum, Maximum | 1, 5 | −4, 1 | 1, 5 | −5, 1 |
|  | Least Squares Mean (SE) |  | −1.1 (0.1) |  | −1.3 (0.1) |
|  | p-value vs. placebo [2] |  |  |  | 0.0380 |
| 8 | N | 200 | 200 | 212 | 212 |
|  | Mean (SD) | 2.7 (1.0) | −1.5 (1.1) | 2.5 (1.0) | −1.8 (1.2) |
|  | 25th Percentile | 2.0 | −2.0 | 2.0 | −3.0 |
|  | Median | 3.0 | −1.0 | 2.5 | −2.0 |
|  | 75th Percentile | 3.0 | −1.0 | 3.0 | −1.0 |
|  | Minimum, Maximum | 1, 5 | −4, 1 | 1, 5 | −5, 1 |
|  | Least Squares Mean (SE) |  | −1.5 (0.1) |  | −1.8 (0.1) |
|  | p-value vs. placebo [2] |  |  |  | 0.0124 |

[1] For each subject, Baseline = Average of Daily IVRS values obtained prior to or on the first dose of double-blind treatment.
[2] The pairwise comparison of the placebo treatment mean to the eszopiclone treatment mean is performed using the analysis of covariance model (ANCOVA) with treatment and site as fixed effects and the baseline as a covariate. The analysis is performed using the SAS MIXED procedure.

TABLE 13

Summary of Change from Baseline in Clinical Global Impression (CGI) - Severity (Intent-to-Treat Population)

|  |  | Placebo | | Eszopiclone 3 mg | |
| --- | --- | --- | --- | --- | --- |
| Visit [1] | Statistic | Observed Value | Change from Baseline | Observed Value | Change from Baseline |
| 9 | N | 236 | 236 | 229 | 229 |
|  | Mean (SD) | 2.7 (1.2) | −1.6 (1.2) | 2.4 (1.2) | −1.9 (1.3) |
|  | 25th Percentile | 2.0 | −3.0 | 1.0 | −3.0 |
|  | Median | 3.0 | −2.0 | 2.0 | −2.0 |
|  | 75th Percentile | 4.0 | −1.0 | 3.0 | −1.0 |
|  | Minimum, Maximum | 1, 6 | −5, 2 | 1, 6 | −5, 1 |
|  | Least Squares Mean (SE) |  | −1.6 (0.1) |  | −1.8 (0.1) |
|  | p-value vs. placebo [2] |  |  |  | 0.0186 |
| 10 (EOT) | N | 191 | 191 | 188 | 188 |
|  | Mean (SD) | 2.4 (1.1) | −1.9 (1.2) | 2.0 (1.0) | −2.3 (1.2) |
|  | 25th Percentile | 1.0 | −3.0 | 1.0 | −3.0 |
|  | Median | 2.0 | −2.0 | 2.0 | −2.0 |
|  | 75th Percentile | 3.0 | −1.0 | 3.0 | −1.0 |
|  | Minimum, Maximum | 1, 5 | −5, 0 | 1, 5 | −5, 1 |
|  | Least Squares Mean (SE) |  | −1.8 (0.1) |  | −2.2 (0.1) |
|  | p-value vs. placebo [2] |  |  |  | 0.0004 |

[1] For each subject, Baseline = Average of Daily IVRS values obtained prior to or on the first dose of double-blind treatment.
[2] The pairwise comparison of the placebo treatment mean to the eszopiclone treatment mean is performed using the analysis of covariance model (ANCOVA) with treatment and site as fixed effects and the baseline as a covariate. The analysis is performed using the SAS MIXED procedure.

TABLE 14

Clinical Global Impression (CGI) - Global Improvement (Intent-to-Treat Population)

| Visit | Statistic | Placebo (N = 274) | Eszopiclone 3 mg (N = 269) |
| --- | --- | --- | --- |
| 4 | N | 250 | 242 |
|  | Mean (SD) | 3.5 (0.7) | 3.3 (0.8) |
|  | 25th Percentile | 3.0 | 3.0 |
|  | Median | 4.0 | 3.0 |
|  | 75th Percentile | 4.0 | 4.0 |
|  | Minimum, Maximum | 1, 5 | 0, 5 |
|  | p-value vs. placebo [1] |  | <.0001 |
| 5 | N | 242 | 241 |
|  | Mean (SD) | 3.0 (0.8) | 2.9 (0.8) |
|  | 25th Percentile | 3.0 | 2.0 |
|  | Median | 3.0 | 3.0 |
|  | 75th Percentile | 4.0 | 3.0 |
|  | Minimum, Maximum | 0, 5 | 1, 4 |
|  | p-value vs. placebo [1] |  | 0.0180 |
| 6 | N | 233 | 233 |
|  | Mean (SD) | 2.8 (0.9) | 2.6 (0.9) |
|  | 25th Percentile | 2.0 | 2.0 |
|  | Median | 3.0 | 3.0 |
|  | 75th Percentile | 3.0 | 3.0 |
|  | Minimum, Maximum | 1, 5 | 1, 6 |
|  | p-value vs. placebo [1] |  | 0.0166 |

[1] The analysis is conducted using an analysis of variance model (ANOVA) with treatment and site as fixed effects. The analysis is performed using the SAS MIXED procedure.

TABLE 15

Clinical Global Impression (CGI) - Global Improvement (Intent-to-Treat Population)

| Visit | Statistic | Placebo (N = 274) | Eszopiclone 3 mg (N = 269) |
|---|---|---|---|
| 7 | N | 222 | 222 |
|   | Mean (SD) | 2.7 (1.1) | 2.4 (1.0) |
|   | 25th Percentile | 2.0 | 2.0 |
|   | Median | 3.0 | 2.0 |
|   | 75th Percentile | 3.0 | 3.0 |
|   | Minimum, Maximum | 1, 5 | 1, 5 |
|   | p-value vs. placebo [1] |  | 0.0011 |
| 8 | N | 200 | 211 |
|   | Mean (SD) | 2.2 (0.9) | 1.9 (0.9) |
|   | 25th Percentile | 2.0 | 1.0 |
|   | Median | 2.0 | 2.0 |
|   | 75th Percentile | 3.0 | 3.0 |
|   | Minimum, Maximum | 1, 4 | 1, 5 |
|   | p-value vs. placebo [1] |  | 0.0057 |
| 9 | N | 236 | 229 |
|   | Mean (SD) | 2.2 (1.1) | 1.9 (1.0) |
|   | 25th Percentile | 1.0 | 1.0 |
|   | Median | 2.0 | 2.0 |
|   | 75th Percentile | 3.0 | 2.0 |
|   | Minimum, Maximum | 1, 6 | 0, 6 |
|   | p-value vs. placebo [1] |  | 0.0009 |

[1] The analysis is conducted using an analysis of variance model (ANOVA) with treatment and site as fixed effects. The analysis is performed using the SAS MIXED procedure.

TABLE 16

Clinical Global Impression (CGI) - Global Improvement (Intent-to-Treat Population)

| Visit | Statistic | Placebo (N = 274) | Eszopiclone 3 mg (N = 269) |
|---|---|---|---|
| 10 (EOT) | N | 190 | 188 |
|   | Mean (SD) | 2.0 (1.0) | 1.6 (0.9) |
|   | 25th Percentile | 1.0 | 1.0 |
|   | Median | 2.0 | 1.0 |
|   | 75th Percentile | 3.0 | 2.0 |
|   | Minimum, Maximum | 1, 5 | 0, 5 |
|   | p-value vs. placebo [1] |  | 0.0003 |

[1] The analysis is conducted using an analysis of variance model (ANOVA) with treatment and site as fixed effects. The analysis is performed using the SAS MIXED procedure.

TABLE 17

Subject Disposition

| Subject Disposition | Placebo n (%) | Esopiclone 3 mg n (%) |
|---|---|---|
| Randomized | 275 (100.0) | 270 (100.0) |
| Completed | 185 (67.3) | 187 (69.3) |
| Discontinued | 89 (32.4) | 83 (30.7) |
| AE | 21 (7.6) | 17 (6.3) |
| Protocol violation | 14 (5.1) | 10 (3.7) |
| Voluntary withdrawal | 21 (7.6) | 19 (7.0) |
| Lost to follow-up | 24 (8.7) | 26 (9.6) |
| Did not meet entry criteria | 3 (1.1) | 4 (1.5) |
| Treatment for Insomnia Failure | 2 (0.7) | 2 (0.7) |
| Other | 4 (1.5) | 5 (1.9) |

Note:
See FIGS. 4-14 for a graphical representation of the data.

The results of this study clearly demonstrate a number of unique and distinct responses, both for sleep and depression, when eszopiclone 3 mg nightly was co-administered with flouxetine HCk 20 mg or 40 mg daily, as discuss below:

1. Co-administration of eszopiclone and fluoxetine was well-tolerated and provided rapid and sustained improvement in sleep in patients with depression-related secondary insomnia. The rapid onset of sleep improvement is an important consideration for adjunctive therapy or co-administration with an antidepressant, such as an SSRI, as the antidepressant effect demonstrated a relatively slower onset.
2. These results indicate that patients co-administered a sedative (e.g., SSRI plus eszopiclone) may be more likely to be resistant to a recurring sleep disturbance which can be a prodromal relapse signal.
3. A pronounced and immediate sleep response was recorded for all three sleep parameters in this trial (sleep onset, WASO, and TST). This response differed in its time course from the observed augmentation effect on antidepressant therapy, which took hold gradually over the course of several weeks, hand in hand with the usually occurring antidepressant effect that is typically seen in this kind of cohort of patients with major depression. These different time courses indicate that separate, but potentially interlinked, biological processes are being affected by eszopiclone, leading to the distinct and temporally divergent improvement responses in sleep and depression.
4. Eszopiclone co-administration significantly improved sleep and augmented the anti-depression response in patients with MDD and insomnia, as shown by the HAMD changes, response rates, and CGI.
5. The augmentation effect observed with eszopiclone was larger than that observed with agents currently used for augmentation therapy, such as lithium.
6. Eszopiclone produced this augmentation effect with little risk to patients, whereas currently commonly used augmentation agents can produce considerable toxicity. In addition co-administration of eszopiclone may specifically reduce undesirable CNS adverse events, such as agitation, confusion, and other symptoms related to the underlying depression.
7. In terms of potential and clinically meaningful benefits to depression patients during treatment initiation, it is important to point out that these results indicate that eszopiclone can help alleviate worsening of sleep during introduction of antidepressants. Insomnia is a common complaint during treatment initiation, and these symptoms may be related to the antidepressant therapy chosen by the clinician, not the underlying depression.
8. The augmentation effect observed at the end of the 8 week treatment period in this study was most pronounced in the most severely depressed patients.
9. These results suggest that the augmentation effect may apply to de novo depressed patients, patients with relapsing depression, as well as patient with refractory depression.
10. The observed augmentation effect size grew gradually over time.
11. Quite unexpectedly, less patients in this study required antidepressant dose escalation to higher dose of fluoxetine, and indicating that co-administration of eszopiclone provided a dose-sparing effect. A dose-sparing effect can lead to significant improvements in efficacy, tolerability, and greater adherence to antidepressant therapy, as well as cost savings for health care payors. In addition, another impact of a dose-sparing effect arising from co-administration of a sedative, such as eszopiclone is that lower likelihood that a second antidepression agent will be needed to treat the depression.
12. These results indicate that co-administration of eszopiclone may have the affect of reducing depression relapse. In this study, the augmentation effect size grows gradually over time, hand in hand with the antidepressant effect, leading to greater improvement in depression in the combination therapy group. These results suggest that these patients receiving co-administration, especially if they receive chronic or long-term treatment with eszopiclone, may be less prone to depression relapse.

13. These results also suggest that co-administration or administration of eszopiclone may delay depression relapse: Depression relapse may be sudden onset for some patients, while for others it might be considered a gradual decline in mood and function which diminishes over time as the patient approaches the state of relapse. The augmentation effect size seen in this study, in and of itself, may delay the onset of depression relapse due to the magnitude of the effect sen in depression measures for those patients who experience a gradual decline. The patients who experience sudden onset of depression relapse may also potentially benefit from the augmentation therapy as the magnitude of the effect of administering eszopiclone may maintain symptoms above a "depression relapse" threshold.

14. These results also suggest the eszopiclone can protect against relapsing depression on its own, after withdrawal of the antidepressant treatment, by suppressing recurrent insomnia or by affecting a separate unknown process in the central nervous system that could either trigger or sustain the emergence of symptoms of depression.

EXAMPLE 2

Adjunctive Eszopiclone with Fluoxetine for MDD and Insomnia: Sleep Effects

Insomnia and depression often co-exist. This study evaluated the efficacy of eszopiclone for insomnia associated with MDD during concurrent fluoxetine treatment.

Methods: Patients (n=545) met DSM-IV criteria for MDD and insomnia, including reported sleep latency (SL)$\geq$30 min (median 73 min), wake time after sleep onset (WASO) $\geq$45 min (median 90 min), and total sleep time (TST)$\leq$6.5h (median 294 min). All patients received fluoxetine QAM, and were randomly assigned to double-blind treatment with eszopiclone 3 mg or placebo QHS for 8 weeks. Subjective sleep and daytime function were assessed weekly.

Results: Compared to placebo, eszopiclone was associated with significantly lower SL and greater TST at each treatment week (p<0.03); significantly lower WASO at Weeks 1, 3-5, and 7-8 (p<0.04); higher ratings across the treatment period in sleep quality and depth (p<0.005); and higher ratings of daytime alertness, ability to concentrate, and well-being (p$\leq$0.02). Combined treatment was well-tolerated. Unpleasant taste was more common with eszopiclone.

Conclusions: Co-administration of eszopiclone with fluoxetine was well-tolerated and associated with rapid, sustained improvement in sleep and daytime symptoms in patients with MDD and insomnia. The rapid sleep improvement with adjunctive eszopiclone may be important, given the relatively slower onset of antidepressant effects with SSRIs.

EXAMPLE 3

Adjunctive Eszopiclone and Fluoxetine in MDD & Insomnia: Depression Effects

Insomnia frequently co-exists with depression. This study evaluated eszopiclone and fluoxetine co-administration in depressed patients with co-morbid insomnia.

Methods: Patients who met DSM-IV criteria for new MDD and insomnia received fluoxetine 20 mg QAM plus either eszopiclone 3 mg (n=275) or placebo (n=270) nightly for 8 weeks. Efficacy was assessed using HAMD17 and Clinical Global Impression Improvement (CGI-I) and Severity (CGI-S). Response=50% decrease from baseline HAMD17; remission=HAMD17$\leq$7.

Results: Eszopiclone co-administration resulted in significantly greater changes in HAMD17 scores at Week 4 (-9.9 vs -8.5 for placebo, p=0.02) with progressive improvement at Week 8 (-13.8 vs -11.8, p<0.001). At Week 8, significantly more eszopiclone patients were responders (74% vs 61%, p<0.009) and remitters (54% vs 41%, p<0.02). Even with removal of insomnia items, significant differences were found at Week 8 (p<0.03). HAMD 17 differences were greater in patients with more severe depression (baseline HAMD 17$\geq$22). CGI-I and CGI-S scores were significantly greater with eszopiclone co-administration (p<0.05). Fluoxetine dose increases were less frequent with in eszopiclone (44% vs 54%; p<0.05). Treatment was well-tolerated; dropouts due to AEs were comparable.

Conclusions: Eszopiclone/fluoxetine co-administration significantly augmented the antidepressant response in patients with MDD and insomnia. The sleep response occurred immediately, followed by augmentation of the antidepressant response.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An improved method of antidepressant therapy utilizing escitalopram or fluoxetine, the improvement comprising administering a therapeutically effective amount of eszopiclone, or a pharmaceutically acceptable salt thereof, thereby accomplishing one or more outcomes selected from the group consisting of augmenting antidepressant response, eliciting a dose sparing effect, reducing depression relapse, improving efficacy of the antidepressant therapy, and improving tolerability of the antidepressant therapy.

2. The method of claim 1, wherein said serotonin reuptake inhibitor is fluoxetine, or a pharmaceutically acceptable salt thereof.

3. The method of claim 2, wherein said serotonin reuptake inhibitor is fluoxetine hydrochloride.

4. The method of claim 1 wherein the serotonin reuptake inhibitor is escitalopram, or a pharmaceutically acceptable salt thereof.

5. The method of claim 1, wherein the outcome comprises augmenting antidepressant response.

6. The method of claim 1, wherein the outcome comprises eliciting a dose sparing effect.

7. The method of claim 1, wherein the outcome comprises reducing depression relapse.

8. The method of claim 1, wherein the outcome comprises improving efficacy of the antidepressant therapy.

9. The method of claim 1, wherein the outcome comprises improving tolerability of the antidepressant therapy.

* * * * *